(12) United States Patent
Zurawski et al.

(10) Patent No.: US 8,961,991 B2
(45) Date of Patent: *Feb. 24, 2015

(54) ANTI-CD40 TARGETED FUSION PROTEINS

(75) Inventors: Gerard Zurawski, Midlothian, TX (US); Jacques F. Banchereau, Dallas, TX (US); Anne-Laure Flamar, Dallas, TX (US); Yves Levy, Paris (FR); Monica Montes, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 555 days.

This patent is subject to a terminal disclaimer.

(21) Appl. No.: 12/717,789

(22) Filed: Mar. 4, 2010

(65) Prior Publication Data

US 2010/0297114 A1 Nov. 25, 2010

Related U.S. Application Data

(60) Provisional application No. 61/159,055, filed on Mar. 10, 2009, provisional application No. 61/159,062, filed on Mar. 10, 2009, provisional application No. 61/159,059, filed on Mar. 10, 2009.

(51) Int. Cl.
| | | |
|---|---|---|
| A61K 39/00 | (2006.01) | |
| A61K 39/12 | (2006.01) | |
| A61K 39/21 | (2006.01) | |
| A61K 39/295 | (2006.01) | |
| C07K 19/00 | (2006.01) | |
| C07K 2/00 | (2006.01) | |
| A61K 39/385 | (2006.01) | |
| C07K 14/005 | (2006.01) | |
| C07K 16/28 | (2006.01) | |
| G01N 33/68 | (2006.01) | |

(52) U.S. Cl.
CPC ............ A61K 39/385 (2013.01); C07K 14/005 (2013.01); C07K 16/2878 (2013.01); G01N 33/6863 (2013.01); *A61K 2039/6056* (2013.01); *A61K 2039/627* (2013.01); *A61K 2039/64* (2013.01); *C07K 2317/77* (2013.01); *C07K 2319/00* (2013.01); *C07K 2319/30* (2013.01); *C12N 2740/16222* (2013.01); *C12N 2740/16322* (2013.01); *C12N 2760/16122* (2013.01)
USPC .................. 424/192.1; 424/134.1; 424/186.1; 424/187.1; 424/188.1; 424/202.1; 530/387.3

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,578,770 A | 3/1986 | Mitani |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,837,028 A | 6/1989 | Allen |
| 4,902,505 A | 2/1990 | Pardridge et al. |
| 4,957,735 A | 9/1990 | Huang |
| 5,004,697 A | 4/1991 | Pardridge |
| 5,019,369 A | 5/1991 | Present et al. |
| 5,055,303 A | 10/1991 | Riley, Jr. |
| 5,188,837 A | 2/1993 | Domb |
| 5,254,342 A | 10/1993 | Shen et al. |
| 5,268,164 A | 12/1993 | Kozarich et al. |
| 5,271,961 A | 12/1993 | Mathiowitz et al. |
| 5,413,797 A | 5/1995 | Khan et al. |
| 5,506,206 A | 4/1996 | Kozarich et al. |
| 5,514,670 A | 5/1996 | Friedman et al. |
| 5,534,496 A | 7/1996 | Lee et al. |
| 5,545,806 A | 8/1996 | Lonberg et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,770,429 A | 6/1998 | Lonberg et al. |
| 5,871,746 A | 2/1999 | Boutillon et al. |
| 6,140,059 A | 10/2000 | Schawaller |
| 6,469,143 B2 | 10/2002 | Sallberg |
| 6,541,011 B2 | 4/2003 | Punnonen et al. |
| 6,573,245 B1 | 6/2003 | Marciani |
| 7,060,495 B2 | 6/2006 | Gehrmann et al. |
| 7,118,751 B1 | 10/2006 | Ledbetter et al. |
| 7,261,897 B2 | 8/2007 | Skeiky et al. |
| 7,456,260 B2 | 11/2008 | Rybak et al. |
| 7,476,386 B1 * | 1/2009 | Gras-Masse et al. ...... 424/184.1 |

(Continued)

FOREIGN PATENT DOCUMENTS

| | | |
|---|---|---|
| AU | 2009270771 A1 | 1/2010 |
| EP | 0491628 | 6/1992 |

(Continued)

OTHER PUBLICATIONS

Rudikoff et al. PNAS 79: 1979-1983. 1982.*
Colman, Research in Immunology 145: 33-36, 1994.*
Kussie et al., J. Immunol. 152: 146-152, 1994.*
Chen et al., EMBO J., 14: 2784-2794, 1995.*
Connick et al. (Journal of Immunology 178: 6975-6983, 2007.*
Gallo (Lancet 1894-1898, 2005.*
Levine (Journal of Virology 82: 11998-12000, 2008.*
Walker et al. (Science 320: 760-764, 2008).*

(Continued)

*Primary Examiner* — Phillip Gambel
(74) *Attorney, Agent, or Firm* — Fulbright & Jaworski LLP

(57) ABSTRACT

The present invention includes compositions and methods for the expression, secretion and use of novel compositions for use as, e.g., vaccines and antigen delivery vectors, to delivery antigens to antigen presenting cells. In one embodiment, the vector is an anti-CD40 antibody, or fragments thereof, and one or more antigenic peptides linked to the anti-CD40 antibody or fragments thereof, including humanized antibodies.

18 Claims, 38 Drawing Sheets

(56) References Cited

U.S. PATENT DOCUMENTS

| | | | |
|---|---|---|---|
| 7,560,534 | B2 | 7/2009 | Deo et al. |
| 8,518,410 | B2* | 8/2013 | Zurawski et al. ........... 424/192.1 |
| 2004/0146948 | A1 | 7/2004 | Britton et al. |
| 2005/0013828 | A1 | 1/2005 | George et al. |
| 2006/0165690 | A1* | 7/2006 | Heath et al. ................ 424/144.1 |
| 2006/0246089 | A1 | 11/2006 | Wu et al. |
| 2008/0181915 | A1 | 7/2008 | Tripp et al. |
| 2008/0199471 | A1 | 8/2008 | Bernett et al. |
| 2008/0233083 | A1 | 9/2008 | Ansari et al. |
| 2008/0241139 | A1 | 10/2008 | Delucia |
| 2008/0241170 | A1 | 10/2008 | Zurawski et al. |
| 2008/0254026 | A1 | 10/2008 | Long et al. |
| 2009/0004194 | A1* | 1/2009 | Kedl ......................... 424/139.1 |
| 2009/0191228 | A1* | 7/2009 | Gebbink et al. ........... 424/184.1 |
| 2009/0238822 | A1 | 9/2009 | George et al. |
| 2009/0280140 | A1* | 11/2009 | Laal et al. .................. 424/190.1 |
| 2010/0135994 | A1* | 6/2010 | Banchereau et al. ...... 424/133.1 |
| 2010/0239575 | A1 | 9/2010 | Banchereau et al. |

FOREIGN PATENT DOCUMENTS

| | | |
|---|---|---|
| EP | 0239400 B1 | 8/1994 |
| EP | 0438474 B1 | 5/1996 |
| EP | 0463151 B1 | 6/1996 |
| EP | 0546073 B1 | 9/1997 |
| EP | 1391464 A1 | 2/2004 |
| JP | 2004192125 A | 7/2004 |
| JP | 2007026135 A | 2/2007 |
| JP | 2009259188 A | 11/2009 |
| WO | 88/01649 A1 | 3/1988 |
| WO | 90/07861 A1 | 7/1990 |
| WO | 01/83755 A2 | 11/2001 |
| WO | 02/28905 A2 | 4/2002 |
| WO | 03/029296 A1 | 4/2003 |
| WO | 2006/128103 A2 | 11/2006 |
| WO | 2007041861 A1 | 4/2007 |
| WO | 2011032161 A1 | 3/2011 |
| WO | 2011140255 A1 | 11/2011 |

OTHER PUBLICATIONS

Austyn, Jonathan M., et al., "Migration Patterns of Dendritic Cells in the Mouse," J. Exp. Med., Feb. 1988, vol. 167, pp. 646-651.

Banchereau, Jacques, et al., "Immunobiology of Dendritic Cells," Annu. Rev. Immunol., (2000), 18:767-811.

Bates, et al., "APCs Express DCIR, a Novel C-Type Lectin Surface Receptor Containing an Immunoreceptor Tyrosine-Based Inhibitory Motif," J. Immunol. (1999) 163:1973-1983.

Beauchamp, Charles O., et al., "A New Procedure for the Synthesis of Polyethylene Glycol-Protein Adducts; Effects on Function, Receptor Recognition, and Clearance of Superoxide Dismutase, Lactoferrin, and a2-Macroglobulin," Analytical Biochemistry 131 (1983), pp. 25-33.

Benton, Trish, et al., "The Use of UCOE Vectors in Combination with a Preadapted Serum Free, Suspension Cell Line Allows for Rapid Production of Large Quantities of Protein," Cytotechnology, (2002), 38:43-46.

Dakappagari, et al., "Internalizing antibodies to the C-Type lectins, L-SIGN and DC-SIGN, inhibit viral glycoprotein binding and deliver antigen to human dendritic cells for the induction of T Cell responses," The Journal of Immunology (2006) 176:426-440.

Dye, Christopher, et al., "Global Burden of Tuberculosis—Estimated Incidence, Prevalence, and Mortality by Country," JAMA, (1999), 282:677-686.

Finn, O., "Cancer Vaccines: Between the Idea and the Reality," Nature Reviews Immunology, (Aug. 2003), 3:630-641.

Hougardy, Jean-Michel, et al., "Heparin-Binding-Hemagglutinin-Induced IFN-y Release as a Diagnostic Tool for Latent Tuberculosis," PLOS ONE, Oct. 2007, Issue 10, 8 pages.

International Search Report and Written Opinion for PCT/US2010/026375, dated Nov. 19, 2010, 8 pages.

International Search Report and Written Opinion for PCT/US2010/026268, dated Dec. 31, 2010, 13 pages.

International Search Report and Written Opinion for PCT/US2010/026273, dated Jan. 9, 2011, 12 pages.

International Search Report and Written Opinion for PCT/US2010/026275, dated Jan. 7, 2011, 13 pages.

Klinguer, et al., "Characterization of a multi-lipopeptides mixture used as an HIV-1 vaccine candidate," Vaccine (2000) 18:259-267.

Langer, R., "Polymer-Controlled Drug Delivery Systems," Acc. Chem. Res., (1993), 26:537-542.

Li, Wei, "Synergistic Antibody Induction by Antigen-CD40 Ligand Fusion Protein as Improved Immunogen," Immunology, 115, (Jun. 2005), pp. 215-222.

Lo-Man, et al., "Anti-tumor immunity provided by a synthetic multiple antigenic glycopeptide displaying a Tri-Tn glycotope," The Journal of Immunology (2001) 166:2849-2854.

Reddy, Manjula P., et al., "Elimination of Fc Receptor-Dependent Effector Functions of a Modified IgG4 Monoclonal Antibody to Human CD4," The Journal of Immunology, (2000), 164; pp. 1925-1933.

Rescigno, Maria, et al., "Bacteria-Induced Neo-Biosynthesis, Stabilization, and Surface Expression of Functional Class I Molecules in Mouse Dendritic Cells," Proc. Natl. Acad. Sci., Apr. 1998, vol. 95, pp. 5229-5234.

Soares, et al., "Three different vaccines based on the 140-amino acid MUC1 peptide with seven tandemly repeated tumor-specific epitopes elicit distinct immune effector mechanisms in wild-type versus MUC1-Transgenic mice with different potential for tumor rejection," The Journal of Immunology (2001) 166:6555-6563.

Steinman, Ralph M., "The Dendritic Cell System and its Role in Immunogenicity," Annual Review Immunology, (1991), 9:271-296.

Van Vliet, Sandra J., et al., "Dendritic Cells and C-Type Lectin Receptors: Coupling Innate to Adaptive Immune Responses," Immunology and Cell Biology, (2008), 86:580-587.

Xiang, Rong, et al., "A Dual-Function DNA Vaccine Encoding Carcinoembryonic Antigen and CD40 Ligand Trimer Induces T Cell-Mediated Protective Immunity Against Colon Cancer in Carcinoembryonic Antigen-Transgenic Mice," The Journal of Immunology, (2001), 167;pp. 4560-4565.

Zhang, Lixin, et al., "An Adenoviral Vector Cancer Vaccine that Delivers a Tumor-Associated Antigen/CD4O-Ligand Fusion Protein to Dendritic Cells," PNAS, Dec. 9, 2003, vol. 100, No. 25, pp. 15101-15106.

Grossman, Claudius, et al., "Enhancement of the Priming Efficacy of DNA Vaccines Encoding Dendritic Cell-Targeted Antigens by Synergistic Toll-Like Receptor Ligands," BMC Immunology, (2009), 10:43, 10 pages.

International Search Report for PCT/JP2012/029802, dated Oct. 18, 2011, 41 pages.

International Search Report for PCT/US2012/030593, dated May 28, 2012, 16 pages.

Xiong, Jin-he, et al., "Expression of B-Cell Naturation Antigen mRNA in Peripheral Blood Mononuclear Cells in Patients with Systemic Lupus Erythematosus," Huaxi Yixue, (2010), 1 page (Abstract Only).

* cited by examiner

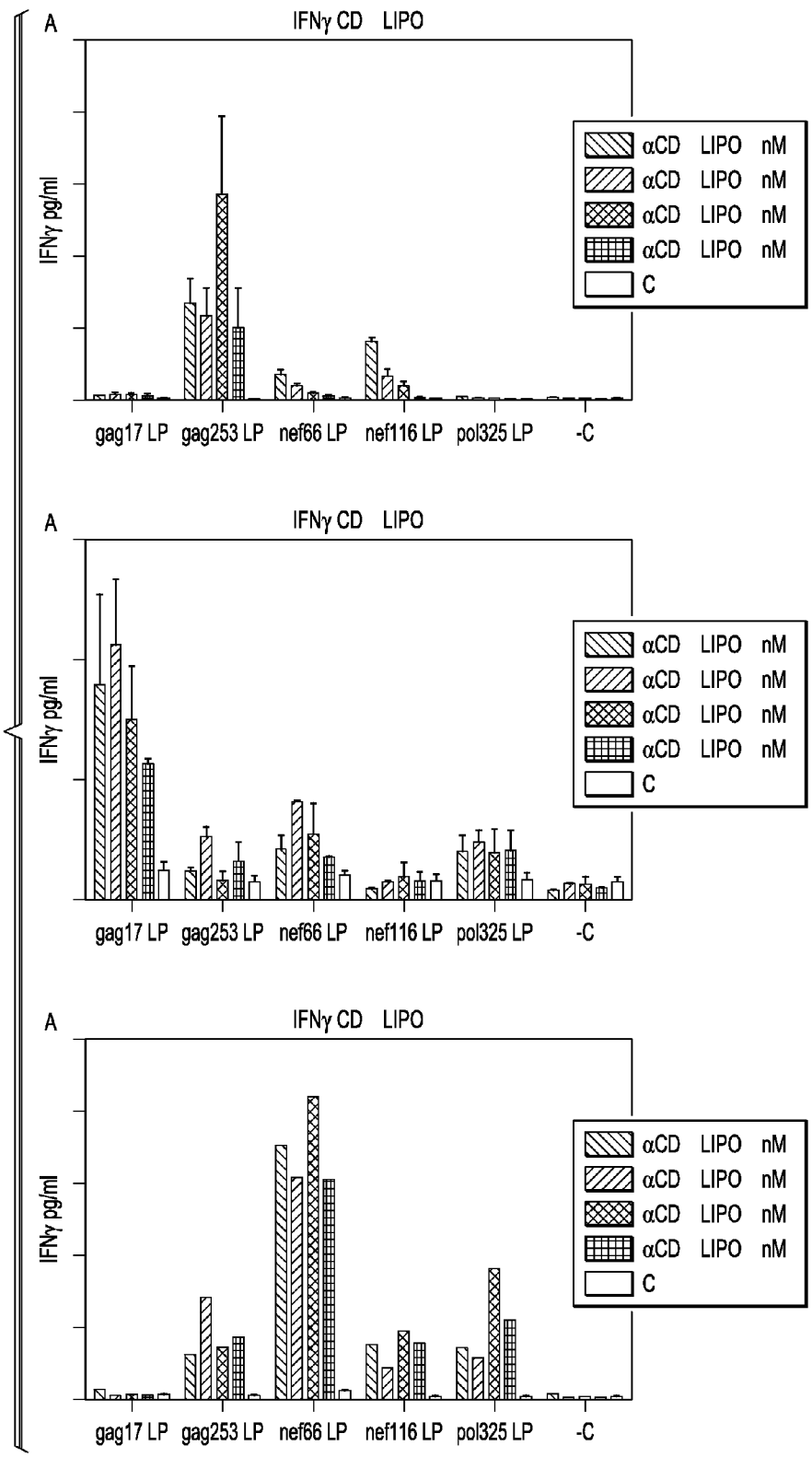

| ID | Construct | Structure | 293F SECRETION |
|---|---|---|---|
| C878 | rAB-pIRES2[mAnti-DCIR_9E8_H-LV-hIgG4H-C-Flex-v1- | CycB1-p1 | ± |
| C895 | rAB-pIRES2[mAnti-DCIR_9E8_H-LV-hIgG4H-C-Flex-v1- | CycB1-p1 — Flex4 | +++ |
| C1124 | rAB-pIRES2[mAnti-DCIR_9E8_H-LV-hIgG4H-C-Flex-v1- | CycB1-p2 | ± |
| C1139 | rAB-pIRES2[mAnti-DCIR_9E8_H-LV-hIgG4H-C-Flex-v1- | CycB1-p2 — Flex3 | ++ |
| C1144 | rAB-pIRES2[mAnti-DCIR_9E8_H-LV-hIgG4H-C-Flex-v1- | CycB1-p1 — Flex4 — CycB1-p2 — Flex3 | NO |
| C1145 | rAB-pIRES2[mAnti-DCIR_9E8_H-LV-hIgG4H-C-Flex-v1- | CycB1-p2 — Flex3 — CycB1-p1 — Flex4 | NO |
| C1162 | rAB-pIRES2[mAnti-DCIR_9E8_H-LV-hIgG4H-C-Flex-v1- | CycB1-p2 — CycB1-p1 — Flex4 | +++ |

ANTI-CD40 TARGETED FUSION PROTEINS

CROSS-REFERENCE TO RELATED APPLICATIONS

This application claims priority to U.S. Provisional Application Ser. No. 61/159,059, filed Mar. 10, 2009, 61/159,055, filed Mar. 10, 2009, 61/159,062, filed Mar. 10, 2009, and, the entire contents of each are incorporated herein by reference.

STATEMENT OF FEDERALLY FUNDED RESEARCH

This invention was made with U.S. Government support under Contract No. 1U19AI057234-0100003 awarded by the NIH. The government has certain rights in this invention.

TECHNICAL FIELD OF THE INVENTION

The present invention relates in general to the field of immunization, and more particularly, to novel anti-CD40 based vaccines.

BACKGROUND OF THE INVENTION

Without limiting the scope of the invention, its background is described in connection with antigen presentation.

One example of vaccines and methods for antigen presentation is taught in U.S. Pat. No. 7,118,751, issued to Ledbetter, et al., for DNA vaccines encoding an amino-terminus antigen linked to a carboxy-terminus domain that binds CD40. Briefly, vaccines are taught that target one or more antigens to a cell surface receptor to improve the antigen-specific humoral and cellular immune response. Antigen(s) linked to a domain that binds to a cell surface receptor are internalized, carrying antigen(s) into an intracellular compartment where the antigen(s) are digested into peptides and loaded onto MHC molecules. T cells specific for the peptide antigens are activated, leading to an enhanced immune response. The vaccine may comprise antigen(s) linked to a domain that binds at least one receptor or a DNA plasmid encoding antigen(s) linked to a domain that binds at least one receptor. A preferred embodiment of the invention targets HIV-1 env antigen to the CD40 receptor, resulting in delivery of antigen to CD40 positive cells, and selective activation of the CD40 receptor on cells presenting HIV-1 env antigens to T cells.

Another example is found in United States Patent Application No. 20080254026, filed by Li, et al., for antagonist anti-CD40 monoclonal antibodies and methods for their use. Briefly, compositions and methods are disclosed for use in therapy for treating diseases mediated by stimulation of CD40 signaling on CD40-expressing cells are provided. The methods comprise administering a therapeutically effective amount of an antagonist anti-CD40 antibody or antigen-binding fragment thereof to a patient in need thereof. The antagonist anti-CD40 antibody or antigen-binding fragment thereof is free of significant agonist activity, but exhibits antagonist activity when the antibody binds a CD40 antigen on a human CD40-expressing cell. Antagonist activity of the anti-CD40 antibody or antigen-binding fragment thereof beneficially inhibits proliferation and/or differentiation of human CD40-expressing cells, such as B cells.

Yet another example is taught in United States Patent Application No. 20080241139, filed by Delucia for an adjuvant combination comprising a microbial TLR agonist, a CD40 or 4-1BB agonist, and optionally an antigen and the use thereof for inducing a synergistic enhancement in cellular immunity Briefly, this application is said to teach adjuvant combinations comprising at least one microbial TLR agonist such as a whole virus, bacterium or yeast or portion thereof such a membrane, spheroplast, cytoplast, or ghost, a CD40 or 4-1BB agonist and optionally an antigen wherein all 3 moieties may be separate or comprise the same recombinant microorganism or virus are disclosed. The use of these immune adjuvants for treatment of various chronic diseases such as cancers and HIV infection is also provided.

United States Patent Application No. 20080199471, filed by Bernett, et al., is directed to optimized CD40 antibodies and methods of using the same. Briefly, this application is said to teach antibodies that target CD40 wherein the antibodies comprise at least one modification relative to a parent antibody, wherein the modification alters affinity to an FcγR or alters effector function as compared to the parent antibody. Also disclosed are methods of using the antibodies of the invention.

Finally, United States Patent Application No. 20080181915, file by Tripp, et al., is directed to a CD40 ligand adjuvant for respiratory syncytial virus. Briefly, this application is said to teach methods and adjuvants for enhancing an immune response to RSV in a host, wherein the methods and adjuvants comprise a source of a CD40 binding protein. Preferably, the CD40 binding protein is CD40L and the source is a vector comprising a promoter operatively linked to a CD40L coding region. The enhanced immune response produced by the adjuvants and methods of the current invention includes both increased expression of Th1 cytokines and increased production of antibody.

SUMMARY OF THE INVENTION

In one embodiment, the present invention is a fusion protein comprising the formula: Antibody(Ab)-Peptide Linker (PL)-Antigen (Ag)x, Ab-(PL-Ag)x; Ab-(Ag-PL)x; Ab-(PL-Ag -PL)x; Ab-(Ag-PL-Ag)x; Ab-(PL-Ag)x-PL; or Ab-(Ag-PL)x-Ag; wherein Ab is an antibody or fragment thereof; wherein PL is at least one peptide linker comprising at least one glycosylation site; wherein Ag is at least one antigen; and wherein x is an integer from 1 to 20 the fusion protein having more stability in solution than the same fusion protein without the glycosylation site. In one aspect, Ag is selected from a viral antigen, a tumor antigen, an infectious disease antigen, an autoimmune antigen, a toxin or combinations thereof. In another aspect, the Ag is a peptide concatemer. In another aspect, the PL is a peptide concatemer. In another aspect, the -(PL-Ag)x, -(Ag-PL)x, -(PL-Ag-PL)x, or -(Ag-PL-Ag)x are located at the carboxy terminus of the Ab heavy chain or fragment thereof. In another aspect, the Ag elicits a humoral immune response and/or cellular immune response in a host. In one aspect, the Ab comprises at least the variable region of anti-CD40__12E12.3F3 (ATCC Accession No. PTA-9854), anti-CD40__12B4.2C10 (Deposit Submission No. HS446, ATCC Accession No. PTA-10653), and anti-CD40__11B6.1C3 (Deposit Submission No. HS440, ATCC Accession No. PTA-10652).

In one aspect, the Ag is selected from autoimmune diseases or disorders associated with antigens involved in autoimmune disease selected from glutamic acid decarboxylase 65 (GAD 65), native DNA, myelin basic protein, myelin proteolipid protein, acetylcholine receptor components, thyroglobulin, and the thyroid stimulating hormone (TSH) receptor. In another aspect, the Ag is selected from infectious disease antigens selected from bacterial, viral, parasitic, and fungal antigens. In another aspect, x comprises 1, 2, 3, 4, 5, 6, 7, 8, 9, 10, 11, 12, 13, 14, 15, 16, 17, 18, or 19. In another aspect, the fusion protein comprises two or more Ags from different antigens separated by at least one PL. In another aspect, the fusion protein comprises two or more Ags separated by at least one PL comprising an alanine and a serine. In another aspect, the Ab is an antibody fragment selected from Fv, Fab, Fab', F(ab')2, Fc, or a ScFv.

In one aspect, the Ab binds specifically to an MHC class I, MHC class II, CD1, CD2, CD3, CD4, CD8, CD11b, CD14, CD15, CD16, CD 19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor, T cell receptor, or lectin. In another aspect, the Ab is an IgA, IgD, IgE, IgG or IgM or isotype thereof. In another aspect, the Ab is a human antibody or a humanized antibody. In another aspect, the PL comprises an alanine and a serine. In another aspect, the PL is selected from: SSVSPTTSVHPTPTSVPPTPTKSSP (SEQ ID NO.: 11); PTSTPADSSTITPTATPTATPTIKG (SEQ ID NO.: 12); TVTPTATATPSAIVTTITPTATTKP (SEQ ID NO.: 13); or TNGSITVAATAPTVTPTVNATPSAA (SEQ ID NO.: 14).

Yet another embodiment of the present invention is a nucleic acid expression vector encoding a fusion protein comprising: a first polynucleotide encoding an antibody light chain or fragment thereof; and a second polynucleotide encoding an antibody heavy chain or fragment thereof; wherein the fusion protein comprises the following formula: Ab-(PL-Ag)x or Ab-(Ag-PL)x; wherein Ab is an antibody or fragment thereof; wherein PL is at least one peptide linker comprising at least one glycosylation site; wherein Ag is at least one antigen; and wherein x is an integer from 1 to 20, the fusion protein having more stability in solution than the same fusion protein without the glycosylation site. In one aspect, the (PL-Ag)x or (Ag-PL)x are located at the carboxy terminus of the Ab heavy chain or fragment thereof. In another aspect, the first and second polynucleotide are on a single expression vector. In another aspect, the Ag is selected from infectious disease antigens selected from bacterial, viral, parasitic, and fungal antigens. In another aspect, x comprises 1, 2, 3, 4, 5, 6, 7, 8, 9, 10, 11, 12, 13, 14, 15, 16, 17, 18, or 19. In another aspect, the fusion protein comprises two or more Ags from different antigens separated by at least one PL. In another aspect, the fusion protein comprises two or more Ags separated by at least on PL comprising an alanine and a serine. In another aspect, the Ab is an antibody fragment selected from Fv, Fab, Fab', F(ab')2, Fc, or a ScFv. In another aspect, the Ab binds specifically to an MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor, T cell receptor, or lectin. In another aspect, the Ab is an IgA, IgD, IgE, IgG or IgM or isotype thereof. In another aspect, the Ab is a human antibody or a humanized antibody. In another aspect, the PL is comprises an alanine and a serine and/or the PL is selected from: SSVSPTTSVHPTPTS-VPPTPTKSSP (SEQ ID NO.: 11); PTST-PADSSTITPTATPTATPTIKG (SEQ ID NO.: 12); TVTPTATATPSAIVTTITPTATTKP (SEQ ID NO.: 13); or TNGSITVAATAPTVTPTVNATPSAA (SEQ ID NO.: 14). In another aspect, the first and second polynucleotides are downstream from a constitutive promoter.

Yet another embodiment of the present invention is a stable, secretable fusion protein comprising the formula: NH$_2$-Ab-(PL-Ag)x-COOH or NH2-Ab-(Ag-PL)x-COOH; wherein Ab is an antibody or fragment thereof; wherein PL is at least one peptide linker comprising at least one glycosylation site; wherein Ag is at least one immunogenic antigen; and wherein x is an integer from 1 to 20, the fusion protein being stable and soluble in solution as compared to an Ab-Ag protein alone that is not soluble or stable.

Another embodiment is a method of stabilizing antigenic peptides comprising: incorporating one or more antigenic peptides that are unstable or insoluble into a fusion protein, wherein the fusion protein has the following structure: Ab-(PL-Ag)x or Ab-(Ag-PL)x; wherein Ab is an antibody or fragment thereof; wherein PL is at least one peptide linker comprising at least one glycosylation site; wherein Ag is at least one antigen; and wherein x is an integer from 1 to 20, the fusion protein being stable and soluble in solution wherein the Ab-Ag is not soluble or stable.

Yet another embodiment of the present invention is a host cell comprising a nucleic acid expression vector comprising: a first polynucleotide encoding an antibody light chain; and a second polynucleotide encoding an antibody heavy chain fusion protein, the fusion protein comprising the following formula: Ab-(PL-Ag)x or Ab-(Ag-PL)x; wherein Ab is an antibody or fragment thereof; wherein PL is at least one peptide linker comprising at least one glycosylation site; wherein Ag is at least one antigen; and wherein x is an integer from 1 to 20, the fusion protein having more stability is solution than the fusion protein without the glycosylation site. In another embodiment, the host cell comprises an expression vector that produces a fusion protein comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an antibody or fragment thereof; wherein PL is at least one peptide linker comprising at least one glycosylation site; wherein Ag is at least one antigen; and wherein x is an integer from 1 to 20, the fusion protein having more stability in solution than the same fusion protein without the glycosylation site.

The present invention also includes a pharmaceutical composition comprising the antibody having the formula comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an antibody or fragment thereof; wherein PL is at least one peptide linker comprising at least one glycosylation site; wherein Ag is at least one antigen; and wherein x is an integer from 1 to 20, the fusion protein having more stability in solution than the same fusion protein without the glycosylation site.

Yet another embodiment of the present invention is a fusion protein comprising the formula: Ab-(PL-Ag)x-(PLy-Agz)n; or Ab-(Ag-PL)x-(PLy-Agz)n; wherein Ab is an antibody or fragment thereof; wherein PL is at least one peptide linker comprising at least one glycosylation site; wherein Ag is at least one antigen; and wherein x is an integer from 1 to 20; wherein n is 0 to 19; and wherein y or z is 0 to 10, wherein the fusion protein has more stability in solution than the same fusion protein without the glycosylation site.

Another embodiment is an isolated and purified vaccine comprising: a heavy chain selected from at least one of SEQ ID NOS.: 6, 7, 8, 9, 10, 16, 17, 18, 19, 20, 36, 37, 96, 97, 98, 99, 110, 111, 112, 118, 119, 134, 136, 138, 146, and 147 that binds specifically to CD40; and a light chain that binds specifically to CD40. In one aspect, the antibody is defined further as a humanized antibody.

Yet another embodiment of the present invention is a fusion protein comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an antibody or fragment thereof; PL is at least one peptide linker comprising at least one glycosylation site; Ag is at least one viral antigen; and x is an integer from 1 to 20. In one aspect, the fusion protein has more stability is solution than the PL without the glycosylation site. In another aspect, the Ag comprises a peptide from an adenovirus, retrovirus, picornavirus, herpesvirus, rotaviruses, hantaviruses, coronavirus, togavirus, flavirvirus, rhabdovirus, paramyxovirus, orthomyxovirus, bunyavirus, arenavirus, reovirus, papilomavirus, parvovirus, poxvirus, hepadnavirus, or spongiform virus. In another aspect, the Ag comprises a peptide from at least one of HIV, CMV, hepatitis A, B, and C, influenza; measles, polio, smallpox, rubella, respiratory syncytial, herpes simplex, varicella zoster, Epstein-Barr, Japanese encephalitis, rabies, flu, or cold viruses.

In another aspect, the Ag is selected from: Nef (66-97): VGFPVTPQVPLRPMTYKAAVDLSHFLKEKGGL (SEQ ID NO.: 1); Nef (116-145): HTQGYFPDWQNYTPGPGVRYPLTFGWLYKL (SEQ ID NO.: 2); Gag p17 (17-35): EKIRLRPGGKKKYKLKHIV (SEQ ID NO.: 3); Gag p17-p24 (253-284): NPPIPVGEIYKRWIILGLNKIVRMYSPTSILD (SEQ ID NO.: 4); or Pol 325-355 (RT 158-188) is: AIFQSSMTKILEPFRKQNPDIVIYQYMDDLY (SEQ ID NO.: 5). In another aspect, the Ag is 19 to 32 residues. In another aspect, the Ag is selected from a cytotoxic T lymphocyte (CTL) epitope identified in the HIV-1 Nef, Gag and Env proteins presented in the context of MHC-class I molecules. In another aspect, the Ag is selected from HIV gp120, gp41, Gag, p17, p24, p2, p'7, p1, p6, Tat, Rev, PR, RT, IN, Vif, Vpr, Vpx, Vpu and Nef. In another aspect, x comprises 1, 2, 3, 4, 5, 6, 7, 8, 9, 10, 11, 12, 13, 14, 15, 16, 17, 18 or 19. In another aspect, the Ag comprises virus peptides from different antigens separated by different peptide linkers. In another aspect, the Ag is separated by at least one PL comprising an alanine and a serine. In another aspect, the fusion protein is selected from SEQ ID NOS.: 21, 22, 23, 24, 25, 26, or 36. In another aspect, the fusion protein is isolated from a cell that comprises a polynucleotide vector that encodes the fusion protein, the polynucleotide vector comprising SEQ ID NOS.: 21, 22, 23, 24, 25, 26, or 36. In another aspect, the Ab comprises SEQ ID NOS.: 37 and 38.

In another aspect, the fusion protein is isolated from a cell that comprises a polynucleotide vector that expresses the fusion protein and the Ab portion comprises SEQ ID NOS.: 39 and 40. In another aspect, Ag is selected from at least one of SEQ ID NOS.: 52-56, 58-60, 61-69, 70-72, or 73-77. In another aspect, the Ag is 17 to 60 residues. In another aspect, the Ag is 8, 10, 12, 14, 15, 16, 18, 19, 20, 25, 30, 35, 40, 45, 50, 55 to 60 residues long. In another aspect, the Ag comprises at least one lipopeptide. In another aspect, the Ag is at the carboxy-terminus and further comprises a carboxy-terminus (Palm)-NH$_2$ group. In another aspect, the PL is selected from: SSVSPTTSVHPTPTSVPPTPTKSSP (SEQ ID NO.: 11); PTSTPADSSTITPTATPTATPTIKG (SEQ ID NO.: 12); TVTPTATATPSAIVTTITPTATTKP (SEQ ID NO.: 13); or TNGSITVAATAPTVTPTVNATPSAA (SEQ ID NO.: 14). In another aspect, the PL comprises an alanine and a serine.

Another embodiment is the present invention is a viral antigen delivery vector comprising: a fusion protein comprising an anti-CD40 antibody or fragment thereof and one or more viral peptides at the carboxy-terminus of the anti-CD40 antibody, wherein when two or more viral peptides are present the viral peptides are separated by the one or more peptide linkers comprising at least one potential glycosylation site. In another aspect, an antigen delivery vector is an anti-CD40 antibody or fragment thereof and two or more viral peptides at the carboxy-terminus of the light chain, the heavy chain or both the light and heavy chains of the anti-CD40 antibody, wherein when two or more viral peptides are separated by the one or more peptide linkers that comprise at least one potential glycosylation site.

Yet another embodiment of the present invention is a method of stabilizing viral peptides comprising: incorporating one or more viral peptides that are unstable or insoluble into a fusion protein with an antibody, wherein the antibody and the viral peptides are separated by one or more peptide linkers that comprise one or more glycosylation sites. Yet another embodiment is a method of enhancing T cell responses comprising: immunizing a subject in need of vaccination with an effective amount of a vaccine comprising the formula: Ab-(PL-Ag)x or Ab-(Ag-PL)x; wherein Ab is an antibody or fragment thereof; PL is at least one peptide linker comprising at least one glycosylation site; Ag is at least one viral antigen; and x is an integer from 1 to 20. In one aspect, the fusion protein has more stability in solution than an identical fusion protein without the glycosylation site. In another aspect, the at least one viral antigen comprise peptides from adenovirus, retrovirus, picornavirus, herpesvirus, rotaviruses, hantaviruses, coronavirus, togavirus, flavirvirus, rhabdovirus, paramyxovirus, orthomyxovirus, bunyavirus, arenavirus, reovirus, papilomavirus, parvovirus, poxvirus, hepadnavirus, or spongiform virus. In another aspect, the at least one viral antigen comprise peptides from at least one of HIV, CMV, hepatitis A, B, and C, influenza; measles, polio, smallpox, rubella; respiratory syncytial, herpes simplex, varicella zoster, Epstein-Barr, Japanese encephalitis, rabies, flu, or cold viruses.

In one aspect, the Ag is selected from: Nef (66-97): VGFPVTPQVPLRPMTYKAAVDLSHFLKEKGGL (SEQ ID NO.: 1); Nef (116-145): HTQGYFPDWQNYTPGPGVRYPLTFGWLYKL (SEQ ID NO.: 2); Gag p17 (17-35): EKIRLRPGGKKKYKLKHIV (SEQ ID NO.: 3); Gag p17-p24 (253-284): NPPIPVGEIYKRWIILGLNKIVRMYSPTSILD (SEQ ID NO.: 4); and/or Pol 325-355 (RT 158-188) is: AIFQSSMTKILEPFRKQNPDIVIYQYMDDLY (SEQ ID NO.: 5). In another aspect, the Ag is 19 to 32 residues and is selected from a cytotoxic T lymphocyte (CTL) epitope identified in the HIV-1 Nef, Gag and Env proteins presented in the context of MHC-class I molecules. In another aspect, the Ag is selected from HIV gp120, gp41, Gag, p17, p24, p2, p'7, p1, p6, Tat, Rev, PR, RT, IN, Vif, Vpr, Vpx, Vpu and Nef. In another aspect, x comprises 1, 2, 3, 4, 5, 6, 7, 8, 9, 10, 11, 12, 13, 14, 15, 16, 17, 18 or 19. In another aspect, the Ag comprises two or more viral antigens from different viruses. In another aspect, PL comprises an alanine and a serine. In another aspect, the vaccine is selected from SEQ ID NOS.: 21, 22, 23, 24, 25, 26 or 36. In another aspect, the Ab comprises SEQ ID NOS.: 37 and 38. In another aspect, the Ag is selected from at least one of SEQ ID NOS.: 52-56, 58-60, 61-69, 70-72, or 73-77. In another aspect, the Ag is 17 to 60 residues. In another aspect, the Ag is 8, 10, 12, 14, 15, 16, 18, 19, 20, 25, 30, 35, 40, 45, 50, 55 to 60 residues long. In another aspect, the Ag is 8, 10, 12, 14, 15, 16, 18, 19, 20, 25, 30, 35, 40, 45, 50, 55 to 60 residues long. In another aspect, the Ag comprise a lipopeptide. In another aspect, the Ag is at the carboxy-terminus and comprises a carboxy-terminus (Palm)-NH$_2$ group. In another aspect, the PL is selected from: SSVSPTTSVHPTPTSVPPTPTKSSP (SEQ ID NO.: 11); PTSTPADSSTITPTATPTATPTIKG (SEQ ID NO.: 12);

TVTPTATATPSAIVTTITPTATTKP (SEQ ID NO.: 13); or TNGSITVAATAPTVTPTVNATPSAA (SEQ ID NO.: 14).

Yet another embodiment of the present invention is a method of making HIV peptide-specific IFNγ producing T cells comprising: immunizing a subject with a fusion protein comprising an anti-CD40 antibody, or fragment thereof, with one or more HIV peptides at the carboxy-terminus of the antibody; and isolating peripheral blood mononuclear cells from the subject, wherein the isolated peripheral mononuclear cells are enriched for anti-HIV IFNγ producing T cells, wherein the anti-CD40 antibody comprises SEQ ID NOS.: 37 and 38 or fragments thereof. In one aspect, the subject is a patient suspected of having an HIV infection. In another aspect, the fusion protein comprises two or more HIV peptides and the peptides are separated by one or more peptide linkers. In another aspect, the fusion protein comprises two or more HIV peptides and the peptides are separated by the one or more peptide linkers comprise glycosylation sequences. In another aspect, the fusion protein comprises two or more HIV peptides and the peptides are separated by one or more peptide linkers comprising an alanine and a serine. In another aspect, the one or more HIV peptides comprise at least one lipopeptide. In another aspect, the one or more HIV peptides comprise a carboxy-terminus (Palm)-NH$_2$ group. In another aspect, the one or more HIV peptides are 19- to 32-amino-acid long and are selected from a cytotoxic T lymphocyte (CTL) epitopes identified in the HIV-1 Nef, Gag and Env proteins in the context of different MHC-class I molecules. In another aspect, the one or more HIV peptides are selected from HIV gp120, gp41, Gag, p17, p24, p2, p'7, p1, p6, Tat, Rev, PR, RT, IN, Vif, Vpr, Vpx, Vpu and Nef. In another aspect, the one or more viral peptides are selected from at least one of: Nef (66-97): VGFPVTPQVPLRPMTYKAAVDLSHFLKEKGGL (SEQ ID NO.: 1); Nef (116-145): HTQGYFPDWQNYTPGPGVRYPLTFGWLYKL (SEQ ID NO.: 2); Gag p17 (17-35): EKIRLRPGGKKKYKLKHIV (SEQ ID NO.: 3); Gag p17-p24 (253-284): NPPIPVGEIYKRWIILGLNKIVRMYSPTSILD (SEQ ID NO.: 4); and/or Pol 325-355 (RT 158-188) is: AIFQSSMTKILEPFRKQNPDIVIYQYMDDLY (SEQ ID NO.: 5).

Yet another embodiment of the present invention is a fusion protein comprising an anti-CD40 antibody, or fragment thereof, with one or more viral peptides at the carboxy-terminus of the antibody separated by a PL comprising at least one alanine and one serine. In one aspect, the one or more viral peptides are HIV peptides. In another aspect, the one or more viral peptides are selected from at least one of: Nef (66-97): VGFPVTPQVPLRPMTYKAAVDLSHFLKEKGGL (SEQ ID NO.: 1); Nef (116-145): HTQGYFPDWQNYTPGPGVRYPLTFGWLYKL (SEQ ID NO.: 2); Gag p17 (17-35): EKIRLRPGGKKKYKLKHIV (SEQ ID NO.: 3); Gag p17-p24 (253-284): NPPIPVGEIYKRWIILGLNKIVRMYSPTSILD (SEQ ID NO.: 4); and/or Pol 325-355 (RT 158-188) is: AIFQSSMTKILEPFRKQNPDIVIYQYMDDLY (SEQ ID NO.: 5).

The present invention also includes a method of making a fusion protein comprising: inserting into an expression vector a nucleic acid construct comprising polynucleotides that encode a protein having the formula: Ab-(PL-Ag)x or Ab-(Ag-PL)x; wherein Ab is an antibody or fragment thereof; PL is at least one peptide linker comprising at least one glycosylation site; Ag is at least one viral antigen; and x is an integer from 1 to 20; and culturing the vector under conditions sufficient to permit expression of the fusion protein. In one aspect, the fusion protein has more stability in solution than an identical fusion protein without the glycosylation site. In another aspect, the at least one viral antigen comprise peptides from an adenovirus, retrovirus, picornavirus, herpesvirus, rotaviruses, hantaviruses, coronavirus, togavirus, flavirvirus, rhabdovirus, paramyxovirus, orthomyxovirus, bunyavirus, arenavirus, reovirus, papilomavirus, parvovirus, poxvirus, hepadnavirus, or spongiform virus. In another aspect, the at least one viral antigen comprise peptides from at least one of HIV, CMV, hepatitis A, B, and C, influenza; measles, polio, smallpox, rubella, respiratory syncytial, herpes simplex, varicella zoster, Epstein-Barr, Japanese encephalitis, rabies, flu, or cold viruses. In another aspect, the fusion protein is the Ab's light chain, the Ab's heavy chain or both the Ab's light and heavy chains. In another aspect, the Ag is selected from: Nef (66-97): VGFPVTPQVPLRPMTYKAAVDLSHFLKEKGGL (SEQ ID NO.: 1); Nef (116-145): HTQGYFPDWQNYTPGPGVRYPLTFGWLYKL (SEQ ID NO.: 2); Gag p17 (17-35): EKIRLRPGGKKKYKLKHIV (SEQ ID NO.: 3); Gag p17-p24 (253-284): NPPIPVGEIYKRWIILGLNKIVRMYSPTSILD (SEQ ID NO.: 4); and/or Pol 325-355 (RT 158-188) is: AIFQSSMTKILEPFRKQNPDIVIYQYMDDLY (SEQ ID NO.: 5).

Yet another embodiment of the present invention includes a method of expanding antigen-specific T cells in vitro comprising: isolating PBMCs from an HIV patient; incubating the isolated PBMCs with an effective amount of a αCD40.LIPO5 HIV peptide vaccine; expanding the PBMCs in the presence of an effective amount of IL-2; harvesting the cells; and assessing the cytokine production by the cells to determine the presence of anti-HIV specific T cells. Another embodiment is an HIV antigen-specific T cells made by the method comprising: isolating PBMCs from an HIV patient; incubating the isolated PBMCs with an effective amount of a αCD40.LIPO5 HIV peptide vaccine; expanding the PBMCs in the presence of an effective amount of IL-2; harvesting the cells; and assessing the cytokine production by the cells to determine the presence of anti-HIV specific T cells. Another embodiment is a method of making a therapeutic vaccine comprising: loading a dendritic cell with αCD40.LIPO5 HIV peptide vaccine comprising: isolating HIV patient monocytes; differentiating the monocytes into dendritic cells with IFNα and GM-CSF; and exposing the differentiated dendritic cells to an αCD40.LIPO5 HIV peptide, wherein the loaded dendritic cells are capable of stimulating autologous HIV-peptide specific T cells in vitro.

The present invention also includes a therapeutic vaccine made by the method comprising: loading a dendritic cell with αCD40.LIPO5 HIV peptide vaccine comprising: isolating HIV patient monocytes; differentiating the monocytes into dendritic cells with IFNα and GM-CSF; and exposing the differentiated dendritic cells to an αCD40.LIPO5 HIV peptide, wherein the loaded dendritic cells are capable of stimulating autologous HIV-peptide specific T cells in vitro. Another embodiment is a therapeutic vaccine comprising a polypeptide comprising at least one of SEQ ID NOS.: 21, 22, 23, 24, 25, 26 or 36. Yet another embodiment is a therapeutic vaccine comprising a fusion protein comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an antibody or fragment thereof; PL is at least one peptide linker comprising at least one glycosylation site; Ag is at least one viral antigen; and x is an integer from 1 to 20.

Yet another embodiment of the present invention includes a fusion protein comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an antibody or fragment thereof; PL is at least one peptide linker comprising at least one glycosylation site; Ag is at least one cancer antigen; and x is an integer from 1 to 20. In one aspect, the fusion protein has more stability in solution than the same fusion protein without the glycosylation site. In another aspect, the Ag is selected from tumor associated antigens selected from CEA, prostate specific antigen (PSA), HER-2/neu, BAGE, GAGE, MAGE 1-4, 6 and 12, MUC-related protein (Mucin) (MUC-1, MUC-2, etc.), GM2 and GD2 gangliosides, ras, myc, tyrosinase, MART (melanoma antigen), MARCO-MART, cyclin B1, cyclin D, Pmel 17(gp100), GnT-V intron V sequence (N-acetylglucoaminyltransferase V intron V sequence), Prostate Ca psm, prostate serum antigen (PSA), PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In another aspect, the Ag is selected from tumor associated antigens comprising antigens from leukemias and lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

In another aspect, the Ag is selected from at least one of: MWVPVVFLTLSVTWIGAAPLILSRIVGG-WECEKHSQPWQVLVASRGRAVCGGVLVHPQWV (SEQ ID NO.:74); LTAAHCIRNKSVILLGRHSLFHPEDT-GQVFQVSHSFPHPLYDMSLLKNRFLRPGDDSSHD (SEQ ID NO.:75); LMLLRLSEPAELTDAVKVMDLPTQE-PALGTTCYASGWGSIEPEEFLTPKKLQCVDLHVIS (SEQ ID NO.:76); NDVCAQVHPQKVTKFMLCAGR-WTGGKSTCSGDSGGPLVCNGV-LQGITSWGSEPCALPERP (SEQ ID NO.:77); or SLYTKV-VHYRKWIKDTIVANP (SEQ ID NO.:78), and fragments thereof. In another aspect, the Ag is selected from at least one of: IMDQVPFSV (SEQ ID NO.:113); ITDQVPFSV (SEQ ID NO.:114); YLEPGPVTV (SEQ ID NO.:115); YLEPG-PVTA (SEQ ID NO.:116); KTWGQYWQV (SEQ ID NO.: 117); DTTEPATPTTPVTTPTTTKVPRNQD-WLGVSRQLRTKAWNRQLYPEWTEAQRLDCWRGGQ VSLKVSNDGPTLIGANASFSIALNFPG-SQKVLPDGQVIWVNNTIINGSQVWG-GQPVYPQETDDACIFPDGGPCPSG-SWSQKRSFVYVWKTWGQYWQVLGGPVSGLSIGTG RAMLGTHTMEVTVYHRRGSQSYVPLAH-SSSAFTITDQVPFSVSVSQLRALDGGNKHFLRNQ (SEQ ID NO.:122); PLTFALQLHDPSGYLAEADL-SYTWDFGDSSGTLISRAXVVTHTYLEPG-PVTAQVVLQAAIPLTSCGSSPVPAS (SEQ ID NO.:124); GTTDGHRPTAEAPNTTAGQVPTTEVVGT-TPGQAPTAEPSGTTSVQVPTTEVI-STAPVQMPTAESTGMTPEKVPVSEVMGT-TLAEMSTPEATGMTPAEVSIVVLSGTTAA (SEQ ID NO.:126); QVTTTEWVETTARELPIPEPEGP-DASSIMSTESITGSLGPLLDGTATLR-LVKRQVPLDCVLYRYGSFSVTLDIVQ (SEQ ID NO.: 128); and GIESAEILQAVPSGEGDAFELTVSCQG-GLPKEACMEISSPGCQPPAQRLCQPV-LPSPACQLVLHQILKGGSGTYCLNVS-LADTNSLAVVSTQLIVPGILLTGQEAGLGQ (SEQ ID NO.:130), and fragments thereof.

In another aspect, the Ag is selected from at least one of: MEMKILRALNFGLGRPLPLHFLRRASKI-GEVDVEQHTLAKYLMELTMLDY (SEQ ID NO.:132); and DWLVQVQMKFRLLQETMYMTVSIIDRFM-QNNCVPKK (SEQ ID NO.:133). In another aspect, the Ag is selected from at least one of: MEHQLLCCEVETIRRAYP-DANLLNDRVLRAMLKAEETCAPSVSYFKCV (SEQ ID NO.:141); QKEVLPSMRKIVATWMLEVCEEQK-CEEEVFPLAMNYLDRFLSLEPVKKSR-LQLLGATCMFVASKMKETIPLTAEKL-CIYTDNSIRPEELLQMELL (SEQ ID NO.:142); LVNKLKWNLAAMTPHDFIEHFLSKMPE-AEENKQIIRKHAQTFVALCATDVKFISNPPSMV (SEQ ID NO.:143); and AAGSVVAAVQGLNLRSPNNFLSYYR-LTRFLSRVIKCDPDCLRACQEQIEALL-ESSLRQAQQNMDPKAAEEEEEEEEVD-LACTPTDVRDVDI (SEQ ID NO.:144), and fragments thereof. In another aspect, the Ag is 19 to 32 amino acids long. In another aspect, the Ag is 17 to 60 amino acids long and is selected from a cytotoxic T lymphocyte (CTL) epitope identified in PSA or cyclin 1. In another aspect, x comprises 1, 2, 3, 4, 5, 6, 7, 8, 9, 10, 11, 12, 13, 14, 15, 16, 17, 18, or 19. In another aspect, the Ag comprises two or more cancer peptides from different cancer antigens separated by the PL. In another aspect, the Ag is separated by at least one PL comprising an alanine and a serine. In another aspect, the Ag is selected from SEQ ID NOS.: 74-78, 79-86, 87-92, 93-95, 113-117, 122-130, 132-133, and 141-144. In another aspect, the Ab comprises SEQ ID NOS.: 38 and 39. In another aspect, the Ab is expressed by a nucleic acid expression vector comprising SEQ ID NOS.: 40 and 41. In another aspect, the PL is selected from: SSVSPTTSVHPTPTSVPPTPTKSSP (SEQ ID NO.: 11); PTSTPADSSTITPTATPTATPTIKG (SEQ ID NO.: 12); TVTPTATATPSAIVTTITPTATTKP (SEQ ID NO.: 13); or TNGSITVAATAPTVTPTVNATPSAA (SEQ ID NO.: 14). In another aspect, the PL comprises an alanine and a serine.

Yet another embodiment of the present invention includes a antigen delivery vector that expresses an anti-CD40 antibody or fragment thereof and two or more cancer peptides at the carboxy-terminus of the light chain, the heavy chain or both the light and heavy chains of the anti-CD40 antibody, wherein when two or more cancer peptides are present, the cancer peptides are separated by the one or more peptide linkers that comprise at least one glycosylation site. In one aspect, the one or more peptide linkers are selected from: SSVSPTTSVHPTPTSVPPTPTKSSP (SEQ ID NO.: 11); PTSTPADSSTITPTATPTATPTIKG (SEQ ID NO.: 12); TVTPTATATPSAIVTTITPTATTKP (SEQ ID NO.: 13); or TNGSITVAATAPTVTPTVNATPSAA (SEQ ID NO.: 14).

Yet another embodiment of the present invention includes an anti-CD40 fusion protein comprising an anti-CD40 antibody or fragment thereof and one or more cancer peptides at the carboxy-terminus of the anti-CD40 antibody, wherein when two or more cancer peptides are present the cancer peptides are separated by the one or more linker peptides that comprise at least one glycosylation site. In one aspect, the antibody fragment is selected from an Fv, Fab, Fab', F(ab')₂, Fc, or a ScFv fragment. In another aspect, the Ag is selected from SEQ ID NOS.: 74-78, 79-86, 87-92, 93-95, 113-117, 122-130, 132-133, and 141-144.

Yet another embodiment of the present invention includes a method of stabilizing cancer peptides comprising: incorporating one or more cancer peptides that are unstable or insoluble into a fusion protein with an antibody, wherein the antibody and the cancer peptides are separated by one or more peptide linkers that comprise one or more glycosylation sites. In another aspect, the fusion protein comprises two or more cancer peptides and the cancer peptides are separated by the one or more peptide linkers. In another aspect, the fusion protein comprises two or more cancer peptides and the peptides are separated by the one or more peptide linkers. In another aspect, the fusion protein comprises two or more cancer peptides and the peptides are separated by one or more linkers comprising an alanine and a serine. In another aspect, the cancer peptide is selected from tumor associated antigens selected from CEA, prostate specific antigen (PSA), HER-2/neu, BAGE, GAGE, MAGE 1-4, 6 and 12, MUC-related protein (Mucin) (MUC-1, MUC-2, etc.), GM2, and GD2, gangliosides, ras, myc, tyrosinase, MART (melanoma antigen), MARCO-MART, cyclin B1, cyclin D, Pmel 17(gp100), GnT-V intron V sequence (N-acetylglucoaminyltransferase V intron V sequence), Prostate Ca psm, prostate serum antigen (PSA), PRAME (melanoma antigen), β-catenin, MUM-1-B (melanoma ubiquitous mutated gene product), GAGE (melanoma antigen) 1, BAGE (melanoma antigen) 2-10, c-ERB2, (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In another aspect, the Ag is selected from tumor associated antigens comprising antigens from leukemias and lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

In another aspect, the Ag is selected from at least one of: MWVPVVFLTLSVTWIGAAPLILSRIVGG-WECEKHSQPWQVLVASRGRAVCGGVLVHPQWV (SEQ ID NO.:74); LTAAHCIRNKSVILLGRHSLFHPEDT-GQVFQVSHSFPHPLYDMSLLKNRFLRPGDDSSHD (SEQ ID NO.:75); LMLLRLSEPAELTDAVKVMDLPTQE-PALGTTCYASGWGSIEPEEFLTPKKLQCVDLHVIS (SEQ ID NO.:76); NDVCAQVHPQKVTKFMLCAGR-WTGGKSTCSGDSGGPLVCNGV-LQGITSWGSEPCALPERP (SEQ ID NO.:77); or SLYTKV-VHYRKWIKDTIVANP (SEQ ID NO.:78).

In another aspect, the Ag is selected from at least one of: IMDQVPFSV (SEQ ID NO.:113); ITDQVPFSV (SEQ ID NO.:114); YLEPGPVTV (SEQ ID NO.:115); YLEPGPVTA (SEQ ID NO.:116); KTWGQYWQV (SEQ ID NO.:117); DTTEPATPTTPVTTPTTTKVPRNQD-WLGVSRQLRTKAWNRQLYPEWTEAQRLD-CWRGGQVSLKVSNDGPTLIGANASF-SIALNFPGSQKVLPDGQVIWVNNTIINGSQVWGGQP VYPQETDDACIFPDGGPCPSGSWSQKRS-FVYVWKTWGQYWQVLGGPVSGLSIGT-GRAMLGTHTMEVTVYHRRGSQSYVPLAH-SSSAFTITDQVPFSVSVSQLRALDGGNKHFLRNQ (SEQ ID NO.:122); PLTFALQLHDPSGYLAEADL-SYTWDFGDSSGTLISRAXVVTHTYLEPG-PVTAQVVLQAAIPLTSCGSSPVPAS (SEQ ID NO.:124); GTTDGHRPTAEAPNTTAGQVPTTEVVGT-TPGQAPTAEPSGTTSVQVPTTEVI-STAPVQMPTAESTGMTPEKVPVSEVMGT-TLAEMSTPEATGMTPAEVSIVVLSGTTAA (SEQ ID NO.:126); QVTTTEWVETTARELPIPEPEGP-DASSIMSTESITGSLGPLLDGTATLR-LVKRQVPLDCVLYRYGSFSVTLDIVQ (SEQ ID NO.: 128); and GIESAEILQAVPSGEGDAFELTVSCQG-GLPKEACMEISSPGCQPPAQRLCQPV-LPSPACQLVLHQILKGGSGTYCLNVS-LADTNSLAVVSTQLIVPGILLTGQEAGLGQ (SEQ ID NO.:130), and fragments thereof.

In another aspect, the Ag is selected from at least one of: MEMKILRALNFGLGRPLPLHFLRRASKI-GEVDVEQHTLAKYLMELTMLDY (SEQ ID NO.:132); and DWLVQVQMKFRLLQETMYMTVSIIDRFM-QNNCVPKK (SEQ ID NO.:133).

In another aspect, the Ag is selected from at least one of: MEHQLLCCEVETIRRAYPDANLLNDRVL-RAMLKAEETCAPSVSYFKCV (SEQ ID NO.:141); QKEVLPSMRKIVATWMLEVCEEQK-CEEEVFPLAMNYLDRFLSLEPVKKSR-LQLLGATCMFVASKMKETIPLTAEKL-CIYTDNSIRPEELLQMELL (SEQ ID NO.:142); LVNKLKWNLAAMTPHDFIEHFLSKMPE-AEENKQIIRKHAQTFVALCATDVKFISNPPSMV (SEQ ID NO.:143); and AAGSVVAAVQGLNLRSPNNFLSYYR-LTRFLSRVIKCDPDCLRACQEQIEALL-ESSLRQAQQNMDPKAAEEEEEEEEEVD-LACTPTDVRDVDI (SEQ ID NO.:144), and fragments thereof. In another aspect, the Ag is 19 to 32 amino acids long. In another aspect, the Ag is 17 to 60 amino acids long and is selected from a cytotoxic T lymphocyte (CTL) epitope identified in PSA or cyclin 1. In another aspect, x comprises 1, 2, 3, 4, 5, 6, 7, 8, 9, 10, 11, 12, 13, 14, 15, 16, 17, 18, or 19. In another aspect, the fusion protein comprises cancer peptides from different antigens separated by different peptide linkers. In another aspect, the fusion protein comprises two or more cancer peptides separated by one or more peptide linkers comprising an alanine and a serine. In another aspect, the antibody comprises SEQ ID NOS.: 38 and 39. In another aspect, the fusion protein is expressed by a nucleic acid expression vector comprising SEQ ID NOS.: 40 and 41. In another aspect, the peptide linker is selected from: SSVSPTTSVHPTPTSVPPTPTKSSP (SEQ ID NO.: 11); PTSTPADSSTITPTATPTATPTIKG (SEQ ID NO.: 12); TVTPTATATPSAIVTTITPTATTKP (SEQ ID NO.: 13); or TNGSITVAATAPTVTPTVNATPSAA (SEQ ID NO.: 14).

Yet another embodiment of the present invention includes a method of enhancing T cell responses comprising: immunizing a subject in need of vaccination with an effective amount of a vaccine comprising a fusion protein comprising an anti-CD40 antibody or portion thereof and one or more cancer peptides linked to the carboxy-terminus of the anti-CD40 antibody. In another aspect, the cancer peptides are selected from tumor associated antigens selected from CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), MARCO-MART, cyclin B1, cyclin D, Pmel 17(gp100), GnT-V intron V sequence (N-acetylglucoaminyltransferase V intron V sequence), Prostate Ca psm, prostate serum antigen (PSA), PRAME (melanoma antigen), β-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In another aspect, the cancer peptides is selected from tumor associated antigens comprising antigens from leukemias and lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

Yet another embodiment of the present invention includes a method of making an anti-CD40-antigen fusion protein comprising: expressing a fusion protein comprising an anti-CD40 antibody or fragment thereof in a host cell, the fusion protein comprising one or more cancer peptides at the carboxy-terminus of the anti-CD40 antibody or fragment thereof, wherein when two or more cancer peptides are separated by one or more linkers, at least one linker comprising a glycosylation site; and isolating the fusion protein. In another aspect, the fusion protein expressed in the host is further isolated and purified. In another aspect, the host is a eukaryotic cell. In another aspect, the cancer peptides are selected from tumor associated antigens selected from CEA, prostate specific antigen (PSA), HER-2/neu, BAGE, GAGE, MAGE 1-4, 6 and 12, MUC-related protein (Mucin) (MUC-1, MUC-2, etc.), GM2 and GD2 gangliosides, ras, myc, tyrosinase, MART (melanoma antigen), MARCO-MART, cyclin B1, cyclin D, Pmel 17(gp100), GnT-V intron V sequence (N-acetylglucoaminyltransferase V intron V sequence), Prostate Ca psm, prostate serum antigen (PSA), PRAME (melanoma antigen), β-catenin, MUM-1-B (melanoma ubiquitous mutated gene product), GAGE (melanoma antigen) 1, BAGE (melanoma antigen) 2-10, c-ERB2, (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In another aspect, the cancer peptides are selected from tumor associated antigens comprising antigens from leukemias and lymphomas, neurological tumors such as astrocytomas or glioblastomas, melanoma, breast cancer, lung cancer, head and neck cancer, gastrointestinal tumors, gastric cancer, colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia. In another aspect, the cancer peptides are selected from at least one of: MWVPVVFLTLSVTWIGAAPLILSRIVGGWECEKHSQP-WQVLVASRGRAVCGGVLVHPQWV (SEQ ID NO.:74); LTAAHCIRNKSVILLGRHSLFHPEDT-GQVFQVSHSFPHPLYDMSLLKNRFLRPGDDSSHD (SEQ ID NO.:75); LMLLRLSEPAELTDAVKVMDLPTQE-PALGTTCYASGWGSIEPEEFLTPKKLQCVDLHVIS (SEQ ID NO.:76); NDVCAQVHPQKVTKFMLCAGR-WTGGKSTCSGDSGGPLVCNGV-LQGITSWGSEPCALPERP (SEQ ID NO.:77); or SLYTKV-VHYRKWIKDTIVANP (SEQ ID NO.:78).

In another aspect, the cancer peptides are selected from at least one of: IMDQVPFSV (SEQ ID NO.:113); ITDQVPFSV (SEQ ID NO.:114); YLEPGPVTV (SEQ ID NO.:115); YLEPGPVTA (SEQ ID NO.:116); KTWGQY-WQV (SEQ ID NO.:117); DTTEPATPTTPVTTPTTT-KVPRNQDWLGVSRQLRTKAWNRQLYPEW-TEAQRLDCWRGGQVSLKVSNDGPTLIGANASFSIAL NFPGSQKVLPDGQVIWVNNTIING-SQVWGGQPVYPQETDDACIFPDGG-PCPSGSWSQKRSFVYVWKTWGQYWQVLG-GPVSGLSIGTGRAMLGTHTMEVTVYHRRGSQSYVP LAHSSSAFTITDQVPFSVSVSQLRALDGGNKHFLRNQ (SEQ ID NO.:122); PLTFALQLHDPSGYLAEADL-SYTWDFGDSSGTLISRAXVVTHTYLEPG-PVTAQVVLQAAIPLTSCGSSPVPAS (SEQ ID NO.:124); GTTDGHRPTAEAPNTTAGQVPTTEVVGT-TPGQAPTAEPSGTTSVQVPTTEVI-STAPVQMPTAESTGMTPEKVPVSEVMGT-TLAEMSTPEATGMTPAEVSIVVLSGTTAA (SEQ ID NO.:126); QVTTTEWVETTARELPIPEPEGP-DASSIMSTESITGSLGPLLDGTATLR-LVKRQVPLDCVLYRYGSFSVTLDIVQ (SEQ ID NO.: 128); and GIESAEILQAVPSGEGDAFELTVSCQG-GLPKEACMEISSPGCQPPAQRLCQPV-LPSPACQLVLHQILKGGSGTYCLNVS-LADTNSLAVVSTQLIVPGILLTGQEAGLGQ (SEQ ID NO.:130), and fragments thereof.

In another aspect, the cancer peptides are selected from at least one of: MEMKILRALNFGLGRPLPLHFLRRASKI-GEVDVEQHTLAKYLMELTMLDY (SEQ ID NO.:132); and DWLVQVQMKFRLLQETMYMTVSIIDRFM-QNNCVPKK (SEQ ID NO.:133).

In another aspect, the cancer peptides are selected from at least one of: MEHQLLCCEVETIRRAYPDANLLNDRVL-RAMLKAEETCAPSVSYFKCV (SEQ ID NO.:141); QKEVLPSMRKIVATWMLEVCEEQK-CEEEVFPLAMNYLDRFLSLEPVKKSR-LQLLGATCMFVASKMKETIPLTAEKL-CIYTDNSIRPEELLQMELL (SEQ ID NO.:142); LVNKLKWNLAAMTPHDFIEHFLSKMPE-AEENKQIIRKHAQTFVALCATDVKFISNPPSMV (SEQ ID NO.:143); and AAGSVVAAVQGLNLRSPNNFLSYYR-LTRFLSRVIKCDPDCLRACQEQIEALL-ESSLRQAQQNMDPKAAEEEEEEEEVD-LACTPTDVRDVDI (SEQ ID NO.:144), and fragments thereof.

Yet another embodiment of the present invention includes a method of expanding antigen-specific T cells in vitro comprising: isolating peripheral blood mononuclear cells (PBMCs) from a cancer patient; incubating the isolated PBMCs with an immunogenic amount of an αCD40-(PL-Ag)x or αCD40-(Ag-PL)x vaccine, wherein Ag is a tumor associated antigen and x is an integer 1 to 20; expanding the PBMCs in the presence of an effective amount of IL-2; harvesting the cells; and assessing the cytokine production by the cells to determine the presence of anti-cancer specific T cells.

Yet another embodiment of the present invention includes a tumor associated antigen-specific T cells made by the method comprising: isolating peripheral blood mononuclear cells (PBMCs) from a cancer patient; incubating the isolated PBMCs with an immunogenic amount of an αCD40-(PL-Ag)x or αCD40-(Ag-PL)x vaccine, wherein Ag is a tumor associated antigen and x is an integer 1 to 20; expanding the PBMCs in the presence of an effective amount of IL-2; harvesting the cells; and assessing the cytokine production by the cells to determine the presence of tumor associated antigen-specific T cells.

Yet another embodiment of the present invention includes a therapeutic vaccine comprising a fusion protein comprising the formula: Ab-(PL-Ag)x; Ab-(Ag-PL)x; Ab-(PL-Ag-PL)x; Ab-(Ag-PL-Ag)x; Ab-(PL-Ag)x-PL; or Ab-(Ag-PL)x-Ag; wherein Ab is an antibody or fragment thereof; PL is at least one peptide linker comprising at least one glycosylation site; Ag is at least one cancer antigen; and x is an integer from 1 to 20.

BRIEF DESCRIPTION OF THE DRAWINGS

For a more complete understanding of the features and advantages of the present invention, reference is now made to the detailed description of the invention along with the accompanying figures and in which:

FIG. 6A-C shows HIV peptide-specific IFN-γ production in PBMCs from HIV patients incubated with various concentrations of anti-CD40.LIPO5 peptide string vaccine. C is the control group, which received no vaccine, and defines the baseline response of the culture to each peptide.

FIG. 8A-B also shows that the αCD40.LIPO5 HIV peptide vaccine elicits gag253, nef66, nef116 and pol1325 peptide-specific responses characterized by production of multiple cytokines (patient A5).

FIG. 12A shows PBMCs from patient A3 treated with the αCD40.LIPO5 HIV peptide vaccine elicit expansion of antigen-specific T cells with specificities to the gag253, nef66, and nef116 regions, but not to the flexible linker sequences. FIG. 12B-1 and 12B-2 shows HIV antigen-specific T cell responses evoked from HIV patient A17 PBMCs incubated with 30 nM of three different HIV5 peptide DC targeting vaccines. FIG. 12C-1 and 12C-2 is a similar study to that show in FIG. 12B-1 and 12B-2, except that the PBMCs are from a different HIV patient (A2).

FIG. 34B shows that full-length Cyclin B1 fused to the C-terminus of either antibody H chain or cohesion fail to be secreted from mammalian 293F cells.

FIG. 38 show a summary of various H chain-Cyclin D1 segment constructs and their relative expressibility as vaccines.

DETAILED DESCRIPTION OF THE INVENTION

Figure 1:
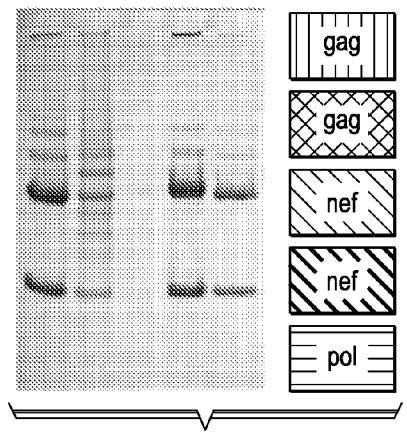
FIG. 1 shows protein A affinity recombinant antibodies fused to various HIV peptides (lanes 1 to 5) secreted from transfected 293F cells, analyzed by reducing SDS.PAGE and Coomassie Brilliant Blue staining

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The invention includes also variants and other modification of an antibody (or "Ab") of fragments thereof, e.g., anti-CD40 fusion protein (antibody is used interchangeably with the term "immunoglobulin"). As used herein, the term "antibodies or fragments thereof," includes whole antibodies or fragments of an antibody, e.g., Fv, Fab, Fab', F(ab')$_2$, Fc, and single chain Fv fragments (ScFv) or any biologically effective fragments of an immunoglobulins that binds specifically to, e.g., CD40. Antibodies from human origin or humanized antibodies have lowered or no immunogenicity in humans and have a lower number or no immunogenic epitopes compared to non-human antibodies. Antibodies and their fragments will generally be selected to have a reduced level or no antigenicity in humans.

As used herein, the terms "Ag" or "antigen" refer to a substance capable of either binding to an antigen binding region of an immunoglobulin molecule or of eliciting an immune response, e.g., a T cell-mediated immune response by the presentation of the antigen on Major Histocompatibility Antigen (MHC) cellular proteins. As used herein, "antigen" includes, but is not limited to, antigenic determinants, haptens, and immunogens which may be peptides, small molecules, carbohydrates, lipids, nucleic acids or combinations thereof. The skilled immunologist will recognize that when discussing antigens that are processed for presentation to T cells, the term "antigen" refers to those portions of the antigen (e.g., a peptide fragment) that is a T cell epitope presented by MHC to the T cell receptor. When used in the context of a B cell mediated immune response in the form of an antibody that is specific for an "antigen", the portion of the antigen that binds to the complementarity determining regions of the variable domains of the antibody (light and heavy) the bound portion may be a linear or three-dimensional epitope. In the context of the present invention, the term antigen is used on both contexts, that is, the antibody is specific for a protein antigen (CD40), but also carries one or more peptide epitopes for presentation by MHC to T cells. In certain cases, the antigens delivered by the vaccine or fusion protein of the present invention are internalized and processed by antigen presenting cells prior to presentation, e.g., by cleavage of one or more portions of the antibody or fusion protein.

As used herein, the term "antigenic peptide" refers to that portion of a polypeptide antigen that is specifically recognized by either B-cells or T-cells. B-cells respond to foreign antigenic determinants via antibody production, whereas T-lymphocytes are the mediate cellular immunity. Thus, antigenic peptides are those parts of an antigen that are recognized by antibodies, or in the context of an MHC, by T-cell receptors.

As used herein, the term "epitope" refers to any protein determinant capable of specific binding to an immunoglobulin or of being presented by a Major Histocompatibility Complex (MHC) protein (e.g., Class I or Class II) to a T-cell receptor. Epitopic determinants are generally short peptides 5-30 amino acids long that fit within the groove of the MHC molecule that presents certain amino acid side groups toward the T cell receptor and has certain other residues in the groove, e.g., due to specific charge characteristics of the groove, the peptide side groups and the T cell receptor. Generally, an antibody specifically binds to an antigen when the dissociation constant is 1 mM, 100 nM or even 10 nM.

As used herein, the term "vector" is used in two different contexts. When using the term "vector" with reference to a vaccine, a vector is used to describe a non-antigenic portion that is used to direct or deliver the antigenic portion of the vaccine. For example, an antibody or fragments thereof may be bound to or form a fusion protein with the antigen that elicits the immune response. For cellular vaccines, the vector for delivery and/or presentation of the antigen is the antigen presenting cell, which is delivered by the cell that is loaded with antigen. In certain cases, the cellular vector itself may also process and present the antigen(s) to T cells and activate an antigen-specific immune response. When used in the context of nucleic acids, a "vector" refers a construct which is capable of delivering, and preferably expressing, one or more genes or polynucleotide sequences of interest in a host cell. Examples of vectors include, but are not limited to, viral vectors, naked DNA or RNA expression vectors, DNA or RNA expression vectors associated with cationic condensing agents, DNA or RNA expression vectors encapsulated in liposomes, and certain eukaryotic cells, such as producer cells.

The compositions and methods of the present invention can be used with a wide variety of peptides and/or protein in which the antibody or fragment thereof and the peptide linker or "PL" create a protein that is stable and/or soluble.

As used herein, the compositions and methods use an antigen delivery vector comprising the formula: Ab-(PL-Ag)x or Ab-(Ag-PL)x; wherein Ab is an antibody or fragment thereof; PL is at least one peptide linker comprising at least one glycosylation site; Ag is at least one viral antigen; and x is an integer from 1 to 20. One example of an antibody for use with the present invention comprises at least the variable region of anti-CD40 12E12.3F3 (ATCC Accession No. PTA-9854), anti-CD40 12B4.2C10 (Deposit Submission No. HS446, ATCC Accession No. PTA-10653), and anti-CD40 11B6.1C3 (Deposit Submission No. HS440, ATCC Accession No. PTA-10652), deposited with the American Type Culture Collection (ATCC), Manassas, Va.

As used herein, the terms "stable" and "unstable" when referring to proteins is used to describe a peptide or protein that maintains its three-dimensional structure and/or activity (stable) or that loses immediately or over time its three-dimensional structure and/or activity (unstable). As used herein, the term "insoluble" refers to those proteins that when produced in a cell (e.g., a recombinant protein expressed in a eukaryotic or prokaryotic cell or in vitro) are not soluble in solution absent the use of denaturing conditions or agents (e.g., heat or chemical denaturants, respectively). The antibody or fragment thereof and the linkers taught herein have been found to convert antibody fusion proteins with the peptides from insoluble and/or unstable into proteins that are stable and/or soluble. Another example of stability versus instability is when the domain of the protein with a stable conformation has a higher melting temperature ($T_m$) than the unstable domain of the protein when measured in the same solution. A domain is stable compared to another domain when the difference in the $T_m$ is at least about 2° C., more preferably about 4° C., still more preferably about 7° C., yet more preferably about 10° C., even more preferably about 15° C., still more preferably about 20° C., even still more preferably about 25° C., and most preferably about 30° C., when measured in the same solution.

As used herein, "polynucleotide" or "nucleic acid" refers to a strand of deoxyribonucleotides or ribonucleotides in either a single- or a double-stranded form (including known analogs of natural nucleotides). A double-stranded nucleic acid sequence will include the complementary sequence. The polynucleotide sequence may encode variable and/or constant region domains of immunoglobulin that are formed into a fusion protein with one or more linkers. For use with the present invention, multiple cloning sites (MCS) may be engineered into the locations at the carboxy-terminal end of the heavy and/or light chains of the antibodies to allow for in-frame insertion of peptide for expression between the linkers. As used herein, the term "isolated polynucleotide" refers to a polynucleotide of genomic, cDNA, or synthetic origin or some combination thereof. By virtue of its origin the "isolated polynucleotide" (1) is not associated with all or a portion of a polynucleotide in which the "isolated polynucleotides" are found in nature, (2) is operably linked to a polynucleotide which it is not linked to in nature, or (3) does not occur in nature as part of a larger sequence. The skilled artisan will recognize that to design and implement a vector having the formula Ab-(PL-Ag)x or Ab-(Ag-PL)x, can be manipulated at the nucleic acid level by using techniques known in the art, such as those taught in Current Protocols in Molecular Biology, 2007 by John Wiley and Sons, relevant portions incorporated herein by reference. Briefly, the Ab, Ag and PL encoding nucleic acid sequences can be inserted using polymerase chain reaction, enzymatic insertion of oligonucleotides or polymerase chain reaction fragments in a vector, which may be an expression vector. To facilitate the insertion of (PL-Ag)x or (Ag-PL)x at the carboxy terminus of the antibody light chain, the heavy chain, or both, a multiple cloning site (MCS) may be engineered in sequence with the antibody sequences.

As used herein, the term "polypeptide" refers to a polymer of amino acids and does not refer to a specific length of the product; thus, peptides, oligopeptides, and proteins are included within the definition of polypeptide. This term also does not refer to or exclude post expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. The term "domain," or "polypeptide domain" refers to that sequence of a polypeptide that folds into a single globular region in its native conformation, and that may exhibit discrete binding or functional properties.

A polypeptide or amino acid sequence "derived from" a designated nucleic acid sequence refers to a polypeptide having an amino acid sequence identical to that of a polypeptide encoded in the sequence, or a portion thereof wherein the portion consists of at least 3-5 amino acids, preferably at least 4-7 amino acids, more preferably at least 8-10 amino acids, and even more preferably at least 11-15 amino acids, or which is immunologically identifiable with a polypeptide encoded in the sequence. This terminology also includes a polypeptide expressed from a designated nucleic acid sequence.

As used herein, "pharmaceutically acceptable carrier" refers to any material that when combined with an immunoglobulin (Ig) fusion protein of the present invention allows the Ig to retain biological activity and is generally non-reactive with the subject's immune system. Examples include, but are not limited to, standard pharmaceutical carriers such as a phosphate buffered saline solution, water, emulsions such as an oil/water emulsion, and various types of wetting agents. Certain diluents may be used with the present invention, e.g., for aerosol or parenteral administration, that may be phosphate buffered saline or normal (0.85%) saline.

The invention provides an CD40 binding molecule comprising at least one immunoglobulin light chain variable domain ($V_L$) which comprises in sequence hypervariable regions $CDR1_L$, $CDR2_L$, and $CDR3_L$, the $CDR1_L$ having the amino acid sequence SASQGISNYLN (SEQ ID NO.:41) the $CDR2_L$ having the amino acid sequence YTSILHS (SEQ ID NO.:42) and the $CDR3_L$ having the amino acid sequence QQFNKLPPT (SEQ ID NO.:43) the amino acid sequences of which are shown in SEQ ID NO. 37; and direct equivalent thereof.

Accordingly the invention provides an CD40 binding molecule which comprises an antigen binding site comprising at least one immunoglobulin heavy chain variable domain ($V_H$) which comprises in sequence hypervariable regions $CDR1_H$, $CDR2_H$ and $CDR3_H$, the $CDR1_H$ having the amino acid sequence GFTFSDYYMY (SEQ ID NO.:44), the $CDR2_H$ having the amino acid sequence YINSGGGSTYYPDTVKG (SEQ ID NO.:45), and the $CDR3_H$ having the amino acid sequence RGLPFHAMDY (SEQ ID NO.:46), the amino acid sequences of which are shown in SEQ ID NO. 38; and direct equivalents thereof.

In one aspect the invention provides a single domain CD40 binding molecule comprising an isolated immunoglobulin light chain comprising a heavy chain variable domain ($V_L$) as defined above. In another aspect the invention provides a single domain CD40 binding molecule comprising an isolated immunoglobulin heavy chain comprising a heavy chain variable domain ($V_H$) as defined above.

In another aspect the invention also provides an CD40 binding molecule comprising both heavy ($V_H$) and light chain ($V_L$) variable domains in which the CD40 binding molecule comprises at least one antigen binding site comprising: a) an immunoglobulin heavy chain variable domain ($V_L$) which comprises in sequence hypervariable regions $CDR1_L$, $CDR2_L$ and $CDR3_L$, the $CDR1_L$ having the amino acid sequence SASQGISNYLN (SEQ ID NO.:41), the $CDR2_L$ having the amino acid sequence YTSILHS (SEQ ID NO.:42), and the $CDR3_L$ having the amino acid sequence QQFNKLPPT (SEQ ID NO.:43), the amino acid sequences of which are shown in SEQ ID. NO. 1, and b) an immunoglobulin light chain variable domain ($V_H$) which comprises in sequence hypervariable regions $CDR1_H$, $CDR2_H$ and $CDR3_H$, the $CDR1_H$ having the amino acid sequence GFTFS-DYYMY (SEQ ID NO.:44), the CDR2' having the amino acid sequence YINSGGGSTYYPDTVKG (SEQ ID NO.:45), and the $CDR3_H$ having the amino acid sequence RGLPFHAMDY (SEQ ID NO.:46), the amino acid sequences of which are shown in SEQ ID NO. 38; and direct equivalents thereof.

Unless otherwise indicated, any polypeptide chain is herein described as having an amino acid sequence starting at the N-terminal end and ending at the C-terminal end. When the antigen binding site comprises both the $V_H$ and $V_L$ domains, these may be located on the same polypeptide molecule or, preferably, each domain may be on a different chain, the $V_H$ domain being part of an immunoglobulin heavy chain or fragment thereof and the $V_L$ being part of an immunoglobulin light chain or fragment thereof.

Non-limiting examples for antigens targeted by the antibodies of the present invention include, but are not limited to: cell surface marker selected from MHC class I, MHC class II, CD1, CD2, CD3, CD4, CD8, CD11b, CD14, CD15, CD16, CD19, CD20, CD29, CD31, CD40,CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor, T cell receptors, lectins, or other immune cell receptors. In one specific example, the antigens that are targeted by the antibody portion of the present invention are specifically expressed by antigen presenting cells, e.g., dendritic cells, Langerhans cells, macrophages, and B cells.

As used herein, the term "CD40 binding molecule" refers to any molecule capable of binding to the CD40 antigen either alone or associated with other molecules having one or more the $V_L$ and $V_H$ CDRs taught herein, in some cases 2, 3, 4, 5, or all 6 CDRs. The binding reaction may be shown by standard methods (qualitative assays) including, for example, a bioassay for determining by blocking the binding of other molecules to CD40 or any kind of binding or activity assays (e.g., activation, reduction or modulation of an immune response), with reference to a negative control test in which an antibody of unrelated specificity but of the same isotype, e.g., an anti-CD25 or anti-CD80 antibody, is used.

The present invention may also be made into a single chain antibody having the variable domains of the heavy and light chains of an antibody covalently bound by a peptide linker usually including from 10 to 30 amino acids, preferably from 15 to 25 amino acids. Therefore, such a structure does not include the constant part of the heavy and light chains and it is believed that the small peptide spacer should be less antigenic than a whole constant part.

As used herein, the term "chimeric antibody" refers to an antibody in which the constant regions of heavy or light chains or both are of human origin while the variable domains of both heavy and light chains are of non-human (e.g., mouse, hamster or rat) origin or of human origin but derived from a different human antibody.

As used herein, the term "CDR-grafted antibody" refers to an antibody in which the hypervariable complementarity determining regions (CDRs) are derived from a donor antibody, such as a non-human (e.g., mouse) antibody or a different human antibody, while all or substantially all the other parts of the immunoglobulin (e.g., the conserved regions of the variable domains, i.e., framework regions), are derived from an acceptor antibody (in the case of a humanized antibody -an antibody of human origin). A CDR-grafted antibody may include a few amino acids of the donor sequence in the framework regions, for instance in the parts of the framework regions adjacent to the hypervariable regions.

As used herein, the term "human antibody" refers to an antibody in which the constant and variable regions of both the heavy and light chains are all of human origin, or substantially identical to sequences of human origin, not necessarily from the same antibody and includes antibodies produced by mice in which the mouse, hamster or rat immunoglobulin variable and constant part genes have been replaced by their human counterparts, e.g. as described in general terms in EP 0546073 B1, U.S. Pat. Nos. 5,545,806, 5,569,825, 5,625,126, 5,633,425, 5,661,016, 5,770,429, EP 0 438474 B1 and EP 0 463151 B1, relevant portions incorporated herein by reference.

The CD40 binding molecule of the invention can be a humanized antibody that comprises the CDRs obtained from the anti-CD40_12E12.3F3, the anti-CD40_11B6.1C3, or the anti-CD40_12B4.2C10 antibodies. One example of a chimeric antibody includes the variable domains of both heavy and light chains are of human origin, for instance those variable domains of the anti-CD40_12E12.3F3 antibody that are part of SEQ ID NO.: 148 and SEQ ID NO.: 149, anti-CD40_12B4.2C10 in SEQ ID NO.: 150 and SEQ ID NO.: 151 or SEQ ID NO.: 152, and/or anti-CD40_11B6.1C3, SEQ ID NO.: 153 and SEQ ID NO.: 154, or combination thereof. The constant region domains preferably also comprise suitable human constant region domains, for instance as described in "Sequences of Proteins of Immunological Interest", Kabat E. A. et al, US Department of Health and Human Services, Public Health Service, National Institute of Health. The nucleic acid sequences can be found in, e.g., SEQ ID NOS.: 8 and 9.

Hypervariable regions may be associated with any kind of framework regions, e.g., of human origin. Suitable framework regions were described Kabat E. A. One heavy chain framework is a heavy chain framework, for instance that of anti-CD40_12E12.3F3 antibody that are part of SEQ ID NO.: 149; anti-CD40_12B4.2C10—SEQ ID NO.: 151 or SEQ ID NO.: 152, and/or anti-CD40_11B6.1C3—SEQ ID NO.: 154, or combination thereof, e.g., $FR1_L$, $FR2_L$, $FR3_L$ and $FR4_L$ regions. In a similar manner, SEQ ID NO. 148 shows the anti-CD40_12E12.3F3 (or the equivalents for anti-CD40_12B4.2C10 and anti-CD40_11B6.1C3, SEQ ID NOS.: 150 and 153, respectively) heavy chain framework that includes the sequence of $FR1_H$, $FR2_H$, $FR3_H$ and $FR4_H$ regions. The CDRs may be added to a human antibody framework, such as those described in U.S. Pat. No. 7,456,260, issued to Rybak, et al., which teach new human variable chain framework regions and humanized antibodies comprising the framework regions, relevant portions and framework sequences incorporated herein by reference. To accomplish the engraftment at a genetic level, the present invention also includes the underlying nucleic acid sequences for the $V_L$ AND $V_H$ regions as well as the complete antibodies and the humanized versions thereof. The nucleic acid sequences of the present invention include SEQ ID NOS.: 155 and 156, which are the anti-CD40 antibody light and the heavy chains, respectively, as well as those nucleic acid sequences that include variable codon usage for the same amino acid sequences and conservative variations thereof having 85, 90, 95 or 100% sequence identity at the nucleic or amino acid level. Likewise, the CDRs may have 85, 90, 95 or 100% sequence identity at the nucleic or amino acid level, individually, in groups or 2, 3, 4 or 5 or all together.

Monoclonal antibodies raised against a protein naturally found in all humans are typically developed in a non-human system e.g. in mice, and as such are typically non-human proteins. As a direct consequence of this, a xenogenic antibody as produced by a hybridoma, when administered to humans, elicits an undesirable immune response that is predominantly mediated by the constant part of the xenogenic immunoglobulin. Xenogeneic antibodies tend to elicit a host immune response, thereby limiting the use of such antibodies as they cannot be administered over a prolonged period of time. Therefore, it is particularly useful to use single chain, single domain, chimeric, CDR-grafted, or especially human antibodies that are not likely to elicit a substantial allogenic response when administered to humans. The present invention includes antibodies with minor changes in an amino acid sequence such as deletion, addition or substitution of one, a few or even several amino acids which are merely allelic forms of the original protein having substantially identical properties.

The inhibition of the binding of CD40 to its receptor may be conveniently tested in various assays including such assays are described hereinafter in the text. By the term "to the same extent" is meant that the reference and the equivalent molecules exhibit, on a statistical basis, essentially identical CD40 binding inhibition curves in one of the assays referred to above. For example, the assay used may be an assay of competitive inhibition of binding of CD40 by the binding molecules of the invention.

Generally, the human anti-CD40 antibody comprises at least: (a) one light chain which comprises a variable domain having an amino acid sequence substantially identical to that shown in SEQ ID NO. 1 starting with the amino acid at position 1 and ending with the amino acid at position 107 and the constant part of a human light chain; and (b) one heavy chain which comprises a variable domain having an amino acid sequence substantially identical to that shown in SEQ ID NO. 2 and the constant part of a human heavy chain. The constant part of a human heavy chain may be of the $\gamma 1$, $\gamma 2$, $\gamma 3$, $\gamma 4$, $\mu$, $\beta 2$, or $\delta$ or $\epsilon$ type, preferably of the $\gamma$-type, whereas the constant part of a human light chain may be of the $\kappa$ or $\lambda$ type (which includes the $\lambda_1$, $\lambda_2$ and $\lambda_3$ subtypes) but is preferably of the $\kappa$ type. The amino acid sequences of the general locations of the variable and constant domains are well known in the art and generally follow the Kabat nomenclature.

A CD40 binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided: (i) DNA molecules encoding a single domain CD40 binding molecule of the invention, a single chain CD40 binding molecule of the invention, a heavy or light chain or fragments thereof of a CD40 binding molecule of the invention; and (ii) the use of the DNA molecules of the invention for the production of a CD40 binding molecule of the invention by recombinant methods.

The present state of the art is such that the skilled worker in the art can synthesize the DNA molecules of the invention given the information provided herein, i.e., the amino acid sequences of the hypervariable regions and the DNA sequences coding for them. A method for constructing a variable domain gene is for example described in EPA 239 400, relevant portions incorporated herein by reference. Briefly, a gene encoding a variable domain of a MAb is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences given in SEQ ID NO. 1 and 3 or 2 and 4 (amino acid and nucleic acid sequences, respectively). These cassettes are often provided with sticky ends so that they can be ligated at the junctions of the framework.

It is not necessary to have access to the mRNA from a producing hybridoma cell line in order to obtain a DNA construct coding for the CD40 binding molecules of the invention. For example, PCT application WO 90/07861 gives full instructions for the production of an antibody by recombinant DNA techniques given only written information as to the nucleotide sequence of the gene, relevant portions incorporated herein by reference. Briefly, the method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector. DNA molecules encoding single chain antibodies may also be prepared by standard methods, for example, as described in WO 88/1649. In view of the foregoing, no hybridoma or cell line deposit is necessary to comply with the criteria of sufficiency of description.

For example, first and second DNA constructs are made that bind specifically to CD40. Briefly, a first DNA construct encodes a light chain or fragment thereof and comprises a) a first part which encodes a variable domain comprising alternatively framework and hypervariable regions, the hypervariable regions being in sequence $CDR1_L$, $CDR2_L$ and $CDR3_L$ the amino acid sequences of which are shown in SEQ ID NO. 1; this first part starting with a codon encoding the first amino acid of the variable domain and ending with a codon encoding the last amino acid of the variable domain, and b) a second part encoding a light chain constant part or fragment thereof which starts with a codon encoding the first amino acid of the constant part of the heavy chain and ends with a codon encoding the last amino acid of the constant part or fragment thereof, followed by a stop codon.

The first part encodes a variable domain having an amino acid sequence substantially identical to the amino acid sequence as shown in SEQ ID NO. 1. A second part encodes the constant part of a human heavy chain, more preferably the constant part of the human γ1 chain. This second part may be a DNA fragment of genomic origin (comprising introns) or a cDNA fragment (without introns).

The second DNA construct encodes a heavy chain or fragment thereof and comprises a) a first part which encodes a variable domain comprising alternatively framework and hypervariable regions; the hypervariable regions being $CDR1_H$ and optionally $CDR2_H$ and $CDR3_H$ the amino acid sequences of which are shown in SEQ ID NO. 2; this first part starting with a codon encoding the first amino acid of the variable domain and ending with a codon encoding the last amino acid of the variable domain, and b) a second part encoding a heavy chain constant part or fragment thereof which starts with a codon encoding the first amino acid of the constant part of the light chain and ends with a codon encoding the last amino acid of the constant part or fragment thereof followed by a stop codon.

The first part encodes a variable domain having an amino acid sequence substantially identical to the amino acid sequence as shown in SEQ ID NO. 2. The first part has the nucleotide sequence as shown in SEQ ID NO. 2 starting with the nucleotide at position 1 and ending with the nucleotide at position 321. Also preferably the second part encodes the constant part of a human light chain, more preferably the constant part of the human κ chain.

The invention also includes CD40 binding molecules in which one or more of the residues of $CDR1_L$, $CDR2_L$, $CDR3_L$, $CDR1_H$, $CDR2_H$ or $CDR3_H$ or the frameworks, typically only a few (e.g. $FR1-4_L$ or $_H$), are changed from the residues shown in SEQ ID NO. 37 and SEQ ID NO. 38; by, e.g., site directed mutagenesis of the corresponding DNA sequences. The invention includes the DNA sequences coding for such changed CD40 binding molecules. In particular the invention includes a CD40 binding molecules in which one or more residues of $CDR1_L$, $CDR2_L$ and/or $CDR3_L$ have been changed from the residues shown in SEQ ID NO. 37 and one or more residues of $CDR1_H$, $CDR2_H$ and/or $CDR3_H$ have been changed from the residues shown in SEQ ID NO. 38.

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, an immunoglobulin gene promoter may be used in B cells. The first and second parts may be separated by an intron, and, an enhancer may be conveniently located in the intron between the first and second parts. The presence of such an enhancer that is transcribed but not translated, may assist in efficient transcription. In particular embodiments the first and second DNA constructs comprise the enhancer of, e.g., a heavy chain human gene.

The desired antibody may be produced in a cell culture or in a transgenic animal. A suitable transgenic animal may be obtained according to standard methods that include micro injecting into eggs the first and second DNA constructs placed under suitable control sequences transferring the so prepared eggs into appropriate pseudo-pregnant females and selecting a descendant expressing the desired antibody.

The invention also provides an expression vector able to replicate in a prokaryotic or eukaryotic cell line, which comprises at least one of the DNA constructs above described. Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin, e.g., a myeloma, hybridoma or a normal immortalized B-cell, which conveniently does not express any endogenous antibody heavy or light chain.

When the antibody chains are produced in a cell culture, the DNA constructs must first be inserted into either a single expression vector or into two separate but compatible expression vectors, the latter possibility being preferred. For expression in mammalian cells it is preferred that the coding sequence of the CD40 binding molecule is integrated into the host cell DNA within a locus which permits or favors high level expression of the CD40 binding molecule.

In a further aspect of the invention there is provided a process for the product of a CD40 binding molecule that comprises: (i) culturing an organism which is transformed with an expression vector as defined above; and (ii) recovering the CD40 binding molecule from the culture.

In accordance with the present invention it has been found that the anti-CD40__12E12.3F3, anti-CD40__12B4.2C10 and/or anti-CD40__11B6.1C3 antibody appears to have binding specificity for the antigenic epitope of human CD40. It is therefore most surprising that antibodies to this epitope, e.g. the anti-CD40__12E12.3F3 antibody, are capable of delivering antigen efficiently into dendritic cells (DCs). Antibodies, in particular chimeric and CDR-grafted antibodies and especially human antibodies, which have binding specificity for the antigenic epitope of mature human CD40; and use of such antibodies for DC antigen loading are novel and are included within the scope of the present invention.

To use the anti-CD40 antibody of the present invention for treatment indications, the appropriate dosage will, of course, vary depending upon, for example, the antibody disclosed herein to be employed, the host, the mode of administration and the nature and severity of the condition being treated. However, in prophylactic use, satisfactory results are generally found at dosages from about 0.05 mg to about 10 mg per kilogram body weight more usually from about 0.1 mg to about 5 mg per kilogram body weight. The frequency of dosing for prophylactic uses will normally be in the range from about once per week up to about once every 3 months, more usually in the range from about once every 2 weeks up to about once every 10 weeks, e.g., once every 4 to 8 weeks. The anti-CD40 antibody of the present can be administered parenterally, intravenously, e.g., into the antecubital or other peripheral vein, intramuscularly, or subcutaneously.

Pharmaceutical compositions of the invention may be manufactured in conventional manner, e.g., in a lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinized blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

One embodiment of the present invention provides an immunoconjugate comprising a humanized antibody of the invention, e.g., a humanized anti-CD40 antibody, linked to one or more effector molecules, antigen(s) and/or a detectable label(s). Preferably, the effector molecule is a therapeutic molecule such as, for example, one or more peptides that comprise one or more T cell epitopes, a toxin, a small molecule, a cytokine or a chemokine, an enzyme, or a radiolabel.

Exemplary toxins include, but are not limited to, Pseudomonas, exotoxin or diphtheria toxin. Examples of small molecules include, but are not limited to, chemotherapeutic compounds such as taxol, doxorubicin, etoposide, and bleiomycin. Exemplary cytokines include, but are not limited to, IL-1, IL-2, IL-4, IL-5, IL-6, and IL-12, IL-17, and IL-25. Exemplary enzymes include, but are not limited to, RNAses, DNAses, proteases, kinases, and caspases. Exemplary radioisotopes include, but are not limited to, $^{32}P$ and $^{125}I$.

As used herein, the term "epitope" refers to a molecule or substance capable of stimulating an immune response. In one example, epitopes include but are not limited to a polypeptide and a nucleic acid encoding a polypeptide, wherein expression of the nucleic acid into a polypeptide is capable of stimulating an immune response when the polypeptide is processed and presented on a Major Histocompatibility Complex (MHC) molecule. Generally, epitopes include peptides presented on the surface of cells non-covalently bound to the binding groove of Class I or Class II MHC, such that they can interact with T cell receptors and the respective T cell accessory molecules.

Proteolytic Processing of Antigens. Epitopes that are displayed by MHC on antigen presenting cells are cleavage peptides or products of larger peptide or protein antigen precursors. For MHC I epitopes, protein antigens are often digested by proteasomes resident in the cell. Intracellular proteasomal digestion produces peptide fragments of about 3 to 23 amino acids in length that are then loaded onto the MHC protein. Additional proteolytic activities within the cell, or in the extracellular milieu, can trim and process these fragments further. Processing of MHC Class II epitopes generally occurs via intracellular proteases from the lysosomal/endosomal compartment. The present invention includes, in one embodiment, pre-processed peptides that are attached to the anti-CD40 antibody (or fragment thereof) that directs the peptides against which an enhanced immune response is sought directly to antigen presenting cells.

To identify epitopes potentially effective as immunogenic compounds, predictions of MHC binding alone are useful but often insufficient. The present invention includes methods for specifically identifying the epitopes within antigens most likely to lead to the immune response sought for the specific sources of antigen presenting cells and responder T cells.

The present invention allows for a rapid and easy assay for the identification of those epitopes that are most likely to produce the desired immune response using the patient's own antigen presenting cells and T cell repertoire. The compositions and methods of the present invention are applicable to any protein sequence, allowing the user to identify the epitopes that are capable of binding to MHC and are properly presented to T cells that will respond to the antigen. Accordingly, the invention is not limited to any particular target or medical condition, but instead encompasses and MHC epitope(s) from any useful source.

As used herein, the term "veneered" refers to a humanized antibody framework onto which antigen-binding sites or CDRs obtained from non-human antibodies (e.g., mouse, rat or hamster), are placed into human heavy and light chain conserved structural framework regions (FRs), for example, in a light chain or heavy chain polynucleotide to "graft" the specificity of the non-human antibody into a human framework. The polynucleotide expression vector or vectors that express the veneered antibodies can be transfected mammalian cells for the expression of recombinant human antibodies which exhibit the antigen specificity of the non-human antibody and will undergo posttranslational modifications that will enhance their expression, stability, solubility, or combinations thereof.

Antigens.

Examples of viral antigens for use with the present invention include, but are not limited to, e.g., HIV, HCV, CMV, adenoviruses, retroviruses, picornaviruses, etc. Non-limiting example of retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens. The at least one viral antigen may be peptides from an adenovirus, retrovirus, picornavirus, herpesvirus, rotaviruses, hantaviruses, coronavirus, togavirus, flavirvirus, rhabdovirus, paramyxovirus, orthomyxovirus, bunyavirus, arenavirus, reovirus, papilomavirus, parvovirus, poxvirus, hepadnavirus, or spongiform virus. In certain specific, non-limiting examples, the at least one viral antigen are peptides obtained from at least one of HIV, CMV, hepatitis A, B, and C, influenza, measles, polio, smallpox, rubella; respiratory syncytial, herpes simplex, varicella zoster, Epstein-Barr, Japanese encephalitis, rabies, flu, and/or cold viruses.

In one aspect, the one or more of the antigenic peptides are selected from at least one of: Nef (66-97): VGFPVTPQVPL-RPMTYKAAVDLSHFLKEKGGL (SEQ ID NO.: 1); Nef (116-145): HTQGYFPDWQNYTPGPGVRYPLTFGW-LYKL (SEQ ID NO.: 2); Gag p17 (17-35): EKIRLRPG-GKKKYKLKHIV (SEQ ID NO.: 3); Gag p17-p24 (253-284): NPPIPVGEIYKRWIILGLNKIVRMYSPTSILD (SEQ ID NO.: 4); or Pol 325-355 (RT 158-188) is: AIFQSSMTKILEPFRKQNPDIVIYQYMDDLY (SEQ ID NO.: 5). In one aspect, the fusion protein peptides are separated by one or more linkers selected from: SSVSPTTS-VHPTPTSVPPTPTKSSP (SEQ ID NO.: 11); PTST-PADSSTITPTATPTATPTIKG (SEQ ID NO.: 12); TVTPTATATPSAIVTTITPTATTKP (SEQ ID NO.: 13); or T NGSITVAATAPTVTPTVNATPSAA (SEQ ID NO.: 14).

Antigenic targets that may be delivered using the anti-CD40-antigen vaccines of the present invention include genes encoding antigens such as viral antigens, bacterial antigens, fungal antigens or parasitic antigens. Pathogens include trypanosomes, tapeworms, roundworms, helminthes, malaria. Tumor markers, such as fetal antigen or prostate specific antigen, may be targeted in this manner Other examples include: HIV env proteins and hepatitis B surface antigen. Administration of a vector according to the present invention for vaccination purposes would require that the vector-associated antigens be sufficiently non-immunogenic to enable long-term expression of the transgene, for which a strong immune response would be desired. In some cases, vaccination of an individual may only be required infrequently, such as yearly or biennially, and provide long-term immunologic protection against the infectious agent. Specific examples of organisms, allergens and nucleic and amino sequences for use in vectors and ultimately as antigens with the present invention may be found in U.S. Pat. No. 6,541, 011, relevant portions incorporated herein by reference, in particular, the tables that match organisms and specific sequences that may be used with the present invention.

Bacterial antigens for use with the anti-CD40-antigen vaccines disclosed herein include, but are not limited to, e.g., bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components, *Mycobacterium tuberculosis* bacterial antigens such as mycolic acid, heat shock protein 65, (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; haemophilus influenza bacterial antigens such as capsular polysaccharides and other haemophilus influenza bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: haemophilus influenza; *Plasmodium falciparum*; neisseria meningitidis; streptococcus pneumoniae; neisseria gonorrhoeae; salmonella serotype typhi; shigella; vibrio cholerae; Dengue Fever; Encephalitides; Japanese Encephalitis; lyme disease; Yersinia pestis; west nile virus; yellow fever; tularemia; hepatitis (viral; bacterial); RSV (respiratory syncytial virus); HPIV 1 and HPIV 3; adenovirus; small pox; allergies and cancers.

Fungal antigens for use with compositions and methods of the invention include, but are not limited to, e.g., candida fungal antigen components; histoplasma fungal antigens such as heat shock protein 60 (HSP60) and other histoplasma fungal antigen components; cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of protozoal and other parasitic antigens include, but are not limited to, e.g., plasmodium falciparum antigens such as merozoite surface antigens, sporozoite surface antigens, circumsporozoite antigens, gametocyte/gamete surface antigens, blood-stage antigen pf 155/RESA and other plasmodial antigen components; toxoplasma antigens such as SAG-1, p30 and other toxoplasmal antigen components; schistosomae antigens such as glutathione-S-transferase, paramyosin, and other schistosomal antigen components; leishmania major and other leishmaniae antigens such as gp63, lipophosphoglycan and its associated protein and other leishmanial antigen components; and trypanosoma cruzi antigens such as the 75-77 kDa antigen, the 56 kDa antigen and other trypanosomal antigen components.

Antigen that can be targeted using the anti-CD40-antigen vaccines of the present invention will generally be selected based on a number of factors, including: likelihood of internalization, level of immune cell specificity, type of immune cell targeted, level of immune cell maturity and/or activation and the like. In this embodiment, the antibodies may be mono- or bi-specific antibodies that include one anti-CD40 binding domain and one binding domain against a second antigen, e.g., cell surface markers for dendritic cells such as, MHC class I, MHC Class II, B7-2, CD18, CD29, CD31, CD43, CD44, CD45, CD54, CD58, CD83, CD86, CMRF-44, CMRF-56, DCIR and/or Dectin-1, and the like; while in some cases also having the absence of CD2, CD3, CD4, CD8, CD14, CD15, CD16, CD19, CD20, CD56, and/or CD57. Examples of cell surface markers for antigen presenting cells include, but are not limited to, MHC class I, MHC Class II, CD45, B7-1, B7-2, IFN-γ receptor and IL-2 receptor, ICAM-1 and/or Fcγ receptor. Examples of cell surface markers for T cells include, but are not limited to, CD3, CD4, CD8, CD14, CD20, CD11b, CD16, CD45 and HLA-DR.

Target antigens on cell surfaces for delivery include those characteristic of tumor antigens typically will be derived from the cell surface, cytoplasm, nucleus, organelles and the like of cells of tumor tissue. Examples of tumor targets for the antibody portion of the present invention include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia.

Examples of antigens that may be delivered alone or in combination to immune cells for antigen presentation using the present invention includes tumor proteins, e.g., mutated oncogenes; viral proteins associated with tumors; and tumor mucins and glycolipids. The antigens may be viral proteins associated with tumors would be those from the classes of viruses noted above. Certain antigens may be characteristic of tumors (one subset being proteins not usually expressed by a tumor precursor cell), or may be a protein that is normally expressed in a tumor precursor cell, but having a mutation characteristic of a tumor. Other antigens include mutant variant(s) of the normal protein having an altered activity or subcellular distribution, e.g., mutations of genes giving rise to tumor antigens.

Specific non-limiting examples of tumor antigens for use in an anti-CD40-fusion protein vaccine include, e.g., CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17(gp100), GnT-V intron V sequence (N-acetylglucoaminyltransferase V intron V sequence), Prostate Ca psm, PRAME (melanoma antigen), β-catenin, MUM-1-B (melanoma ubiquitous mutated gene product), GAGE (melanoma antigen) 1, MAGE, BAGE (melanoma antigen) 2-10, c-ERB2 (Her2/neu), DAGE, EBNA (Epstein-Barr Virus nuclear antigen) 1-6, gp75, human papilloma virus (HPV) E6 and E7, p53, lung resistance protein (LRP), Bcl-2, Ki-67, Cyclin B1, gp100, Survivin, and NYESO-1

In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., SLE or MG. In such diseases, it can be desirable to direct an ongoing antibody-mediated (i.e., a Th2-type) immune response to the relevant autoantigen towards a cellular (i.e., a Th1-type) immune response. Alternatively, it can be desirable to prevent onset of or decrease the level of a Th2 response to the autoantigen in a subject not having, but who is suspected of being susceptible to, the relevant autoimmune disease by prophylactically inducing a Th1 response to the appropriate autoantigen. Autoantigens of interest include, without limitation: (a) with respect to SLE, the Smith protein, RNP ribonucleoprotein, and the SS-A and SS-B proteins; and (b) with respect to MG, the acetylcholine receptor. Examples of other miscellaneous antigens involved in one or more types of autoimmune response include, e.g., endogenous hormones such as luteinizing hormone, follicular stimulating hormone, testosterone, growth hormone, prolactin, and other hormones.

Antigens involved in autoimmune diseases, allergy, and graft rejection can be used in the compositions and methods of the invention. For example, an antigen involved in any one or more of the following autoimmune diseases or disorders can be used in the present invention: diabetes, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor.

Examples of antigens involved in allergy include pollen antigens such as Japanese cedar pollen antigens, ragweed pollen antigens, rye grass pollen antigens, animal derived antigens such as dust mite antigens and feline antigens, histocompatiblity antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

It will be appreciated by those of skill in the art that the sequence of any protein effector molecule may be altered in a manner that does not substantially affect the functional advantages of the effector protein. For example, glycine and alanine are typically considered to be interchangeable as are aspartic acid and glutamic acid and asparagine and glutamine. One of skill in the art will recognize that many different variations of effector sequences will encode effectors with roughly the same activity as the native effector. The effector molecule and the antibody may be conjugated by chemical or by recombinant means as described above. Chemical modifications include, for example, derivitization for the purpose of linking the effector molecule and the antibody to each other, either directly or through a linking compound, by methods that are well known in the art of protein chemistry. Both covalent and noncovalent attachment means may be used with the humanized antibodies of the present invention.

The procedure for attaching an effector molecule to an antibody will vary according to the chemical structure of the moiety to be attached to the antibody. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule. Alternatively, the antibody can be derivatized to expose or to attach additional reactive functional groups, e.g., by attachment of any of a number of linker molecules such as those available from Pierce Chemical Company, Rockford Ill.

The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker that is cleavable under conditions present at the tumor site (e.g. when exposed to tumor-associated enzymes or acidic pH) may be used.

Exemplary chemical modifications of the effector molecule and the antibody of the present invention also include derivitization with polyethylene glycol (PEG) to extend time of residence in the circulatory system and reduce immunogenicity, according to well known methods (See for example, Lisi, et al., Applied Biochem. 4:19 (1982); Beauchamp, et al., Anal Biochem. 131:25 (1982); and Goodson, et al., Bio/Technology 8:343 (1990)).

The present invention contemplates vaccines for use in both active and passive immunization embodiments Immunogenic compositions, proposed to be suitable for use as a vaccine, may be prepared most readily directly from immunogenic T-cell stimulating peptides prepared in a manner disclosed herein. The final vaccination material is dialyzed extensively to remove undesired small molecular weight molecules and/or lyophilized for more ready formulation into a desired vehicle. In certain embodiment of the present invention, the compositions and methods of the present invention are used to manufacture a cellular vaccine, e.g., the antigen-delivering anti-CD40 binding portion of the antibody is used to direct the antigen(s) to an antigen presenting cell, which then "loads" the antigen onto MHC proteins for presentation. The cellular vaccine is, therefore, the antigen presenting cell that has been loaded using the compositions of the present invention to generate antigen-loaded antigen presenting cells.

When the vaccine is the anti-CD40 binding protein itself, e.g., a complete antibody or fragments thereof, then these "active ingredients" can be made into vaccines using methods understood in the art, e.g., U.S. Pat. Nos. 4,608,251; 4,601,903; 4,599,231; 4,599,230; and 4.578,770 relevant portions incorporated herein by reference. Typically, such vaccines are prepared as injectables, e.g., as liquid solutions or suspensions or solid forms suitable for re-suspension in liquid prior to injection. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

The vaccines are administered in a manner compatible with the dosage formulation, and in such amount as will be therapeutically effective and immunogenic. The quantity to be administered depends on the subject to be treated, including, e.g., the capacity of the individual's immune system to generate an immune response. Precise amounts of cells or active ingredient required to be administered depend on the judgment of the practitioner. However, suitable dosage ranges are of the order of a few thousand cells (to millions of cells) for cellular vaccines. For standard epitope or epitope delivery vaccines then the vaccine may be several hundred micrograms active ingredient per vaccination. Suitable regimes for initial administration and booster shots are also variable, but are typified by an initial administration followed by subsequent inoculations or other administrations.

The manner of application may vary widely, however, certain embodiments herein will most likely be delivered intravenously or at the site of a tumor or infection directly. Regardless, any of the conventional methods for administration of a vaccine are applicable. The dosage of the vaccine will depend on the route of administration and will vary according to the size of the host.

In many instances, it will be desirable to have multiple administrations of the vaccine, e.g., four to six vaccinations provided weekly or every other week. A normal vaccination regimen will often occur in two to twelve week intervals or from three to six week intervals. Periodic boosters at intervals of 1-5 years, usually three years, may be desirable to maintain protective levels of the immune response or upon a likelihood of a remission or re-infection. The course of the immunization may be followed by assays for, e.g., T cell activation, cytokine secretion or even antibody production, most commonly conducted in vitro. These immune response assays are well known and may be found in a wide variety of patents and as taught herein.

The vaccine of the present invention may be provided in one or more "unit doses" depending on whether the nucleic acid vectors are used, the final purified proteins, or the final vaccine form is used. Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. Unit dose of the present invention may conveniently be described in terms of DNA/kg (or protein/Kg) body weight, with ranges between about 0.05, 0.10, 0.15, 0.20, 0.25, 0.5, 1, 10, 50, 100, 1,000 or more mg/DNA or protein/kg body weight are administered.

Likewise, the amount of anti-CD40-antigen vaccine delivered can vary from about 0.2 to about 8.0 mg/kg body weight. Thus, in particular embodiments, 0.4 mg, 0.5 mg, 0.8 mg, 1.0 mg, 1.5 mg, 2.0 mg, 2.5 mg, 3.0 mg, 4.0 mg, 5.0 mg, 5.5 mg, 6.0 mg, 6.5 mg, 7.0 mg and 7.5 mg of the vaccine may be delivered to an individual in vivo. The dosage of vaccine to be administered depends to a great extent on the weight and physical condition of the subject being treated as well as the route of administration and the frequency of treatment. A pharmaceutical composition that includes a naked polynucleotide prebound to a liposomal or viral delivery vector may be administered in amounts ranging from 1 µg to 1 mg polynucleotide to 1 µg to 100 mg protein. Thus, particular compositions may include between about 1 µg, 5 µg, 10 µg, 20 µg, 30 µg, 40 µg, 50 µg, 60 µg, 70 µg, 80 µg, 100 µg, 150 µg, 200 µg, 250 µg, 500 µg, 600 µg, 700 µg, 800 µg, 900 µg or 1,000 µg polynucleotide or protein that is bound independently to 1 µg, 5 µg, 10 µg, 20 µg, 3.0 µg, 40 µg 50 µg, 60 µg, 70 µg, 80 µg, 100 µg, 150 µg, 200 µg, 250 µg, 500 µg, 600 µg, 700 µg, 800 µg, 900 µg, 1 mg, 1.5 mg, 5 mg, 10 mg, 20 mg, 30 mg, 40 mg, 50 mg, 60 mg, 70 mg, 80 mg, 90 mg or 100 mg vector.

Antibodies of the present invention may optionally be covalently or non-covalently linked to a detectable label. Detectable labels suitable for such use include any composition detectable by spectroscopic, photochemical, biochemical, immunochemical, electrical, optical or chemical methods. Useful labels in the present invention include magnetic beads (e.g., DYNABEADS®), fluorescent dyes (e.g., fluorescein isothiocyanate, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Methods of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The antibody and/or immunoconjugate compositions of this invention are particularly useful for parenteral administration, such as intravenous administration or administration into a body cavity. The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunoconjugate composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly.

Polymers can be used for ion-controlled release of immunoconjugate compositions of the present invention. Various degradable and non-degradable polymeric matrices for use in controlled drug delivery are known in the art (Langer, R., Accounts Chem. Res. 26:537-542 (1993)). For example, the block copolymer, poloxamer 407® exists as a viscous yet mobile liquid at low temperatures but forms a semisolid gel at body temperature, hydroxyapatite has been used as a microcarrier for controlled release of proteins, and/or liposomes may be used for controlled release as well as drug targeting of the lipid-capsulated drug. Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, relevant portions of each of which are incorporated herein by reference.

Among various uses of the immunoconjugates of the invention are included a variety of disease conditions caused by specific human cells that may be eliminated by the toxic action of the fusion protein. For example, for the humanized anti-CD40 12E12.3F3 (ATCC Accession No. PTA-9854), anti-CD40 12B4.2C10 (Deposit Submission No. HS446, ATCC Accession No. PTA-10653), and anti-CD40 11B6.1C3 (Deposit Submission No. HS440, ATCC Accession No. PTA-10652)), deposited with the American Type Culture Collection (ATCC), Manassas, Va., antibodies disclosed herein, one preferred application for immunoconjugates is the treatment of malignant cells expressing CD40.

In another embodiment, this invention provides kits for the delivery of antigens, e.g., CD40 or an immunoreactive fragment thereof, conjugated or in the form of a fusion protein with one or more T cell or B cell epitopes. A "biological sample" as used herein is a sample of biological tissue or fluid that contains the antigen. Such samples include, but are not limited to, tissue from biopsy, blood, and blood cells (e.g., white cells). Preferably, the cells are lymphocytes, e.g., dendritic cells. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human. The antibodies of the invention may also be used in vivo, for example, as a diagnostic tool for in vivo imaging.

Kits will typically comprise a nucleic acid sequence that encodes an antibody of the present invention (or fragment thereof) with one or more framework portions or multiple cloning sites at the carboxy-terminal end into which the coding sequences for one or more antigens may be inserted. In some embodiments, the antibody will be a humanized anti-CD40 Fv fragment, such as an scFv or dsFv fragment. In addition the kits will typically include instructional materials disclosing methods of use of an antibody of the present invention (e.g. for loading into dendritic cells prior to immunization with the dendritic cells, which can be autologous dendritic cells). The kits may also include additional components to facilitate the particular application for which the kit is designed. Thus, for example, the kit may additionally contain methods of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In another set of uses for the invention, immunoconjugates targeted by antibodies of the invention can be used to purge targeted cells from a population of cells in a culture. For example, if a specific population of T cells is preferred, the immunoconjugates of the present invention may be used to enrich a population of T cells having the opposite effect of the on-going immune response. Thus, for example, cells cultured from a patient having a cancer can be purged of cancer cells by providing the patient with dendritic cells that were antigen loaded using the antibodies of the invention as a targeting moiety for the antigens that will trigger an immune response against the cancer, virus or other pathogen. Likewise, the immunoconjugates can be used to increase the population of regulatory T cells or drive the immune response toward or away from a cytotoxic T cell response or even drive a B cell response.

EXAMPLE 1

Anti-CD40—HIV Peptides Vaccine

Five 19- to 32-amino-acid long sequences were selected from a multiplicity of cytotoxic T lymphocyte (CTL) epitopes identified in the HIV-1 Nef, Gag and Env proteins in the context of different MHC-class I molecules. It has been reported that CTL responses can be induced efficiently by lipopeptide vaccines in mice, in primates, and in humans. The five HIV peptides were then modified in C-terminal position by a (Palm)-NH2 group and the five HIV peptide sequences have been well described in the scientific literature [e.g., Characterization of a multi-lipopeptides mixture used as an HIV-1 vaccine candidate (1999) Klinguer et al., Vaccine, Volume 18, 259-267] and in a patent application [Cytotoxic T lymphocyte-inducing lipopeptides and use as vaccines. Gras-Masse H. et al., Patent No. EPO491628 (1992 Jun. 24); U.S. Pat. No. 5,871,746 (1999 Feb. 16)].

A very desirable HIV vaccine would be composed of recombinant anti-dendritic cell receptor antibody fused to the above HIV peptides. The present invention includes compositions and methods to efficiently produce proteins and HIV vaccines.

The sequences shown below are the amino-acid sequences of the five selected HIV peptides and the amino-acid positions within each HIV protein are in brackets.

```
                                          (SEQ ID NO.: 1)
Nef (66-97) is: VGFPVTPQVPLRPMTYKAAVDLSHFLKEKGGL (SEQ ID NO.: 2)
Nef (116-145) is: HTQGYFPDWQNYTPGPGVRYPLTFGWLYKL (SEQ ID NO.: 3)
Gag p17 (17-35) is: EKIRLRPGGKKKYKLKHIV (SEQ ID NO.: 4)
Gag p17-p24 (253-284) is: NPPIPVGEIYKRWIILGLNKIVRM
YSPTSILD (SEQ ID NO.: 5)
Pol 325-355 (RT 158-188) is: AIFQSSMTKILEPFRKQNPDI
VIYQYMDDLY
```

The sequence below is a hIgG4 heavy chain (H)—HIV gag17 fusion protein where the Gag p17 (17-35) region is shown in bold. The underlined AS residues are joining sequences.
[mAnti-DCIR_9E8_H-LV-hIgG4H-C-Pep-gag17] C655 is:

```
                                          (SEQ ID NO.: 6)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKASEKIRLRPGGKKKYKLKHIVAS.
```

The sequence below is an H chain—HIV gag253 fusion protein where the Gag p17-p24 (253-284) region is shown in bold. The underlined AS residues are joining sequences.
[mAnti-DCIR_9E8_H-LV-hIgG4H-C-Pep-gag253] C656 is:

```
                                          (SEQ ID NO.: 7)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKASNPPIPVGEIYKRWIILGLNKIVRMYSPTSILDAS.
```

The sequence below is an H chain—HIV nef116 fusion protein where the Nef (116-145) region is shown in bold. The underlined AS residues are joining sequences.
[mAnti-DCIR_9E8_H-LV-hIgG4H-C-Pep-nef116] C680 is:

(SEQ ID NO.: 8)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>HTQGYFPDWQNYTPGPGVRYPLTFGWLYKL<u>AS</u>.

The sequence below is a H chain—HIV nef66 fusion protein where the Nef (66-97) region is shown shaded in bold. The underlined AS residues are joining sequences.
[mAnti-DCIR_9E8_H-LV-hIgG4H-C-Pep-nef66] C679 is:

(SEQ ID NO.: 9)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>VGFPVTPQVPLRPMTYKAAVDLSHFLKEKGGL<u>AS</u>.

The sequence below is a H chain—HIV pol158 fusion protein where the Pol 325-355 (RT 158-188) region is shown in bold. The underlined AS residues are joining sequences.
[mAnti-DCIR_9E8_H-LV-hIgG4H-C-Pep-pol158] C667 is:

(SEQ ID NO.: 10)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>AIFQSSMTKILEPFRKQNPDIVIYQYMDDLY<u>AS</u>.

FIG. 1 shows protein A affinity purified recombinant antibodies fused to various HIV peptides (lanes 1 to 5) secreted from transfected 293F cells, analyzed by reducing SDS.PAGE and Coomassie Brilliant Blue staining. Expression vectors for the H chains fused to various C-terminal HIV peptides coding regions were co-transfected with the matching light chain (L) plasmid into transient 293F cells for three days before harvesting the supernatant for subsequent purification. Cell number and DNA amount were constant between transfections. Since the protein A affinity matrix was used in excess, the SDS.PAGE analysis defines both the production yield and the H chain integrity of the various vaccine constructs. Lanes 1, 4 and 5 (upper bands) show that the H chains fused directly to HIV gag17, nef66 and pol158 peptides can be well-secreted. Lane 2 shows that the H chain fused directly to HIV gag253 peptide expresses poorly. Lane 3 shows that the H chain fused directly to HIV nef116 peptide is not expressed at all.

Surprisingly, it was found that the use of flexible potentially glycosylated inter-peptide coding region linker sequences improves the secretion of intact recombinant antibody-HIV peptides fusion proteins.

The flexible linker sequences used are derived from cellulosomal anchoring scaffoldin B precursor [Bacteroides cellulosolvens] and have been described by the present inventors in co-pending U.S. Patent Application Ser. No. 61/081,234 relevant portions incorporated herein by reference.

The sequences shown below are the 25-amino-acid long sequences of the four selected peptide linker sequences. The underlined sequences are predicted N-linked glycosylation sites.

```
                                    (SEQ ID NO.: 11)
Flex1 is: SSVSPTTSVHPTPTSVPPTPTKSSP (SEQ ID NO.: 12)
Flex2 is: PTSTPADSSTITPTATPTATPTIKG (SEQ ID NO.: 13)
Flex3 is: TVTPTATATPSAIVTTITPTATTKP (SEQ ID NO.: 14)
Flex4 is: T NGS ITVAATAPTVTPTV NATPSAA
```

These sequences [the linkers shows in bold and underlined regions obtained from cohesion] are derived from the inter-cohesin domain spacers of the bacterial protein >gi|50656899|gb|AAT79550.1| cellulosomal anchoring scaffoldin B precursor [Bacteroides cellulosolvens]:

(SEQ ID NO.: 15)
MQSPRLKRKILSVILAVCYIISSFSIQFAATPQVNIIIGSAQGIPGSTVKVPINLQNVPEIGINNCDFTIKF

DSDILDFNSVEAGDIVPLPVASFSSNNSKDIIKFLFSDATQGNMPINENGLFAVISFKIKDNAQKGISNI

KVSSYGSFSGMSGKEMQSLSPTFFSGSIDVSDVSTSKLDVKVGNVEGIAGTEVNVPITFENVPDNGI

```
-continued
NNCNFTLSYDSNALEFLTTEAGNIIPLAIADYSSYRSMEGKIKFLFSDSSQGTRSIKNDGVFANIKFKI

KGNAIRDTYRIDLSELGSFSSKQNNNLKSIATQFLSGSVNVKDIESSVSPTTSVHPTPTSVPPTPTKS

SPGNKMKIQIGDVKANQGDTVIVPITFNEVPVMGVNNCNFTLAYDKNIMEFISADAGDIVTLPMAN

YSYNMPSDGLVKFLYNDQAQGAMSIKEDGTFANVKFKIKQSAAFGKYSVGIKAIGSISALSNSKLIP

IESIFKDGSITVTNKPIVNIEIGKVKVKAGDKIKVPVEIKDIPSIGINNCNFTLKYNSNVLKYVSNEAGT

IVPAPLANLSINKPDEGIIKLLFSDASQGGMPIKDNGIFVNLEFQAVNDANIGVYGLELDTIGAFSGIS

SAKMTSIEPQFNNGSIEIFNSAQTPVPSNTEVQTPTNTISVTPTNNSTPTNNSTPKPNPLYNLNVNIG

EISGEAGGVIEVPIEFKNVPDFGINNCDFSVKYDKSIFEYVTYEAGSIVKDSIVNLACMENSGIINLLF

NDATQSSSPIKNNGVFAKLKFKINSNAASGTYQINAEGYGKFSGNLNGKLTSINPIFENGIINIGNVT

VKPTSTPADSSTITPTATPTATPTIKGTPTVTPIYWMNVLIGNMNAAIGEEVVVPIEFKNVPPFGIN

NCDFKLVYDSNALELKKVEAGDIVPEPLANLSSNKSEGKIQFLFNDASQGSMQIENGGVFAKITFKV

KSTAASGIYNIRKDSVGSFSGLIDNKMTSIGPKFTDGSIVVGTVTPTATATPSAIVTTITPTATTKPI

ATPTIKGTPTATPMYWMNVVIGKMNAEVGGEVVVPIEFNNVPSFGINNCDFKLVYDATALELKNV

EAGDIIKTPLANFSNNKSEEGKISFLFNDASQGSMQIENGGVFAKITFKVKSTTATGVYDLRKDLVG

SFSGLKDNKMTSIGAEFTNGSITVAATAPTVTPTVNATPSAATPTVTPTATATPSVTIPTVTPTATA

TPSVTIPTVTPTATATPSAATPTVTPTATATPSVTIPTVTPTVTATPSDTIPTVTPTATATPSAIVTTITP

TATAKPIATPTIKGTPTATPMYWMNVVIGKMNAEVGGEVVVPIEFKNVPSFGINNCDFKLVYDATA

LELKNVEAGDIIKTPLANFSNNKSEEGKISFLFNDASQGSMQIENGGVSAKITFKVKSTTAIGVYDIR

KDLIGSFSGLKDSKMTSIGAEFTNGSIVATTAPTVTPTATATPSVTIPTVTPTATATPGTATPGTATP

TATATPGAATPTETATPSVMIPTVTPTATATPTATATPTVKGTPTIKPVYKMNVVIGRVNVVAGEE

VVVPVEFKNIPAIGVNNCNFVLEYDANVLEVKKVDAGEIVPDALINFGSNNSDEGKVYFLFNDALQ

GRMQIANDGIFANITFKVKSSAAAGIYNIRKDSVGAFSGLVDKLVPISAEFTDGSISVESAKSTPTAT

ATGTNVTPTVAATVTPTATPASTTPTATPTATSTVKGTPTATPLYSMNVIIGKVNAEASGEVVVPVE

FKDVPSIGINNCNFILEYDASALELDSAEAGEIVPVPLGNFSSNNKDEGKIYFLFSDGTQGRMQIVND

GIFAKIKFKVKSTASDGTYYIRKDSVGAFSGLIEKKIIKIGAEFTDGSITVRSLTPTPTVTPNVASPTPT

KVVAEPTSNQPAGPGPITGTIPTATTTATATPTKASVATATPTATPIVVVEPTIVRPGYNKDADLAVF

ISSDKSRYEESSIITYSIEYKNIGKVNATNVKIAAQIPKFTKVYDAAKGAVKGSEIVWMIGNLAVGES

YTKEYKVKVDSLTKSEEYTDNTVTISSDQTVDIPENITTGNDDKSTIRVMLYSNRFTPGSHSSYILGY

KDKTFKPKQNVTRAEVAAMFARIMGLTVKDGAKSSYKDVSNKHWALKYIEAVTKSGIFKGYKDS

TFHPNAPITRAELSTVIFNYLHLNNIAPSKVHFTDINKHWAKNYIEEIYRFKLIQGYSDGSFKPNNNIT

RAEVVTMINRMLYRGPLKVKVGSFPDVSPKYWAYGDIEEASRNHKYTRDEKDGSEILIE.
```

The sequence below is a heavy chain (H)

peptide sequences [italics] are linked via a spacer f1 [shown in bold]. The underlined AS residues are joining sequences.
[mAnti-DCIR_9E8_H-LV-hIgG4H-C-gag17-f1-nef116] C692 is:

(SEQ ID NO.: 17)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>*EKIRLRPGGKKKYKLKHIV*<u>AS</u>SSVSPTTSVHPTPTSVPPTPTKSSP

<u>AS</u>*HTQGYFPDWQNYTPGPGVRYPLTFGWLYKL*<u>AS</u>.

Figure 2:
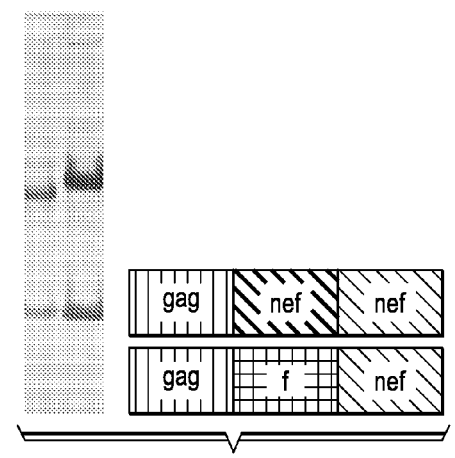
FIG. 2 shows protein A affinity purified recombinant antibodies fused to various HIV peptides (Lanes 1 and 2) secreted from transfected 293F cells, then analyzed by reducing SDS.PAGE and Coomassie Brilliant Blue staining.

FIG. 2 shows protein A affinity purified recombinant antibodies fused to various HIV peptides (Lanes 1 and 2) secreted from transfected 293F cells, then analyzed by reducing SDS.PAGE and Coomassie Brilliant Blue staining. Expression vectors for the H chains fused to various C-terminal HIV peptides coding regions were co-transfected with the matching L chain plasmid into transient 293F cells for three days before harvesting the supernatant for subsequent purification. Lanes 1 and 2 (upper bands) show that the H chains fused directly to a HIV peptide string of gag17-nef66-nef116 can be well-secreted. Also the H chain product containing a HIV peptide string of gag17 and nef116 separated by the flexible spacer f1 (Lane 2) is also well expressed. Thus HIV nef116 peptide, which is not expressed as a secreted product when directly fused to the H chain alone, can be well-expressed when appended in certain other peptide and flexible string contexts. Note that the H chain fused directly to gag17-f1-nef116 [82 residues] migrates slower than H chain with gag17-nef66-nef116 [89 residues] this suggests that the flexible linker f1 is glycosylated, possibly also enhancing the production of the secreted gag17-f1-nef116 fusion antibody versus gag17-nef66-nef116 fusion antibody.

The sequence below is an H chain—HIV peptides string of gag17-gag253-nef66 fusion protein where each HIV peptide sequence [shaded in italics] is separated by a inter-peptide spacer f [shown in bold]. In this case, a 27-amino-acid long linker flex-v1(v1) [shown in bold italics] derived from cellulosomal anchoring scaffoldin B precursor [Bacteroides cellulosolvens regions in bold-italics-underlined] was inserted between the H chain C-terminus and the HIV peptides-flexible spacers string. The underlined AS residues are joining sequences.
[mAnti-DCIR_9E8_H-LV-hIgG4H-C-Flex-v1-Pep-gag17-f1-gag253-f2-nef66] C711 is:

(SEQ ID NO.: 18)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>*QTPTNTISVTPTNNSTPTNNSNPKPNP*<u>AS</u>EKIRLRPGGKKKYKLKH

IV<u>AS</u>SSVSPTTSVHPTPTSVPPTPTKSSP<u>AS</u>NPPIPVGEIYKRWIILGLN

*KIVRMYSPTSILD*<u>AS</u>PTSTPADSSTITPTATPTATPTIKG<u>AS</u>*VGFPVTPQ*

*VPLRPMTYKAAVDLSHFLKEKGGL*<u>AS</u>.

The sequence below is an H chain—HIV peptides string of pol158-gag17-nef66-nef116-gag253 fusion protein where peptide sequences are shaded in grey. The underlined AS residues are joining sequences.
[mAnti-DCIR_9E8_H-LV-hIgG4H-C-Pep-pol158-gag17-nef66-nef116-gag253] C713 is:

(SEQ ID NO.: 19)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>AIFQSSMTKILEPFRKQNPDIVIYQYMDDLY<u>AS</u>EKIRLRPGGKKKY

KLKHIV<u>AS</u>VGFPVTPQVPLRPMTYKAAVDLSHFLKEKGGL<u>AS</u>HTQGYFPD

WQNYTPGPGVRYPLTFGWLYKL<u>AS</u>NPPIPVGEIYKRWIILGLNKIVRMYS

PTSILD<u>AS</u>.

Figure 3:
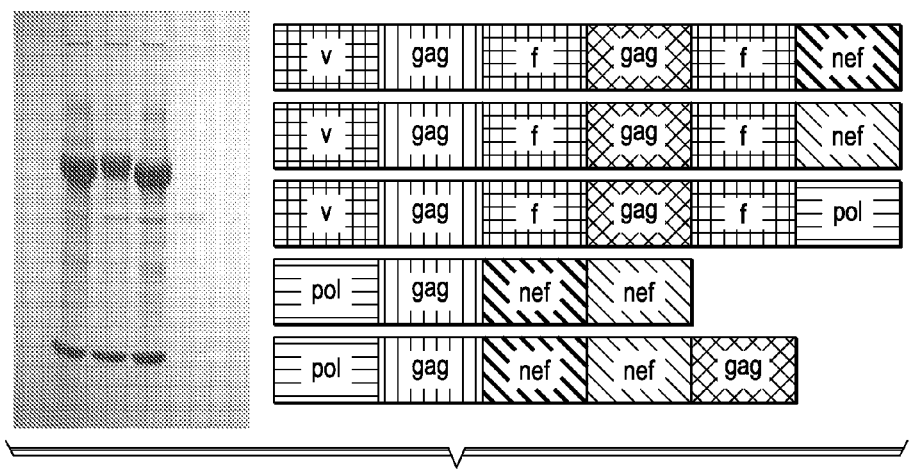
FIG. 3 shows protein A affinity purified recombinant antibodies fused to various HIV peptide strings (Lanes 1 to 5) secreted from transfected 293F cells, then analyzed by reducing SDS.PAGE and Coomassie Brilliant Blue staining

FIG. 3 shows protein A affinity purified recombinant antibodies fused to various HIV peptide strings (Lanes 1 to 5) secreted from transfected 293F cells, then analyzed by reducing SDS.PAGE and Coomassie Brilliant Blue staining Expression vectors for the H chains fused to various C-terminal HIV peptides coding regions were co-transfected with the matching L chain plasmid into transient 293F cells for three days before harvesting the supernatant for subsequent purification. Lanes 1, 2 and 3 (upper bands) show that the 4 HIV peptides-flexible spacers fused to H chain via the flexible linker flex-v1 can be well-secreted. However, a string of 4 HIV peptides fused directly to H chain is not expressed at all (Lane 4, upper band). Also, lane 5 (upper band) shows that a string of 5 HIV peptides fused directly to H chain is not expressed at all. This result suggests that certain combinations and contexts of flexible linkers and HIV peptide coding sequences can enhance secretion of recombinant antibody-HIV peptide fusion proteins (Lanes 1, 2 and 3).

The sequence below is for an H chain—HIV peptides string of gag17-gag253-nef66-nef116-pol158 fusion protein where each HIV peptide sequence [shaded in italics] is separated by an inter-peptide spacer f [shown in bold]. The flexible linker flex-v1 (v1) [shown in bold-italics] was inserted between the H chain C-terminus and the HIV peptides-flexible spacers string. The underlined AS residues are joining sequences.

[mAnti-DCIR_9E8_H-LV-hIgG4H-C-hIgG4H-Flex-v1-Pep-gag17-f1-gag253-f2-nef116-f3-nef66-f4-pol158] C825 is:

(SEQ ID NO.: 20)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKAS*QTPTNTISVTPTNNSTPTNNSNPKPNP*ASEKIRLRPGGKKKYKLKH

IVASSSVSPTTSVHPTPTSVPPTPTKSSPASNPPIPVGEIYKRWIILGLN

KIVRMYSPTSILDASPTSTPADSSTITPTATPTATPTIKGASHTQGYFPD

WQNYTPGPGVRYPLTFGWLYKLASTVTPTATATPSAIVTTITPTATTKPA

SVGFPVTPQVPLRPMTYKAAVDLSHFLKEKGGLASTNGSITVAATAPTVT

PTVNATPSAAASAIFQSSMTKILEPFRKQNPDIVIYQYMDDLYAS.

Figure 4:
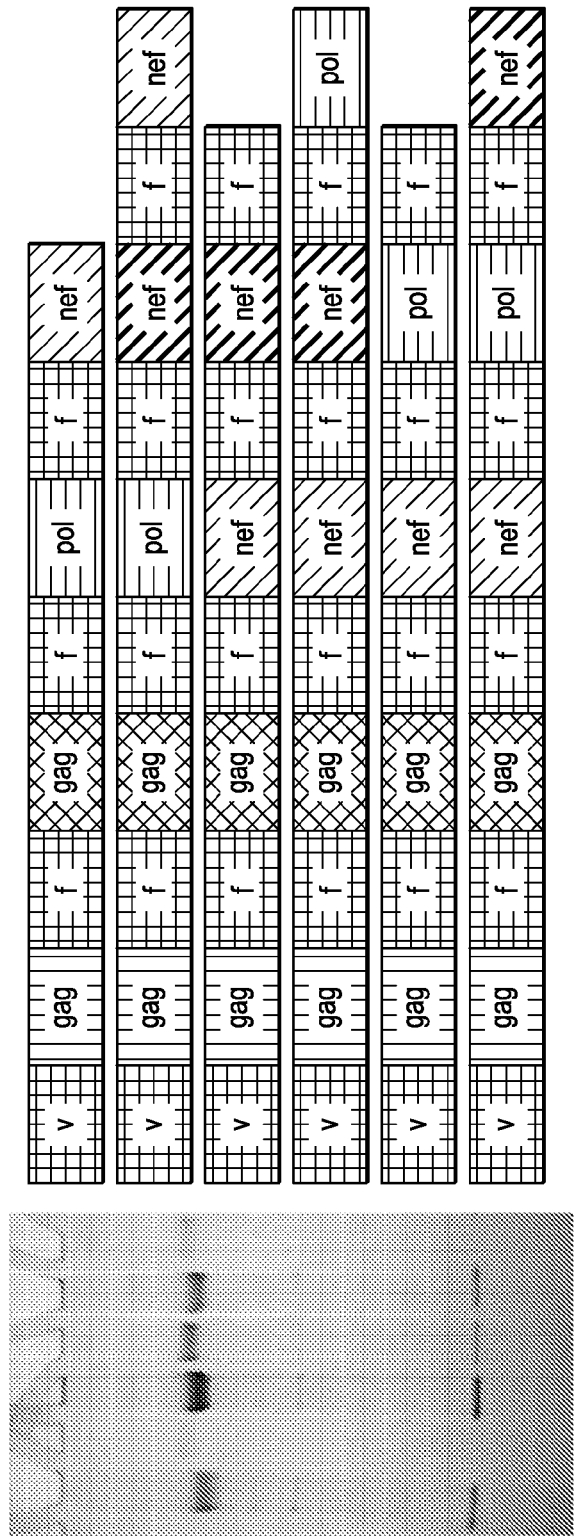
FIG. 4 shows protein A affinity purified recombinant antibodies fused to various HIV peptide strings (Lanes 1 to 6) secreted from transfected 293F cells, then analyzed by reducing SDS.PAGE and Coomassie Brilliant Blue staining FIG. 5 describes the protocol used in vitro to assay the potency of αCD40.LIPO5 HIV peptide fusion recombinant antibody (αCD40.LIPO5 rAb) to elicit the expansion of antigen-specific T cells in the context of a PBMC culture.

FIG. 4 shows protein A affinity purified recombinant antibodies fused to various HIV peptide strings (Lanes 1 to 6) secreted from transfected 293F cells, then analyzed by reducing SDS.PAGE and Coomassie Brilliant Blue staining Expression vectors for the H chains fused to various C-terminal HIV peptides coding regions were co-transfected with the matching L chain plasmid into transient 293F cells for three days before harvesting the supernatant for subsequent purification. Lanes 1, 3 and 5 (upper bands) show that the string of 4 HIV peptides-flexible spacers fused to H chain via the flexible linker flex-v1 can be well-secreted. Lanes 2 and 6 (upper bands) show that the string of 5 HIV peptides-flexible spacers fused to H chain via the flexible linker flex-v1 expresses poorly. However certain combinations and contexts of HIV peptide coding sequences enhance secretion of recombinant antibody-HIV peptide fusion proteins (Lanes 3 and 4). Thus H chain fused to a string of 5 HIV peptides-flexible spacers via the flexible linker flex-v1 can be well-expressed when appended in certain other peptide and flexible string contexts (Lane 4).

The present invention includes compositions and methods for flexible potentially glycosylated inter-peptide coding region linker sequences and combinations of such HIV peptide coding regions that are particularly favorable to efficient secretion of recombinant anti-DC receptor antibody-HIV peptide fusion vaccines.

The use of inter-structural domain linker sequences derived from cellulose-degrading bacteria as preferred inter-domain linker sequences in protein engineering—particularly those with highly predicted glycosylation sites. Desirable properties of these sequences are i) inherent flexibility, thereby facilitating separation of linked domains which should greatly help their correct folding and maintaining B cell receptor access to conformationally-dependent antigen epitopes; ii) glycosylation, thereby helping secretion and solubility of the intact produced fusion protein, and also protecting of the linker sequences from culture medium proteases.

Certain combinations of HIV peptide coding regions favor secretion and that particular flexible linker sequences inserted between the HIV peptide coding sequences can also help secretion of intact HIV peptide string vaccines—principles that can also be applied to solve similar issues for other preferred peptide antigens.

DNA sequences of preferred linker and antigen coding sequences. Joining sequence codons and stop codons are in bold:

[mAnti-DCIR_9E8_H-LV-hIgG4H-C-Pep-gag17] C655 is:

(SEQ ID NO.: 21)
GCTAGTGAGAAGATCCGGCTGCGGCCCGGCGGCAAGAAGAAGTACAAGCT

GAAGCACATCGTGGCTAGCTGA

[mAnti-DCIR_9E8_H-LV-hIgG4H-C-Pep-nef66] C679 is:

(SEQ ID NO.: 22)
GCTAGTGTGGGCTTCCCCGTGACCCCCAGGTGCCCCTGCGGCCCATGAC

CTACAAGGCCGCCGTGGACCTGAGCCACTTCCTGAAGGAGAAGGGCGGC

CTGGCTAGCTGA

[mAnti-DCIR_9E8_H-LV-hIgG4H-C-Pep-pol158] C667 is:

(SEQ ID NO.: 23)
GCTAGTGCCATCTTCCAGAGCAGCATGACCAAGATCCTGGAGCCCTTCCG

GAAGCAGAACCCCGACATCGTGATCTACCAGTACATGGACGACCTGTACG

CTAGCTGA

[mAnti-DCIR_9E8_H-LV-hIgG4H-C-Flex-v1-Pep-gag253] C681 is:

(SEQ ID NO.: 24)
GCTAGTCAGACCCCCACCAACACCATCAGCGTGACCCCCACCAACAACAG

CACCCCCACCAACAACAGCAACCCCAAGCCCAACCCCGCTAGTAACCCCC

CCATCCCCGTGGGCGAGATCTACAAGCGGTGGATCATCCTGGGCCTGAAC

AAGATCGTGCGGATGTACAGCCCCACCAGCATCCTGGACGCTAGCTGA

[mAnti-DCIR_9E8 H-LV-hIgG4H-Flex-v1-Pep-gag17-nef116] C686 is:

(SEQ ID NO.: 25)
GCTAGTCAGACCCCCACCAACACCATCAGCGTGACCCCCACCAACAACA

GCACCCCCACCAACAACAGCAACCCCAAGCCCAACCCCGCTAGTGAGAA

GATCCGGCTGCGGCCCGGCGGCAAGAAGAAGTACAAGCTGAAGCACATC

GTGGCTAGTCACACCCAGGGCTACTTCCCCGACTGGCAGAACTACACCC

CCGGCCCCGGCGTGCGGTACCCCCTGACCTTCGGCTGGCTGTACAAGCT

GGCTAGCTGA

[mAnti-DCIR_9E8_H-LV-hIgG4H-C-hIgG4H-Flex-v1-Pep-gag17-f1-gag253-f2-nef116-f3-nef66-f4-pol158] C825 is:

(SEQ ID NO.: 26)
GCTAGTCAGACCCCCACCAACACCATCAGCGTGACCCCCACCAACAACAGCACCCCCACCAA

CAACAGCAACCCCAAGCCCAACCCCGCTAGTGAGAAGATCCGGCTGCGGCCCGGCGGCAAGA

AGAAGTACAAGCTGAAGCACATCGTGGCTAGTAGCAGCGTGAGCCCCACCACCAGCGTGCAC

CCCACCCCCACCAGCGTGCCCCCCACCCCCACCAAGAGCAGCCCCGCTAGTAACCCCCCCATC

CCCGTGGGCGAGATCTACAAGCGGTGGATCATCCTGGGCCTGAACAAGATCGTGCGGATGTAC

AGCCCCACCAGCATCCTGGACGCTAGTCCCACCAGCACCCCCGCCGACAGCAGCACCATCACC

CCCACCGCCACCCCCACCGCCACCCCCACCATCAAGGGCGCTAGTCACACCCAGGGCTACTTC

CCCGACTGGCAGAACTACACCCCCGGCCCCGGCGTGCGGTACCCCCTGACCTTCGGCTGGCTG

TACAAGCTGGCTAGTACCGTGACCCCCACCGCCACCGCCACCCCCAGCGCCATCGTGACCACC

ATCACCCCCACCGCCACCACCAAGCCCGCTAGTGTGGGCTTCCCCGTGACCCCCCAGGTGCCC

CTGCGGCCCATGACCTACAAGGCCGCCGTGGACCTGAGCCACTTCCTGAAGGAGAAGGGCGGC

CTGGCTAGTACCAACGGCAGCATCACCGTGGCCGCCACCGCCCCCACCGTGACCCCCACCGTG

AACGCCACCCCCAGCGCCGCCGCTAGTGCCATCTTCCAGAGCAGCATGACCAAGATCCTGGA

GCCCTTCCGGAAGCAGAACCCCGACATCGTGATCTACCAGTACATGGACGACCTGTACGCTAG

CTGA.

DNA sequences of preferred linker and antigen coding sequences. Joining sequence codons are in bold:

Nef (66-97) is:

(SEQ ID NO.: 27)
GCTAGTGTGGGCTTCCCCGTGACCCCCCAGGTGCCCCTGCGGCCCATGA

CCTACAAGGCCGCCGTGGACCTGAGCCACTTCCTGAAGGAGAAGGGCGG

CCTGGCTAGC

Nef (116-145) is:

(SEQ ID NO.: 28)
GCTAGTCACACCCAGGGCTACTTCCCCGACTGGCAGAACTACACCCCCG

GCCCCGGCGTGCGGTACCCCCTGACCTTCGGCTGGCTGTACAAGCTGGC

TAGC

Gag p17 (17-35) is:

(SEQ ID NO.: 29)
GCTAGTGAGAAGATCCGGCTGCGGCCCGGCGGCAAGAAGAAGTACAAGCT

GAAGCACATCGTGGCTAGC

Gag p17-p24 (253-284) is:

(SEQ ID NO.: 30)
GCTAGTAACCCCCCCATCCCCGTGGGCGAGATCTACAAGCGGTGGATCAT

CCTGGGCCTGAACAAGATCGTGCGGATGTACAGCCCCACCAGCATCCTGG

ACGCTAGC

Pol 325-355 (RT 158-188) is:

(SEQ ID NO.: 31)
GCTAGTGCCATCTTCCAGAGCAGCATGACCAAGATCCTGGAGCCCTTCCG

GAAGCAGAACCCCGACATCGTGATCTACCAGTACATGGACGACCTGTAC

GCTAGC

Flex1 is:

(SEQ ID NO.: 32)
GCTAGTAGCAGCGTGAGCCCCACCACCAGCGTGCACCCCACCCCCACCAG

CGTGCCCCCCACCCCCACCAAGAGCAGCCCCGCTAGC

Flex2 is:

(SEQ ID NO.: 33)
GCTAGTCCCACCAGCACCCCCGCCGACAGCAGCACCATCACCCCCACCGC

CACCCCCACCGCCACCCCCACCATCAAGGGCGCTAGC

Flex3 is:

(SEQ ID NO.: 34)
GCTAGTACCGTGACCCCCACCGCCACCGCCACCCCCAGCGCCATCGTGAC

CACCATCACCCCCACCGCCACCACCAAGCCCGCTAGC

Flex4 is:

(SEQ ID NO.: 35)
GCTAGTACCAACGGCAGCATCACCGTGGCCGCCACCGCCCCCACCGTGAC

CCCCACCGTGAACGCCACCCCCAGCGCCGCCGCTAGC

The present invention includes compositions and methods for assembling constructs encoding HIV peptides and Flexible linker sequences. The H chain expression vectors typically have a Nhe I site [g|ctage] appended to the H chain C-terminal residue codon, or [for flex-v1 vectors] to the C-terminal codon of the flex-v1 sequence. Flexible linker sequences or HIV peptide sequences have an Spe I site [a|letagt] preceding the N-terminal flexible linker or HIV peptide codon, a Nhe I site appended to the C-terminal flexible linker or HIV peptide codon, followed by a TGA stop codon, followed by a Eco RI site, followed by a Not I site. Such flexible linker or HIV peptide Spe I-Not I fragments are inserted into the H chain vector prepared with Nhe I-Not I digestion. Nhe I and Spe I are compatible sites, but when ligated [g|ctagt] is no longer either a Nhe I or Spe I site. Thus additional Spe I-Not I flexible linker or HIV peptide fragments can be inserted into the new Nhe I-Not I interval distal to the initial flexible linker or HIV peptide. In this way, strings of HIV peptide and/or flexible linker coding regions can be appended to the expression vector H chain coding region.

EXAMPLE 2

HIV Peptides Vaccine—In Vitro Antigen-Targeting Biology

Anti-CD40.LIPO5 HIV peptides vaccine tests on HIV patients in vitro. To study the ability of αCD40.LIPO5 HIV peptide fusion recombinant antibody (αCD40.LIPO5 rAb) to mediate antigen presentation, the fusion rAb was added to blood cells from HIV-infected individuals and measured cytokine production form peripheral blood mononuclear cells (PBMCs).

Figure 5:
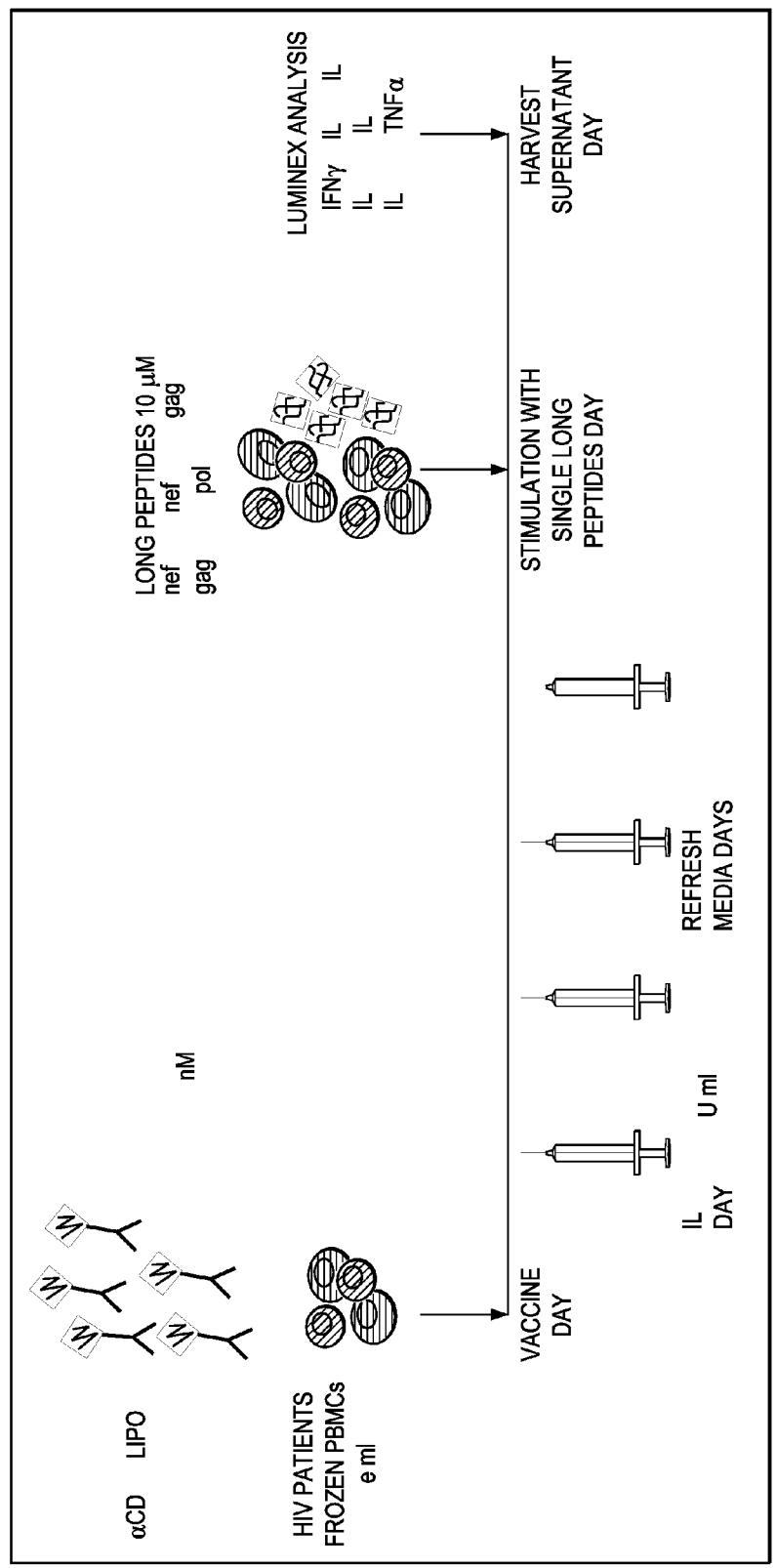

FIG. 5 describes the protocol used in vitro to assay the potency of αCD40.LIPO5 HIV peptide fusion recombinant antibody (αCD40.LIPO5 rAb) to elicit the expansion of antigen-specific T cells in the context of a PBMC culture. Briefly, PBMCs ($2 \times 10^6$ cells/ml) from apheresis of HIV patients are incubated with a dose range of αCD40.LIPO5 HIV peptide vaccine. On day 2, 100 U/ml IL-2 are added to the culture and then, the media is refreshed every 2 days with 100 U/ml IL-2. On day 10 the expanded cells are challenged for 48 h with the individual long peptides corresponding to the 5 HIV peptide sequences incorporated in the αCD40.LIPO5 HIV peptide fusion rAb. Then, culture supernatants are harvested and assessed for cytokine production (by the T cells with T cell receptor [TCR] specificities for peptide sequences) using multiplex beads assay (Luminex). Antigen-specific cytokine production detected in such an assay, if it depends on the presence of the anti-CD40.LIPO5 HIV peptide vaccine, reflects vaccine uptake by antigen presenting cells [APC] in the culture, and processing [proteolytic degradation] and presentation of peptides on MHC. The antigen-MHC complexes are recognized by T cells with TCR that recognize only the particular HIV antigen-MHC complex. In a HIV patient, such cells are likely to be memory T cells that expanded in the patient in response to the HIV infection.

Figure 6A:
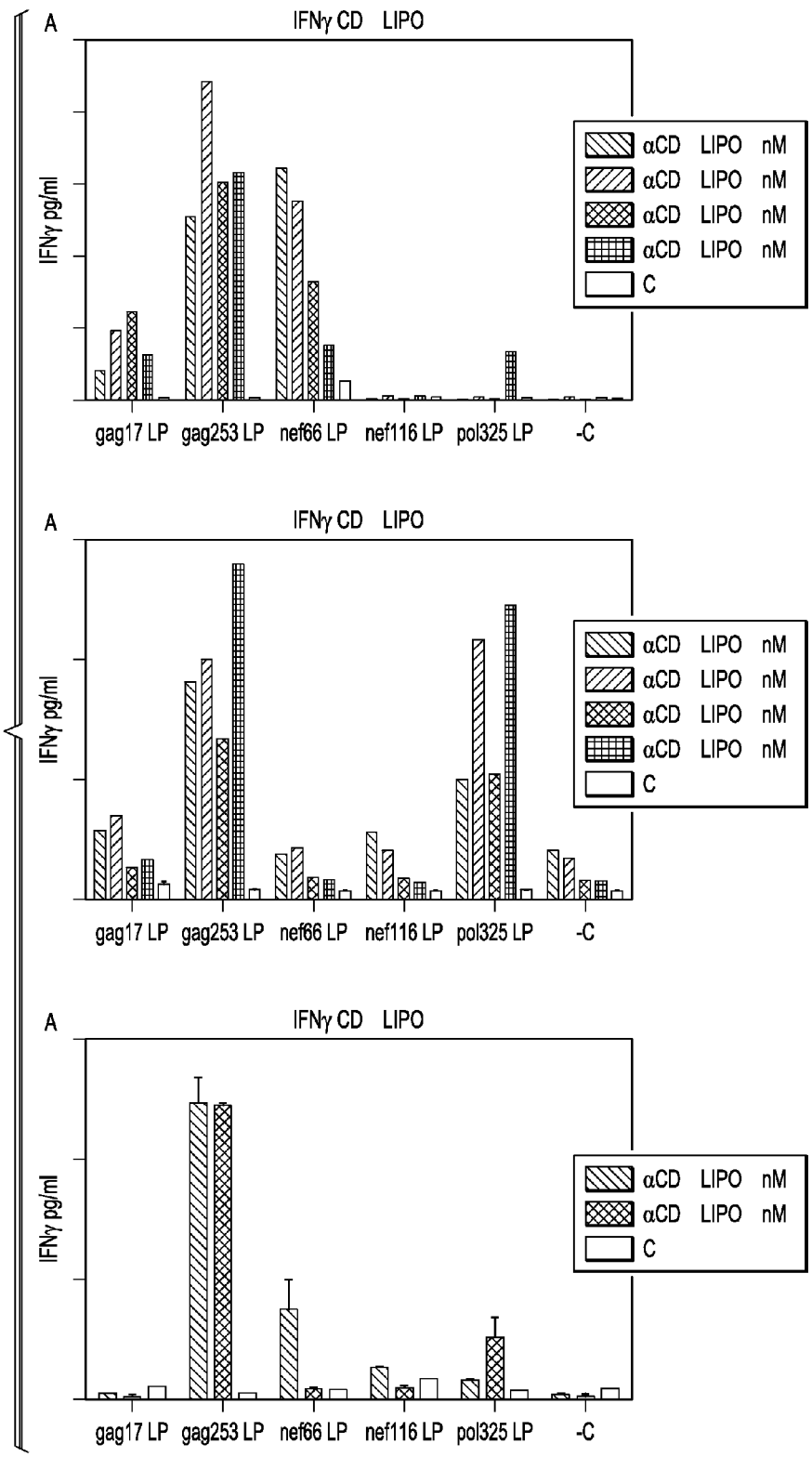
Figure 6C:
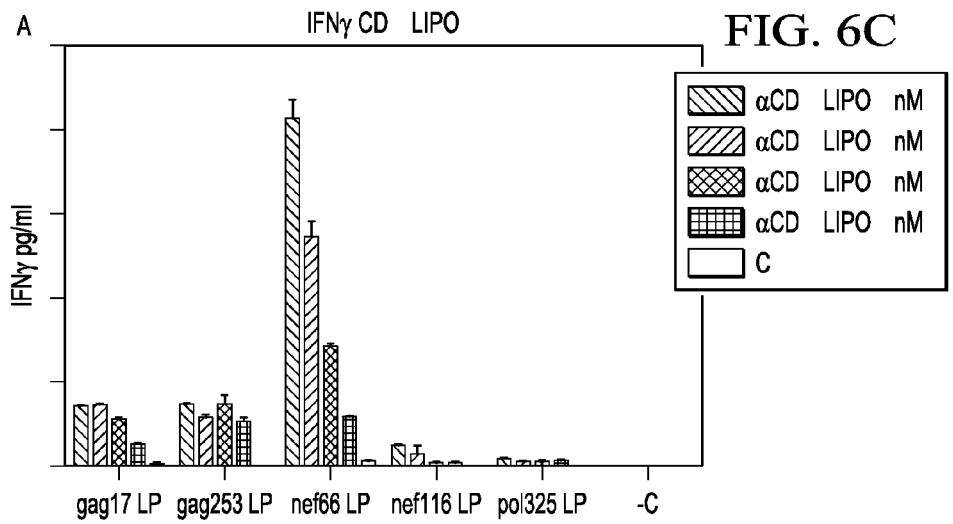

Epitopes from all 5 HIV peptide regions of the vaccine can be presented by APCs. The scheme in FIG. 5 was used to assay the in vitro expansion of HIV peptide-specific T cells in response to anti-CD40.LIPO5 peptide vaccine. Results from 7 individuals are shown in FIG. 6A-C and indicate that the aCD40.LIPO5 HIV peptide fusion rAb elicited HIV peptide-specific IFN-γ responses in all of the patients studied. Thus, the α-CD40.LIPO5 HIV peptide fusion rAb allows DCs to cross-present at least 1 or 2 different peptides out of the 5 peptides within the vaccine to the T cells of each individual. However, the set of HIV peptides that stimulated IFN γ production was different for each patient—most likely reflecting different pools of memory T cells for HIV specificity.

FIG. 6A-C shows the HIV peptide-specific IFN γ production in PBMCs from HIV patients incubated with various concentrations of anti-CD40.LIPO5 peptide string vaccine. C is the control group, which received no vaccine, and defines the baseline response of the culture to each peptide.

Figure 7:
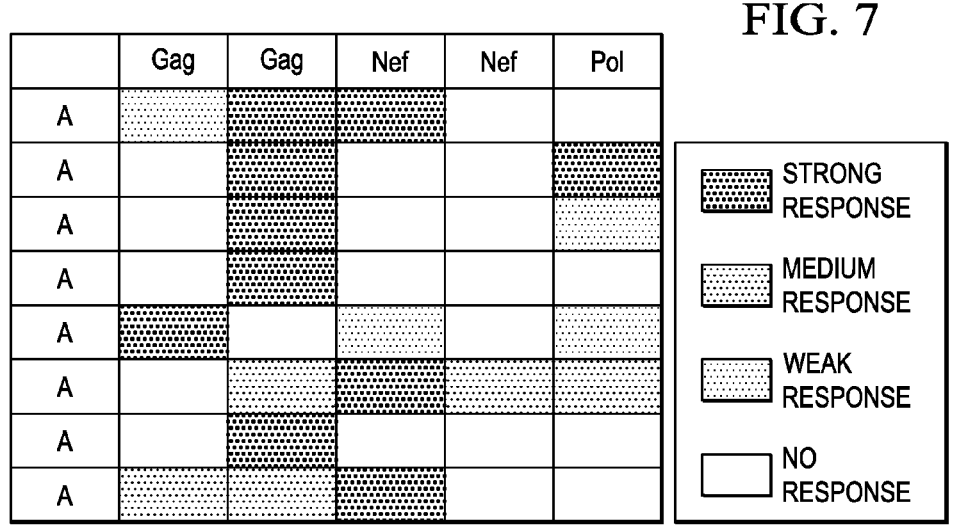
FIG. 7 is a summary of αCD40.LIPO5 peptide vaccine responses against the 5 peptide regions from 8 HIV patients.

FIG. 7 is a summary of αCD40.LIPO5 peptide vaccine responses against the 5 peptide regions from 8 HIV patients. The data are based on peptide-specific IFN-γ production. FIG. 7 shows that the antigen-specific responses observed in 8 HIV patients. The data demonstrate that all HIV peptide regions on the vaccine have the capacity to be processed and presented to T cells—assuming the likely situation that responses to these peptides will only be observed if the appropriate TCR-bearing cells are present. Thus, each patient has a characteristic spectrum of such cells.

Figure 8A:
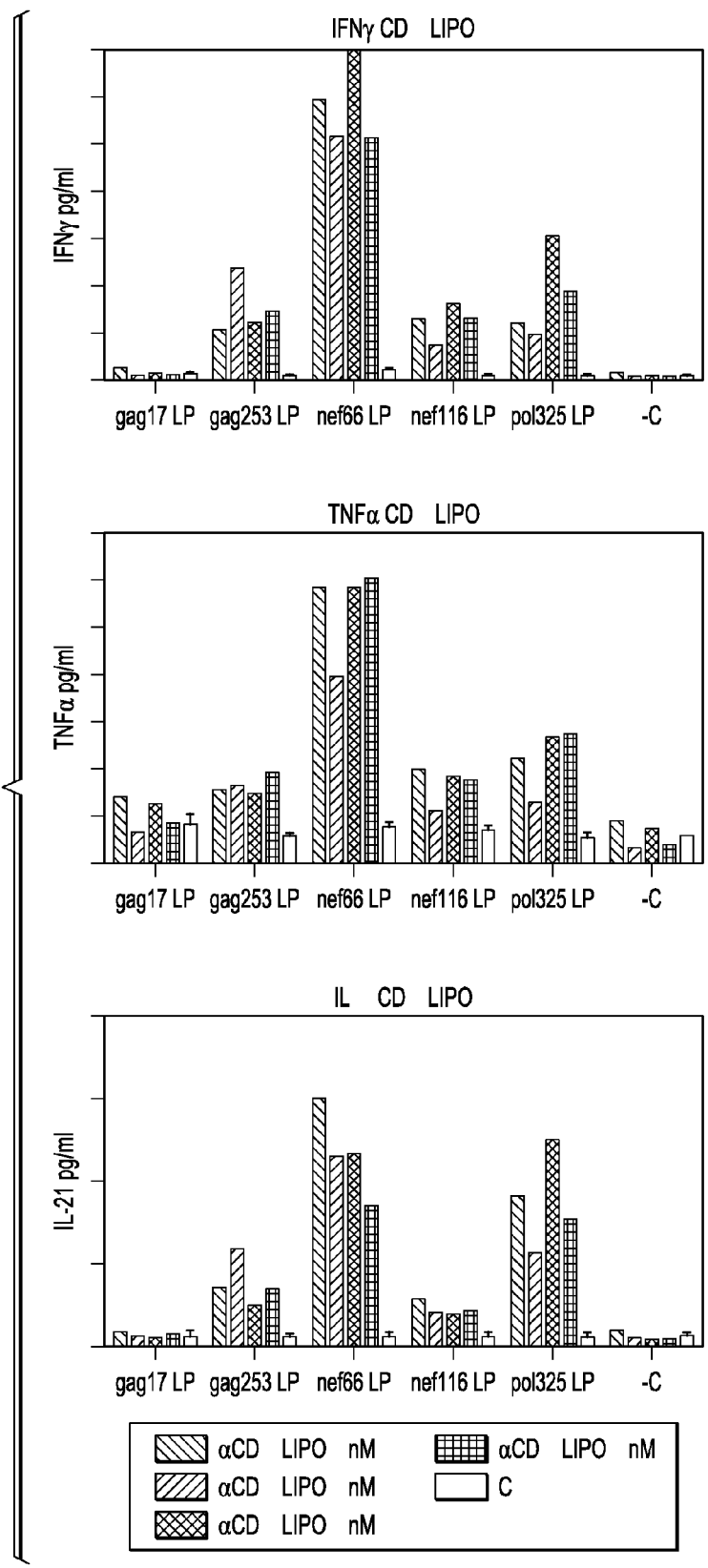
FIG. 8A-B shows that the αCD40.LIPO5 HIV peptide vaccine elicits expansion of HIV peptide-specific T cells capable of secreting multiple cytokines—a desirable feature in a vaccine.
Figure 8B:
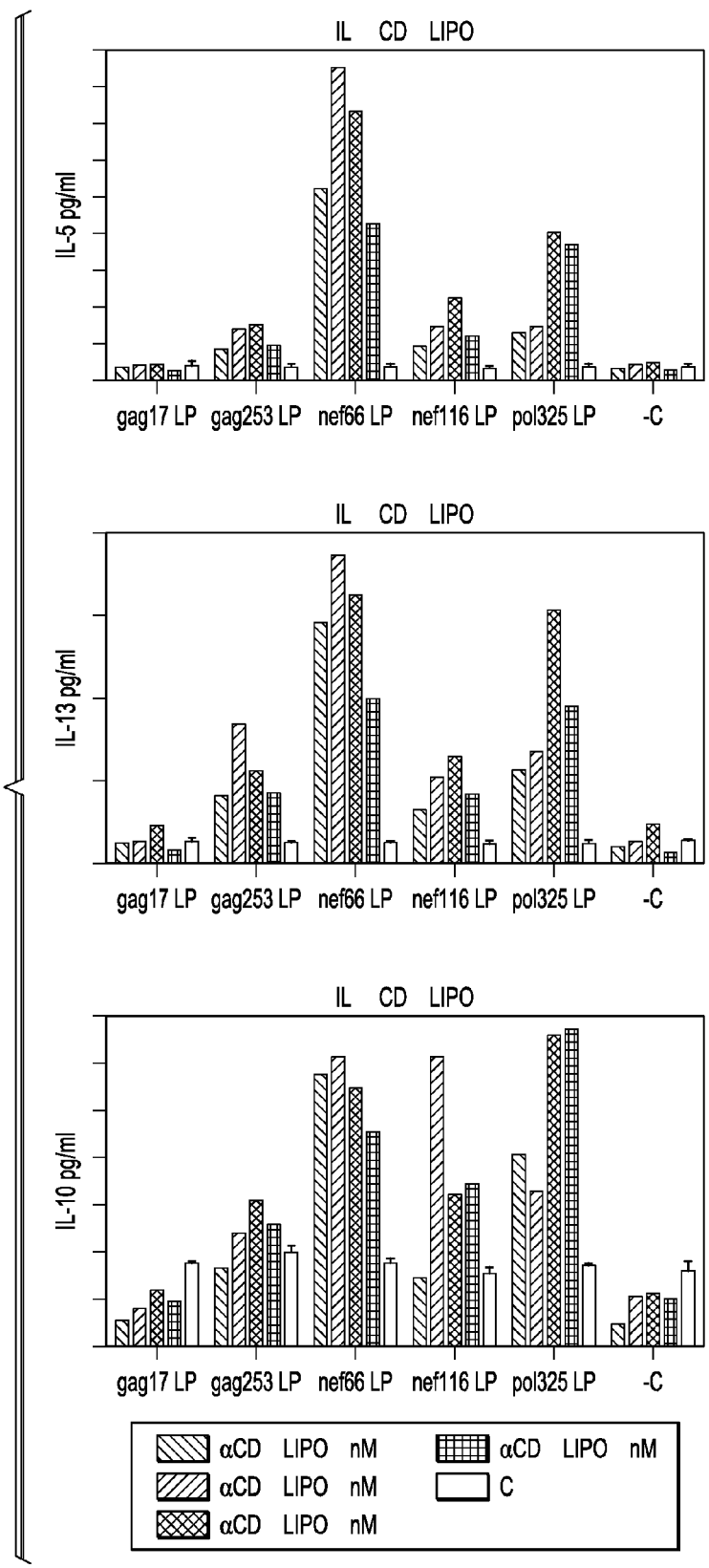

The αCD40.LIPO5 peptide vaccine can evoke the proliferation of antigen-specific T cells capable of secreting a wide spectrum of cytokines FIG. 8A-B shows that αCD40.LIPO5 HIV peptide vaccine elicits expansion of HIV peptide-specific T cells capable of secreting multiple cytokines—a desirable feature in a vaccine. In FIG. 8A-B αCD40.LIPO5 HIV peptide vaccine elicits gag253, nef66, nef116 and pol325 peptide-specific responses characterized by production of multiple cytokines. This is patient A5.

Anti-CD40.LIPO5 HIV peptide vaccination of ex vivo DCs.

Figure 9:
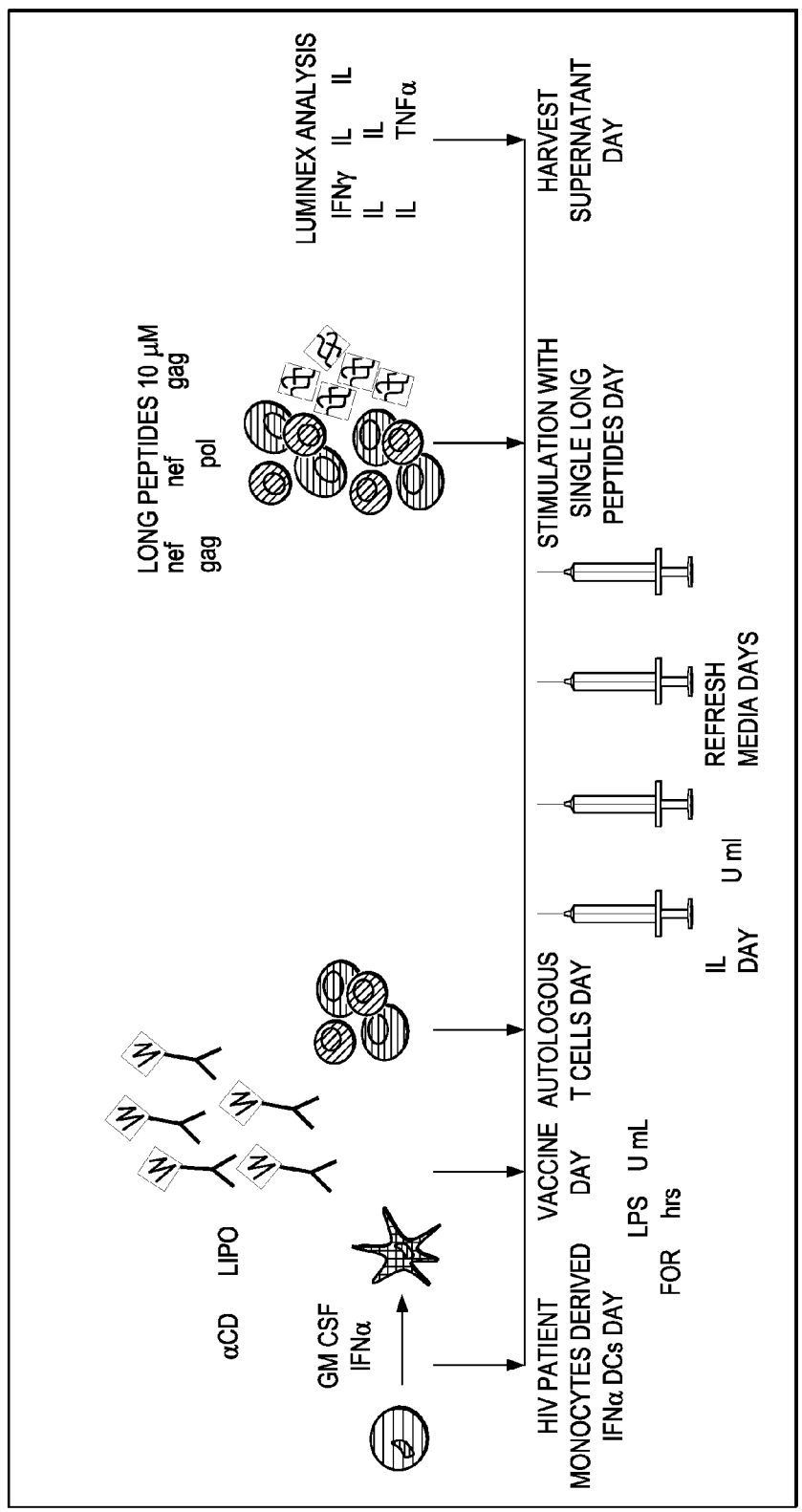
FIG. 9 shows the protocol for testing αCD40.LIPO5 HIV peptide vaccine for its ability to direct the expansion of antigen-specific T cells resulting from targeted uptake by DCs and presentation of peptide epitopes on their surface MHC complex.

FIG. 9 shows the protocol for testing αCD40.LIPO5 HIV peptide vaccine for its ability to direct the expansion of antigen-specific T cells resulting from targeted uptake by DCs and presentation of peptide epitopes on their surface MHC complex. Briefly, HIV patient monocytes are differentiated into DCs by culture for2 days with IFNα and GM-CSF. Different doses αCD40.LIPO5 HIV peptide vaccine or a mix of the 5 peptides are then added for 18 h. Autologous T cells were added to the co-culture (at a ratio of 1:20) on day 3. On day 5, 100 U/ml IL-2 are added to the culture and then, the media is refreshed every 2 days with 100 U/ml IL-2. On day 10 the expanded cells are rechallenged for 48 h with the individual long peptides corresponding to the 5 HIV peptide sequences incorporated in the αCD40.LIPO5 HIV peptide fusion rAb. Then, culture supernatants are harvested and assessed for cytokine production using Luminex.

Figure 10A:
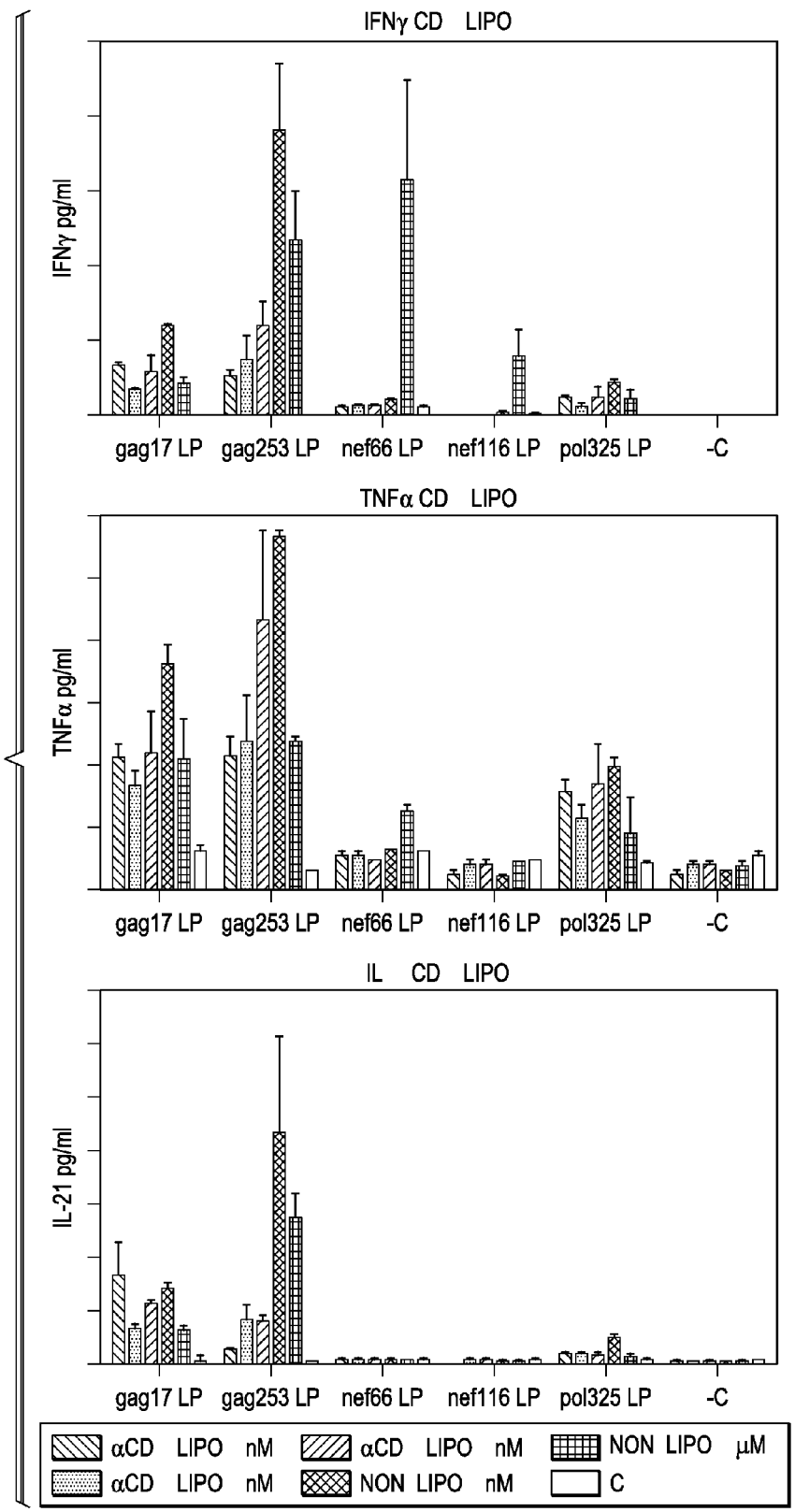
FIG. 10A-B shows the cytokine secretion in response to HIV peptides from DC-T cell co-cultures treated with various doses of αCD40.LIPO5 HIV peptide vaccine (patient A10).
Figure 10B:
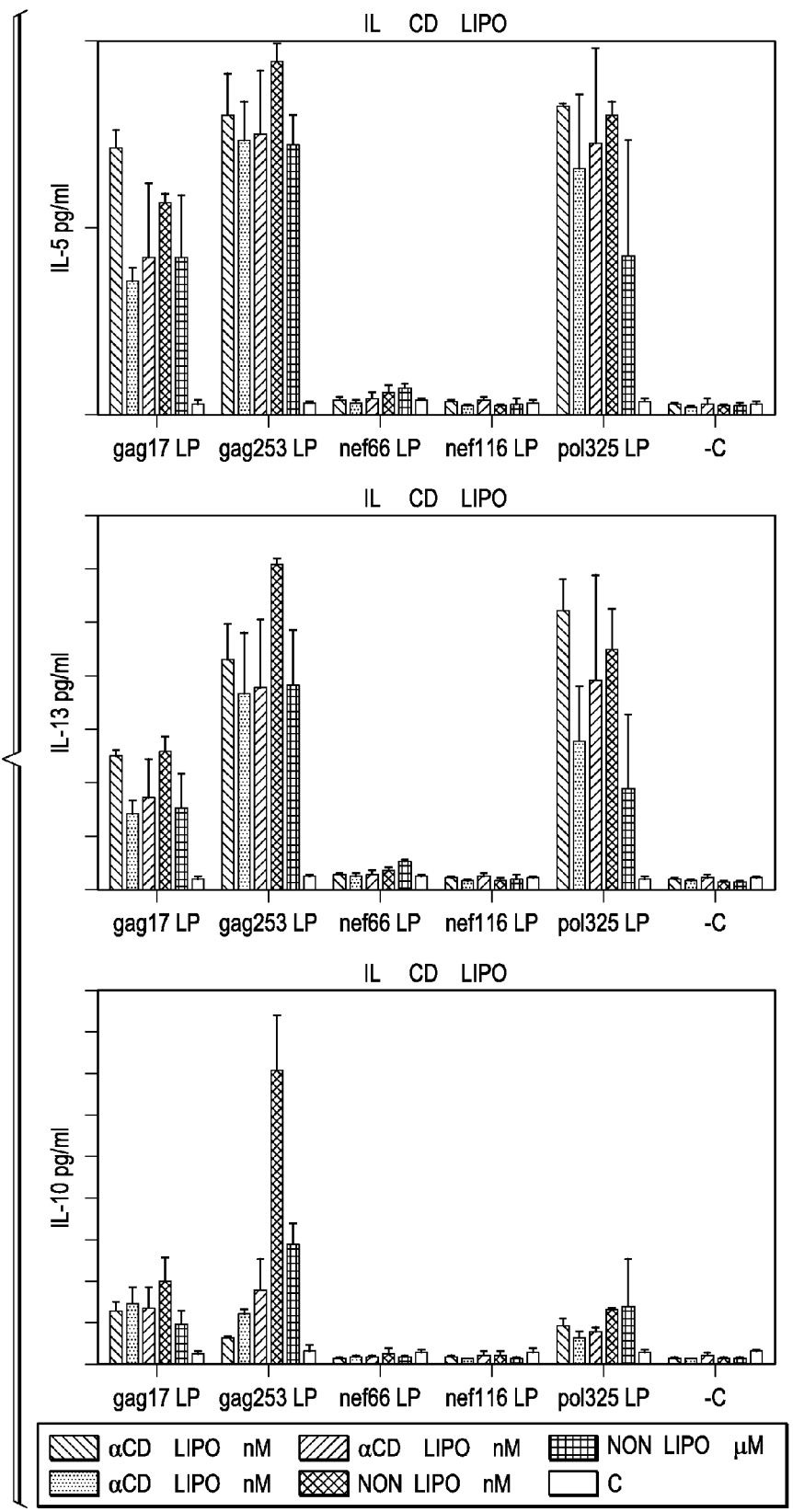
Figure 11A:
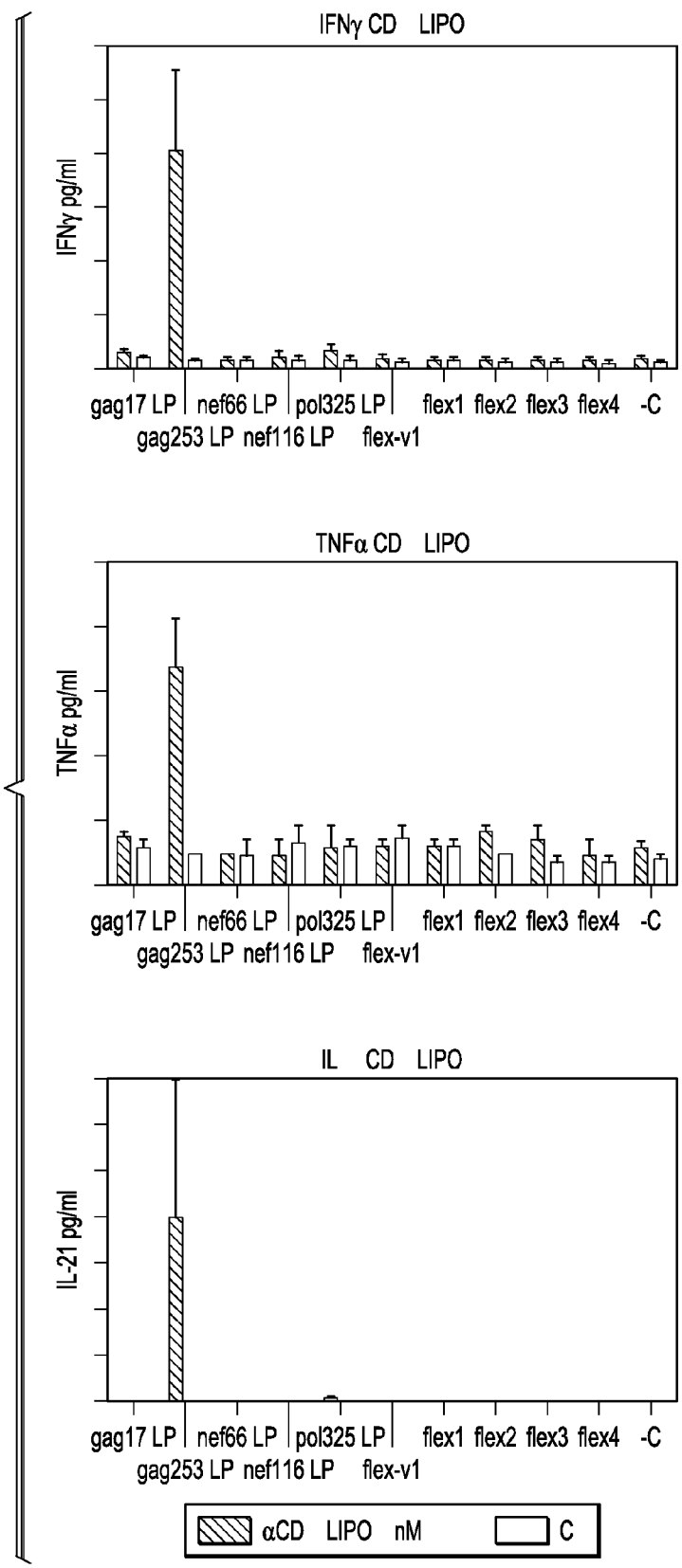
FIG. 11A-B shows PBMCs from patient A4 treated with the αCD40.LIPO5 HIV peptide vaccine elicit expansion of antigen-specific T cells with specificity to the gag253 region, but not to the flexible linker sequences.
Figure 11B:
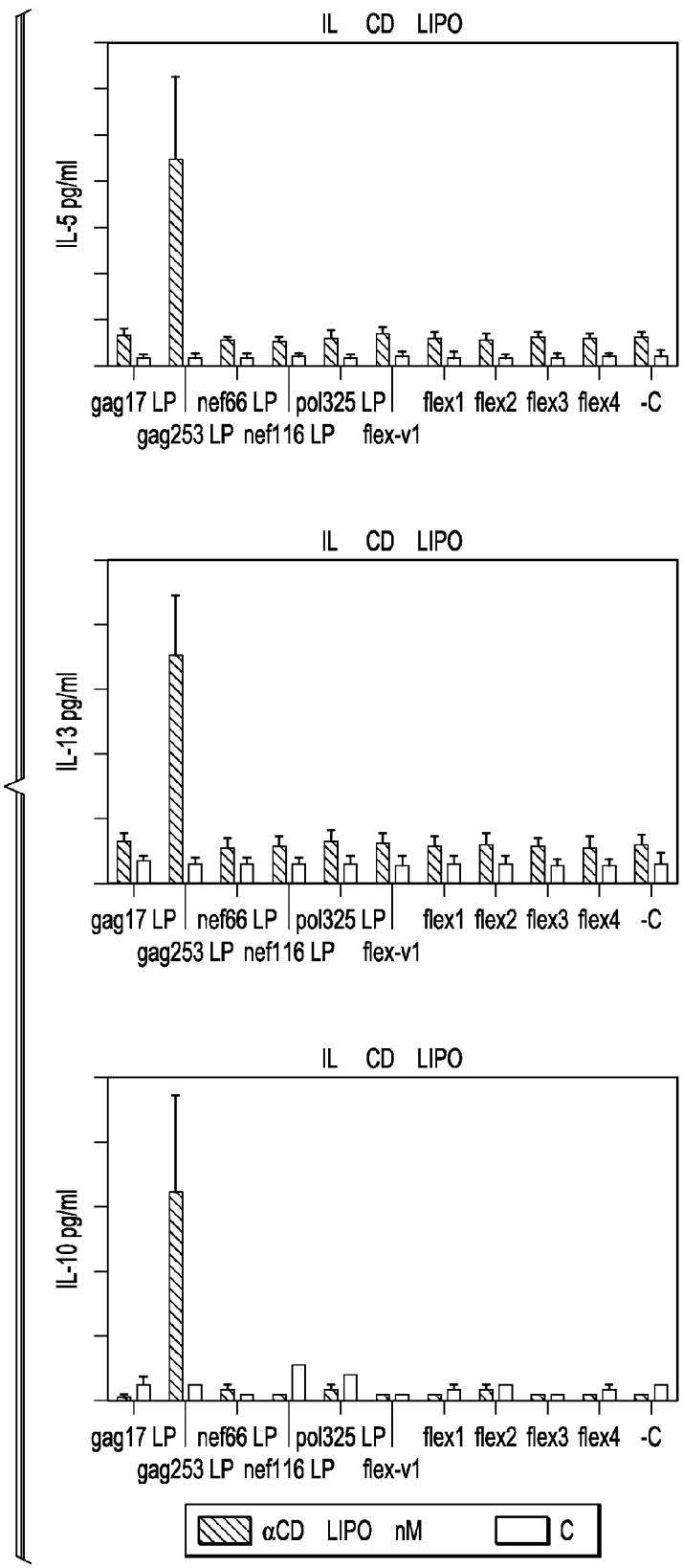

FIG. 10A-B shows the cytokine secretion in response to HIV peptides from DC-T cell co-cultures treated with various doses of αCD40.LIPO5 HIV peptide vaccine. This is patient A10. The results in the patient A10 shown in FIG. 10 demonstrate expansion of antigen-specific T cells corresponding to epitopes within the gag17, gag253, and pol325 HIV peptide regions. In most instances, there is concordance of responses between αCD40.LIPO5 HIV peptide vaccine and non-LIPO5 vaccine [mixture of 5 non-lipidated HIV peptides with sequences corresponding to those in the αCD40.LIPO5 HIV peptide vaccine]. Thus, the αCD40.LIPO5 HIV peptide vaccine functions well in this in vitro setting where cultured DCs effectively process and present the HIV antigens to T cells. This exemplifies use of the αCD40.LIPO5 HIV peptide vaccine for ex vivo vaccination, whereby the 'vaccinated DCs' would be cryopreserved for future re-injection into the same patient.

αCD40.LIPO5 HIV peptide vaccine—possible immune effect of the flexible linker regions. It is possible that the flexible linker sequences interspersing the HIV peptide sequences within the αCD40.LIPO5 HIV peptide vaccine themselves contain T cell epitopes. FIG. 11A-B shows that patient A4 does not appear to have a significant pool of memory T cells with specificities to the five flexible linker sequences within αCD40.LIPO5 HIV peptide vaccine. In FIG. 11A-B, PBMCs from patient A4 treated with the αCD40.LIPO5 HIV peptide vaccine elicit expansion of antigen-specific T cells with specificity to the gag253 region, but not to the flexible linker sequences. The protocol describe in FIG. 9 was used, with the flexible linker long peptides corresponding in sequence to the bold areas, the HIV peptides are in bold-italics, shown in the sequence below.

αCD40.LIPO5 HIV peptide vaccine heavy chain sequence showing flexible linker regions in bold, joining sequences underlined and HIV peptide regions shaded in bold italics.

(SEQ ID NO.: 36)

QVTLKESGPGILQPSQTLSLTCSFSGFSLSTSGMGLSWIRQPSGKGLEWLAHIYWDDDKRYNPSLKS

RLTISKDTSSNQVFLKITIVDTADAATYYCARSSHYYGYGYGGYFDVWGAGTTVTVSSAKTKGPS

VFPLAPCSRSTSESTAALGCLVKDYFPEPVTVSWNSGALTSGVHTFPAVLQSSGLYSLSSVVTVPSS

SLGTKTYTCNVDHKPSNTKVDKRVESKYGPPCPPCPAPEFEGGPSVFLFPPKPKDTLMISRTPEVTC

VVVDVSQEDPEVQFNWYVDGVEVHNAKTKPREEQFNSTYRVVSVLTVLHQDWLNGKEYKCKVS

NKGLPSSIEKTISKAKGQPREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKSLSLSLGKASQTPTNTIS

VTPTNNSTPTNNSNPKPNPASEKIRLRPGGKKKYKLKHIVASSSVSPTTSVHPTPTSVPPTPTKSSP

ASNPPIPVGEIYKRWIILGLNKIVRMYSPTSILDASPTSTPADSSTITPTATPTATPTIKGASHTQGY

FPDWQNYTPGPGVRYPLTFGWLYKLASTVTPTATATPSAIVTTITPTATTKPASVGFPVTPQVPLR

PMTYKAAVDLSHFLKEKGGLASTNGSITVAATAPTVTPTVNATPSAAASAIFQSSMTKILEPFRKQ

NPDIVIYQYMDDLYAS.

Figure 12A:
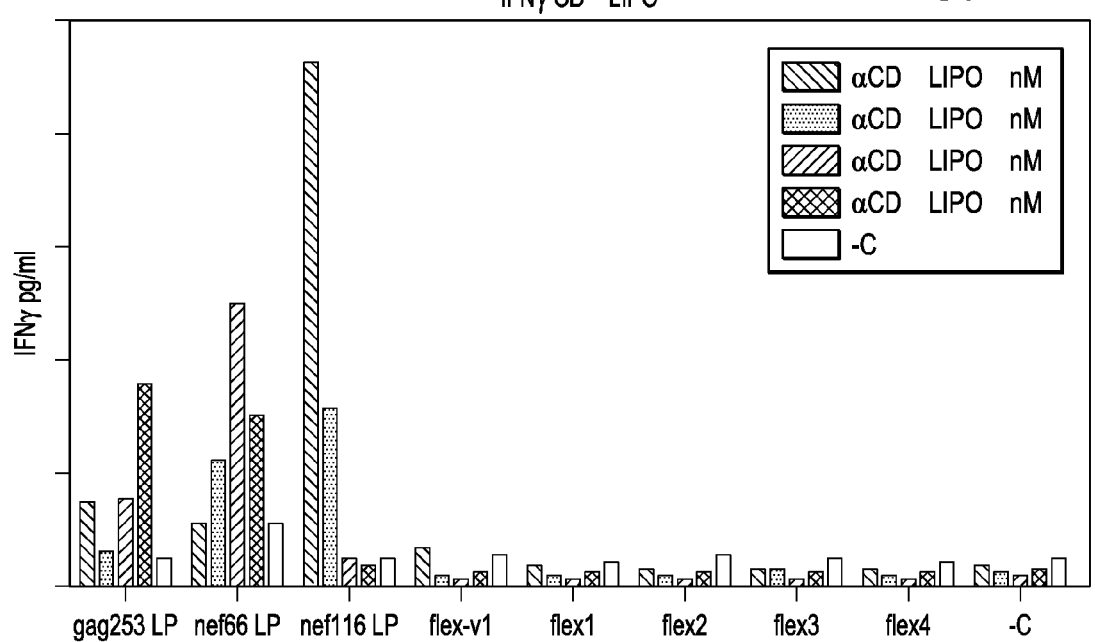
FIG. 12A is the αCD40.LIPO5 HIV peptide vaccine heavy chain sequence showing flexible linker regions in bold, joining sequences underlined and HIV peptide regions shaded in grey.

In FIG. 12A, the PBMCs from patient A3 treated with the αCD40.LIPO5 HIV peptide vaccine elicit expansion of antigen-specific T cells with specificities to the gag253, nef66, and nef116 regions, but not to the flexible linker sequences. The protocol described in FIG. 1 was used, with the flexible linker long peptides corresponding in sequence to the bold areas shown in FIG. 8A-B.

Figures 1, 12B:
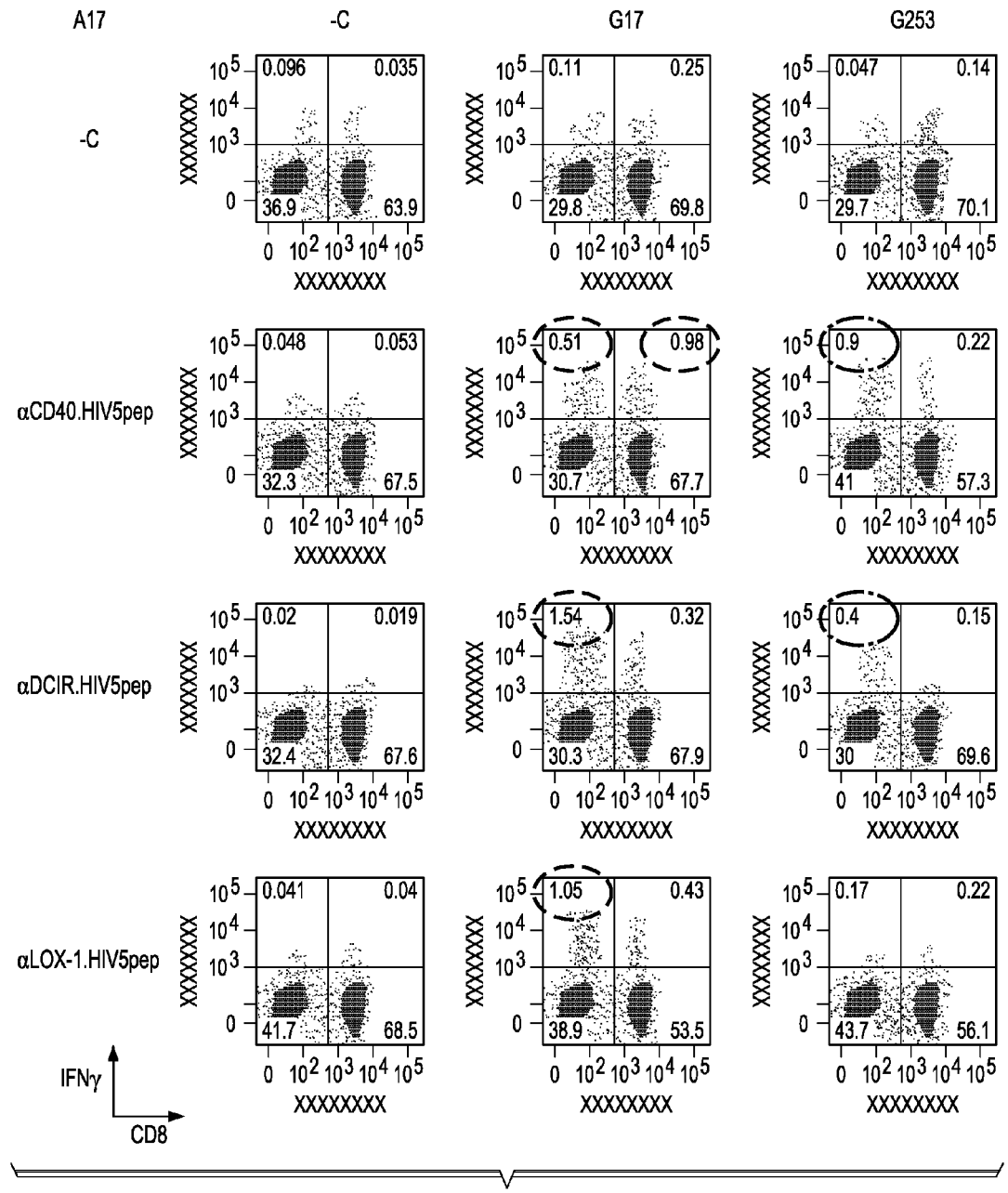
Figures 2, 12B:
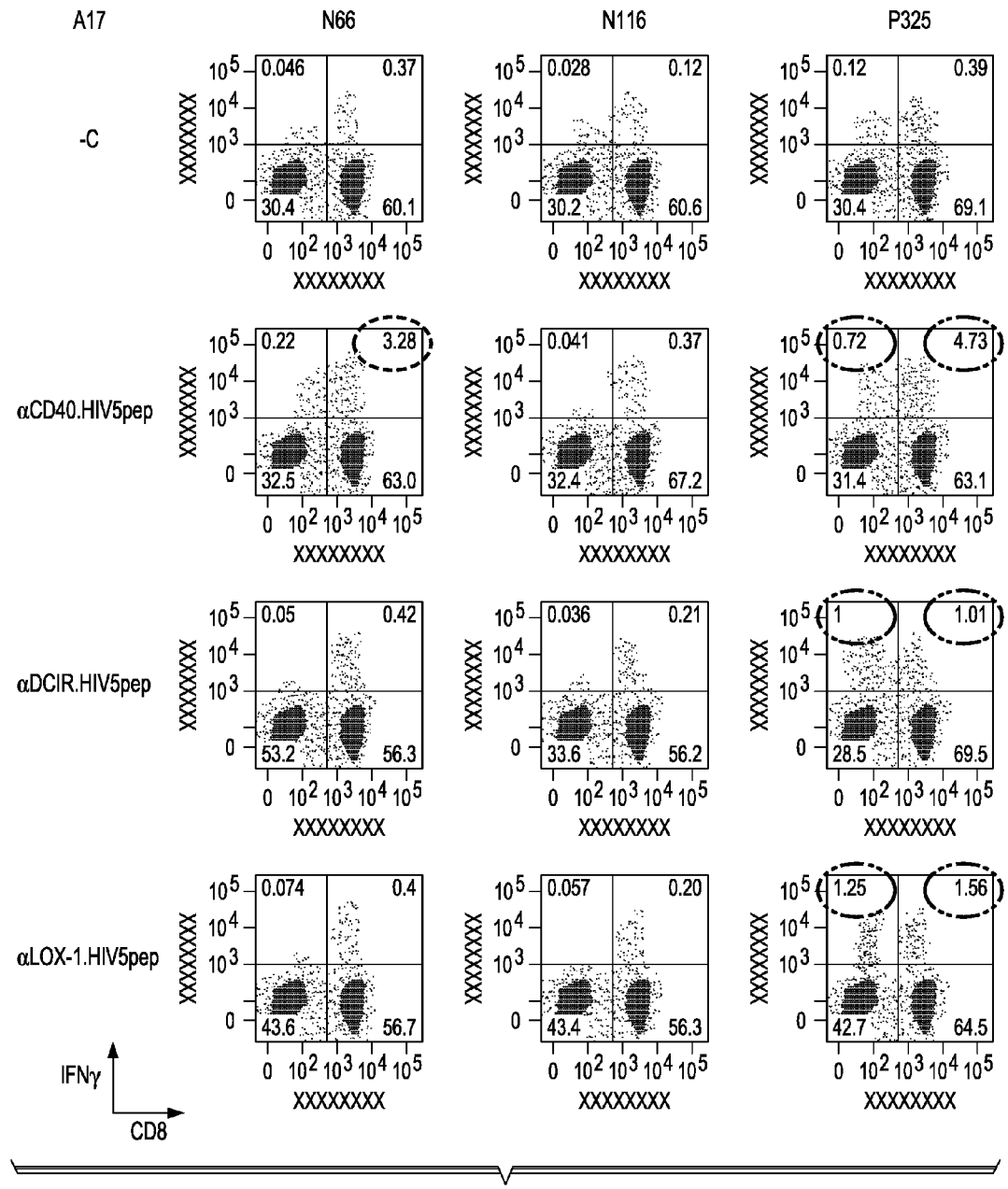

FIG. 12B-1 and 12B-2 shows HIV antigen-specific T cell responses evoked from HIV patient A17 PBMCs incubated with 30 nM of three different HIV5 peptide DC targeting vaccines. Cells were cultured for 10 days with IL-2 and then stimulated with individual long peptides corresponding to the 5 HIV peptide sequences encompassed within the DC-targeting vaccines. After 1 hr brefeldin A was added and incubation continued for a further 5 hrs before staining for FACS analysis. The FACS plots show IFN and CD8 staining on CD3+ T cells. Circles indicate significant vaccine-evoked expansion of IFN+ cells compared to cells from PBMCs cultured without vaccine. CD8− cells are CD4+ T cells. The data show that that anti-CD40.HIV5pep vaccine evokes a strong expansion of nef66 (N66)-specific CD8+ T cells which is not seen with the other DC targeting vehicles.

These are data based on the LIPO5 HIV peptide string. For example the anti-CD40 H chain is anti-CD40__12E12.3F3_H-LV-hIgG4H-C-Flex-v1-Pep-gag17-f1-gag253-f2-nef116-f3-nef66-f4-pol158] with sequence:

(SEQ ID NO.: 37)

EVKLVESGGGLVQPGGSLKLSCATSGFTFSDYYMYWVRQTPEKRLEWVAYINSGGGSTYYPDTVK

GRFTISRDNAKNTLYLQMSRLKSEDTAMYYCARRGLPFHAMDYWGQGTSVTVSSAKTKGPSVFPL

APCSRSTSESTAALGCLVKDYFPEPVTVSWNSGALTSGVHTFPAVLQSSGLYSLSSVVTVPSSSLGT

KTYTCNVDHKPSNTKVDKRVESKYGPPCPPCPAPEFEGGPSVFLFPPKPKDTLMISRTPEVTCVVVD

VSQEDPEVQFNWYVDGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSLGKASQTPTNTISVTPT

NNSTPTNNSNPKPNPASEKIRLRPGGKKKYKLKHIVASSSVSPTTSVHPTPTSVPPTPTKSSPASNPPI

PVGEIYKRWIILGLNKIVRMYSPTSILDASPTSTPADSSTITPTATPTATPTIKGASHTQGYFPDWQNY

TPGPGVRYPLTFGWLYKLASTVTPTATATPSAIVTTITPTATTKPASVGFPVTPQVPLRPMTYKAAV

DLSHFLKEKGGLASTNGSITVAATAPTVTPTVNATPSAAASAIFQSSMTKILEPFRKQNPDIVIYQYM

DDLYAS.

Figures 1, 12C:
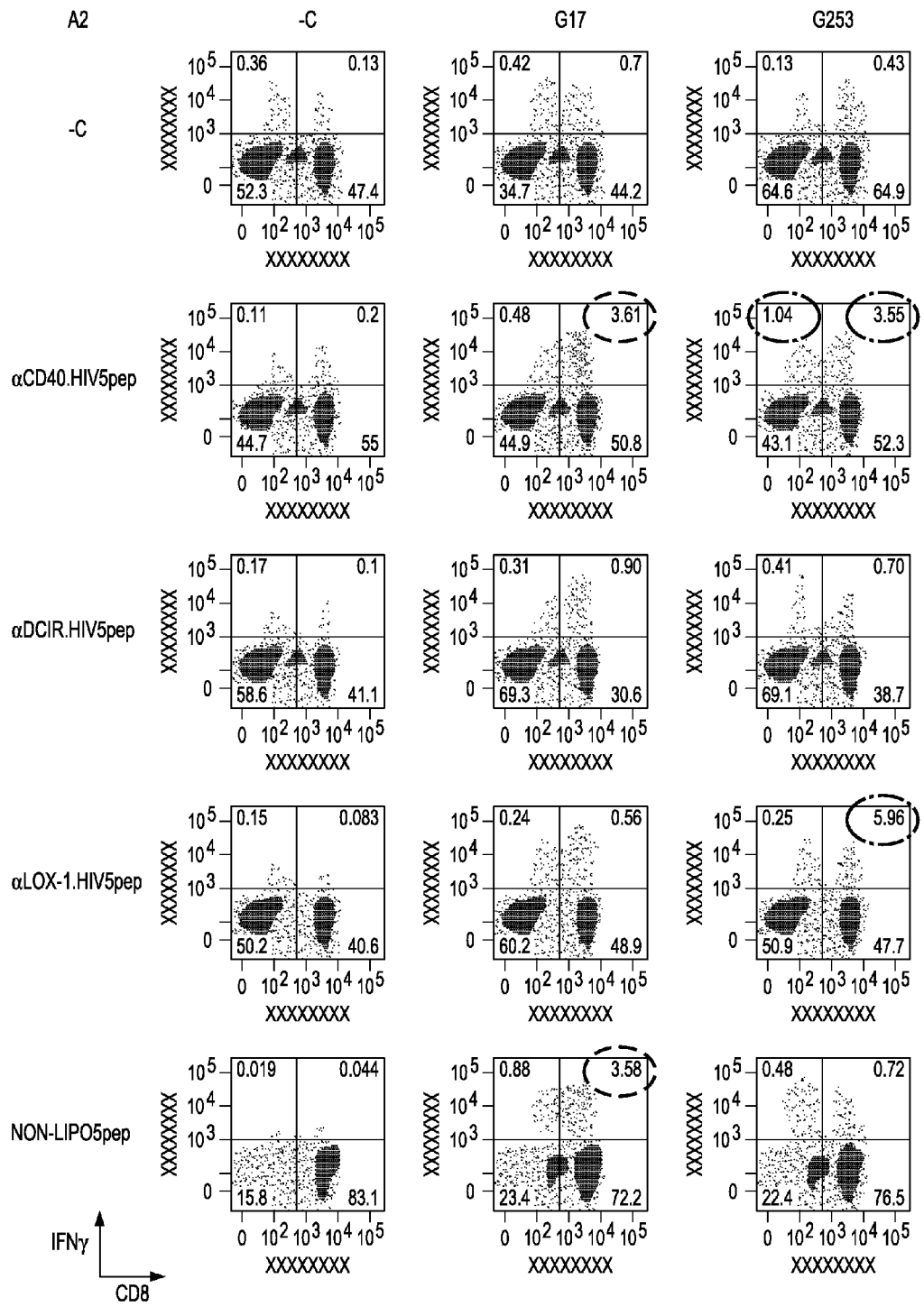
Figures 2, 12C:
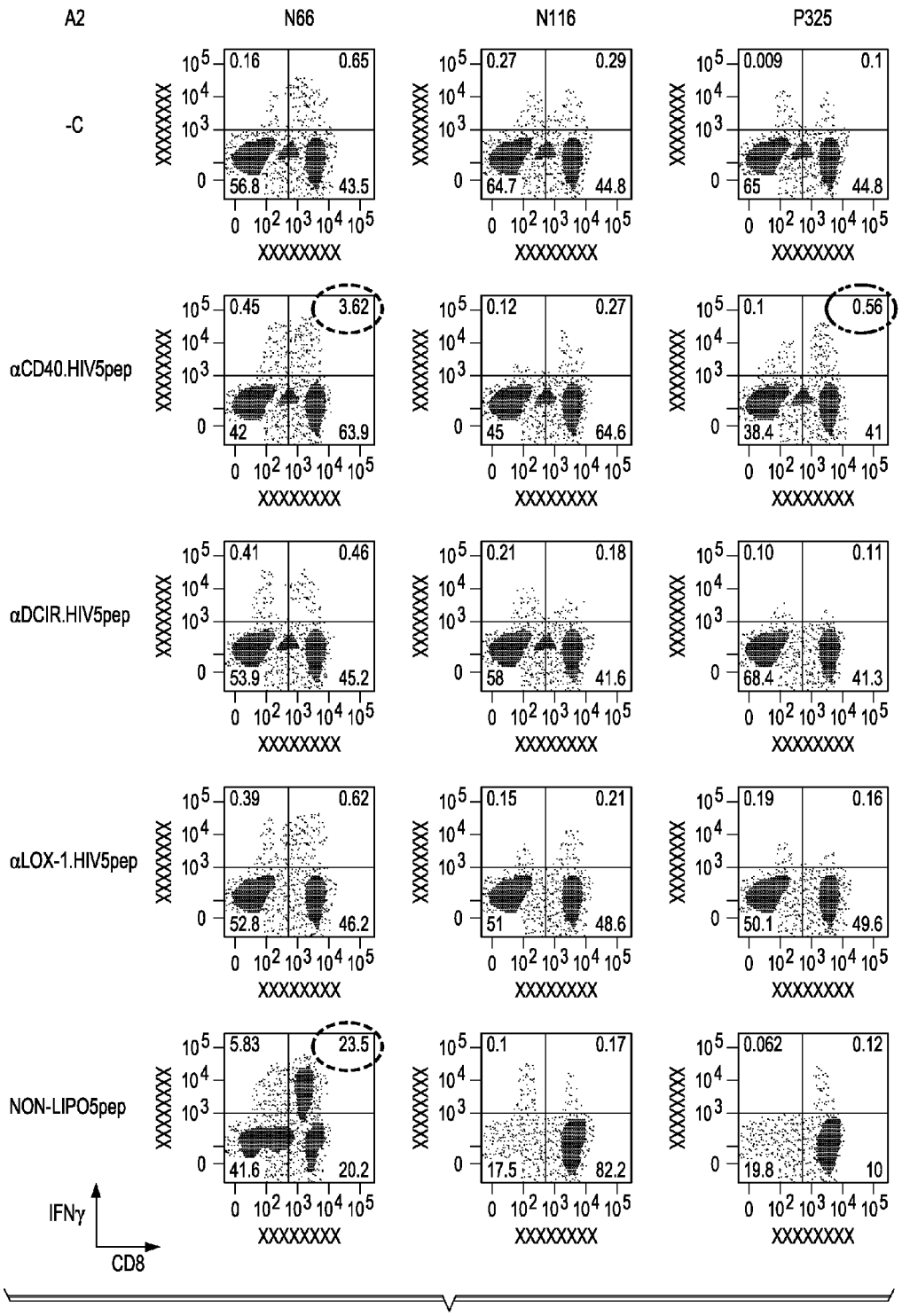

FIG. 12C-1 and 12C-2 is a similar study to that show in FIG. 12B-1 and 12B-2, except that the PBMCs are from a different HIV patient (A2). The data show antigen-specific CD4+ and CD8+ T cell responses evoked by anti-CD40.HIV5pep but not the other DC-targeting vaccines, or by a mixture of the peptides themselves.

Figure 12D:
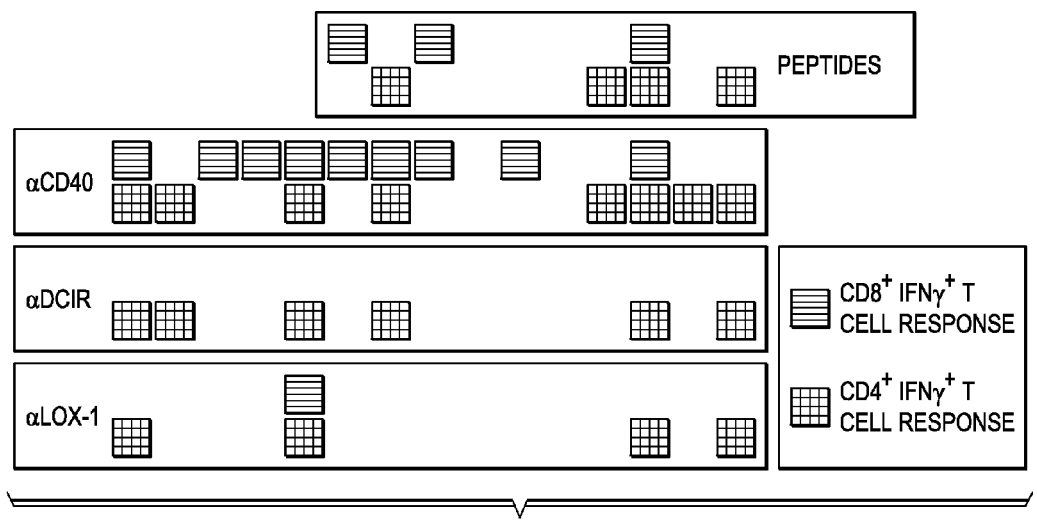
FIG. 12D shows 15 different HIV peptide responses [5 peptide regions sampled in 3 patients], it was found that the anti-CD40.HIV5pep vaccine was superior to anti-DCIR.HIV5pep, anti-LOX-1.HIV5pep and non-LIPO5 mix for eliciting a broad range of HIV peptide-specific CD8+ and CD4+ T responses.

FIG. 12D shows that, based on analysis of 15 different HIV peptide responses [5 peptide regions sampled in 3 patients], anti-CD40.HIV5pep vaccine is clearly superior to anti-DCIR.HIV5pep, anti-LOX-1.HIV5pep and non-LIPO5 mix for eliciting a broad range of HIV peptide-specific CD8+ and CD4+ T responses.

The immunogenicity of the flexible linker sequences is of concern for the αCD40.LIPO5 HIV peptide vaccine design. The limited datasets shown above, testing recall of T cells with specificities for epitopes within the flexible linker sequences, suggest that the human repertoire against these sequences is variable. Also, the ability of these sequences to prime responses de novo is untested. Responses to the αCD40.LIPO5 HIV peptide vaccine in monkeys can be tested using the present invention. If necessary, certain less desirable epitopes within these regions can be identified by a combination of predictive computational means and peptide stimulation scans, and then eliminated by introducing mutational changes that abrogate the TCR interaction.

The anti-CD40 binding molecule includes a light chain having the following amino acid sequence (SEQ ID NO. 38). The variable region of the antibody light chain is underlined and the CDRs are bolded (SEQ ID NOS.: 42, 43 and 44, respectively).

(SEQ ID NO.: 38)
MMSSAQFLGLLLLCFQGTRC<u>DIQMTQTTSSLSASLGDRVTISCSASQGIS</u>
<u>NYLNWYQQKPDGTVKLLIYYTSILHSGVPSRFSGSGSGTDYSLTIGNLEP</u>
<u>EDIATYYCQQFNKLPPTF</u>GGGTKLEIKRTVAAPSVFIFPPSDEQLKSGTA
SVVCLLNNFYPREAKVQWKVDNALQSGNSQESVTEQDSKDSTYSLSSTL
TLSKADYEKHKVYACEVTHQGLSSPVTKSFNRGEC.

The anti-CD40 binding molecule includes a heavy chain having the following sequence. The variable region of the antibody light chain is underlined and the CDRs are bolded (SEQ ID NOS.: 45, 46 and 47, respectively).

(SEQ ID NO.: 39)
MNLGLSLIFLVLVLKGVQ<u>CEVKLVESGGGLVQPGGSLKLSCATSGFTFSDYYMYWVRQTP</u>
<u>EKRLEWVAYINSGGGSTYYPDTVKGRFTISRDNAKNTLYLQMSRLKSEDTAMYYCARRGLPFH</u>
<u>AMDYWGQGTSVTVS</u>SAKTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVESKYGPPCPPCPAPEFEGG
PSVFLFPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQEGNVFSCSVMHEALH
NHYTQKSLSLSLGKAS.

In one aspect the nucleic acid that encodes the light chain comprises the SEC ID NO. The variable region of the antibody light chain nucleic acid sequence is underlined and the CDRs are bolded.

(SEQ ID NO.: 40)
ATGATGTCCTCTGCTCAGTTCCTTGGTCTCCTGTTGCTCTGTTTTCAAGGTACCAGATGT
<u>GATATCCAGATGACACAGACTACATCCTCCCTGTCTGCCTCTCTAGGAGACAGAGTCACCATC</u>
<u>AGTTGCAGTGCAAGTCAGGGCATTAGCAATTATTTAAACTGGTATCAGCAGAAACCAGATG</u>
<u>GAACTGTTAAACTCCTGATCTATTACACATCAATTTTACACTCAGGAGTCCCATCAAGGTTCA</u>
<u>GTGGCAGTGGGTCTGGGACAGATTATTCTCTCACCATCGGCAACCTGGAACCTGAAGATATTG</u>
<u>CCACTTACTATTGTCAGCAGTTTAATAAGCTTCCTCCGACGTTCGGTGGAGGCACCAAACTC</u>
GAGATCAAACGAACTGTGGCTGCACCATCTGTCTTCATCTTCCCGCCATCTGATGAGCAGTTGA
AATCTGGAACTGCCTCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCACAGAGCAGGACA
GCAAGGACAGCACCTACAGCCTCAGCAGCACCCTGACGCTGAGCAAAGCAGACTACGAGAAA
CACAAAGTCTATGCCTGCGAAGTCACCCATCAGGGCCTGAGCTCGCCCGTCACAAAGAGCTTC
AACAGGGGAGAGTGTTAG.

In one aspect the nucleic acid that encodes the heavy chain comprises the SEQ ID NO.:40. The variable region of the antibody heavy chain nucleic acid sequence is underlined and the CDRs are bolded.

the framework of SEQ ID NO.:39. In another aspect, the donor CDR sequences are from ANTI-CD40_12E12.3F3 and further, wherein the antibody or fragment thereof specifically binds to CD40.

(SEQ ID NO.: 41)

ATGAACTTGGGGCTCAGCTTGATTTTCCTTGTCCTTGTTTTAAAAGGTGTCCAGTGT<u>GA</u>

<u>AGTGAAGCTGGTGGAGTCTGGGGGAGGCTTAGTGCAGCCTGGAGGGTCCCTGAAACTCTCCTG</u>

<u>TGCAACCTCTGGATTCACTTTCAGTGACTATTACATGTATTGGGTTCGCCAGACTCCAGAGA</u>

<u>AGAGGCTGGAGTGGGTCGCATACATTAATTCTGGTGGTGGTAGCACCTATTATCCAGACAC</u>

<u>TGTAAAGGGCCGATTCACCATCTCCAGAGACAATGCCAAGAACACCCTGTACCTGCAAATGA</u>

<u>GCCGGCTGAAGTCTGAGGACACAGCCATGTATTACTGTCAAGACGGGGGTTACCGTTCCAT</u>

<u>GCTATGGACTATTGGGGTCAAGGAACCTCAGTCACCGTCTCCT</u>CAGCCAAAACGAAGGGCCC

ATCCGTCTTCCCCCTGGCGCCCTGCTCCAGGAGCACCTCCGAGAGCACAGCCGCCCTGGGCTG

CCTGGTCAAGGACTACTTCCCCGAACCGGTGACGGTGTCGTGGAACTCAGGCGCCCTGACCAG

CGGCGTGCACACCTTCCCGGCTGTCCTACAGTCCTCAGGACTCTACTCCCTCAGCAGCGTGGTG

ACCGTGCCCTCCAGCAGCTTGGGCACGAAGACCTACACCTGCAACGTAGATCACAAGCCCAGC

AACACCAAGGTGGACAAGAGAGTTGAGTCCAAATATGGTCCCCCATGCCCACCCTGCCCAGCA

CCTGAGTTCGAAGGGGGACCATCAGTCTTCCTGTTCCCCCCAAAACCCAAGGACACTCTCATG

ATCTCCCGGACCCCTGAGGTCACGTGCGTGGTGGTGGACGTGAGCCAGGAAGACCCCGAGGTC

CAGTTCAACTGGTACGTGGATGGCGTGGAGGTGCATAATGCCAAGACAAAGCCGCGGGAGGA

GCAGTTCAACAGCACGTACCGTGTGGTCAGCGTCCTCACCGTCCTGCACCAGGACTGGCTGAA

CGGCAAGGAGTACAAGTGCAAGGTCTCCAACAAAGGCCTCCCGTCCTCCATCGAGAAACCAT

CTCCAAAGCCAAAGGGCAGCCCCGAGAGCCACAGGTGTACACCCTGCCCCCATCCCAGGAGG

AGATGACCAAGAACCAGGTCAGCCTGACCTGCCTGGTCAAAGGCTTCTACCCCAGCGACATCG

CCGTGGAGTGGGAGAGCAATGGGCAGCCGGAGAACAACTACAAGACCACGCCTCCCGTGCTG

GACTCCGACGGCTCCTTCTTCCTCTACAGCAGGCTAACCGTGGACAAGAGCAGGTGGCAGGAG

GGGAATGTCTTCTCATGCTCCGTGATGCATGAGGCTCTGCACAACCACTACACACAGAAGAGC

CTCTCCCTGTCTCTGGGTAAAGCTAGCTGA.

A humanized antibody includes the heavy chain variable region ($V_H$) and a light chain variable region ($V_L$), wherein the framework regions of the heavy chain and light chain variable regions are from a donor human antibody, and wherein the light chain complementarity determining regions (CDRs) have at least 80%, 90%, 95% or higher identity to $CDR1_L$ having the amino acid sequence SASQGISNYLN (SEQ ID NO.:41), the $CDR2_L$ having the amino acid sequence YTSILHS (SEQ ID NO.:42) and the $CDR3_L$ having the amino acid sequence QQFNKLPPT (SEQ ID NO.:43); and wherein the heavy chain complementarity determining regions comprise at least 80%, 90%, 95% or higher identity to the $CDR1_H$, $CDR2_H$ and $CDR3_H$, the $CDR1_H$ having the amino acid sequence GFTFSDYYMY (SEQ ID NO.:45), the $CDR2_H$ having the amino acid sequence YINSGGGSTYYP-DTVKG (SEQ ID NO.:46), and the $CDR3_H$ having the amino acid sequence RGLPFHAMDY (SEQ ID NO.:47). For example, the humanized antibody may comprise a VL framework having at least 95% identity to the framework of SEQ ID NO.:38 and a VH framework that has at least 95% identity to

EXAMPLE 3

Prostate-Specific Antigen (PSA), Cycline D1, MART-1, Influenza Viral Nucleoprotein (NP) and HA1 Subunit of Influenza Viral Hemagglutinin (H1N1, PR8) and Peptide Screen Internalization of anti-CD40 mAb. $1\times10^6$ IL-4DCs were incubated for 1 h in ice with 3 mg/ml human gamma globulin in PBS containing 3% BSA to block non-specific binding Cells were pulsed for 30 minutes on ice with Alexa 568 labeled anti-CD40 mAb (all at 20 ng/ml final concentration in non-specific block). Cells were then washed and allowed to internalize surface bound antibodies for different times, between 0 and 90 minutes, at 37° C. Following internalization, cells were washed twice with ice-cold PBS containing 1% BSA and 0.05% sodium azide (PBA) and fixed in ice-cold 1% methanol-free formaldehyde (MFF) in PBS overnight at 4° C. Cells were permeablized in PBS 3% BSA containing 0.5% saponin (PBAS) for 20 minutes at 4° C., and transferred to a 96-well round bottom polypropylene microtiter plate. After washing twice with ice-cold PBAS, cells were incubated for 1 h on ice with 3 mg/ml human gamma globulin in PBAS. BODIPY-phalloidin diluted in PBAS and incubated with cells for 1 hour in ice. Cells were further stained with TOPRO-II, as a nuclear counterstain. Slides were imaged on a Leica SP1 confocal microscope. Cells. Monoclonal antibodies for cell surface staining were purchased from BD Biosciences (CA). Monocytes ($1 \times 10^6$/ml) from healthy donors were cultured in Cellgenics media (France) containing GM-CSF (100 ng/ml) and IL-4 (50 ng/ml) or GM-CSF (100 ng/ml) and IFNα (500 Units/ml) (R&D, CA). For IFNDCs, cells were fed on day 1 with IFNα and GM-CSF. For IL-4DCs, the same amounts of cytokines were supplemented into the media on day one and day three. PBMCs were isolated from Buffy coats using Percoll™ gradients (GE Healthcare, Buckinghamshire, UK) by density gradient centrifugation. Total CD4+ and CD8+ T cells were purified by using StemCell kits (CA).

Peptides. 15-mers (11 amino acid overlapping) for prostate-specific antigen (PSA), Cycline D1, MART-1 influenza viral nucleoprotein (NP) and HA1 subunit of influenza viral hemagglutinin (H1N1, PR8), were synthesized (Mimotopes).

DCs and T cell co-culture and cytokine expressions. $5 \times 10^3$ DCs loaded with recombinant fusion proteins (anti-CD40-HA1, Control Ig-HA1, anti-CD40-PSA, anti-CD40-Cyclin D1, anti-CD40-MART-1, anti-MARCO-MART-1, and control Ig-MART-1) were co-cultured with $2 \times 10^5$ CFSE-labeled CD4+ T cells for 8 days. Proliferation was tested by measuring CFSE dilution after staining cells with anti-CD4 antibody labeled with APC.

For measuring the expression of intracellular IFNγ, CD4+ T cells were restimulated with 1-5 uM of indicated peptides for 5 h in the presence of Brefeldin A. In separate experiments, CD4+ T cells were restimulated with peptides indicated for 36 h, and then cytokines secreted by CD4+ T cells were measured by the Luminex.

CD8+ T cells were co-cultured with DCs for 10 days in the presence of 20 units/ml IL-2 and 20 units/ml IL-7. On day 10 of the culture, CD8+ T cells were stained with anti-CD8 and tetramers indicated.

CTL assay. On day 10 of the culture, a 5-h $^{51}$Cr release assay was performed. T2 cells pulsed with $^{51}$Cr first and then labeled with 10 uM HLA-A2 epitope of MART-1 or 1 nM epitope of influenza viral M1. T2 cells without peptide were used as control. The mean of triplicate samples was calculated, and the percentage of specific lysis was determined using the following formula: percentage of specific lysis=100×(experimental $^{51}$Cr release–control $^{51}$Cr release)/(maximum $^{51}$Cr release–control $^{51}$Cr release). The maximum release refers to counts from targets in 2.5% Triton X-100.

Preparation of mAbs specific for human CD40. Receptor ectodomain.hIgG (human IgG1Fc) and AP (human placental alkaline phosphatase) fusion proteins were produced for immunizing mice and screening mAbs, respectively. A mammalian vector for human IgFc fusion proteins was engineered as described [*J. Immunol.* 163: 1973-1983 (1999)]. The mammalian expression vector for receptor ectodomain.AP proteins was generated using PCR to amplify cDNA for AP resides 133-1581 (gb|BC009647|) while adding a proximal in-frame Xho I site and a distal 6C-terminal His residues followed by a TGA stop codon and Not I site. This Xho I-Not I fragment replaced the human IgG Fc coding sequence in the above ectodomain.IgG vector. Fusion proteins were produced using the FreeStyle™ 293 Expression System (Invitrogen, CA) according to the manufacturer's protocol (1 mg total plasmid DNA with 1.3 ml 293Fectin reagent/L of transfection). Receptor ectodomain.hIgG was purified by 1 ml HiTrap protein A affinity chromatography (GE Healthcare, CA) eluted with 0.1 M glycine, pH 2.7. Fractions were neutralized with 2M Tris, and then dialyzed against PBS.

Mouse mAbs were generated by conventional technology. Briefly, six-week-old BALB/c mice were immunized i.p. with 20 μg of receptor ectodomain.hIgGFc fusion protein with Ribi adjuvant, then boosted with 20 μg antigen ten days and fifteen days later. After three months, the mice were boosted again three days prior to taking the spleens. Three to four days after a final boosting, draining lymph nodes (LN) were harvested. B cells from spleen or LN cells were fused with SP2/O-Ag 14 cells (ATCC). Hybridoma supernatants were screened to analyze mAbs specific to the receptor ectodomain fusion protein compared to the fusion partner alone, or to the receptor ectodomain fused to alkaline phosphatase [*J. Immunol.* 163: 1973-1983 (1999)]. Positive wells were then screened in FACS using 293F cells transiently transfected with expression plasmids encoding full-length receptor cDNAs. Selected hybridomas were single cell cloned and expanded in CELLine flasks (Integra, CA). Hybridoma supernatants were mixed with an equal volume of 1.5 M glycine, 3 M NaCl, 1× PBS, pH 7.8 (binding buffer) and tumbled with MabSelect resin (GE Healthcare, CA) (800 μl/5 ml supernatant). The resin was washed with binding buffer and eluted with 0.1 M glycine, pH 2.7. Following neutralization with 2 M Tris, mAbs were dialyzed against PBS.

Expression and purification of recombinant mAbs. Total RNA was prepared from hybridoma cells using RNeasy kit (Qiagen, CA) and used for cDNA synthesis and PCR (SMART RACE kit, BD Biosciences) using supplied 5' primers and gene specific 3' primers (mIgGκ, 5'ggatggtgggaagatggatacagttggtgcagcatc3' (SEQ ID NO.:48); mIgG2a, 5'ccaggcatcctagagtcaccgaggagccagt3') (SEQ ID NO.:49). PCR products were then cloned (pCR2.1 TA kit, Invitrogen) and characterized by DNA sequencing (MC Lab, CA). Using the derived sequences for the mouse heavy (H) and light (L) chain variable (V)-region cDNAs, specific primers were used to PCR amplify the signal peptide and V-regions while incorporating flanking restriction sites for cloning into expression vectors encoding downstream human IgGκ or IgG4H regions. The vector for expression of chimeric mVκ-hIgκ was built by amplifying residues 401-731 (gi|63101937|) flanked by Xho I and Not I sites and inserting this into the Xho I-Not I interval of pIRES2-DsRed2 (BD Biosciences). PCR was used to amplify the mAb Vκ region from the initiator codon, appending a Nhe I or Spe I site then CACC, to the region encoding (e.g., residue 126 of gi|76779294|), appending a distal Xho I site. The PCR fragment was then cloned into the Nhe I-Not I interval of the above vector. The control human IgGκ sequence corresponds to gi|49257887| residues 26-85 and gi|21669402| residues 67-709. The control human IgG4H vector corresponds to residues 12-1473 of gi|19684072| with S229P and L236E substitutions, which stabilize a disulphide bond and abrogate residual FcR interaction [*J. Immunol.* 164: 1925-1933 (2000)], inserted between the Bgl II and Not I sites of pIRES2-DsRed2 while adding the sequence 5'gctagctgattaattaa 3' instead of the stop codon. PCR was used to amplify the mAb VH region from the initiator codon, appending CACC then a Bgl II site, to the region encoding residue 473 of gi|19684072|. The PCR fragment was then cloned into the Bgl II-Apa I interval of the above vector.

Expression and purification of Flu HA1 fusion protein. The Flu HA1 antigen coding sequence is a CipA protein [*Clostridium. thermocellum*] gi|479126| residues 147-160, preceding hemagglutinin [Influenza A virus (A/Puerto Rico/8/34(H1N1))] gi|126599271| residues 18-331, with a P321L change and with 6 C-terminal His residues was inserted between the H chain vector Nhe I and Not I sites to encode recombinant antibody-HA1 fusion proteins (rAb.HA1). Similarly, recombinant antibody-PSA fusion proteins (rAb.PSA) were encoded by inserting gi|34784812| prostate specific antigen residues 101-832 with proximal sequence GCTAGCGATACAACAGAACCTGCAACAC-CTACAACACCTGTAACAACACCGACAA-CAACACTTCTAGCGC (SEQ ID NO.:50) (Nhe I site and CipA spacer) and a distal Not I site into the same H chain vector. Recombinant antibody proteins were expressed and purified as described above for hFc fusion proteins. In some cases the rAb.antigen coding region and the corresponding L chain coding region were transferred to separate cetHS-puro UCOE vectors (Millipore, Calif.). The use of UCOE vectors in combination with a preadapted serum free, suspension cell line allowed for rapid production of large quantities of protein [*Cytotechnology* 38, 43-46 (2002).] CHO-S cells grown in CD-CHO with GlutaMAX and HT media supplement (Invitrogen) were seeded at $5\times10^5$ ml 24 h prior to transfection in 500 ml Corning Ehrlenmyer flasks and incubated in 8% $CO_2$ at 125 rpm. On the day of transfection, $1.2\times10^7$ cells with viability at least 95% were added to a final volume of 30 ml in a 125 ml flask in CD-CHO with GlutaMAX. 48 µl of FreeStyle Max reagent (Invitrogen) in 0.6 ml of OptiPRO SFM (Invitrogen) was added with gentle mixing to 24 µg of Sce I-linearized light chain vector and 24 µg of Sce I-linearized H chain vector mixed and sterile filtered in 0.6 ml of OptiPRO SFM. After 20 min, the DNA-lipid complex was slowly added to the 125 ml CHO-S culture flask with swirling. Cells were incubated 24 h before adding 30 ml of a combined media solution of CD-CHO with CHO-M5 (Sigma, CO363 component of CHO Kit 1) containing 5 µg/ml of puromycin (A.G. Scientific, CA), 2× GlutaMAX and 0.25× Pen/Strep (Invitrogen). At day 2 another 5 µg/ml of puromycin was added directly to the culture and selection was allowed to proceed ~10-14 days while following cell viability from six days post transfection. The viable cell count dropped and when the viable density is $\sim2\text{-}3\times10^6$/ml, the cells were transferred to fresh selection medium (CD CHO-S+CHO M5 with 2× GlutaMAX, 0.25× Pen/Strep, 10 µg/ml Puromycin) at 1E6/ml. Frozen cell stocks were prepared when viability reached >90%. Cells were split in selection medium when cell density exceeded $2\times10^6$/ml until scaled to 4×250 ml in 500 ml flasks. Supernatant was harvested when cell viability dropped below 80% with a maximum final cell density $\sim7\times10^6$/ml. Endotoxin levels were less than 0.2 units/ml.

Expression and purification of recombinant Flu M1 and MART-1 proteins. PCR was used to amplify the ORF of Influenza A/Puerto Rico/8/34/Mount Sinai (H1N1) M1 gene while incorporating an Nhe I site distal to the initiator codon and a Not I site distal to the stop codon. The digested fragment was cloned into pET-28b(+) (Novagen), placing the M1 ORF in-frame with a His6 tag, thus encoding His.Flu M1 protein. A pET28b (+) derivative encoding an N-terminal 169 residue cohesin domain from *C. thermocellum* (unpublished) inserted between the Nco I and Nhe I sites expressed Coh.His. For expression of Cohesin-Flex-hMART-1-PeptideA-His, the sequence GACACCACCGAGGCCCGCCACCCCCAC-CCCCCCGTGACCACCCCCACCACCAC-CGACCGGAAGGGCACCACCGCCGAG-GAGCTGGCCGGCATCGGCATCCTGACCGTGATCCT GGGCGGCAAGCGGACCAACAACAGCAC-CCCCACCAAGGGCGAATTCTGCA-GATATCCATCACACTGGCGGCCG (SEQ ID NO.:51) (encoding DTTEARHPHPPVTTPTTDRKGT TAEELAGIGILTV ILGGKRTNNSTPTKGEFCRYPSHWRP (SEQ ID NO.: 52)—the italicized residues are the immunodominant HLA-A2-restricted peptide and the underlined residues surrounding the peptide are from MART-1) was inserted between the Nhe I and Xho I sites of the above vector. The proteins were expressed in *E. coli* strain BL21 (DE3) (Novagen) or T7 Express (NEB), grown in LB at 37° C. with selection for kanamycin resistance (40 µg/ml) and shaking at 200 rounds/min to mid log phase growth when 120 mg/L IPTG was added. After three hours, the cells were harvested by centrifugation and stored at −80° C. *E. coli* cells from each 1 L fermentation were resuspended in 30 ml ice-cold 50 mM Tris, 1 mM EDTA pH 8.0 (buffer B) with 0.1 ml of protease inhibitor Cocktail II (Calbiochem, CA). The cells were sonicated on ice 2×5 min at setting 18 (Fisher Sonic Dismembrator 60) with a 5 min rest period and then spun at 17,000 r.p.m. (Sorvall SA-600) for 20 min at 4° C. For His.Flu M1 purification the 50 ml cell lysate supernatant fraction was passed through 5 ml Q Sepharose beads and 6.25 ml 160 mM Tris, 40 mM imidazole, 4 M NaCl pH 7.9 was added to the Q Sepharose flow through. This was loaded at 4 ml/min onto a 5 ml HiTrap chelating HP column charged with Ni++. The column-bound protein was washed with 20 mM $NaPO_4$, 300 mM NaCl pH 7.6 (buffer D) followed by another wash with 100 mM $H_3COONa$ pH 4.0. Bound protein was eluted with 100 mM $H_3COONa$ pH 4.0. The peak fractions were pooled and loaded at 4 ml/min onto a 5 ml HiTrap S column equilibrated with 100 mM $H_3COONa$ pH 5.5, and washed with the equilibration buffer followed by elution with a gradient from 0-1 M NaCl in 50 mM $NaPO_4$ pH 5.5. Peak fractions eluting at about 500 mM NaCl were pooled. For Coh.Flu M1.His purification, cells from 2 L of culture were lysed as above. After centrifugation, 2.5 ml of Triton X114 was added to the supernatant with incubation on ice for 5 min. After further incubation at 25° C. for 5 min, the supernatant was separated from the Triton X114 following centrifugation at 25° C. The extraction was repeated and the supernatant was passed through 5 ml of Q Sepharose beads and 6.25 ml 160 mM Tris, 40 mM imidazole, 4 M NaCl pH 7.9 was added to the Q Sepharose flow through. The protein was then purified by $Ni^{++}$ chelating chromatography as described above and eluted with 0-500 mM imidazole in buffer D.

Figure 13:
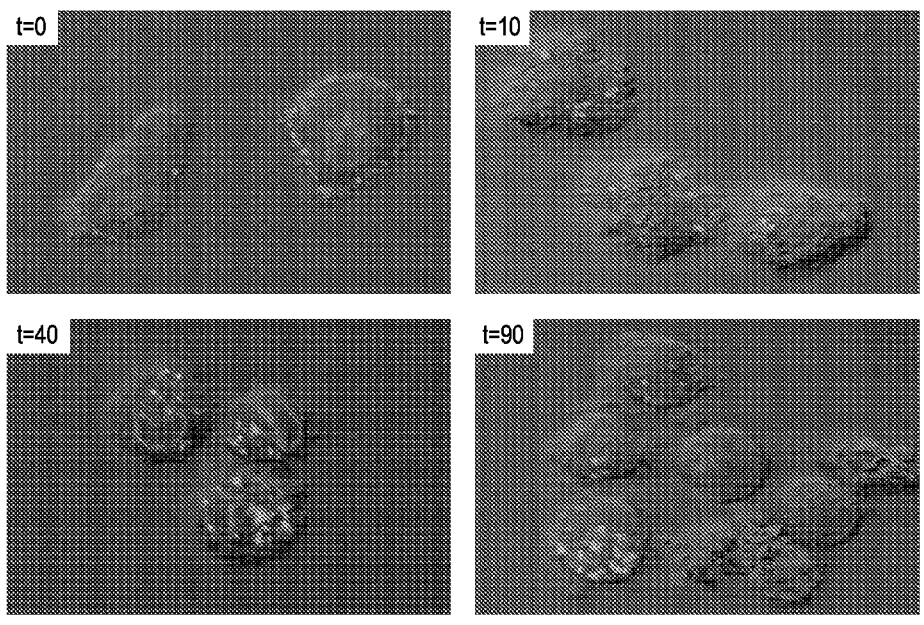
FIG. 13 shows the internalization of anti-CD40 mAb:IL-4DC. IL-4DCs were treated with 500 ng/ml of anti-CD40-Alexa 568.

FIG. 13 shows the internalization of anti-CD40 mAb:IL-4DC. IL-4DCs were treated with 500 ng/ml of anti-CD40-Alexa 568.

Figure 14:
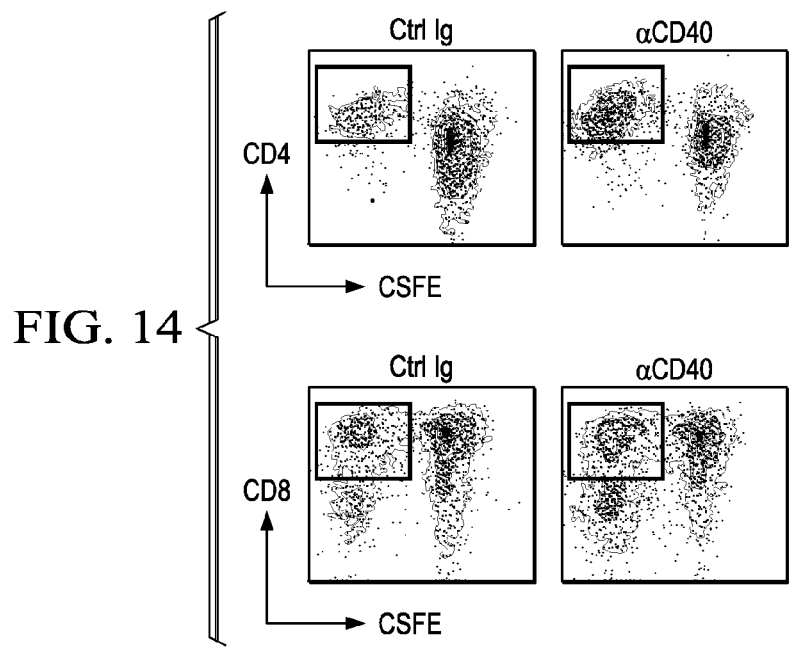
FIG. 14 shows CD4 and CD8 T cell proliferation by DCs targeted with anti-CD40-HA1. 5×10e3IFNDCs loaded with 2 ug/ml of anti-CD40-HA or control Ig-HA1 were co-cultured with CFSE-labeled an assay, if it depends on the presence of the anti-CD40.LIPO5 HIV peptide vaccine, reflects vaccine uptake by antigen presenting cells [APC] in the culture, and processing [proteolytic degradation] and presentation of peptides on MHC. The antigen-MHC complexes are recognized by T cells with TCR that recognize only the particular HIV antigen-MHC complex. In a HIV patient, such cells are likely to be memory T cells that expanded in the patient in response to the HIV infection.

FIG. 14 shows CD4 and CD8 T cell proliferation by DCs targeted with anti-CD40-HA1. 5×10e3 IFNDCs loaded with 2 ug/ml of anti-CD40-HA or control Ig-HA1 were co-cultured with CFSE-labeled autologous CD4+ or CD8+ T cells (2×10e5) for 7 days. Cells were then then stained with anti-CD4 or anti-CD8 antibodies. Cell proliferation was tested by measuring CFSE-dilution.

Figure 15:
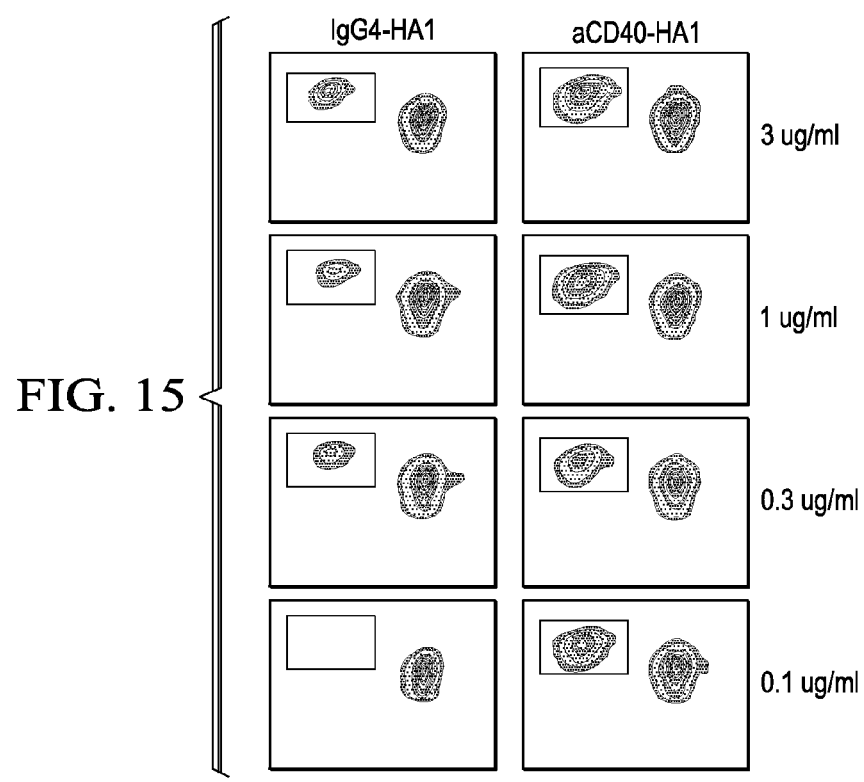
FIG. 15 shows a titration of HA1 fusion protein on CD4+ T proliferation. IFNDCs (5K) loaded with fusion proteins were co-cultured with CFSE-labeled CD4+ T cells (200K) for 7 days.

FIG. 15 shows a titration of HA1 fusion protein on CD4+ T proliferation. IFNDCs (5K) loaded with fusion proteins were co-cultured with CFSE-labeled CD4+ T cells (200K) for 7 days.

Figure 16:
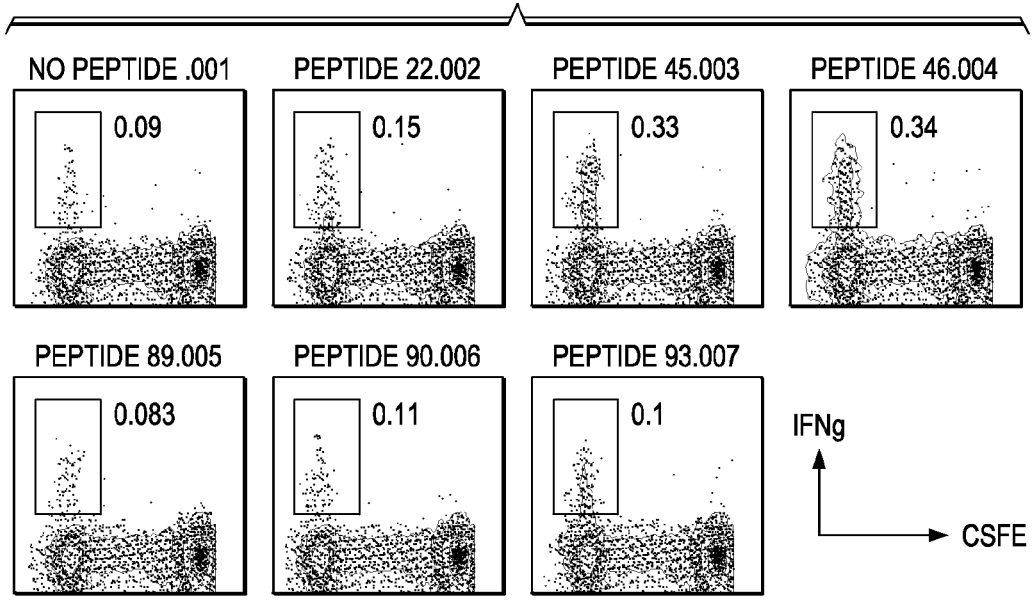
FIG. 16 shows IFNDCs targeted with anti-CD40-HA1 activate HA1-specific CD4+ T cells. CD4+ T cells were re-stimulated with DCs loaded with 5 uM of indicated peptides, and then intracellular IFNγ was stained.

FIG. 16 shows IFNDCs targeted with anti-CD40-HA1 activate HA1-specific CD4+ T cells. CD4+ T cells were restimulated with DCs loaded with 5 uM of indicated peptides, and then intracellular IFNγ was stained.

Figure 17:
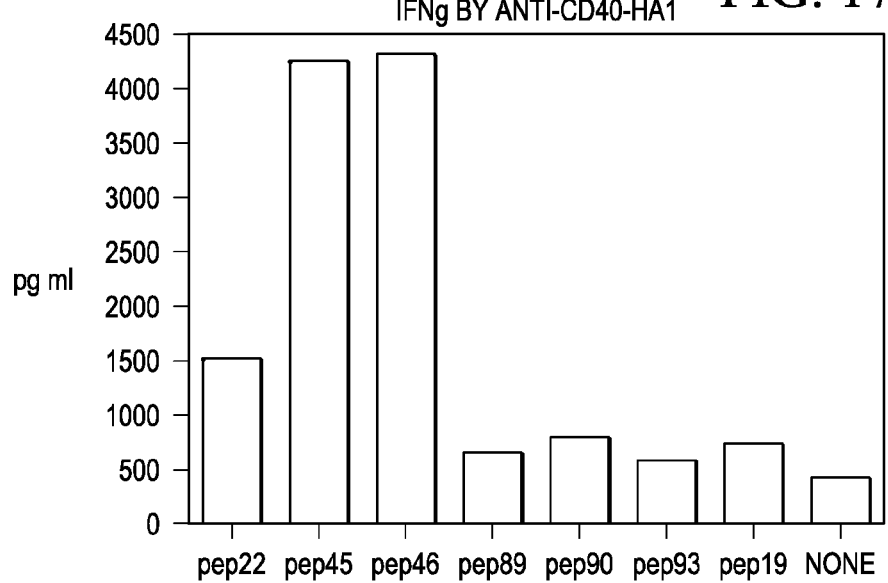
FIG. 17 shows IFNDCs targeted with anti-CD40-HA1 activate HA1-specific CD4+ T cells. CD4+ T cells were re-stimulated with DCs loaded with indicated peptides for 36h, and then culture supernatant was analyzed for measuring IFNγ.

FIG. 17 shows IFNDCs targeted with anti-CD40-HA1 activate HA1-specific CD4+ T cells. CD4+ T cells were restimulated with DCs loaded with indicated peptides for 36 h, and then culture supernatant was analyzed for measuring IFNγ.

Figure 18:
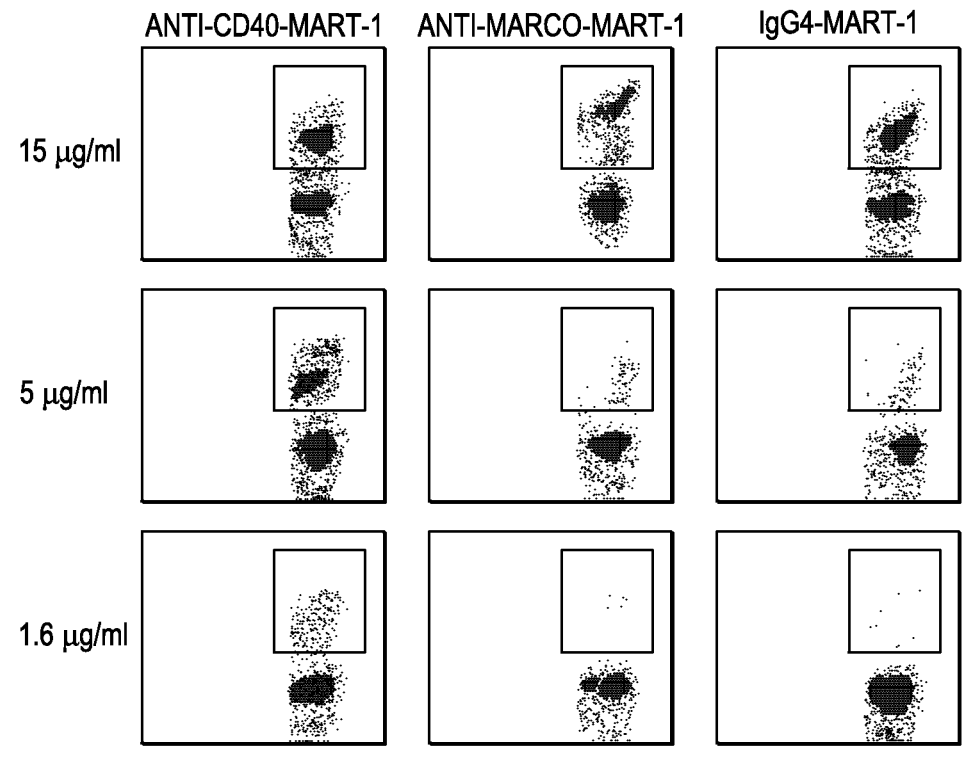
FIG. 18 shows that targeting CD40 results in enhanced cross-priming of MART-1 specific CD8+ T cells. IFNDCs (5K/well) loaded with fusion proteins were co-cultured with purified CD8+ T cells for 10 days. Cells were stained with anti-CD8 and tetramer. Cells are from healthy donors (HLA-A*0201+).

FIG. 18 shows that targeting CD40 results in enhanced cross-priming of MART-1 specific CD8+ T cells. IFNDCs (5K/well) loaded with fusion proteins were co-cultured with purified CD8+ T cells for 10 days. Cells were stained with anti-CD8 and tetramer. Cells are from healthy donors (HLA-A*0201+).

Figure 19:
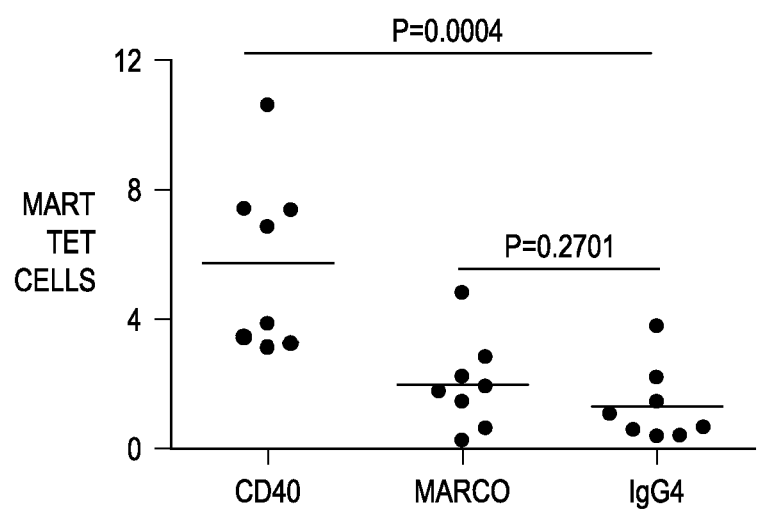
FIG. 19 shows targeting CD40 results in enhanced cross-priming of MART-1 specific CD8+ T cells (Summary of 8-repeated experiments using cells from different healthy donors).

FIG. 19 shows targeting CD40 results in enhanced cross-priming of MART-1 specific CD8+ T cells (Summary of 8-repeated experiments using cells from different healthy donors).

Figure 20:
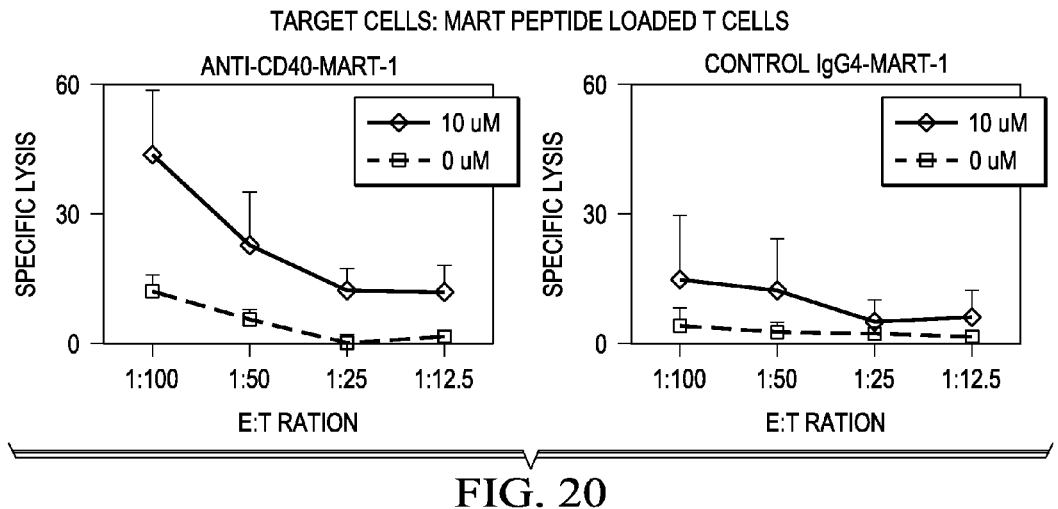
FIG. 20 shows CD8+ CTL induced with IFNDCs targeted with anti-CD40-MART-1 are functional. CD8+ T cells co-cultured with IFNDCs targeted with fusion proteins were mixed with T2 cells loaded with 10 uM peptide epitope.

FIG. 20 shows CD8+ CTL induced with IFNDCs targeted with anti-CD40-MART-1 are functional. CD8+ T cells co-cultured with IFNDCs targeted with fusion proteins were mixed with T2 cells loaded with 10 uM peptide epitope.

Figure 21:
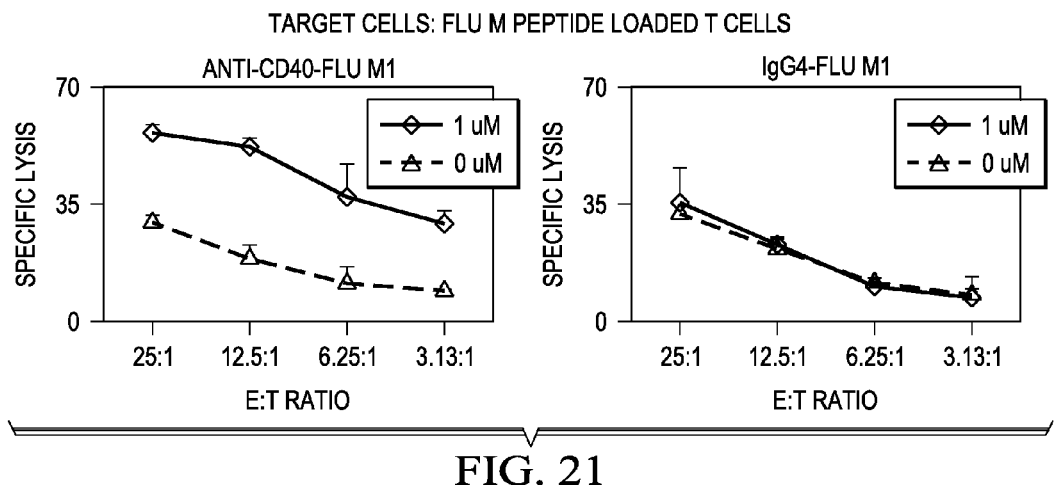
FIG. 21 shows CD8+ CTL induced with IFNDCs targeted with anti-CD40-Flu M1 are functional. CD8+ T cells co-cultured with IFNDCs targeted with fusion proteins were mixed with T2 cells loaded with 1.0 nM peptide epitope.

FIG. 21 shows CD8+ CTL induced with IFNDCs targeted with anti-CD40-Flu M1 are functional. CD8+ T cells co-cultured with IFNDCs targeted with fusion proteins were mixed with T2 cells loaded with 1.0 nM peptide epitope.

Figure 22:
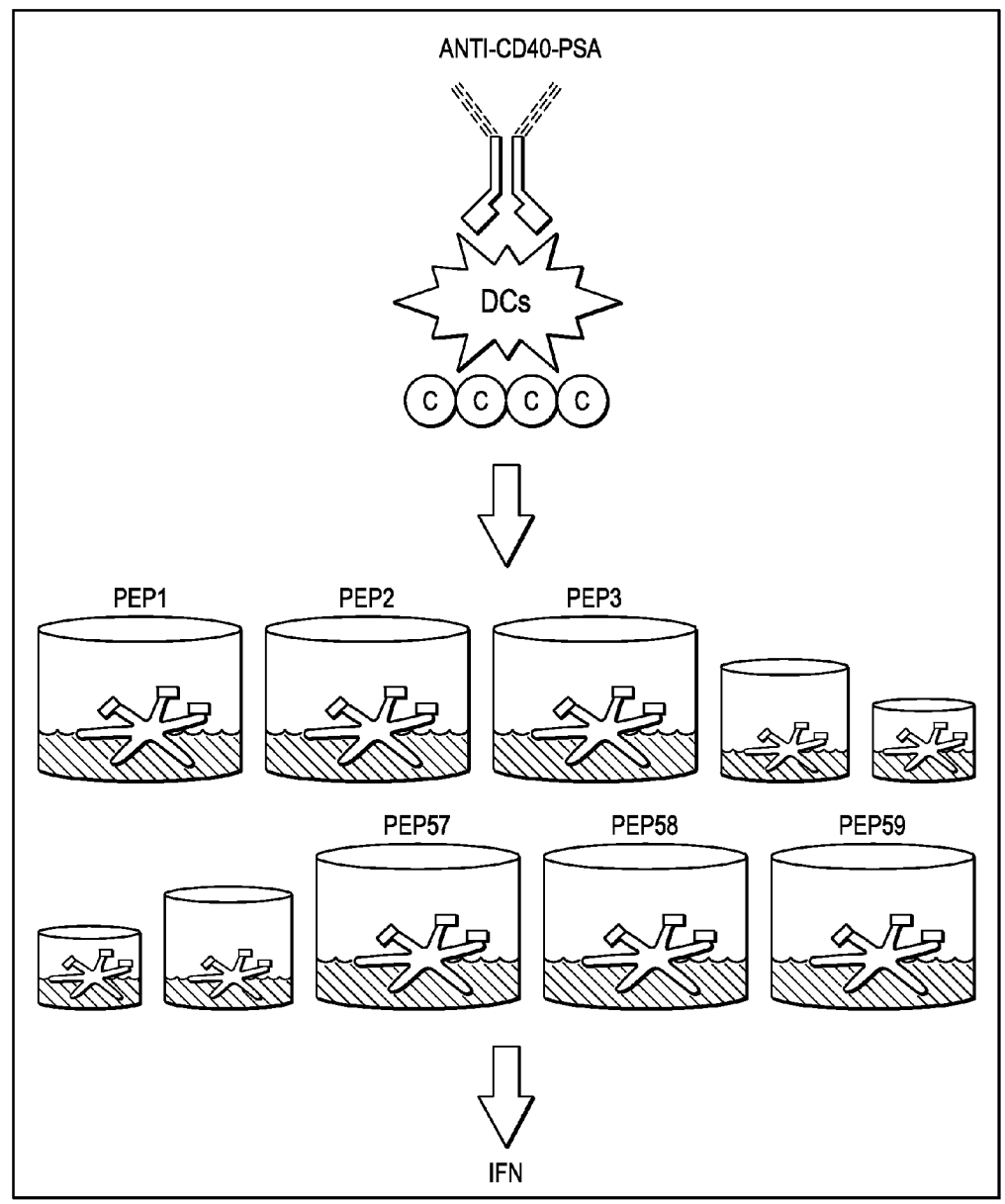
FIG. 22 shows an outline of protocol to test the ability a vaccine composed of anti-CD4012E12 linked to PSA (prostate specific antigen) to elicit the expansion from a naïve T cell population. PSA-specific CD4+ T cells corresponding to a broad array of PSA epitopes. Briefly, DCs derived by culture with IFNα and GM-CSF of monocytes from a healthy donor are incubated with the vaccine. The next day, cells are placed in fresh medium and pure CD4+ T cells from the same donor are added. Several days later, PSA peptides are added and, after four hours, secreted gamma-IFN levels in the culture supernatants are determined.

FIG. 22 shows an outline of protocol to test the ability a vaccine composed of anti-CD4012E12 linked to PSA (prostate specific antigen) to elicit the expansion from a naïve T cell population. PSA-specific CD4+ T cells corresponding to a broad array of PSA epitopes. Briefly, DCs derived by culture with IFNα and GM-CSF of monocytes from a healthy donor are incubated with the vaccine. The next day, cells are placed in fresh medium and pure CD4+ T cells from the same donor are added. Several days later, PSA peptides are added and, after four hours, secreted gamma-IFN levels in the culture supernatants are determined.

Figure 23:
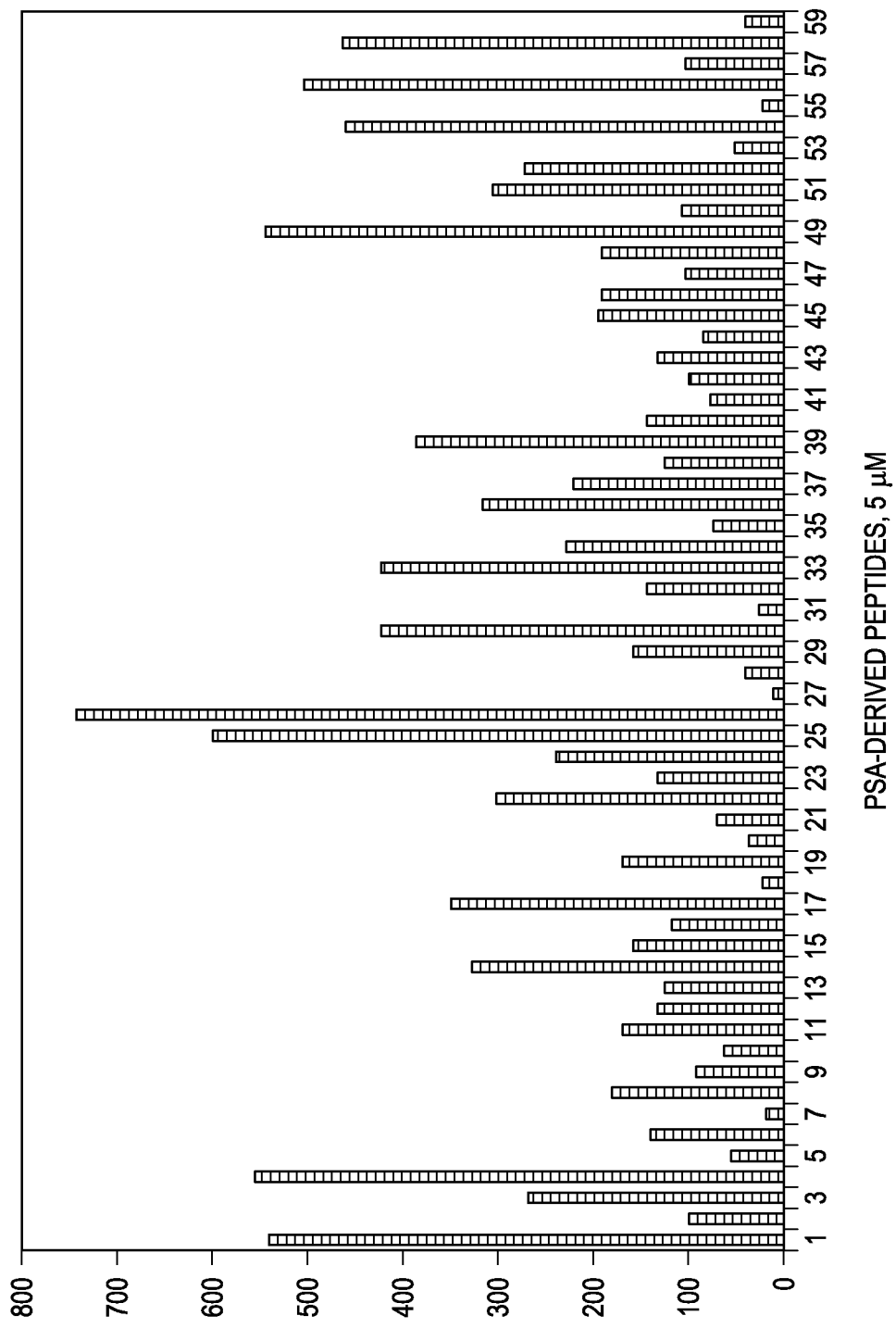
FIG. 23 shows that many PSA peptides elicit potent gamma-IFN-production responses indicating that anti-CD4012E12 and similar anti-CD40 agents can efficiently deliver antigen to DCs, resulting in the priming of immune responses against multiple epitopes of the antigen.

FIG. 23 shows that many PSA peptides elicit potent gamma-IFN-production responses indicating that anti-CD4012E12 and similar anti-CD40 agents can efficiently deliver antigen to DCs, resulting in the priming of immune responses against multiple epitopes of the antigen. The peptide mapping of PSA antigens. 5×10e3 IFNDCs loaded with 2 ug/ml of anti-CD40-PSA were co-cultured with purified autologous CD4+ T cells (2×10e5) for 8 days. Cells were then restimulated with 5 uM of individual peptides derived from PSA for 36 h. The amount of IFNγ was measured by Luminex. Cells are from healthy donors.

Figure 24:
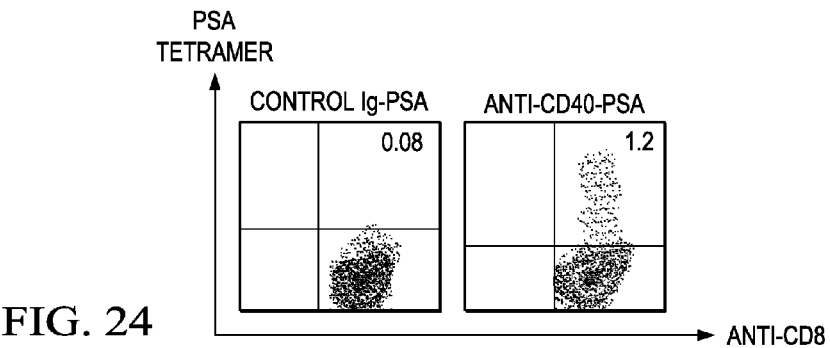
FIG. 24 shows DCs targeted with anti-CD40-PSA induce PSA-specific CD8+ T cell responses. IFNDCs were targeted with 1 ug mAb fusion protein with PSA. Purified autologous CD8+ T cells were co-cultured for 10 days. Cells were stained with anti-CD8 and PSA (KLQCVDLHV)-tetramer. Cells are from a HLA-A*0201 positive healthy donor. The results demonstrate that anti-CD40 effectively deliver PSA to the DCs, which in turn elicit the expansion of PSA-specific CD8+ T cells.

FIG. 24 shows DCs targeted with anti-CD40-PSA induce PSA-specific CD8+ T cell responses. IFNDCs were targeted with 1 ug mAb fusion protein with PSA. Purified autologous CD8+ T cells were co-cultured for 10 days. Cells were stained with anti-CD8 and PSA (KLQCVDLHV)-tetramer. Cells are from a HLA-A*0201 positive healthy donor. The results demonstrate that anti-CD40 effectively deliver PSA to the DCs, which in turn elicit the expansion of PSA-specific CD8+ T cells. Briefly, 5×10e3 IFNDCs loaded with 2 ug/ml of anti-CD40-PSA were co-cultured with purified autologous CD8+ T cells (2×10e5) for 10 days. Cells were then stained with tetramer. Cells are from HLA-0*201 positive healthy donor.

Figure 25:
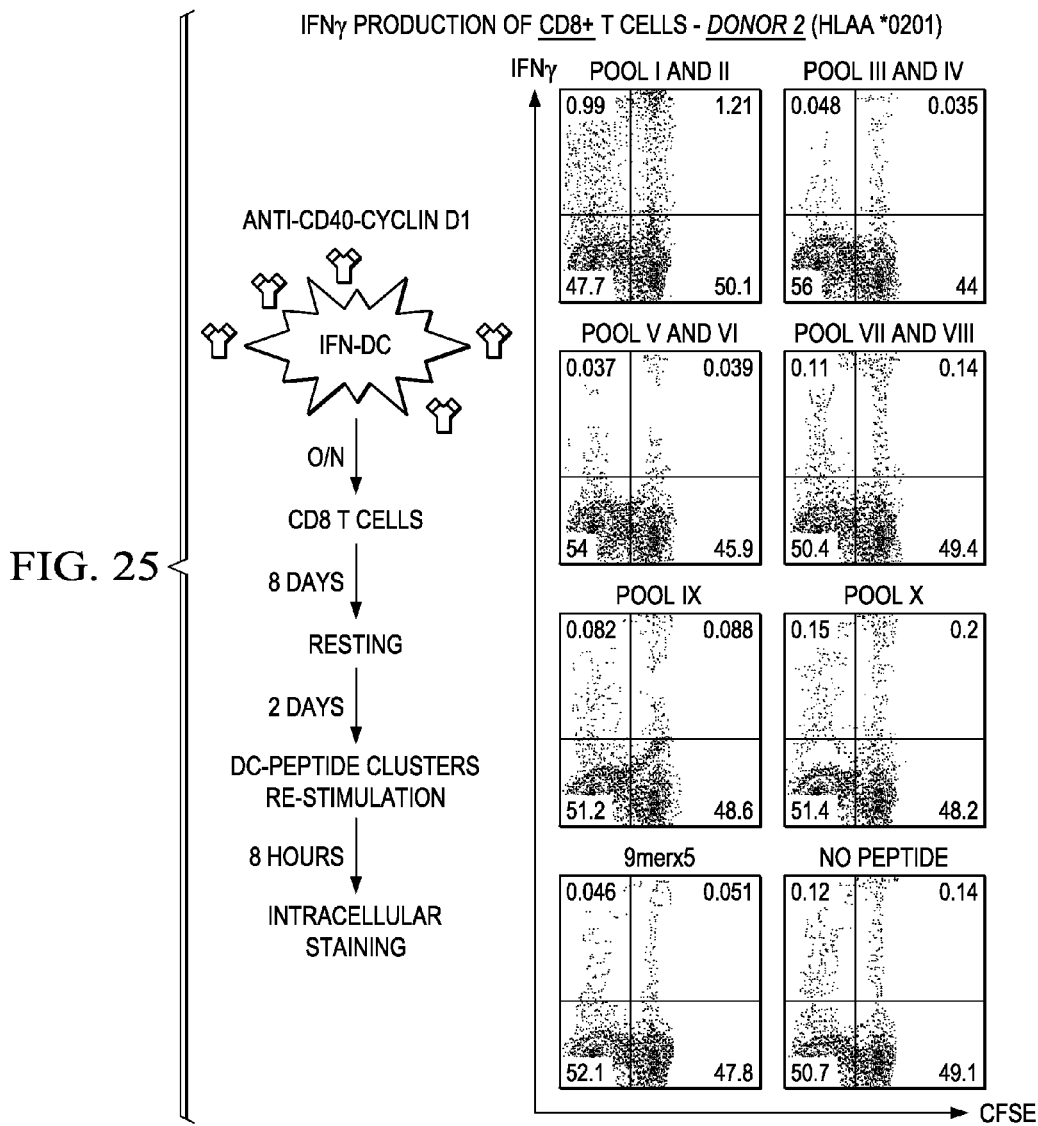
FIG. 25 a scheme (left) and the IFNγ production by T cells of the pools of peptides and control for Donor 2. 5×10e3 IFNDCs loaded with 2 ug/ml of anti-CD40-Cyclin D1 were co-cultured with purified autologous CD4+ T cells (2×10e5) for 8 days. Cells were then re-stimulated with with 5 uM of individual peptides derived from CyclinD1 for 5 h in the presence of Brefeldin A. Cells were stained for measuring intracellular IFNγ expression.

FIG. 25 a scheme (left) and the IFNγ production by T cells of the pools of peptides and control for Donor 2. 5×10e3 IFNDCs loaded with 2 ug/ml of anti-CD40-Cyclin D1 were co-cultured with purified autologous CD4+ T cells (2×10e5) for 8 days. Cells were then restimulated with with 5 uM of individual peptides derived from CyclinD1 for 5 h in the presence of Brefeldin A. Cells were stained for measuring intracellular IFNγ expression.

Figure 26:
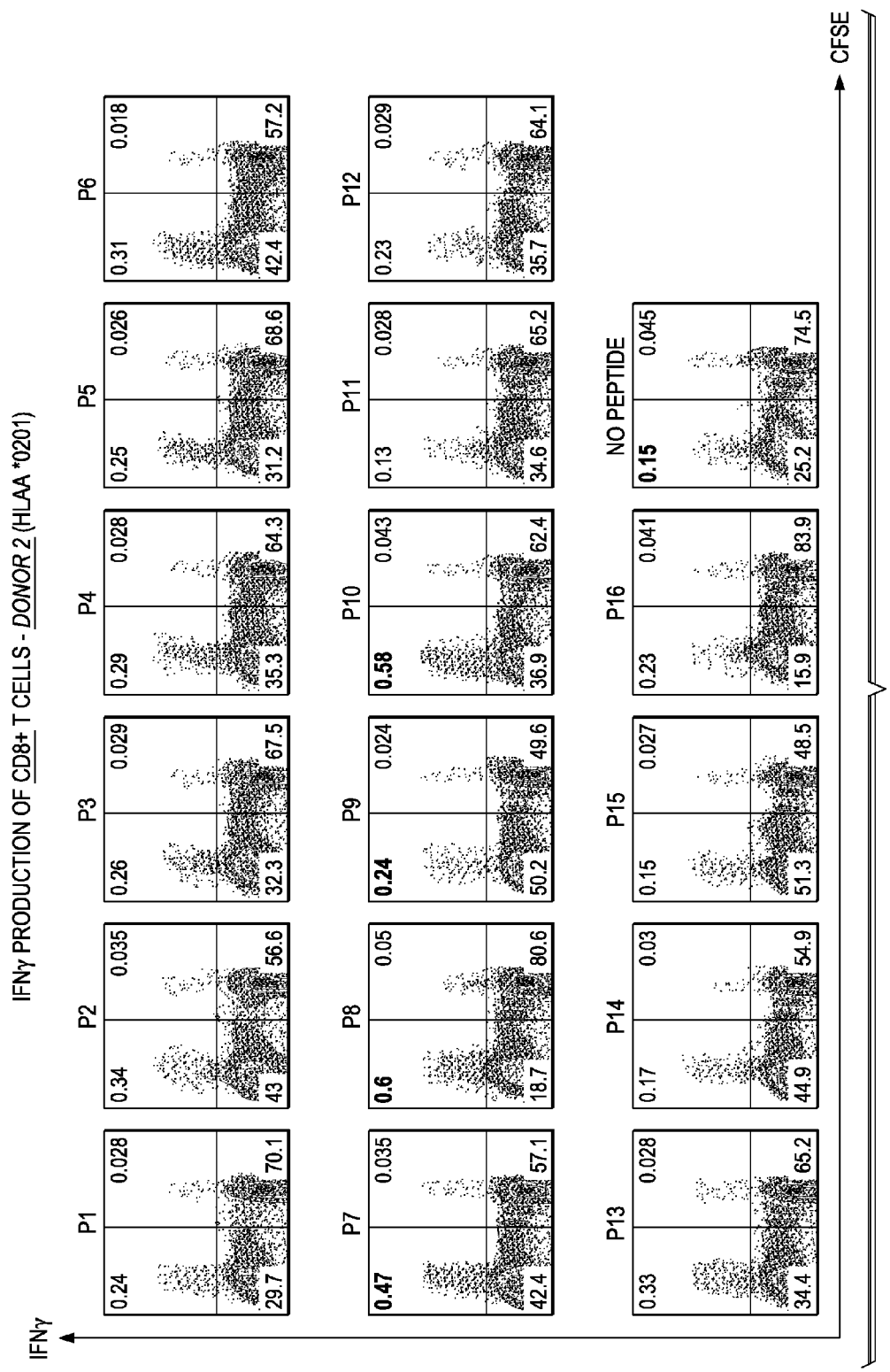
FIG. 26 shows a peptide scan and IFNγ production by T cells obtained from the pools of peptides shown in FIG. 25 and control for Donor 2. 5×10e3 IFNDCs loaded with 2 ug/ml of anti-CD40-Cyclin D1 were co-cultured with purified autologous CD4+ T cells (2×10e5) for 8 days. Cells were then re-stimulated with 5 uM of individual peptides derived from CyclinD1 for 5h in the presence of Brefeldin A. Cells were stained for measuring intracellular IFNγ expression.

FIG. 26 shows a peptide scan and IFNγ production by T cells obtained from the pools of peptides shown in FIG. 25 and control for Donor 2. 5×10e3 IFNDCs loaded with 2 ug/ml of anti-CD40-Cyclin D1 were co-cultured with purified autologous CD4+ T cells (2×10e5) for 8 days. Cells were then restimulated with 5 uM of individual peptides derived from CyclinD1 for 5 h in the presence of Brefeldin A. Cells were stained for measuring intracellular IFNγ expression.

In conclusion, delivering antigens to DCs, the most potent antigen presenting cells, via CD40 is an efficient way to induce and activate antigen specific both CD4+ and CD8+ T cell-mediated immunity. Thus, vaccines made of anti-CD40 mAb will induce potent immunity against cancer and infections.

Peptide Information:
HA1 Sequences:

```
                                      (SEQ ID NO.: 53)
MKANLLVLLCALAAADADTICIGYHANNSTDTVDTVLEKNVTVTHSVNLL
EDSHNGKLCR (SEQ ID NO.: 54)
LKGIAPLQLGKCNIAGWLLGNPECDPLLPVRSWSYIVETPNSENGICYPG
DFIDYEELRE (SEQ ID NO.: 55)
QLSSVSSFERFEIFPKESSWPNHNTNGVTAACSHEGKSSFYRNLLWLT
EKEGSYPKLKNS (SEQ ID NO.: 56)
YVNKKGKEVLVLWGIHHPPNSKEQQNLYQNENAYVSVVTSNYNRRFTP
EIAERPKVRDQA (SEQ ID NO.: 57)
GRMNYYWTLLKPGDTIIFEANGNLIAPMYAFALSRGFGSGIITSNASMHE
CNTKCQTPLG (SEQ ID NO.: 58)
AINSSLPYQNIHPVTIGECPKYVRSAKLRMVTGLRNIPSI
```

Sequences of Peptides in FIG. 17

```
Peptide 22: SSFERFEIFPKESSWPN   (SEQ ID NO.: 59)

Peptide 45: GNLIAPWYAFALSRGFG   (SEQ ID NO.: 60)

Peptide 46: WYAFALSRGFGSGIITS   (SEQ ID NO.: 61)
```

NP Sequences:

```
                                      (SEQ ID NO.: 62)
MASQGTKRSYEQMETDGERQNATEIRASVGKMIGGIGRFYIQMCTELKLS
DYEGRLIQNS (SEQ ID NO.: 63)
LTIERMVLSAFDERRNKYLEEHPSAGKDPKKTGGPIYRRVNGKWMRELIL
YDKEEIRRIW (SEQ ID NO.: 64)
RQANNGDDATAGLTHMMIWHSNLNDATYQRTRALVRTGMDPRMCSLMQ
GSTLPRRSGA

AG (SEQ ID NO.: 65)
AAVKGVGTMVMELVRMIKRGINDRNFWRGENGRKTRIAYERMCNILKGK
FQTAAQKAM

MD (SEQ ID NO.: 66)
QVRESRNPGNAEFEDLTFLARSALILRGSVAHKSCLPACVYGPAVASG
YDFEREGYSLVG (SEQ ID NO.: 67)
IDPFRLLQNSQVYSLIRPNENPAHKSQLVWMACHSAAFEDLRVLSFIKG
TKVLPRGKLST (SEQ ID NO.: 68)
RGVQIASNENMETMESSTLELRSRYWAIRTRSGGNTNQQRASAGQISI
QPTFSVQRNLPF (SEQ ID NO.: 69)
DRTTIMAAFNGNTEGRTSDMRTEIIRMMESARPEDVSFQGRGVFELSDE
KAASPIVPSFD (SEQ ID NO.: 70)
MSNEGSYFFGDNAEEYDN
```

Sequences of Peptides in FIG. 23

```
Peptide 22: GKWVRELVLYDKEEIRR    (SEQ ID NO.: 71)

Peptide 33: RTGMDPRMCSLMQGSTL    (SEQ ID NO.: 72)

Peptide 46: MCNILKGKFQTAAQKAM    (SEQ ID NO.: 73)
```

Prostate Specific Antigen (PSA) Sequence

```
                                        (SEQ ID NO.: 74)
MWVPVVFLTLSVTWIGAAPLILSRIVGGWECEKHSQPWQVLVASRGRAVC
GGVLVHPQWV (SEQ ID NO.: 75)
LTAAHCIRNKSVILLGRHSLFHPEDTGQVFQVSHSFPHPLYDMSLLKNRF
LRPGDDSSHD (SEQ ID NO.: 76)
LMLLRLSEPAELTDAVKVMDLPTQEPALGTTCYASGWGSIEPEEFLTPKK
LQCVDLHVIS (SEQ ID NO.: 77)
NDVCAQVHPQKVTKFMLCAGRWTGGKSTCSGDSGGPLVCNGVLQGITS
WGSEPCALPERP (SEQ ID NO.: 78)
SLYTKVVHYRKWIKDTIVANP
```

Sequences of Peptides in FIG. 23

```
Peptide 1:  APLILSRIVGGWECE      (SEQ ID NO.: 79)

Peptide 4:  ECEKHSQPWQVLVAS      (SEQ ID NO.: 80)

Peptide 25: GDDSSHDLMLLRLSE      (SEQ ID NO.: 81)

Peptide 26: SHDLMLLRLSEPAEL      (SEQ ID NO.: 82)

Peptide 49: SGDSGGPLVCNGVLQ      (SEQ ID NO.: 83)

Peptide 54: GSEPCALPERPSLYT      (SEQ ID NO.: 84)

Peptide 56: ERPSLYTKVVHYRKW      (SEQ ID NO.: 85)

Peptide 58: VVHYRKWIKDTIVAN      (SEQ ID NO.: 86)
```

Cyclin D1 Sequence

```
                                        (SEQ ID NO.: 87)
MRSYRFSDYLHMSVSFSNDMDLFCGEDSGVFSGESTVDFSSSEVDSWPGD
SIACFIEDER (SEQ ID NO.: 88)
HFVPGHDYLSRFQTRSLDASAREDSVAWILKVQAYYNFQPLTAYLAVNYM
DRFLYARRLP (SEQ ID NO.: 89)
ETSGWPMQLLAVACLSLAAKMEEILVPSLFDFQVAGVKYLFEAKTIKRME
LLVLSVLDWR (SEQ ID NO.: 90)
LRSVTPFDFISFFAYKIDPSGTFLGFFISHATEIILSNIKEASFLEYWPS
SIAAAAILCV (SEQ ID NO.: 91)
ANELPSLSSVVNPHESPETWCDGLSKEKIVRCYRLMKAMAIENNRLNTPK
VIAKLRVSVR (SEQ ID NO.: 92)
ASSTLTRPSDESSFSSSSPCKRRKLSGYSWVGDETSTSN
```

Sequences of Peptides in FIG. 26.

```
Peptide 7:  DRVLRAMLKAEETCA      (SEQ ID NO.: 93)

Peptide 8:  RAMLKAEETCAPSVS      (SEQ ID NO.: 94)

Peptide 10: TCAPSVSYFKCVQKE      (SEQ ID NO.: 95)
```

MART-1 Antigen. MART-1 is a tumor-associated melanocytic differentiation antigen. Vaccination with MART-1 antigen may stimulate a host cytotoxic T-cell response against tumor cells expressing the melanocytic differentiation antigen, resulting in tumor cell lysis.

Figure 27:
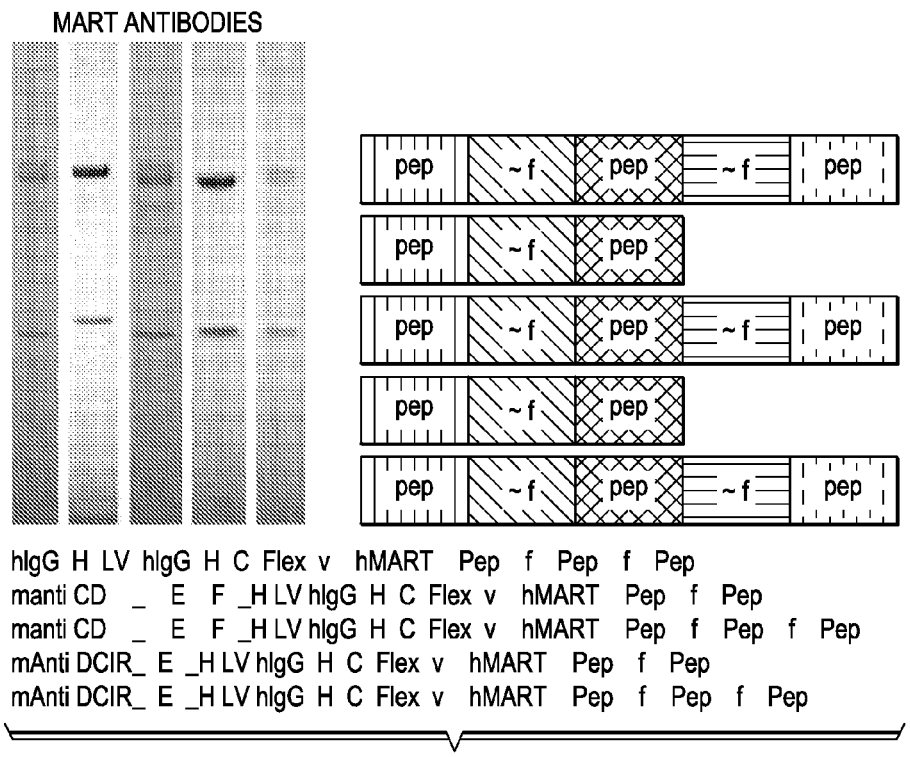
FIG. 27 shows the expression and construct design for anti-CD40-MART-1 peptide antibodies.
Figure 28:
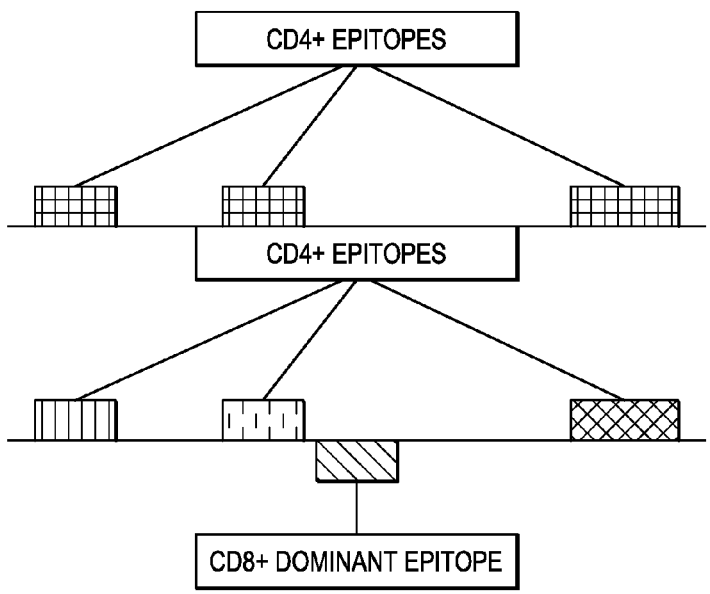
FIG. 28 is a summary of the CD4+ and CD8+ immunodominant epitopes for MART-1.

FIG. 27 shows the expression and construct design for anti-CD40-MART-1 peptide antibodies. FIG. 28 is a summary of the CD4$^+$ and CD8$^+$ immunodominant epitopes for MART-1. FIGS. 27 and 28 show the use of the flexible linker technology to permit the successful expression of recombinant anti-DC receptor targeting antibodies fused to significant (~⅔) parts of human MART-1. Recombinant antibody fused at the H chain C-terminus to the entire MART-1 coding region is not at all secreted from production mammalian cells [not shown]. The Flex-v1-hMART-1-Pep-3-f4-Pep-1 adduct is particularly well expressed and is one preferred embodiment of a MART-1-targeting vaccine, as is the Flex-v1-hMART-1-Pep-3-f4-Pep-1-f3-Pep-2 adduct which bears a maximum load of MART-1 epitopes. Slide 2 of the MART-1 powerpoint presentation shows that these adducts can be successfully appended to multiple anti-DC receptor vehicles.

The sequence below is a H chain—hMART-1 peptides string of pep3-pep1-pep2 fusion protein where each hMART1 peptide sequence [bold-italics] is separated by a inter-peptide spacer f [shown in bold]. In this case, a 27-amino-acid long linker flex-v1 (v1) [italics] derived from cellulosomal anchoring scaffoldin B precursor [Bacteroides cellulosolvens-described in the gag-nef vaccine invention disclosure] was inserted between the H chain C-terminus and the hMART1 peptides-flexible spaces string. The underlined AS residues are joining sequences.

[manti-CD40_12E12.3F3_H-LV-hIgG4H-C-Flex-v1-hMART-1-Pep-3-f4-Pep-1] C981 is:

```
                                                (SEQ ID NO.: 96)
EVKLVESGGGLVQPGGSLKLSCATSGFTFSDYYMYWVRQTPEKRLEWVAYINSGGGSTYY

PDTVKGRFTISRDNAKNTLYLQMSRLKSEDTAMYYCARRGLPFHAMDYWGQGTSVTVSSAKTKG

PSVFPLAPCSRSTSESTAALGCLVKDYFPEPVTVSWNSGALTSGVHTFPAVLQSSGLYSLSSVVTVP

SSSLGTKTYTCNVDHKPSNTKVDKRVESKYGPPCPPCPAPEFEGGPSVFLFPPKPKDTLMISRTPEVT
```

-continued

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKSLSLSLGKASQTPTNTIS

VTPTNNSTPTNNSNPKPNP<u>AS</u>*GFDHRDSKVSLQEKNCEPVVPNAPPAYEKLSAEQSPPPYSP*<u>AS</u>TNGS

ITVAATAPTVTPTVNATPSAA<u>AS</u>*MPREDAHFIYGYPKKGHGHSYTTAEEAAGIGILTVILG*AS

[manti-CD40_12E12.3F3_H-LV-hIgG4H-C-Flex-v1-hMART-1-Pep-3-f4-Pep-1-f3-Pep-2] C978 is:

(SEQ ID NO.: 97)

EVKLVESGGGLVQPGGSLKLSCATSGFTFSDYYMYWVRQTPEKRLEWVAYINSGGGSTYY

PDTVKGRFTISRDNAKNTLYLQMSRLKSEDTAMYYCARRGLPFHAMDYWGQGTSVTVSSAKTKG

PSVFPLAPCSRSTSESTAALGCLVKDYFPEPVTVSWNSGALTSGVHTFPAVLQSSGLYSLSSVVTVP

SSSLGTKTYTCNVDHKPSNTKVDKRVESKYGPPCPPCPAPEFEGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKSLSLSLGKASQTPTNTIS

VTPTNNSTPTNNSNPKPNP<u>AS</u>*GFDHRDSKVSLQEKNCEPVVPNAPPAYEKLSAEQSPPPYSP*<u>AS</u>TNGS

ITVAATAPTVTPTVNATPSAA<u>AS</u>*MPREDAHFIYGYPKKGHGHSYTTAEEAAGIGILTVILG*<u>AS</u>TVT

PTATATPSAIVTTITPTATTKP<u>AS</u>VLLLIGCWYCRRRNGYRALMDKSLHVGTQCALTRRCPQEGAS

[mAnti-DCIR_9E8_H-LV-hIgG4H-C-Flex-v1-hMART-1-Pep-3-f4-Pep-1] C1012 is:

(SEQ ID NO.: 98)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKASQTPTNTISVTPTNNSTPTNNSNPKPNP<u>AS</u>*GFDHRDSKVSLQEKNC*

*EPVVPNAPPAYEKLSAEQSPPPYSP*<u>AS</u>TNGSITVAATAPTVTPTVNATPS

AA<u>AS</u>*MPREDAHFIYGYPKKGHGHSYTTAEEAAGIGILTVILG*<u>AS</u>

[mAnti-DCIR_9E8_H-LV-hIgG4H-C-Flex-v1-hMART-1-Pep-3-f4-Pep-1-f3-Pep-2] C1013 is:

(SEQ ID NO.: 99)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

-continued

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

ASQTPTNTISVTPTNNSTPTNNSNPKPNP<u>AS</u>*GFDHRDSKVSLQEKNC*

*EPVVPNAPPAYEKLSAEQSPPPYSP*<u>AS</u>TNGSITVAATAPTVTPTVNATPS

AA<u>AS</u>*MPREDAHFIYGYPKKGHGHSYTTAEEAAGIGILTVILG*<u>AS</u>TVTPTA

TATPSAIVTTITPTATTKP<u>AS</u>VLLLIGCWYCRRRNGYRALMDKSL

HVGTQCALTRRCPQE<u>AS</u>

MART-1 DNA Sequence:
MART-1 constructs with 3 peptides, Start/stop sites are underlined, peptide 1 is bold, peptide 2 is bold-italics and peptide 3 is bold-underlined:

(SEQ ID NO.: 100)
AACACCGACAACAACAGATGATCTGGATGCA<u>GCTAGT</u>GGGTTTGATCATC

GGGACAGCAAAGTGTCTCTTCAAGAGAAAAACTGTGAACCTGTGGTTCCC

AATGCTCCACCTGCTTATGAGAAACTCTCTGCAGAACAGTCACCACCACC

TTATTCACCTGCTAGTACCAACGGCAGCATCACCGTGGCCGCCACCGCCC

CCACCGTGACCCCCACCGTGAACGCCACCCCAGCGCCGCCGCTAGT

*ATGCCAAGAGAAGATGCTCACTTCATCTATGGTTACCCCAAGAAGGGG*

```
                                           -continued
CACGGCCACTCTTACACCACGGCTGAAGAGGCCGCTGGGATCGGCAT

CCTGACAGTGATCCTGGGAGCTAGTACCGTGACCCCCACCGCCACCGCCA

CCCCCAGCGCCATCGTGACCACCATCACCCCCACCGCCACCACCAAGCCC

GCTAGTGTCTTACTGCTCATCGGCTGTTGGTATTGTAGAAGACGAAATGG

ATACAGAGCCTTGATGGATAAAAGTCTTCATGTTGGCACTCAATGTGCCT

TAACAAGAAGATGCCCACAAGAAGGGtgaGCGGCCGCATCGAAGAGCTCG

GTACCCGGGATCCTCTAGAGTCGACCTGCAGCATGC
```

Peptide 3 is bold followed by the Flex-4 amino acid sequence—underlined.

```
                                          (SEQ ID NO.: 101)
GFDHRDSKVSLQEKNCEPVVPNAPPAYEKLSAEQSPPPYSPASTNGSITV

AATAPTVTPT
```

Peptide 1 is bold followed by the Flex-3 amino acid sequence—underlined.

```
                                          (SEQ ID NO.: 102)
VNATPSAAASMPREDAHFIYGYPKKGHGHSYTTAEEAAGIGILTVILGAS

TVTPTATATP
```

Peptide 3 is bold.

```
                                          (SEQ ID NO.: 103)
SAIVTTITPTATTKPASVLLLIGCWYCRRRNGYRALMDKSLHVGTQCALT

RRCPQEG
```

MART1-Peptide 3 the italicized portion is the CD4+ immunodominant epitope.

```
                                          (SEQ ID NO.: 104)
GFDHRDSKVSLQEKNCEPVVPNAPPAYEKLSAEQSPPPYSP
```
Flex-4

```
                                          (SEQ ID NO.: 105)
ASTNGSITVAATAPTVTPTVNATPSAAAS
```

MART1-Peptide 1 the italicized portion is the CD4+ immunodominant epitope and the underlined-italicized portion is the CD8+ immunodominant epitope

```
                                          (SEQ ID NO.: 106)
MPREDAHFIYGYPKKGHGHSYTTAEEAAGIGILTVILG
                                          (SEQ ID NO.: 107)
Flex-3: ASTVTPTATATPSAIVTTITPTATTKPAS
```

MART1-Peptide 2 the italicized portion is the CD4+ immunodominant epitope.

```
                                          (SEQ ID NO.: 108)
VLLLIGCWYCRRRNGYRALMDKSLHVGTQCALTRRCPQEG
```

MART1 constructs with two peptides:

Peptide 3 is bold-italics-underlined, flex-4 is bold and Peptide 1 is bold-italics-underlined:

```
                                          (SEQ ID NO.: 109)
GFDHRDSKVSLQEKNCEPVVPNAPPAYEKLSAEQSPPPYSPASTNGSITV

AATAPTVTPTVNATPSAAASMPREDAHFIYGYPKKGHGHSYTTA

EEAAGIGILTVILGAS
```

Protein Sequence: C978. rAB-cetHS-puro[manti-CD40__12E12.3F3_H-LV-hIgG4H-C-Flex-v1-hMART-1-Pep-3 (bold-italics-underlined)-f4 (bold)-Pep-1 (bold-italics)-f3 (italics)-Pep-2 (bold-underlined)]

```
                                          (SEQ ID NO.: 110)
MNLGLSLIFLVLVLKGVQCEVKLVESGGGLVQPGGSLKLSCATSGFTFSD

YYMYWVRQTPEKRLEWVAYINSGGGSTYYPDTVKGRFTISRDNAKNTLYL

QMSRLKSEDTAMYYCARRGLPFHAMDYWGQGTSVTVSSAKTKGPSVFPLA

PCSRSTSESTAALGCLVKDYFPEPVTVSWNSGALTSGVHTFPAVLQSSGL

YSLSSVVTVPSSSLGTKTYTCNVDHKPSNTKVDKRVESKYGPPCPPCPAP

EFEGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEAL

HNHYTQKSLSLSLGKASQTPTNTISVTPTNNSTPTNNSNPKPNPAS

GFDHRDSKVSLQEKNCEPVVPNAPPAYEKLSAEQSPPPYSPASTNGSITV

AATAPTVTPTVNATPSAAASMPREDAHFIYGYPKKGHGHSYTTAEE

AAGIGILTVILGASTVTPTATATPSAIVTTITPTATTKPASVLLLIGCWY

CRRRNGYRALMDKSLHVGTQCALTRRCPQEGAS
```

Protein Sequence: C981. rAB-cetHS-puro [manti-CD40__12E12.3F3_H-LV-hIgG4H-C-Flex-v1-hMART-1-Pep-3 (bold-italics-underlined)-f4-(bold)-Pep-1](bold-underlined)

```
                                          (SEQ ID NO.: 111)
MNLGLSLIFLVLVLKGVQCEVKLVESGGGLVQPGGSLKLSCATSGFTFSD

YYMYWVRQTPEKRLEWVAYINSGGGSTYYPDTVKGRFTISRDNAKNTLYL

QMSRLKSEDTAMYYCARRGLPFHAMDYWGQGTSVTVSSAKTKGPSVFPLA

PCSRSTSESTAALGCLVKDYFPEPVTVSWNSGALTSGVHTFPAVLQSSGL

YSLSSVVTVPSSSLGTKTYTCNVDHKPSNTKVDKRVESKYGPPCPPCPAP

EFEGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSSI

EKTISKAKGQPREPQVYTLPPSQEEMTKNQVSLTCLVKGFYPSDIAVEWE

SNGQPENNYKTTPPVLDSDGSFFLYSRLTVDKSRWQEGNVFSCSVMHEAL

HNHYTQKSLSLSLGKASQTPTNTISVTPTNNSTPTNNSNPKPNPAS

GFDHRDSKVSLQEKNCEPVVPNAPPAYEKLSAEQSPPPYSPASTNGSITV

AATAPTVTPTVNATPSAAASMPREDAHFIYGYPKKGHGHSYTTAEEAAGI

GILTVILGAS
```

GP100 Antigen. GP100 antigen is a melanoma-associated antigen. When administered in a vaccine formulation, gp100 antigen may stimulate a cytotoxic T cell HLA-A2.1-restricted immune response against tumors that express this antigen, which may result in a reduction in tumor size.

GP100 ectodomain coding region fused to recombinant antibody H chain coding region is not at all secreted by production mammalian cells [not shown]. The total sequence is shown below—italics residues are the leader sequence and the transmembrane domain, the peptides are in bold-italics and the transmembrane domain is italics-underlined.

(SEQ ID NO.: 112)
MDLVLKRCLLHLAVIGALLAVGATKVPRNQDWLGVSRQLRTKAWNRQLYP

EWTEAQRLDCWRGGQVSLKVSNDGPTLIGANASFSIALNFPGSQKVLPDG

QVIWVNNTIINGSQVWGGQPVYPQETDDACIFPDGGPCPSGSWSQKRSFV

YVW*KTWGQYWQV*LGGPVSGLSIGTGRAMLGTHTMEVTVYHRRGSRSYVPL

AHSSSAFT*ITDQVPFSV*SVSQLRALDGGNKHFLRNQPLTFALQLHDPSGY

LAEADLSYTWDFGDSSGTLISRALVVTHT*YLEPGPVTA*QVVLQAAIPLTS

CGSSPVPGTTDGHRPTAEAPNTTAGQVPTTEVVGTTPGQAPTAEPSGTTS

VQVPTTEVISTAPVQMPTAESTGMTPEKVPVSEVMGTTLAEMSTPEATGM

TPAEVSIVVLSGTTAAQVTTTEWVETTARELPIPEPEGPDASSIMSTESI

TGSLGPLLDGTATLRLVKRQVPLDCVLYRYGSFSVTLDIVQGIESAEILQ

AVPSGEGDAFELTVSCQGGLPKEACMEISSPGCQPPAQRLCQPVLPSPAC

QLVLHQILKGGSGTYCLNVSLADTNSLAVVSTQLIMPGQEAGLGQ*VPLIV*

*GILLVLMAVVLASLIYRRRLMKQDFSVPQLPHSSSHWLRLPRIFCSCPIG*

*ENSPLLSGQQV*

Known HLA-A0201 restricted peptides sequences are: GP100 M: 209-217 (2M): IMDQVPFSV (SEQ ID NO.:113); 209-217 WT: ITDQVPFSV (SEQ ID NO.:114) GP100 M: 280-288 (9V): YLEPGPVTV (SEQ ID NO.:115) 280-288 WT: YLEPGPVTA (SEQ ID NO.:116) GP100 WT: 154-162: KTWGQYWQV (SEQ ID NO.:117)

FIG. 29-33 show the gp100 adducts which were successfully expressed as secreted anti-DC receptor targeting vaccines. These employed the use of the flexible linker sequences and fragmentation and shuffling of the gp100 ectodomain coding region. Preferred embodiments of gp100 vaccine adducts are described.

Figure 29:
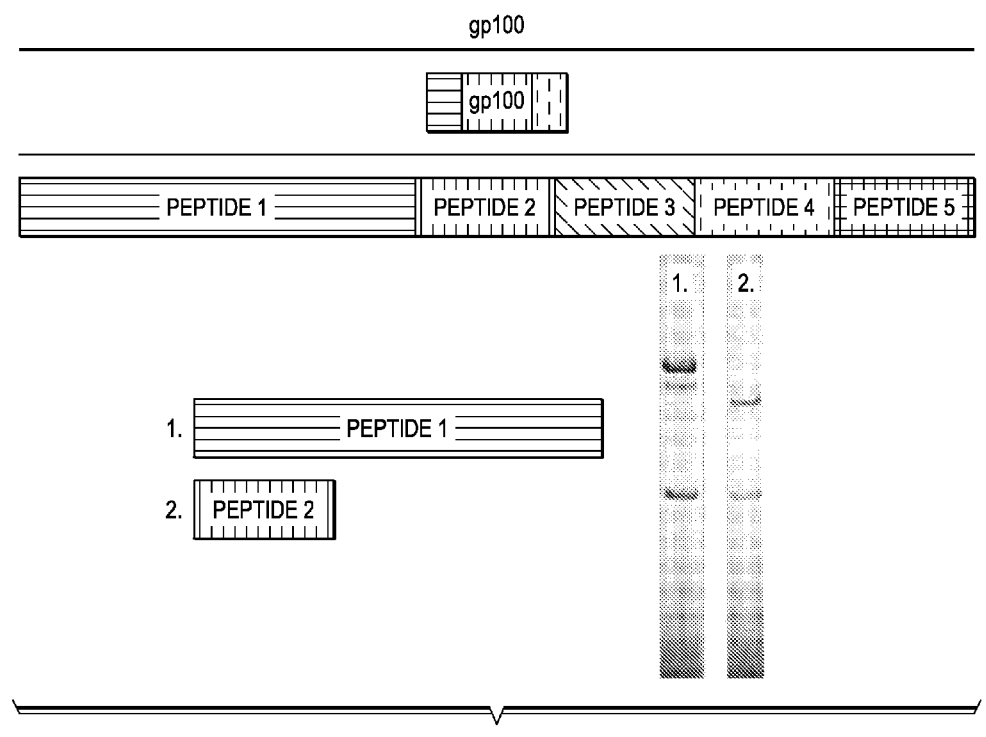
FIG. 29 shows the expression and construct design for anti-CD40-gp100 peptide antibodies.
Figure 30:
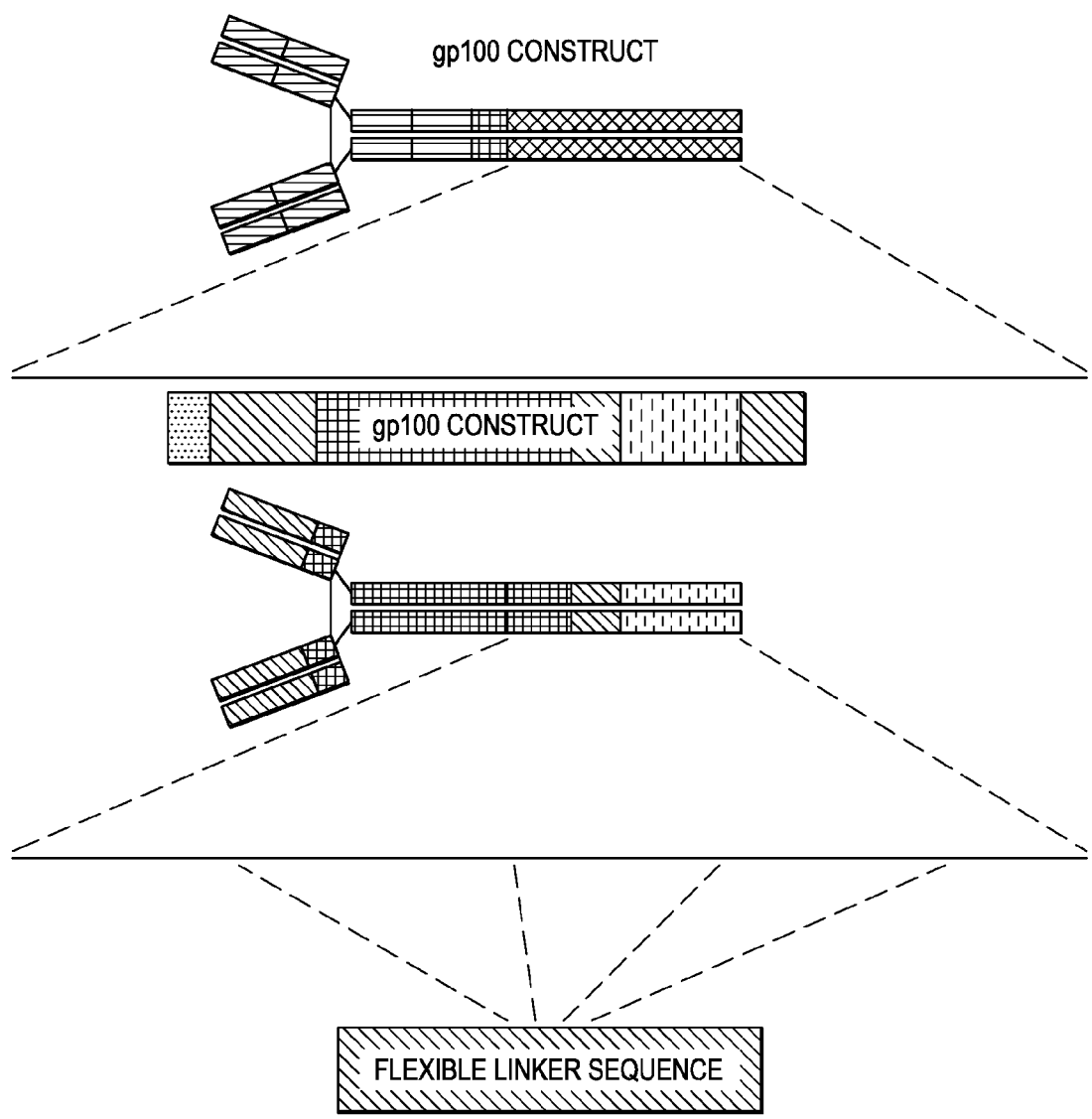
FIG. 30 shows the design for additional anti-CD40-gp100 peptide antibodies.
Figure 31:
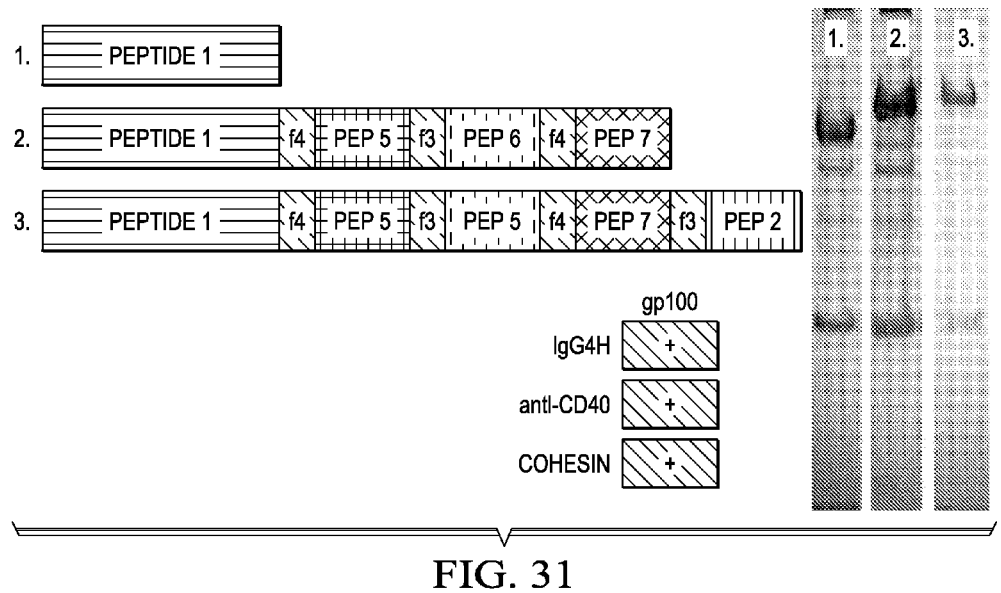
FIG. 31 shows the expression and construct design for additional anti-CD40-gp100 peptide antibodies.
Figure 32:
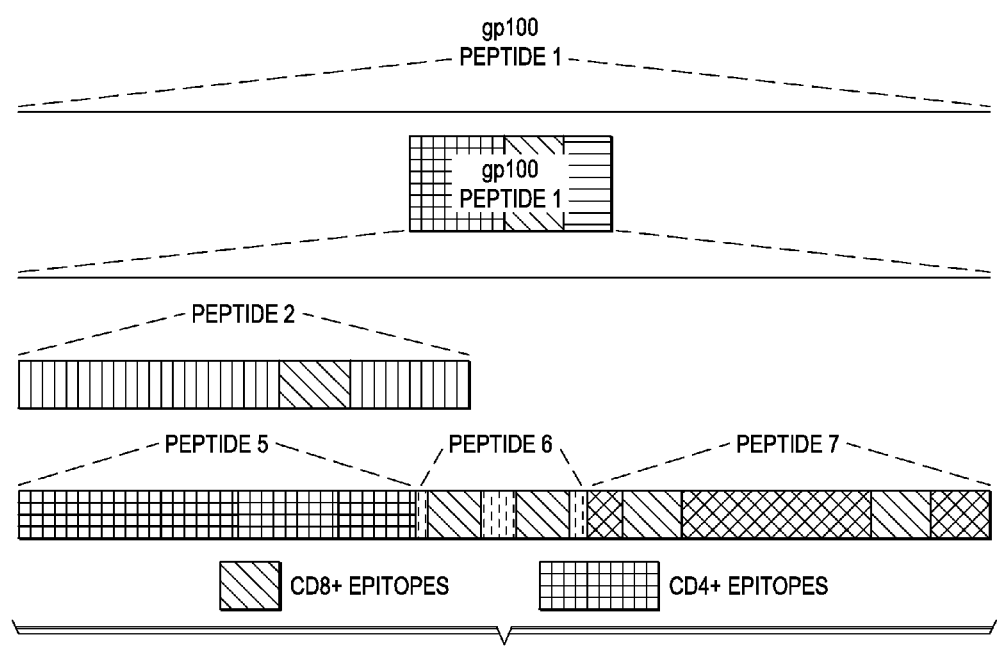
FIG. 32 is a summary of the CD4+ and CD8+ immunodominant epitopes for gp100.
Figure 33:
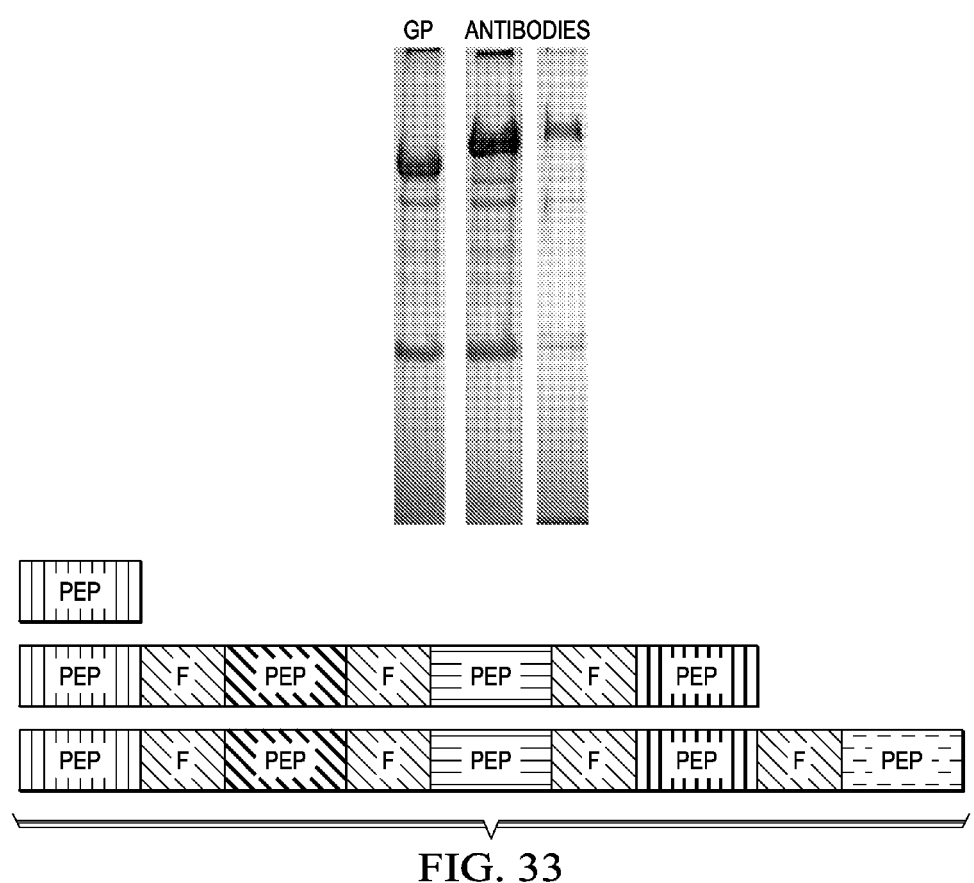
FIG. 33 shows the expression and construct design for additional anti-CD40-gp100 peptide antibodies.

FIG. 29 shows the expression and construct design for anti-CD40-gp100 peptide antibodies. FIG. 30 shows the design for additional anti-CD40-gp100 peptide antibodies. FIG. 31 shows the expression and construct design for additional anti-CD40-gp100 peptide antibodies. FIG. 32 is a summary of the CD4+ and CD8+ immunodominant epitopes for gp100. FIG. 33 shows the expression and construct design for additional anti-CD40-gp100 peptide antibodies.

rAB-cetHS-puro[manti-CD40__12E12.3F3_H-LV-hIgG4H-C-Flex-hgp100-Pep-1-f4-Pep-3-f3-Pep-4-f4-Pep-5-f3-Pep-2] C1285 the peptides are bold-italics, flexible linkers are bold and the underlined AS residues are joining sequences:

(SEQ ID NO.: 118)
EVKLVESGGGLVQPGGSLKLSCATSGFTFSDYYMYWVRQTPEKRLEWVAYINSGGGSTYY

PDTVKGRFTISRDNAKNTLYLQMSRLKSEDTAMYYCARRGLPFHAMDYWGQGTSVTVSSAKTKG

PSVFPLAPCSRSTSESTAALGCLVKDYFPEPVTVSWNSGALTSGVHTFPAVLQSSGLYSLSSVVTVP

SSSLGTKTYTCNVDHKPSNTKVDKRVESKYGPPCPPCPAPEFEGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKSLSLSLGKASDTTEPAT

PTTPVTTPTTTKVPRNQDWLGVSRQLRTKAWNRQLYPEWTEAQRLDCWRGGQVSLKVSNDGPTLI

GANASFSIALNFPGSQKVLPDGQVIWVNNTIINGSQVWGGQPVYPQETDDACIFPDGGPCPSGSWS

QKRSFVYVWKTWGQYWQVLGGPVSGLSIGTGRAMLGTHTMEVTVYHRRGSQSYVPLAHSSSAFTI

TDQVPFSVSVSQLRALDGGNKHFLRNQASTNGSITVAATAPTVTPTVNATPSAAADGTTDGHRPT

TEAPNTTAGQVPTTEVVGTTPGQAPTAEPSGTTSVQVPTTEVISTAPVQMPTAESTGMTPEKVPVSE

VMGTTLAEMSTPEATGMTPAEVSIVVLSGTTAAASTVTPTATATPSAIVTTITPTATTKPASQVTT

TEWVETTARELPIPEPEGPDASSIMSTESITGSLGPLLDGTATLRLVKRQVPLDCVLYRYGSFSVTLD

IVQASTNGSTTVAATAPTVTPTVNATPSAAAGIESAEILQAVPSGEGDAFELTVSCQGGLPKEAC

MEISSPGCQPPAQRLCQPVLPSPACQLVLHQILKGGSGTYCLNVSLADTNSLAVVSTQLIVPGILLTG

QEAGLGQASTVTPTATATPSAIVTTITPTATTKPASPLTFALQLHDPSGYLAEADLSYTWDFGDSS

GTLISRALVVTHTYLEPGPVTAQVVLQAAIPLTSCGSSPVPAS rAB-cetHS-puro[hIgG4H-C-Flex-hgp100-Pep-1-f4-Pep-3-f3-Pep-4-f4-Pep-5-f3-Pep-2] C1286:

(SEQ ID NO.: 119)

RLQLQESGPGLLKPSVTLSLTCTVSGDSVASSSYYWGWVRQPPGKGLEWIGTINFSGNMYY

SPSLRSRVTMSADMSENSFYLKLDSVTAADTAVYYCAAGHLVMGFGAHWGQGKLVSVSPASTKG

PSVFPLAPCSRSTSESTAALGCLVKDYFPEPVTVSWNSGALTSGVHTFPAVLQSSGLYSLSSVVTVP

SSSLGTKTYTCNVDHKPSNTKVDKRVESKYGPPCPPCPAPEFEGGPSVFLFPPKPKDTLMISRTPEVT

CVVVDVSQEDPEVQFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFYPSDIAVEWESNGQPENN

YKTTPPVLDSDGSFFLYSRLTVDKSRWQEGNVFSCSVMHEALHNHYTQKSLSLSLGKA<u>S</u>*DTTEPAT*

*PTTPVTTPTTTKVPRNQDWLGVSRQLRTKAWNRQLYPEWTEAQRLDCWRGGQVSLKVSNDGPTLI*

*GANASFSIALNFPGSQKVLPDGQVIWVNNTILNGSQVWGGQPVYPQETDDACIFPDGGPCPSGSWS*

*QKRSFVYVWKTWGQYWQVLGGPVSGLSIGTGRAMLGTHTMEVTVYHRRGSQSYVELAHSSSAFTI*

*TDQVPFSVSVSQLRAIDGGNKHFLRNQ*<u>AS</u>TNGSITVAATAPTVTPTVNATPSAA<u>AS</u>GTTDGHRPT

TEAPNTTAGQVPTTEVVGTTPGQAPTAEPSGTTSVQVPTTEVISTAPVQMPTAESTGMTPEKVPVSE

VMGTTLAEMSTPEATGMTPAEVSIVVLSGTTAA<u>AS</u>TVTPTATATPSAIVTTITPTATTKPA<u>S</u>*QVTT*

*TEWVETTARELPIPEPEGPDASSIMSTESITGSLGPLLDGTATLRLVKRQVPLDCVLYRYGSFSVTLD*

*IVQ*<u>AS</u>TNGSITVAATAPTVTPTVNATPSAA<u>AS</u>*GIESAEIIQAVPSGEGDAFELTVSCQGGLPKEAC*

*MEISSPGCQPPAQRLQQPVLPSPACQLVLHQILKGGSGTYCLNVSLADTNSLAVVSTQLIVPGILLTG*

*QEAGLGQ*<u>AS</u>TVTPTATATPSAIVTTITPTATTKPA<u>S</u>PLTFALQLHDPSGYLAEADLSYTWDFGDSS

GTLISRALVVTHTYLEPGPVTAQVVLQAAIPLTSCGSSFVP<u>AS</u> gp100:—Nucleic Acid Sequence. Peptide 1—underlined, Peptide 2—italics, Peptide 3—bold, Peptide 4—bold-underlined, Peptide 5 bold-italics.

(SEQ ID NO.: 120)

<u>GATACAACAGAACCTGCAACACCTACAACACCTGTAACAACACCGACAACAACAAAAGTACC</u>

<u>CAGAAACCAGGACTGGCTTGGTGTCTCAAGGCAACTCAGAACCAAAGCCTGGAACAGGCAGC</u>

<u>TGTATCCAGAGTGGACAGAAGCCCAGAGACTTGACTGCTGGAGAGGTGGTCAAGTGTCCCTCA</u>

<u>AGGTCAGTAATGATGGGCCTACACTGATTGGTGCAAATGCCTCCTTCTCTATTGCCTTGAACTT</u>

<u>CCCTGGAAGCCAAAAGGTATTGCCAGATGGGCAGGTTATCTGGGTCAACAATACCATCATCAA</u>

<u>TGGGAGCCAGGTGTGGGGAGGACAGCCAGTGTATCCCCAGGAAACTGACGATGCCTGCATCTT</u>

<u>CCCTGATGGTGGACCTTGCCCATCTGGCTCTTGGTCTCAGAAGAGAAGCTTTGTTTATGTCTGG</u>

<u>AAGACCTGGGGCCAATACTGGCAAGTTCTAGGGGCCCAGTGTCTGGGCTGAGCATTGGGACA</u>

<u>GGCAGGGCAATGCTGGGCACACACACCATGGAAGTGACTGTCTACCATCGCCGGGGATCCCAG</u>

<u>AGCTATGTGCCTCTTGCTCATTCCAGCTCAGCCTTCACCATTACTGACCAGGTGCCTTTCTCCGT</u>

<u>GAGCGTGTCCCAGTTGCGGGCCTTGGATGGAGGGAACAAGCACTTCCTGAGAAATCAGGCTAG</u>

TACCAACGGCAGCATCACCGTGGCCGCCACCGCCCCCACCGTGACCCCCACCGTGAACGCCAC

CCCCAGCGCCGCCGCTAGT*GGCACCACAGATGGGCACAGGCCAACTGCAGAGGCCCCTAACACCA*

*CAGCTGGCCAAGTGCCTACTACAGAAGTTGTGGGTACTACACCTGGTCAGGCGCCAACTGCAGAGC*

*CCTCTGGAACCACATCTGTGCAGGTGCCAACCACTGAAGTCATAAGCACTGCACCTGTGCAGATGCC*

*AACTGCAGAGAGCACAGGTATGACACCTGAGAAGGTGCCAGTTTCAGAGGTCATGGGTACCACACTG*

*GCAGAGATGTCAACTCCAGAGGCTACAGGTATGACACCTGCAGAGGTATCAATTGTGGTGCTTTCTG*

```
GAACCACAGCTGCAGCTAGTACCGTGACCCCCACCGCCACCGCCACCCCCAGCGCCATCGTGAC

CACCATCACCCCCACCGCCACCACCAAGCCCGCTAGTCAGGTAACAACTACAGAGTGGGTG

GAGACCACAGCTAGAGAGCTACCTATCCCTGAGCCTGAAGGTCCAGATGCCAGCTCAAT

CATGTCTACGGAAAGTATTACAGGTTCCCTGGGCCCCCTGCTGGATGGTACAGCCACCTT

AAGGCTGGTGAAGAGACAAGTCCCCCTGGATTGTGTTCTGTATCGATATGGTTCCTTTTC

CGTCACCCTGGACATTGTCCAGGCTAGTACCAACGGCAGCATCACCGTGGCCGCCACCGCCC

CCACCGTGACCCCCACCGTGAACGCCACCCCCAGCGCCGCCGCTAGTGGTATTGAAAGTGCC

GAGATCCTGCAGGCTGTGCCGTCCGGTGAGGGGGATGCATTTGAGCTGACTGTGTCCTG

CCAAGGCGGGCTGCCCAAGGAAGCCTGCATGGAGATCTCATCGCCAGGGTGCCAGCCCC

CTGCCCAGCGGCTGTGCCAGCCTGTGCTACCCAGCCCAGCCTGCCAGCTGGTTCTGCAC

CAGATACTGAAGGGTGGCTCGGGGACATACTGCCTCAATGTGTCTCTGGCTGATACCAA

CAGCCTGGCAGTGGTCAGCACCCAGCTTATCGTGCCTGGGATTCTTCTCACAGGTCAAGA

AGCAGGCCTTGGGCAGTAAGCTAGTACCGTGACCCCCACCGCCACCGCCACCCCCAGCGCCA

TCGTGACCACCATCACCCCCACCGCCACCACCAAGCCCGCTAGTCCTCTGACCTTTGCCCTCCA

GCTCCATGACCCTAGTGGCTATCTGGCTGAAGCTGACCTCTCCTACACCTGGGACTTTGGAGACA

GTAGTGGAACCCTGATCTCTCGGGCACYTGTGGTCACTCATACTTACCTGGAGCCTGGCCCAGTC

ACTGCCCAGGTGGTCCTGCAGGCTGCCATTCCTCTCACCTCCTGTGGCTCCTCCCCAGTTCCA

GCTAGC TGA
```

GP100-Peptide 1—Nucleic Acid Sequence.

(SEQ ID NO.: 121)
```
GATACAACAGAACCTGCAACACCTACAACACCTGTAACAACACCGACAAC
AACAAAAGTACCCAGAAACCAGGACTGGCTTGGTGTCTCAAGGCAACTCA
GAACCAAAGCCTGGAACAGGCAGCTGTATCCAGAGTGGACAGAAGCCCAG
AGACTTGACTGCTGGAGAGGTGGTCAAGTGTCCCTCAAGGTCAGTAATGA
TGGGCCTACACTGATTGGTGCAAATGCCTCCTTCTCTATTGCCTTGAACT
TCCCTGGAAGCCAAAAGGTATTGCCAGATGGGCAGGTTATCTGGGTCAAC
AATACCATCATCAATGGGAGCCAGGTGTGGGGAGGACAGCCAGTGTATCC
CCAGGAAACTGACGATGCCTGCATCTTCCCTGATGGTGGACCTTGCCCAT
CTGGCTCTTGGTCTCAGAAGAGAAGCTTTGTTTATGTCTGGAAGACCTGG
GGCCAATACTGGCAAGTTCTAGGGGCCCAGTGTCTGGGCTGAGCATTGG
GACAGGCAGGGCAATGCTGGGCACACACACCATGGAAGTGACTGTCTACC
ATCGCCGGGGATCCCAGAGCTATGTGCCTCTTGCTCATTCCAGCTCAGCC
TTCACCATTACTGACCAGGTGCCTTTCTCCGTGAGCGTGTCCCAGTTGCG
GGCCTTGGATGGAGGGAACAAGCACTTCCTGAGAAATCAG
```

Protein Sequence:

(SEQ ID NO.: 122)
```
DTTEPATPTTPVTTPTTTKVPRNQDWLGVSRQLRTKAWNRQLYPEWTEAQ
RLDCWRGGQVSLKVSNDGPTLIGANASFSIALNFPGSQKVLPDGQVIWVN
NTIINGSQVWGGQPVYPQETDDACIFPDGGPCPSGSWSQKRSFVYVWKTW
GQYWQVLGGPVSGLSIGTGRAMLGTHTMEVTVYHRRGSQSYVPLAHSSSA
FTITDQVPFSVSVSQLRALDGGNKHFLRNQ
```

GP100-Peptide 3

(SEQ ID NO.: 123)
```
GGCACCACAGATGGGCACAGGCCAACTGCAGAGGCCCCTAACACCACAGC
TGGCCAAGTGCCTACTACAGAAGTTGTGGGTACTACACCTGGTCAGGCGC
CAACTGCAGAGCCCTCTGGAACCACATCTGTGCAGGTGCCAACCACTGAA
GTCATAAGCACTGCACCTGTGCAGATGCCAACTGCAGAGAGCACAGGTAT
GACACCTGAGAAGGTGCCAGTTTCAGAGGTCATGGGTACCACACTGGCAG
AGATGTCAACTCCAGAGGCTACAGGTATGACACCTGCAGAGGTATCAATT
GTGGTGCTTTCTGGAACCACAGCTGCA
```

Protein Sequence:

(SEQ ID NO.: 124)
```
GTTDGHRPTAEAPNTTAGQVPTTEVVGTTPGQAPTAEPSGTTSVQVPTTE
VISTAPVQMPTAESTGMTPEKVPVSEVMGTTLAEMSTPEATGMTPAEVSI
VVLSGTTAA
```

GP100-Peptide 4:

(SEQ ID NO.: 125)
```
CAGGTAACAACTACAGAGTGGGTGGAGACCACAGCTAGAGAGCTACCTAT
CCCTGAGCCTGAAGGTCCAGATGCCAGCTCAATCATGTCTACGGAAAGTA
```

-continued
TTACAGGTTCCCTGGGCCCCCTGCTGGATGGTACAGCCACCTTAAGGCTG

GTGAAGAGACAAGTCCCCCTGGATTGTGTTCTGTATCGATATGGTTCCTT

TTCCGTCACCCTGGACATTGTCCAG

Protein Sequence:

(SEQ ID NO.: 126)
QVTTTEWVETTARELPIPEPEGPDASSIMSTESITGSLGPLLDGTATLRL

VKRQVPLDCVLYRYGSFSVTLDIVQ

GP100-Peptide 5

(SEQ ID NO.: 127)
GGTATTGAAAGTGCCGAGATCCTGCAGGCTGTGCCGTCCGGTGAGGGGA

TGCATTTGAGCTGACTGTGTCCTGCCAAGGCGGGCTGCCCAAGGAAGCCT

GCATGGAGATCTCATCGCCAGGGTGCCAGCCCCCTGCCCAGCGGCTGTGC

CAGCCTGTGCTACCCAGCCCAGCCTGCCAGCTGGTTCTGCACCAGATACT

GAAGGGTGGCTCGGGGACATACTGCCTCAATGTGTCTCTGGCTGATACCA

ACAGCCTGGCAGTGGTCAGCACCCAGCTTATCGTGCCTGGGATTCTTCTC

ACAGGTCAAGAAGCAGGCCTTGGGCAG

Protein Sequence:

(SEQ ID NO.: 128)
GIESAEILQAVPSGEGDAFELTVSCQGGLPKEACMEISSPGCQPPAQRLC

QPVLPSPACQLVLHQILKGGSGTYCLNVSLADTNSLAVVSTQLIVPGILL

TGQEAGLGQ

GP100-Peptide 2

(SEQ ID NO.: 129)
CCTCTGACCTTTGCCCTCCAGCTCCATGACCCTAGTGGCTATCTGGCTGA

AGCTGACCTCTCCTACACCTGGGACTTTGGAGACAGTAGTGGAACCCTGA

TCTCTCGGGCACYTGTGGTCACTCATACTTACCTGGAGCCTGGCCCAGTC

ACTGCCCAGGTGGTCCTGCAGGCTGCCATTCCTCTCACCTCCTGTGGCTC

CTCCCCAGTTCCAGCTAGC

Protein Sequence:

(SEQ ID NO.: 130)
PLTFALQLHDPSGYLAEADLSYTWDFGDSSGTLISRAXVVTHTYLEPGPV

TAQVVLQAAIPLTSCGSSPVPAS

Cyclin B1 Antigen. Cyclin B1 also known as CCNB1 is a human gene that encodes a regulatory protein involved in mitosis. Cyclin B1 complexes with p34(cdc2) to form the maturation-promoting factor (MPF). Two alternative transcripts are known that are the result of alternative transcription initiation sites. A first transcript encodes a constitutively expressed transcript. The second transcript is a cell cycle-regulated transcript expressed predominantly during G2/M phase.

Figure 34A:
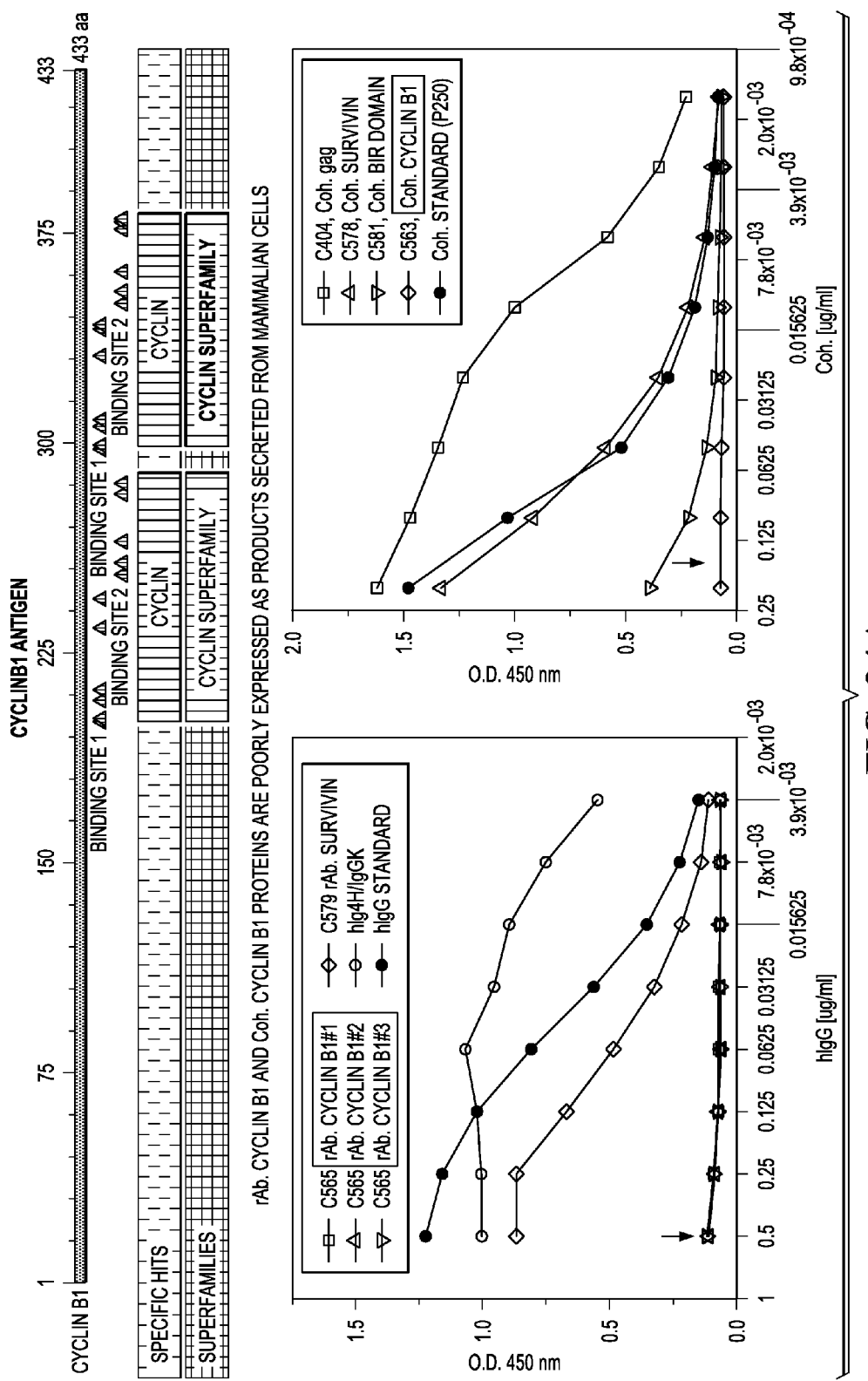
FIG. 34A shows that full-length Cyclin B1 fused to the C-terminus of either antibody H chain or cohesion fail to be secreted from mammalian 293F cells.

FIGS. 34A and 34B shows that full-length Cyclin B1 fused to the C-terminus of either antibody H chain or cohesion fail to be secreted from mammalian 293F cells. The data are anti-human Fc and anti-cohesin ELISA on serial dilutions of transfection supernatants. rAb.Cyclin B1 and Coh.Cyclin B1 proteins are poorly expressed as products secreted from mammalian cells.

The following amino acid sequence is human cyclin B1. Two peptide regions known to contain T cell epitopes are highlighted in bold-underlined and italics-underlined.

(SEQ ID NO.: 131)
MALRVTRNSKINAENKAKINMAGAKRVPTAPAATSKPGLRPRTALGDIGN

KVSEQLQAKMPMKKEAKPSATGKVIDKKLPKPLEKVPMLVPVPVSEPVPE

PEPEPEPEPVKEEKLSPEPILVDTASPSPMETSGCAPAEEDLCQAFSDVI

LAVNDVDAEDGADPNLCSEYVKDIYAYLRQLEEEQAVRPKYLLGREVTGN

MRAILIDWLVQVQMKFRLLQETMYMTVSIIDRFMQNNCVPKKMLQLVGVT

AMFIASKYEEMYPPEIGDFAFVTDNTYTKHQIRQ*MEMKILRALNFGLGRP*

*LPLHFLRRASKIGEVDVEQHTLAKYLMETMLDY*DMVHFPPSQIAAGAFCL

ALKILDNGEWTPTLQHYLSYTEESLLPVMQHLAKNVVMVNQGLTKHMTVK

NKYATSKHAKISTLPQLNSALVQDLAKAVAKVHHHHHH

Peptide-1

(SEQ ID NO.: 132)
MEMKILRALNFGLGRPLPLHFLRRASKIGEVDVEQHTLAKYLMELTMLDY

Peptide-2

(SEQ ID NO.: 133)
DWLVQVQMKFRLLQETMYMTVSIIDRFMQNNCVPKK

Figure 35:
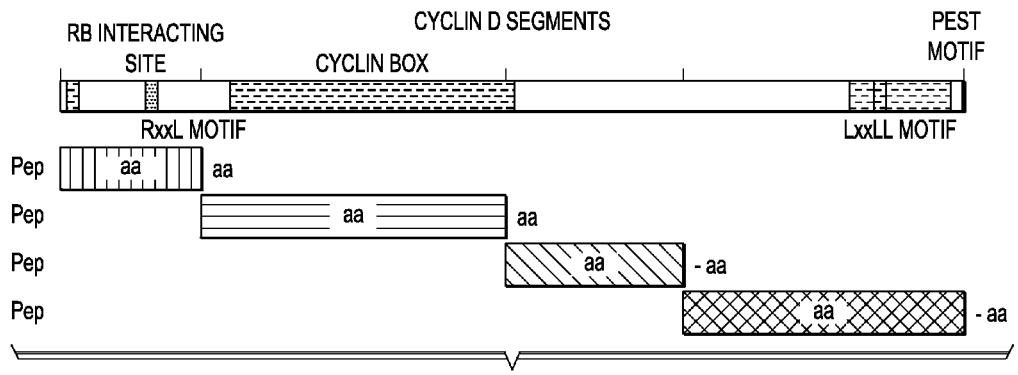
FIG. 35 shows Cyclin B1 segmentation strategy based on known or predicted structural domain regions.

FIG. 35 shows a summary of relative expression levels of prototype Cyclin B1 vaccines secreted from transfected mammalian 293F cells. The flexible linker sequences facilitate secretion.

C1189 rAB-cetHS-puro[manti-CD40_12E12.3F3_H-LV-hIgG4H-C-Flex-v1 (bold)-hCyclinB1-Peptide-2(italics)-Peptide-1 (bold-italics)-f4 (bold)] [AS linkers—underlined]

(SEQ ID NO.: 134)
EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVSSAKTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGKASQT

PTNTISVTPTNNSTPTNNSNPKPNPAS*DWLVQVQMKFRLLQETMYMTVSI

IDRFMQNNCVPKK*AS*MEMKILRALNFGLGRPLPLHFLRRAS*KIGEVDVE

QHTLAKYLMELTMLDY*ASTNDSITVAATAPTVTPTVNATPSAAAS

Above is the sequence of the mature secreted H chain for one form of anti-CD4012E12-cyclin B1 vaccine. The AS residues are from joining restriction sites. The DNA coding sequence is shown below, and this includes the signal peptide.

(SEQ ID NO.: 135)

```
ATGAACTTGGGGCTCAGCTTGATTTTCCTTGTCCTTGTTTTAAAAGGTGTCCAGTGTGAAGTGA
AGCTGGTGGAGTCTGGGGGAGGCTTAGTGCAGCCCGGAGGGTCCCTGAAACTCTCCTGTGCAA
CCTCTGGATTCACTTTCAGTGACTATTACATGTATTGGGTTCGCCAGACTCCAGAGAAGAGGCT
GGAGTGGGTCGCATACATTAATTCTGGTGGTGGTAGCACCTATTATCCAGACACTGTAAAGGG
CCGATTCACCATCTCCAGAGACAATGCCAAGAACACCCTGTACCTGCAAATGAGCCGGCTGAA
GTCTGAGGACACAGCCATGTATTACTGTGCAAGACGGGGGTTACCGTTCCATGCTATGGACTA
TTGGGGTCAAGGAACCTCAGTCACCGTCTCCTCAGCCAAAACGAAGGGCCCATCCGTCTTCCC
CCTGGCGCCCTGCTCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCC
AGCAGCTTGGGCACGAAGACCTACACCTGCAACGTAGATCACAAGCCCAGCAACACCAAGGT
GGACAAGAGAGTTGAGTCCAAATATGGTCCCCCATGCCCACCCTGCCCAGCACCTGAGTTCGA
AGGGGGACCATCAGTCTTCCTGTTCCCCCCAAAACCCAAGGACACTCTCATGATCTCCCGGAC
CCCTGAGGTCACGTGCGTGGTGGTGGACGTGAGCCAGGAAGACCCCGAGGTCCAGTTCAACTG
GTACGTGGATGGCGTGGAGGTGCATAATGCCAAGACAAAGCCGCGGGAGGAGCAGTTCAACA
GCACGTACCGTGTGGTCAGCGTCCTCACCGTCCTGCACCAGGACTGGCTGAACGGCAAGGAGT
ACAAGTGCAAGGTCTCCAACAAAGGCCTCCCGTCCTCCATCGAGAAAACCATCTCCAAAGCCA
AAGGGCAGCCCCGAGAGCCACAGGTGTACACCCTGCCCCCATCCCAGGAGGAGATGACCAAG
AACCAGGTCAGCCTGACCTGCCTGGTCAAAGGCTTCTACCCCAGCGACATCGCCGTGGAGTGG
GAGAGCAATGGGCAGCCGGAGAACAACTACAAGACCACGCCTCCCGTGCTGGACTCCGACGG
CTCCTTCTTCCTCTACAGCAGGCTAACCGTGGACAAGAGCAGGTGGCAGGAGGGGAATGTCTT
CTCATGCTCCGTGATGCATGAGGCTCTGCACAACCACTACACACAGAAGAGCCTCTCCCTGTCT
CTGGGTAAAGCTAGTCAGACCCCCACCAACACCATCAGCGTGACCCCCACCAACAACAGCACC
CCCACCAACAACAGCAACCCCAAGCCCAACCCCGCTAGTGACTGGCTAGTACAGGTTCAAATG
AAATTCAGGTTGTTGCAGGAGACCATGTACATGACTGTCTCCATTATTGATCGGTTCATGCAGA
ATAATTGTGTGCCCAAGAAGGCTAGTATGGAAATGAAGATTCTAAGAGCTTTAAACTTTGGTC
TGGGTCGGCCTCTACCTTTGCACTTCCTTCGGAGAGCATCTAAGATTGGAGAGGTTGATGTCGA
GCAACATACTTTGGCCAAATACCTGATGGAACTAACTATGTTGGACTATGCTAGTACCAACGA
CAGCATCACCGTGGCCGCCACCGCCCCCACCGTGACCCCCACCGTGAACGCCACCCCCAGCGC
CGCCGCTAGCTGA
```

C1143 rAB-cetHS-puro[manti-CD40__12E12.3F3_H-LV-hIgG4H-C-Flex-v1 (bold)-hCyclinB1-Peptide-2(italics)-f3 (bold)] [AS linkers—underlined].

(SEQ ID NO.: 136)

EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVSSAKTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK<u>AS</u>QT

PTNTISVTPTNNSTPTNNSNPKPNP<u>AS</u>*DWLVQVQMKFRLLQETMYMTVSI*

*IDRFMQNNCVPKK*<u>AS</u>TVTPTATATPSAIVTTITPTATTKP<u>AS</u>

Above is the sequence of the mature secreted H chain for one form of anti-CD4012E12-cyclin B1 vaccine. The AS residues are from joining restriction sites. The DNA coding sequence is shown below, and this includes the signal peptide.

(SEQ ID NO.: 137)

```
ATGAACTTGGGGCTCAGCTTGATTTTCCTTGTCCTTGTTTTAAAAGGTGTCCAGTGTGAAGTGA
AGCTGGTGGAGTCTGGGGGAGGCTTAGTGCAGCCCGGAGGGTCCCTGAAACTCTCCTGTGCAA
CCTCTGGATTCACTTTCAGTGACTATTACATGTATTGGGTTCGCCAGACTCCAGAGAAGAGGCT
GGAGTGGGTCGCATACATTAATTCTGGTGGTGGTAGCACCTATTATCCAGACACTGTAAAGGG
CCGATTCACCATCTCCAGAGACAATGCCAAGAACACCCTGTACCTGCAAATGAGCCGGCTGAA
GTCTGAGGACACAGCCATGTATTACTGTGCAAGACGGGGGTTACCGTTCCATGCTATGGACTA
TTGGGGTCAAGGAACCTCAGTCACCGTCTCCTCAGCCAAAACGAAGGGCCCATCCGTCTTCCC
CCTGGCGCCCTGCTCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCC
AGCAGCTTGGGCACGAAGACCTACACCTGCAACGTAGATCACAAGCCCAGCAACACCAAGGT
GGACAAGAGAGTTGAGTCCAAATATGGTCCCCCATGCCCACCCTGCCCAGCACCTGAGTTCGA
AGGGGGACCATCAGTCTTCCTGTTCCCCCCAAAACCCAAGGACACTCTCATGATCTCCCGGAC
CCCTGAGGTCACGTGCGTGGTGGTGGACGTGAGCCAGGAAGACCCCGAGGTCCAGTTCAACTG
GTACGTGGATGGCGTGGAGGTGCATAATGCCAAGACAAAGCCGCGGGAGGAGCAGTTCAACA
GCACGTACCGTGTGGTCAGCGTCCTCACCGTCCTGCACCAGGACTGGCTGAACGGCAAGGAGT
ACAAGTGCAAGGTCTCCAACAAAGGCCTCCCGTCCTCCATCGAGAAAACCATCTCCAAAGCCA
AAGGGCAGCCCCGAGAGCCACAGGTGTACACCCTGCCCCCATCCCAGGAGGAGATGACCAAG
AACCAGGTCAGCCTGACCTGCCTGGTCAAAGGCTTCTACCCCAGCGACATCGCCGTGGAGTGG
GAGAGCAATGGGCAGCCGGAGAACAACTACAAGACCACGCCTCCCGTGCTGGACTCCGACGG
CTCCTTCTTCCTCTACAGCAGGCTAACCGTGGACAAGAGCAGGTGGCAGGAGGGGAATGTCTT
CTCATGCTCCGTGATGCATGAGGCTCTGCACAACCACTACACACAGAAGAGCCTCTCCCTGTCT
CTGGGTAAAGCTAGTCAGACCCCCACCAACACCATCAGCGTGACCCCACCAACAACAGCACC
CCCACCAACAACAGCAACCCCAAGCCCAACCCCGCTAGTGACTGGCTAGTACAGGTTCAAATG
AAATTCAGGTTGTTGCAGGAGACCATGTACATGACTGTCTCCATTATTGATCGGTTCATGCAGA
ATAATTGTGTGCCCAAGAAGGCTAGTACCGTGACCCCCACCGCCACCGCCACCCCCAGCGCCA
TCGTGACCACCATCACCCCCACCGCCACCACCAAGCCCGCTAGCTGA
```

C911 rAB-cetHS-puro[manti-CD40__12E12.3F3_H-LV-hIgG4H-C-Flex-v1 (bold)-hCyclinB1-Peptide-1 (italics)-f4 (bold)]

(SEQ ID NO.: 138)

EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVSSAKTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGKASQT

PTNTISVTPTNNSTPTNNSNPKPNPASMEMKILRALNFGLGRPLPLHFLR

RASKIGEVDVEQHTLAKYLMELTMLDYASTNGSITVAATAPTVTPTVNAT

PSAAAS

C911 rAB-cetHS-puro [manti-CD40__12E12.3F3_H-LV-hIgG4H-C-Flex-v1 (bold)-hCyclinB1-Peptide-1 (italics)-f4 (bold)] nucleic acid sequence.

(SEQ ID NO.: 139)

```
ATGAACTTGGGGCTCAGCTTGATTTTCCTTGTCCTTGTTTTAAAAGGTGTCCAGTGTGAAGTGA
AAGCTGGTGGAGTCTGGGGGAGGCTTAGTGCAGCCCGGAGGGTCCCTGAAACTCTCCTGTGCAA
```

-continued

```
CCTCTGGATTCACTTTCAGTGACTATTACATGTATTGGGTTCGCCAGACTCCAGAGAAGAGGCT
GGAGTGGGTCGCATACATTAATTCTGGTGGTGGTAGCACCTATTATCCAGACACTGTAAAGGG
CCGATTCACCATCTCCAGAGACAATGCCAAGAACACCCTGTACCTGCAAATGAGCCGGCTGAA
GTCTGAGGACACAGCCATGTATTACTGTGCAAGACGGGGGTTACCGTTCCATGCTATGGACTA
TTGGGGTCAAGGAACCTCAGTCACCGTCTCCTCAGCCAAAACGAAGGGCCCATCCGTCTTCCC
CCTGGCGCCCTGCTCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCC
AGCAGCTTGGGCACGAAGACCTACACCTGCAACGTAGATCACAAGCCCAGCAACACCAAGGT
GGACAAGAGAGTTGAGTCCAAATATGGTCCCCCATGCCCACCCTGCCCAGCACCTGAGTTCGA
AGGGGGACCATCAGTCTTCCTGTTCCCCCCAAAACCCAAGGACACTCTCATGATCTCCCGGAC
CCCTGAGGTCACGTGCGTGGTGGTGGACGTGAGCCAGGAAGACCCCGAGGTCCAGTTCAACTG
GTACGTGGATGGCGTGGAGGTGCATAATGCCAAGACAAAGCCGCGGGAGGAGCAGTTCAACA
GCACGTACCGTGTGGTCAGCGTCCTCACCGTCCTGCACCAGGACTGGCTGAACGGCAAGGAGT
ACAAGTGCAAGGTCTCCAACAAAGGCCTCCCGTCCTCCATCGAGAAAACCATCTCCAAAGCCA
AAGGGCAGCCCCGAGAGCCACAGGTGTACACCCTGCCCCCATCCCAGGAGGAGATGACCAAG
AACCAGGTCAGCCTGACCTGCCTGGTCAAAGGCTTCTACCCCAGCGACATCGCCGTGGAGTGG
GAGAGCAATGGGCAGCCGGAGAACAACTACAAGACCACGCCTCCCGTGCTGGACTCCGACGG
CTCCTTCTTCCTCTACAGCAGGCTAACCGTGGACAAGAGCAGGTGGCAGGAGGGGAATGTCTT
CTCATGCTCCGTGATGCATGAGGCTCTGCACAACCACTACACACAGAAGAGCCTCTCCCTGTCT
CTGGGTAAAGCTAGTCAGACCCCCACCAACACCATCAGCGTGACCCCCACCAACAACAGCACC
CCCACCAACAACAGCAACCCCAAGCCCAACCCCGCTAGTATGGAAATGAAGATTCTAAGAGCT
TTAAACTTTGGTCTGGGTCGGCCTCTACCTTTGCACTTCCTTCGGAGAGCATCTAAGATTGGAG
AGGTTGATGTCGAGCAACATACTTTGGCCAAATACCTGATGGAACTAACTATGTTGGACTATG
CTAGTACCAACGGCAGCATCACCGTGGCCGCCACCGCCCCCACCGTGACCCCACCGTGAACG
CCACCCCCAGCGCCGCCGCTAGCTGA
```

D-type Cyclin Antigen. D-type cyclins are predominantly expressed in the G1 phase of the cell cycle. The expression pattern of cyclin D1 has been extensively studied in certain cancer types including lymphoma and non-small cell lung cancer. Approximately 30 percent of breast carcinomas are Cyclin D1 positive. Over expression of Cyclin D1 is now a well established criterion for the diagnosis of Mantle Cell Lymphoma, a malignant, non-Hodgkin's lymphoma which is characterized by a unique chromosomal translocation t(11;14).

Cyclin D1—Peptide 1—bold, Peptide 2—bold-underlined, Peptide-3 italics, Peptide 4—underlined.

(SEQ ID NO.: 140)
MEHQLLCCEVETIRRAYPDANLLNDRVLRAMLKAEETCAPSVSYFKCVQK
EVLPSMRKIVATWMLEVCEEQKCEEEVFPLAMNYLDRFLSLEPVKKSRLQ
LLGATCMFVASKMKETIPLTAEKLCIYTDNSIRPEELLQMELLLVNKLKW
NLAAMTPHDFIEHFLSKMPEAEENKQIIRKHAQTFVALCATDVKFISNPP

*SMV*AAGSVVAAVQGLNLRSPNNFLSYYRLTRFLSRVIKCDPDCLRACQEQ
IEALLESSLRQAQQNMDPKAAEEEEEEEEVDLACTPTDVRDVDI

Pep-1:

(SEQ ID NO.: 141)
MEHQLLCCEVETIRRAYPDANLLNDRVLRAMLKAEETCAPSVSYFKCV

Pep-2

(SEQ ID NO.: 142)
QKEVLPSMRKIVATWMLEVCEEQKCEEEVFPLAMNYLDRFLSLEPVKKSR
LQLLGATCMFVASKMKETIPLTAEKLCIYTDNSIRPEELLQMELL

Pep-3

(SEQ ID NO.: 143)
LVNKLKWNLAAMTPHDFIEHFLSKMPEAEENKQIIRKHAQTFVALCATDV
KFISNPPSMV

Pep-4

(SEQ ID NO.: 144)
AAGSVVAAVQGLNLRSPNNFLSYYRLTRFLSRVIKCDPDCLRACQEQIEA

LLESSLRQAQQNMDPKAAEEEEEEEEVDLACTPTDVRDVDI

Flex-4 Sequence

TNGSITVAATAPTVTPTVNATPSAA (SEQ ID NO.: 14)

Flex-3 Sequence

TVTPTATATPSAIVTTITPTATTKP (SEQ ID NO.: 13)

Flex-Var1

QTPTNTISVTPTNNSTPTNNSNPKPNP (SEQ ID NO.: 145)

FIG. 35 shows Cyclin B1 segmentation strategy based on known or predicted structural domain regions.

Figure 36:
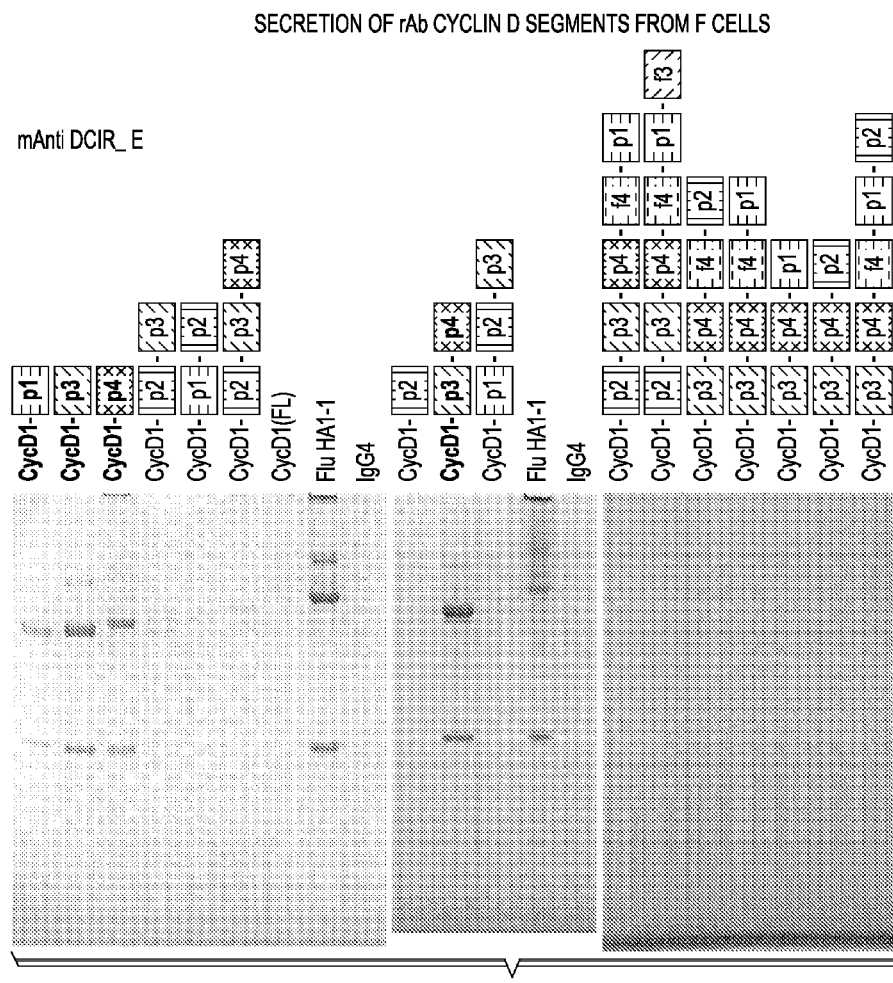
FIG. 36 shows that Cyclin D1 segments p1, p3, and p4, but not p2 express well as direct fusions to the H chain C-terminus.

FIG. 36 shows that Cyclin D1 segments p1, p3, and p4, but not p2 express well as direct fusions to the H chain C-terminus. These are transient transfections of the H chain vectors co-transfected with the L chain expression vector into 293F cells and the supernatants harvested after 48-72 hours of expression. The Cyclin D1 p3+p4 segments joined together at the H chain C-terminus also express well, but various other combinations, with and without interspersed flex segments do not express, or express very poorly.

Figure 37:
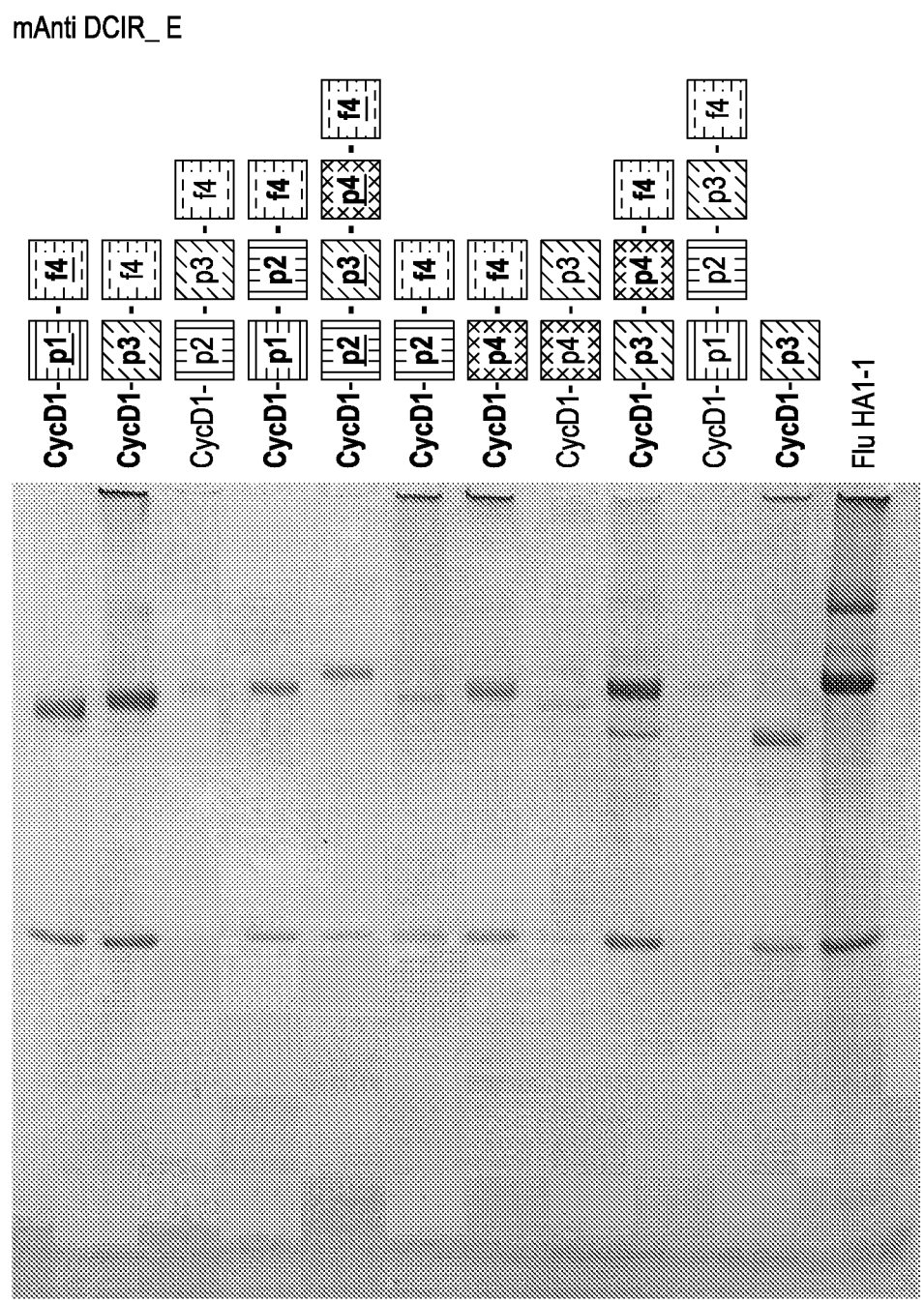
FIG. 37 shows the relative expression levels of various Cyclin D1 segments as direct fusions to the H chain C-terminus in various combinations with flexible linker sequences.

FIG. 37 shows the relative expression levels of various Cyclin D1 segments as direct fusions to the H chain C-terminus in various combinations with flexible linker sequences. These are transient transfections of the H chain vectors co-transfected with the L chain expression vector into 293F cells and the supernatants harvested after 48-72 hours of expression. The Cyclin D1 p2+p3+p4+f4 segments joined together at the H chain C-terminus also express well enough for vaccine production.

Sequences of useful anti-DCIR 9E8—cyclin D1H chain fusion proteins are below.

1082 is rAB-pIRES2[mAnti-DCIR__9E8_H-LV-hIgG4H-C-Flex-v1 (bold)-hCyclinD1-Pep-1 (italics)-f4 (bold)-]

QVTLKESGPGILQPSQTLSLTCSFSGFSLSTSGMGLSWIRQPSGKGLEWL (SEQ ID NO.: 146)

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>QTPTNTISVTPTNNSTPTNNSNPKPNP<u>AS</u>*MEHQLLCCEVETIRRAYPDAN*

*LLNDRVLRAMLKAEETCAPSVSYFKCV*<u>AS</u>TNGSITVAATAPTVTPTVNATPSAA<u>AS</u>

C1086 is rAB-pIRES2[mAnti-DCIR__9E8_H-LV-hIgG4H-C-Flex-v1 (bold)-hCyclinD1-Pep-2—(bold)-Pep-3 (bold-underlined)-Pep-4 (italics)-f4)(bold)]

(SEQ ID NO.: 147)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>QTPTNTISVTPTNNSTPTNNSNPKPNP<u>AS</u>QKEVLPSMRKIVATWML

EVCEEQKCEEEVFPLAMNYLDRFLSLEPVKKSRLQLLGATCMFVASKMKE

TIPLTAEKLCIYTDNSIRPEELLQMELL<u>LVNKLKWNLAAMTPHDFIEHFL</u>

<u>SKMPEAEENKQIIRKHAQTFVALCATDVKFISNPPSMV</u>*AAGSVVAAVQGL*

*NLRSPNNFLSYYRLTRFLSRVIKCDPDCLRACQEQIEALLESSLRQAQQN*

*MDPKAAEEEEEEEEVDLACTPTDVRDVDI*<u>AS</u>TNGSITVAATAPTVTPTV

NATPSAA<u>AS</u>

Figure 38:
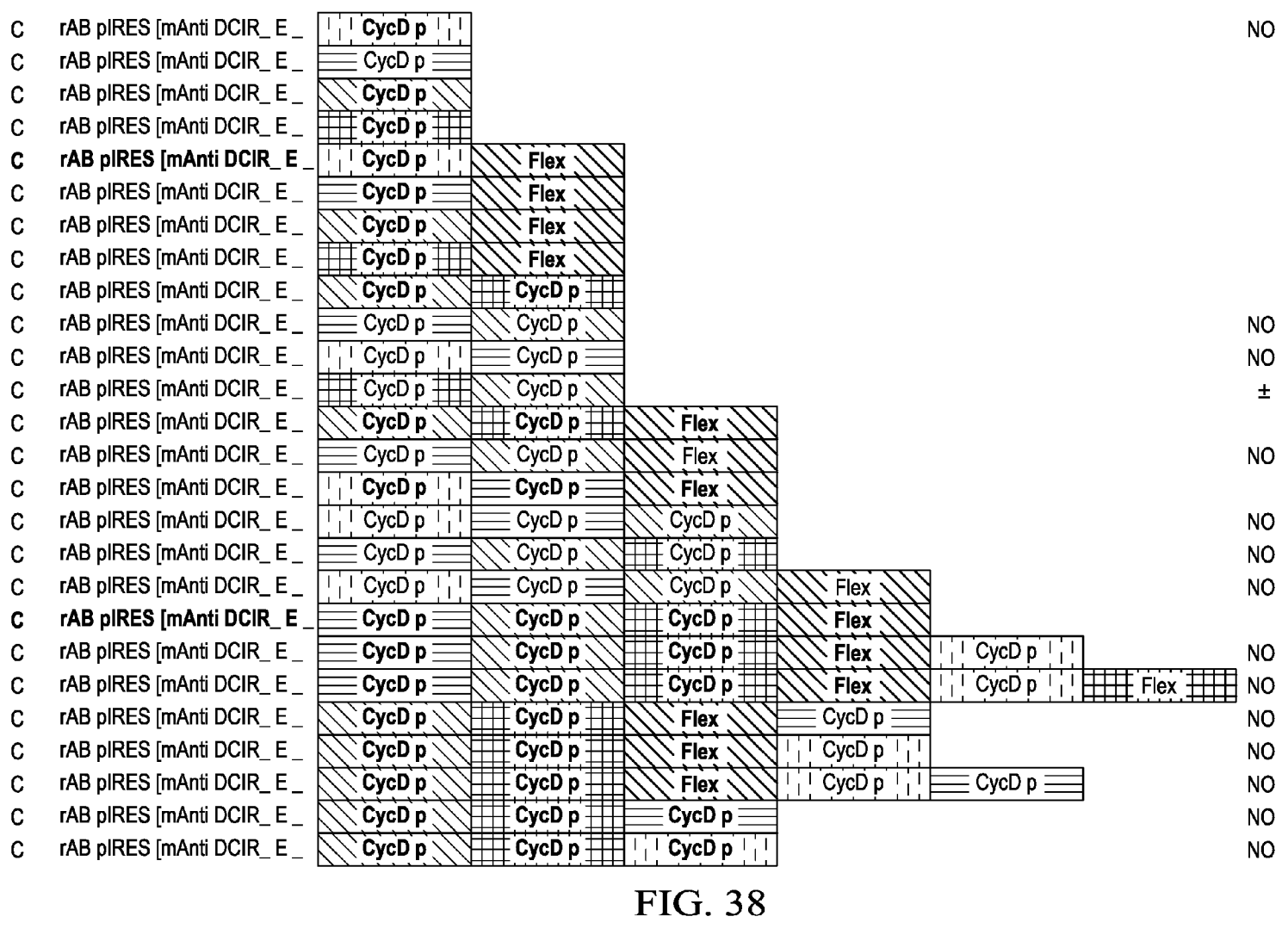

FIG. 38 show a summary of various H chain-Cyclin D1 segment constructs and their relative expressibility as vaccines.

Figure 39:
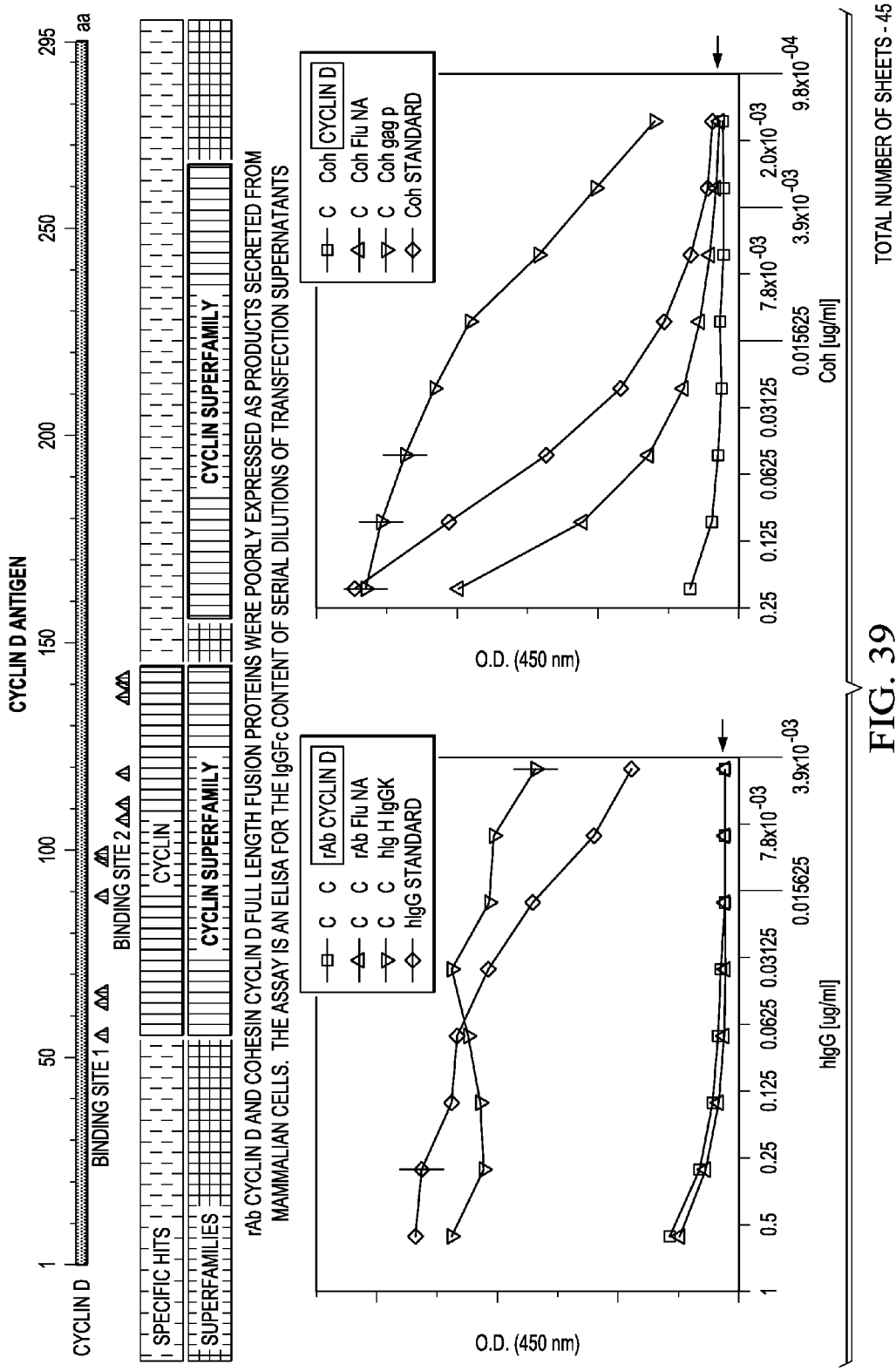
FIG. 39 shows that full-length Cyclin D1 fused to the C-terminus of a DC targeting antibody H chain is very poorly expressed as a secreted recombinant antibody.

FIG. 39 above shows that full-length Cyclin D1 fused to the C-terminus of a DC targeting antibody H chain is very poorly expressed as a secreted recombinant antibody.

anti-CD40__12E12.3F3 anti-CD40__12E12.3F3_H-V-hIgG4H-C—underlined region shows the Heavy chain V region amino acid sequence:

(SEQ ID NO.: 148)
MNLGLSLIFLVLVLKGVQC<u>EVKLVESGGGLVQPGGSLKLSCATSGFTFSD</u>
<u>YYMYWVRQTPEKRLEWVAYINSGGGSTYYPDTVKGRFTISRDNAKNTLYL</u>
<u>QMSRLKSEDTAMYYCARRGLPFHAMDYWGQGTSVTFVS</u>SAKTKGPSVFPL
APCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPPCPA
PEFEGGPSVFLFPPKPKDTLMISRTPEVTCVVVDVSQEDPEVQFNWYVDG
VEVHNAKTKPREEQFNSTYRVVSVLTVLHQDWLNGKEYKCKVSNKGLPSS
IEKTISKAKGQPREPQVYTLPPSQEEMTKNQVSLTCLVKGFYPSDIAVEW
ESNGQPENNYKTTPPVLDSDGSFFLYSRLTVDKSRWQEGNVFSCSVMHEA
LHNHYTQKSLSLSLGKAS anti-CD40__12E12.3F3_K-V-hIgGK-C—underlined region shows the Light chain V region amino acid sequence (SEQ ID NO.: 149)
MMSSAQFLGLLLLCFQGTRC<u>DIQMTQTTSSLSASLGDRVTISCSASQGIS</u>
<u>NYLNWYQQKPDGTVKLLIYYTSILHSGVPSRFSGSGSGTDYSLTIGNLEP</u>
<u>EDIATYYCQQFNKLPPTFGGGTKLEIK</u>RTVAAPSVFIFPPSDEQLKSGTA
SVVCLLNNFYPREAKVQWKVDNALQSGNSQESVTEQDSKDSTYSLSSTLT
LSKADYEKHKVYACEVTHQGLSSPVTKSFNRGECanti-CD40__12B4.2C10
anti-CD40__12B4.2C10 Heavy Chain:

(SEQ ID No.: 150)
MEWSWIFLFLLSGTAGVHSEVQLQQSGPELVKPGASVKMSCKASGYTFTD
YVLHWVKQKPGQGLEWIGYINPYNDGTKYNEKFKGKATLTSDKSSSTAYM
ELSSLTSEDSAVYYCARGYPAYSGYAMDYWGQGTSVTVSSAKT<u>TPP</u>SVYP
LAPGSAAQTNSMVTLGCLVKGYFPEPVTVTWNSGSLSSGVHTFPAVLQKG
EFV anti-CD40__12B4.2C10 Light Chain:

(SEQ ID No.: 151)
MMSSAQFLGLLLLCFQGTRCDIQMTQTTSSLSASLGDRVTISCRASQDIS
NYLNWYQQKPDGTVKLLIYYTSRLHSGVPSRFSGSGSGTDYSLTISN<u>LEQ</u>
EDIATYFCHHGNTLPWTFGGGTKLEIKRADAAPTVSIFPPSSEQLTSGGA
SVVCFLNNFYPKDINVKWKIDGSERQNGVLNSWTDQDSKDSTYSMSSTLT
LTKDEYERHNSYTCEATHKTSTSPIVKSFNRNEC anti-CD40__12B4.2C10 Light Chain—alternative clone (17K6)

(SEQ ID No.: 152)
MDFQVQIFSFLLISASVIMSRGQIVLTQSPAILSASPGEKVTMTCSASSS
VSYMRYQQKPGSSPKPWIYGTSNLASGVPARFSGSGSGTSYSLTISSME
AEDAATYYCQQYHSYPLTFGAGTK<u>LEL</u>KRADAAPTVSIFPPSSEQLTSGG
ASVVCFLNNFYPKDINVKWKIDGSERQNGVLNSWTDQDSKDSTYSMSSTL
TLTKDEYERHNSYTCEATHKTSTSPIVKSFNREC anti-CD40__11B6.1C3
anti-CD40__11B6.1C3 Heavy Chain:

(SEQ ID No.: 153)
MGWSWIFLFLLSGTAGVLSEVQLQQSGPELVKPGASVKISCKASGYSFTG
YYMHWVKQSHVKSLEWIGRINPYNGATSYNQNFKDKASLTVDKSSSTAYM
ELHSLTSEDSAVYYCAREDYVYWGQGTTLTVSSAKT<u>TPP</u>SVYPLAPGSAA
QTNSMVTLGCLVKGYFPEPVTVTWNSGSLSSGVHTFPAVLQKGEFV anti-CD40__11B6.1C3 Light Chain:

(SEQ ID No.: 154)
MKLPVRLLVLMFWIPASSSDVVMTQTPLSLPVSLGDQASISCRSSQSLVH
SNGNTYLHWYLQKPGQSPKLLIYKVSNRFSGVPDRFSGSGSGTDFALKIS
RVEAEDLGVYFCSQSTHVPWTFGGGTK<u>LEI</u>KRADAAPTVSIFPPSEQLTS
GGASVVCFLNNFYPKDINVKWKIDGSERQNGVLNSWTDQDSKDSTYSMSS
TLTLTKDEYERHNSYTCEATHKTSTSPIVKSFNRNEC

[anti-CD40__12E12.3F3_K-V-hIgGK-C]—underlined region shows the Light chain V region sequence (SEQ ID NO.: 155)
ATGATGTCCTCTGCTCAGTTCCTTGGTCTCCTGTTGCTCTGTTTTCAAGG
TACCAGATGTGATATCCAGATGACACAGACTACATCCTCCCTGTCTGCCT
CTCTAGGAGACAGAGTCACCATCAGTTGCAGTGCAAGTCAGGGCATTAGC
AATTATTTAAACTGGTATCAGCAGAAACCAGATGGAACTGTTAAACTCCT
GATCTATTACACATCAATTTTACACTCAGGAGTCCCATCAAGGTTCAGTG
GCAGTGGGTCTGGGACAGATTATTCTCTCACCATCGGCAACCTGGAACCT
GAAGATATTGCCACTTACTATTGTCAGCAGTTTAATAAGCTTCCTCCGAC
GTTCGGTGGAGGCACCAAACTCGAGATCAAACGAACTGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTATGCCTGCGAAGTCAC
CCATCAGGGCCTGAGCTCGCCCGTCACAAAGAGCTTCAACAGGGGAGAGT
GTTAG

[anti-CD40__12E12.3F3_H-V-hIgG4H-C]—underlined region shows the Heavy chain V region sequence:

(SEQ ID NO.: 156)
ATGAACTTGGGGCTCAGCTTGATTTTCCTTGTCCTTGTTTTAAAAGGTGT
CCAGTGTGAAGTGAAGCTGGTGGAGTCTGGGGGAGGCTTAGTGCAGCCTG
GAGGGTCCCTGAAACTCTCCTGTGCAACCTCTGGATTCACTTTCAGTGAC
TATTACATGTATTGGGTTCGCCAGACTCCAGAGAAGAGGCTGGAGTGGGT

CGCATACATTAATTCTGGTGGTGGTAGCACCTATTATCCAGACACTGTAA
AGGGGCCGATTCACCATCTCCAGAGACAATGCCAAGAACACCCTGTACCTG
CAAATGAGCCGGCTGAAGTCTGAGGACACAGCCATGTATTACTGTGCAAG
ACGGGGGTTACCGTTCCATGCTATGGACTATTGGGGTCAAGGAACCTCAG
TCACCGTCTCCTCAGCCAAAACGAAGGGCCCATCCGTCTTCCCCCTGGCG
CCCTGCTCCAGGAGCACCTCCGAGAGCACAGCCGCCCTGGGCTGCCTGGT
CAAGGACTACTTCCCCGAACCGGTGACGGTGTCGTGGAACTCAGGCGCCC
TGACCAGCGGCGTGCACACCTTCCCGGCTGTCCTACAGTCCTCAGGACTC
TACTCCCTCAGCAGCGTGGTGACCGTGCCCTCCAGCAGCTTGGGCACGAA
GACCTACACCTGCAACGTAGATCACAAGCCCAGCAACACCAAGGTGGACA
AGAGAGTTGAGTCCAAATATGGTCCCCCATGCCCACCCTGCCCAGCACCT
GAGTTCGAAGGGGGACCATCAGTCTTCCTGTTCCCCCCAAAACCCAAGGA
CACTCTCATGATCTCCCGGACCCCTGAGGTCACGTGCGTGGTGGTGGACG
TGAGCCAGGAAGACCCCGAGGTCCAGTTCAACTGGTACGTGGATGGCGTG
GAGGTGCATAATGCCAAGACAAAGCCGCGGGAGGAGCAGTTCAACAGCAC
GTACCGTGTGGTCAGCGTCCTCACCGTCCTGCACCAGGACTGGCTGAACG
GCAAGGAGTACAAGTGCAAGGTCTCCAACAAAGGCCTCCCGTCCTCCATC
GAGAAAACCATCTCCAAAGCCAAAGGGCAGCCCCGAGAGCCACAGGTGTA
CACCCTGCCCCCATCCCAGGAGGAGATGACCAAGAACCAGGTCAGCCTGA
CCTGCCTGGTCAAAGGCTTCTACCCCAGCGACATCGCCGTGGAGTGGGAG
AGCAATGGGCAGCCGGAGAACAACTACAAGACCACGCCTCCCGTGCTGGA
CTCCGACGGCTCCTTCTTCCTCTACAGCAGGCTAACCGTGGACAAGAGCA
GGTGGCAGGAGGGGAATGTCTTCTCATGCTCCGTGATGCATGAGGCTCTG
CACAACCACTACACACAGAAGAGCCTCTCCCTGTCTCTGGGTAAAGCTAG
CTGA anti-CD40__12B4.2C10_H-V-hIgG4H-C heavy chain (SEQ ID NO.: 157)
ATGGAATGGAGTTGGATATTTCTCTTTCTTCTGTCAGGAACTGCAGGTGT
CCACTCTGAGGTCCAGCTGCAGCAGTCTGGACCTGAGCTGGTAAAGCCTG
GGGCTTCAGTGAAGATGTCCTGCAAGGCTTCTGGATACACATTCACTGAC
TATGTTTTGCACTGGGTGAAACAGAAGCCTGGGCAGGGCCTTGAGTGGAT
TGGATATATTAATCCTTACAATGATGGTACTAAGTACAATGAGAAGTTCA
AAGGCAAGGCCACACTGACTTCAGACAAATCCTCCAGCACAGCCTACATG
GAGCTCAGCAGCCTGACCTCTGAGGACTCTGCGGTCTATTACTGTGCAAG
GGGCTATCCGGCCTACTCTGGGTATGCTATGGACTACTGGGGTCAAGGAA
CCTCAGTCACCGTCTCCTCAGCCAAAACG<u>AAGGGCCCA</u>TCCGTCTTCCCC
CTGGCGCCCTGCTCCAGGAGCACCTCCGAGAGCACAGCCGCCCTGGGCTG
CCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGG
CACGAAGACCTACACCTGCAACGTAGATCACAAGCCCAGCAACACCAAGG
TGGACAAGAGAGTTGAGTCCAAATATGGTCCCCCATGCCCACCCTGCCCA
GCACCTGAGTTCGAAGGGGACCATCAGTCTTCCTGTTCCCCCCAAAACC
CAAGGACACTCTCATGATCTCCCGGACCCCTGAGGTCACGTGCGTGGTGG
TGGACGTGAGCCAGGAAGACCCCGAGGTCCAGTTCAACTGGTACGTGGAT
GGCGTGGAGGTGCATAATGCCAAGACAAAGCCGCGGGAGGAGCAGTTCAA
CAGCACGTACCGTGTGGTCAGCGTCCTCACCGTCCTGCACCAGGACTGGC
TGAACGGCAAGGAGTACAAGTGCAAGGTCTCCAACAAAGGCCTCCCGTCC
TCCATCGAGAAAACCATCTCCAAAGCCAAAGGGCAGCCCCGAGAGCCACA
GGTGTACACCCTGCCCCCATCCCAGGAGGAGATGACCAAGAACCAGGTCA
GCCTGACCTGCCTGGTCAAAGGCTTCTACCCCAGCGACATCGCCGTGGAG
TGGGAGAGCAATGGGCAGCCGGAGAACAACTACAAGACCACGCCTCCCGT
GCTGGACTCCGACGGCTCCTTCTTCCTCTACAGCAGGCTAACCGTGGACA
AGAGCAGGTGGCAGGAGGGGAATGTCTTCTCATGCTCCGTGATGCATGAG
GCTCTGCACAACCACTACACACAGAAGAGCCTCTCCCTGTCTCTGGGTAA
AGCTAGCTGA anti-CD40__12B4.2C10_K-V-hIgGK-C (variant 1) light chain (SEQ ID NO.: 158)
ATGGATTTTCAAGTGCAGATTTTCAGCTTCCTGCTAATCAGTGCCTCAGT
CATAATGTCCAGGGGACAAATTGTTCTCACCCAGTCTCCAGCAATCCTGT
CTGCATCTCCAGGGGAGAAGGTCACCATGACCTGCAGTGCCAGCTCAAGT
GTAAGTTACATGTACAGGTACCAGCAGAAGCCAGGATCCTCACCCAAACC
CTGGATTTATGGCACATCCAACCTGGCTTCTGGAGTCCCTGCTCGCTTCA
GTGGCAGTGGATCTGGGACCTCTTATTCTCTCACAATCAGCAGCATGGAG
GCTGAAGATGCTGCCACTTATTACTGCCAGCAATATCATAGTTACCCGCT
CACGTTCGGTGCTGGGACCAAG<u>CTCGAG</u>ATCAAACGAACTGTGGCTGCAC
CATCTGTCTTCATCTTCCCGCCATCTGATGAGCAGTTGAAATCTGGAACT
GCCTCTGTTGTGTGCCTGCTGAATAACTTCTATCCCAGAGAGGCCAAAGT
ACAGTGGAAGGTGGATAACGCCCTCCAATCGGGTAACTCCCAGGAGAGTG
TCACAGAGCAGGACAGCAAGGACAGCACCTACAGCCTCAGCAGCACCCTG
ACGCTGAGCAAAGCAGACTACGAGAAACACAAAGTCTATGCCTGCGAAGT
CACCCATCAGGGCCTGAGCTCGCCCGTCACAAAGAGCTTCAACAGGGGAG
AGTGTTAG anti-CD40__12B4.2C10_K-V-hIgGK-C (Variant 2) light chain (SEQ ID NO.: 159)
ATGATGTCCTCTGCTCAGTTCCTTGGTCTCCTGTTGCTCTGTTTTCAAGG
TACCAGATGTGATATCCAGATGACACAGACTACATCCTCCCTGTCTGCCT
CTCTGGGAGACAGAGTCACCATCAGTTGCAGGGCAAGTCAGGACATTAGC -continued
AATTATTTAAACTGGTATCAGCAGAAACCAGATGGAACTGTTAAACTCCT

GATCTACTACACATCAAGATTACACTCAGGAGTCCCATCAAGGTTCAGTG

GCAGTGGGTCTGGAACAGATTATTCTCTCACCATTAGCAACCTGGAGCAA

GAAGATATTGCCACTTACTTTTGCCATCATGGTAATACGCTTCCGTGGAC

GTTCGGTGGAGGCACCAAG<u>CTCGAG</u>ATCAAACGAACTGTGGCTGCACCAT

CTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG

CTGAGCAAAGCAGACTACGAGAAACACAAAGTCTATGCCTGCGAAGTCAC

CCATCAGGGCCTGAGCTCGCCCGTCACAAAGAGCTTCAACAGGGGAGAGT

GTTAG anti-CD40__11B6.1C3_H-V-hIgG4H-C heavy chain (SEQ ID NO.: 160)
ATGGGATGGAGCTGGATCTTTCTCTTTCTCCTGTCAGGAACTGCAGGTGT

CCTCTCTGAGGTCCAGCTGCAACAGTCTGGACCTGAGCTGGTGAAGCCTG

GGGCTTCAGTGAAGATATCCTGCAAGGCTTCTGGTTACTCATTCACTGGC

TACTACATGCACTGGGTGAAGCAAAGCCATGTAAAGAGCCTTGAGTGGAT

TGGACGTATTAATCCTTACAATGGTGCTACTAGCTACAACCAGAATTTCA

AGGACAAGGCCAGCTTGACTGTAGATAAGTCCTCCAGCACAGCCTACATG

GAGCTCCACAGCCTGACATCTGAGGACTCTGCAGTCTATTACTGTGCAAG

AGAGGACTACGTCTACTGGGGCCAAGGCACCACTCTCACAGTCTCCTCAG

CCAAAACG<u>AAGGGCCC</u>ATCCGTCTTCCCCCTGGCGCCCTGCTCCAGGAGC

ACCTCCGAGAGCACAGCCGCCCTGGGCTGCCTGGTCAAGGACTACTTCCC

CGAACCGGTGACGGTGTCGTGGAACTCAGGCGCCCTGACCAGCGGCGTGC

ACACCTTCCCGGCTGTCCTACAGTCCTCAGGACTCTACTCCCTCAGCAGC

GTGGTGACCGTGCCCTCCAGCAGCTTGGGCACGAAGACCTACACCTGCAA

CGTAGATCACAAGCCCAGCAACACCAAGGTGGACAAGAGAGTTGAGTCCA

AATATGGTCCCCCATGCCCACCCTGCCCAGCACCTGAGTTCGAAGGGGGA

CCATCAGTCTTCCTGTTCCCCCCAAAACCCAAGGACACTCTCATGATCTC

CCGGACCCCTGAGGTCACGTGCGTGGTGGTGGACGTGAGCCAGGAAGACC

CCGAGGTCCAGTTCAACTGGTACGTGGATGGCGTGGAGGTGCATAATGCC

AAGACAAAGCCGCGGGAGGAGCAGTTCAACAGCACGTACCGTGTGGTCAG

CGTCCTCACCGTCCTGCACCAGGACTGGCTGAACGGCAAGGAGTACAAGT

GCAAGGTCTCCAACAAAGGCCTCCCGTCCTCCATCGAGAAAACCATCTCC

AAAGCCAAAGGGCAGCCCCGAGAGCCACAGGTGTACACCCTGCCCCCATC

CCAGGAGGAGATGACCAAGAACCAGGTCAGCCTGACCTGCCTGGTCAAAG

GCTTCTACCCCAGCGACATCGCCGTGGAGTGGGAGAGCAATGGGCAGCCG

GAGAACAACTACAAGACCACGCCTCCCGTGCTGGACTCCGACGGCTCCTT

CTTCCTCTACAGCAGGCTAACCGTGGACAAGAGCAGGTGGCAGGAGGGGA

ATGTCTTCTCATGCTCCGTGATGCATGAGGCTCTGCACAACCACTACACA

CAGAAGAGCCTCTCCCTGTCTCTGGGTAAAGCTAGCTGA anti-CD40__11B6.1C3_K-V-hIgGK-C light chain (SEQ ID NO.: 161)
ATGAAGTTGCCTGTTAGGCTGTTGGTGCTGATGTTCTGGATTCCTGCTTC

CAGCAGTGATGTTGTGATGACCCAAACTCCACTCTCCCTGCCTGTCAGTC

TTGGAGATCAAGCCTCCATCTCTTGCAGATCTAGTCAGAGCCTTGTACAC

AGTAATGGAAACACCTATTTACATTGGTACCTGCAGAAGCCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCGCACTCAAGATCAGT

AGAGTGGAGGCTGAGGATCTGGGAGTTTATTTCTGCTCTCAAAGTACACA

TGTTCCGTGGACGTTCGGTGGAGGCACCAAG<u>CTCGAG</u>ATCAAACGAACTG

TGGCTGCACCATCTGTCTTCATCTTCCCGCCATCTGATGAGCAGTTGAAA

TCTGGAACTGCCTCTGTTGTGTGCCTGCTGAATAACTTCTATCCCAGAGA

GGCCAAAGTACAGTGGAAGGTGGATAACGCCCTCCAATCGGGTAACTCCC

AGGAGAGTGTCACAGAGCAGGACAGCAAGGACAGCACCTACAGCCTCAGC

AGCACCCTGACGCTGAGCAAAGCAGACTACGAGAAACACAAAGTCTATGC

CTGCGAAGTCACCCATCAGGGCCTGAGCTCGCCCGTCACAAAGAGCTTCA

ACAGGGGAGAGTGTTAG

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A fusion protein comprising the formula:
Ab-(Ag-PL-Ag)x;
wherein Ab is an antibody or fragment thereof comprising at least the variable region of the antibody anti-CD40_12B4.2C10 (ATCC Submission No. HS446, Accession No. PTA-10653) or of the antibody anti-CD40_11B6.1C3 (ATCC Submission No. HS440, Accession No. PTA-10652);
wherein PL is at least one peptide linker comprising at least one glycosylation site;
wherein Ag is at least one antigen, at least one of which is SEQ ID NO:5; and
wherein x is an integer from 1 to 20, the fusion protein having more stability in solution than the same fusion protein without the glycosylation site.

2. The fusion protein of claim 1, wherein at least one of the Ag or the PL is a peptide concatemer.

3. The fusion protein of claim 1, wherein the -(Ag-PL-Ag)x is located at the carboxy terminus of the Ab heavy chain or fragment thereof.

4. The fusion protein of claim 1, wherein the Ag elicits at least one of a humoral or a cellular immune response in a host.

5. The fusion protein of claim 1, wherein the Ab comprises variable domains having sequence identity with a heavy chain variable domain of SEQ ID NOS: 150 or 153 or light chain variable domains of SEQ ID NOS: 151, 152 or 154, or both.

6. The fusion protein of claim 1, wherein x comprises 1, 2, 3, 4, 5, 6, 7, 8, 9, 10, 11, 12, 13, 14, 15, 16, 17, 18, or 19.

7. The fusion protein of claim 1, wherein the Ab is an antibody fragment selected from Fv, Fab, Fab', F(ab')$_2$, Fc, or a ScFv.

8. The fusion protein of claim 1, wherein the Ab binds specifically to CD40.

9. The fusion protein of claim 1, wherein the Ab is an IgA, IgD, IgE, IgG or IgM or isotype thereof.

10. The fusion protein of claim 1, wherein the Ab is a human antibody or a humanized antibody.

11. The fusion protein of claim 1, wherein the Pl, comprises an alanine and a serine.

12. The fusion protein of claim 1, wherein the PL is: SSVSPTTSVHPTPTSVPPTPTKSSP (SEQ ID NO: 11).

13. A stable, secretable fusion protein comprising the formula:

NH$_2$-Ab-(Ag-PL-Ag)x-COON;

wherein Ab is an antibody or fragment thereof comprising at least the variable region of the antibody anti-CD40_12B4.2C10 (ATCC Submission No. HS446, Accession No. PTA-10653) or of the antibody anti-CD40_11B6.1C3 (ATCC Submission No. HS440, Accession No. PTA-10652);

wherein PL is at least one peptide linker comprising at least one glycosylation site;

wherein Ag is at least one immunogenic antigen, at least one of which is SEQ ID NO: 5; and wherein x is an integer from 1 to 20, the fusion protein being stable and soluble in solution as compared to an Ab-Ag protein alone that is not soluble or stable.

14. A pharmaceutical composition comprising the fusion protein of claim 1.

15. A fusion protein comprising the formula:

Ab-(Ag-PL-Ag)x;

wherein Ab is an antibody or fragment thereof comprising at least the variable region of the antibody anti-CD40_12B4.2C10 (ATCC Submission No. HS446, Accession No. PTA-10653) or of the antibody anti-CD40_11B6.1C3 (ATCC Submission No. HS440, Accession No. PTA-10652);

wherein PL is at least one peptide linker comprising at least one glycosylation site;

wherein Ag is at least one antigen, at least one of which is SEQ ID NO:5; and wherein x is an integer from 1 to 20; and wherein the fusion protein has more stability in solution than the same fusion protein without the glycosylation site.

16. The fusion protein of claim 1, further comprising at least one other Ag selected from SEQ ID NOS: 1-4.

17. The stable, secretable fusion protein of claim 13, further comprising at least one other Ag selected from SEQ ID NOS: 1-4.

18. The fusion protein of claim 15, further comprising at least one other Ag selected from SEQ ID NOS: 1-4.

* * * * *

UNITED STATES PATENT AND TRADEMARK OFFICE
CERTIFICATE OF CORRECTION

PATENT NO. : 8,961,991 B2  
APPLICATION NO. : 12/717789  
DATED : February 24, 2015  
INVENTOR(S) : Gerard Zurawski et al.

Page 1 of 1

It is certified that error appears in the above-identified patent and that said Letters Patent is hereby corrected as shown below:

In the Claims

Column 278, Claim 11, on line 64, delete "PI" and insert -- PL -- therefor.

Column 279, Claim 13, on line 3, delete "COON" and insert -- COOH -- therefor.

Signed and Sealed this  
Eleventh Day of August, 2015

Michelle K. Lee  
*Director of the United States Patent and Trademark Office*

SEQUENCE LISTING

```
<160> NUMBER OF SEQ ID NOS: 161

<210> SEQ ID NO 1
<211> LENGTH: 32
<212> TYPE: PRT
<213> ORGANISM: Artificial Sequence
<220> FEATURE:
<223> OTHER INFORMATION: Synthetic peptide.

<400> SEQUENCE: 1

Val Gly Phe Pro Val Thr Pro Gln Val Pro Leu Arg Pro Met Thr Tyr
1               5                   10                  15

Lys Ala Ala Val Asp Leu Ser His Phe Leu Lys Glu Lys Gly Gly Leu
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic peptide.

<400> SEQUENCE: 2

His Thr Gln Gly Tyr Phe Pro Asp Trp Gln Asn Tyr Thr Pro Gly Pro
1               5                   10                  15

Gly Val Arg Tyr Pro Leu Thr Phe Gly Trp Leu Tyr Lys Leu
            20                  25                  30

<210> SEQ ID NO 3
<211> LENGTH: 19
<212> TYPE: PRT
<213> ORGANISM: Artificial Sequence
<220> FEATURE:
<223> OTHER INFORMATION: Synthetic peptide.

<400> SEQUENCE: 3

Glu Lys Ile Arg Leu Arg Pro Gly Gly Lys Lys Lys Tyr Lys Leu Lys
1               5                   10                  15

His Ile Val

<210> SEQ ID NO 4
<211> LENGTH: 32
<212> TYPE: PRT
<213> ORGANISM: Artificial Sequence
<220> FEATURE:
<223> OTHER INFORMATION: Synthetic peptide.
```

```
<400> SEQUENCE: 4

Asn Pro Pro Ile Pro Val Gly Glu Ile Tyr Lys Arg Trp Ile Ile Leu
1               5                   10                  15

Gly Leu Asn Lys Ile Val Arg Met Tyr Ser Pro Thr Ser Ile Leu Asp
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic peptide.

<400> SEQUENCE: 5

Ala Ile Phe Gln Ser Ser Met Thr Lys Ile Leu Glu Pro Phe Arg Lys
1               5                   10                  15

Gln Asn Pro Asp Ile Val Ile Tyr Gln Tyr Met Asp Asp Leu Tyr
            20                  25                  30

<210> SEQ ID NO 6
<211> LENGTH: 475
<212> TYPE: PRT
<213> ORGANISM: Artificial Sequence
<220> FEATURE:
<223> OTHER INFORMATION: Synthetic peptide.

<400> SEQUENCE: 6

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Tyr Phe
            100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Glu
225                 230                 235                 240
```

```
Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Glu Lys Ile Arg Leu Arg Pro Gly Gly Lys
    450                 455                 460

Lys Lys Tyr Lys Leu Lys His Ile Val Ala Ser
465                 470                 475

<210> SEQ ID NO 7
<211> LENGTH: 488
<212> TYPE: PRT
<213> ORGANISM: Artificial Sequence
<220> FEATURE:
<223> OTHER INFORMATION: Synthetic peptide.

<400> SEQUENCE: 7

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
        115                 120                 125
```

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Asn Pro Pro Ile Pro Val Gly Glu Ile Tyr
450                 455                 460

Lys Arg Trp Ile Ile Leu Gly Leu Asn Lys Ile Val Arg Met Tyr Ser
465                 470                 475                 480

Pro Thr Ser Ile Leu Asp Ala Ser
                485

<210> SEQ ID NO 8
<211> LENGTH: 486
<212> TYPE: PRT
<213> ORGANISM: Artificial Sequence
<220> FEATURE:
<223> OTHER INFORMATION: Synthetic peptide.

<400> SEQUENCE: 8

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Tyr Phe
            100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
```

```
                    420                 425                 430
Met His Glu Ala Leu His Asn His Tyr Thr Gln Lys Ser Leu Ser Leu
                435                 440                 445

Ser Leu Gly Lys Ala Ser His Thr Gln Gly Tyr Phe Pro Asp Trp Gln
            450                 455                 460

Asn Tyr Thr Pro Gly Pro Gly Val Arg Tyr Pro Leu Thr Phe Gly Trp
465                 470                 475                 480

Leu Tyr Lys Leu Ala Ser
                485

<210> SEQ ID NO 9
<211> LENGTH: 488
<212> TYPE: PRT
<213> ORGANISM: Artificial Sequence
<220> FEATURE:
<223> OTHER INFORMATION: Synthetic peptide.

<400> SEQUENCE: 9

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Gly Met Gly Leu Ser Trp Ile Arg Gln Pro Ser Gly Lys Gly Leu Glu
            35                  40                  45

Trp Leu Ala His Ile Tyr Trp Asp Asp Asp Lys Arg Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Gly Tyr Phe
                100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
```

```
                290                 295                 300
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
                435                 440                 445

Ser Leu Gly Lys Ala Ser Val Gly Phe Pro Val Thr Pro Gln Val Pro
                450                 455                 460

Leu Arg Pro Met Thr Tyr Lys Ala Ala Val Asp Leu Ser His Phe Leu
465                 470                 475                 480

Lys Glu Lys Gly Gly Leu Ala Ser
                485

<210> SEQ ID NO 10
<211> LENGTH: 487
<212> TYPE: PRT
<213> ORGANISM: Artificial Sequence
<220> FEATURE:
<223> OTHER INFORMATION: Synthetic peptide.

<400> SEQUENCE: 10

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Gly Met Gly Leu Ser Trp Ile Arg Gln Pro Ser Gly Lys Gly Leu Glu
                35                  40                  45

Trp Leu Ala His Ile Tyr Trp Asp Asp Lys Arg Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Gly Tyr Phe
                100                 105                 110

Asp Val Trp Gly Ala Gly Thr Thr Val Thr Val Ser Ser Ala Lys Thr
                115                 120                 125

Lys Gly Pro Ser Val Phe Pro Leu Ala Pro Cys Ser Arg Ser Thr Ser
                130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
```

```
                      165                 170                 175
Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
        210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Ala Ile Phe Gln Ser Ser Met Thr Lys Ile
    450                 455                 460

Leu Glu Pro Phe Arg Lys Gln Asn Pro Asp Ile Val Ile Tyr Gln Tyr
465                 470                 475                 480

Met Asp Asp Leu Tyr Ala Ser
                485

<210> SEQ ID NO 11
<211> LENGTH: 25
<212> TYPE: PRT
<213> ORGANISM: Artificial Sequence
<220> FEATURE:
<223> OTHER INFORMATION: Synthetic peptide.

<400> SEQUENCE: 11

Ser Ser Val Ser Pro Thr Thr Ser Val His Pro Thr Pro Thr Ser Val
1               5                   10                  15

Pro Pro Thr Pro Thr Lys Ser Ser Pro
            20                  25
```

```
<210> SEQ ID NO 12
<211> LENGTH: 25
<212> TYPE: PRT
<213> ORGANISM: Artificial Sequence
<220> FEATURE:
<223> OTHER INFORMATION: Synthetic peptide.

<400> SEQUENCE: 12

Pro Thr Ser Thr Pro Ala Asp Ser Ser Thr Ile Thr Pro Thr Ala Thr
1               5                   10                  15

Pro Thr Ala Thr Pro Thr Ile Lys Gly
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic peptide.

<400> SEQUENCE: 13

Thr Val Thr Pro Thr Ala Thr Ala Thr Pro Ser Ala Ile Val Thr Thr
1               5                   10                  15

Ile Thr Pro Thr Ala Thr Thr Lys Pro
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic peptide.

<400> SEQUENCE: 14

Thr Asn Gly Ser Ile Thr Val Ala Ala Thr Ala Pro Thr Val Thr Pro
1               5                   10                  15

Thr Val Asn Ala Thr Pro Ser Ala Ala
            20                  25

<210> SEQ ID NO 15
<211> LENGTH: 2299
<212> TYPE: PRT
<213> ORGANISM: Bacteroides cellulosolvens

<400> SEQUENCE: 15

Met Gln Ser Pro Arg Leu Lys Arg Lys Ile Leu Ser Val Ile Leu Ala
1               5                   10                  15

Val Cys Tyr Ile Ile Ser Ser Phe Ser Ile Gln Phe Ala Ala Thr Pro
            20                  25                  30

Gln Val Asn Ile Ile Gly Ser Ala Gln Gly Ile Pro Gly Ser Thr
        35                  40                  45

Val Lys Val Pro Ile Asn Leu Gln Asn Val Pro Glu Ile Gly Ile Asn
    50                  55                  60

Asn Cys Asp Phe Thr Ile Lys Phe Asp Ser Asp Ile Leu Asp Phe Asn
65                  70                  75                  80

Ser Val Glu Ala Gly Asp Ile Val Pro Leu Pro Val Ala Ser Phe Ser
                85                  90                  95

Ser Asn Asn Ser Lys Asp Ile Ile Lys Phe Leu Phe Ser Asp Ala Thr
            100                 105                 110

Gln Gly Asn Met Pro Ile Asn Glu Asn Gly Leu Phe Ala Val Ile Ser
        115                 120                 125
```

-continued

```
Phe Lys Ile Lys Asp Asn Ala Gln Lys Gly Ile Ser Asn Ile Lys Val
    130                 135                 140
Ser Ser Tyr Gly Ser Phe Ser Gly Met Ser Gly Lys Glu Met Gln Ser
145                 150                 155                 160
Leu Ser Pro Thr Phe Phe Ser Gly Ser Ile Asp Val Ser Asp Val Ser
                165                 170                 175
Thr Ser Lys Leu Asp Val Lys Val Gly Asn Val Glu Gly Ile Ala Gly
            180                 185                 190
Thr Glu Val Asn Val Pro Ile Thr Phe Glu Asn Val Pro Asp Asn Gly
        195                 200                 205
Ile Asn Asn Cys Asn Phe Thr Leu Ser Tyr Asp Ser Asn Ala Leu Glu
    210                 215                 220
Phe Leu Thr Thr Glu Ala Gly Asn Ile Ile Pro Leu Ala Ile Ala Asp
225                 230                 235                 240
Tyr Ser Ser Tyr Arg Ser Met Glu Gly Lys Ile Lys Phe Leu Phe Ser
                245                 250                 255
Asp Ser Ser Gln Gly Thr Arg Ser Ile Lys Asn Asp Gly Val Phe Ala
            260                 265                 270
Asn Ile Lys Phe Lys Ile Lys Gly Asn Ala Ile Arg Asp Thr Tyr Arg
        275                 280                 285
Ile Asp Leu Ser Glu Leu Gly Ser Phe Ser Ser Lys Gln Asn Asn Asn
    290                 295                 300
Leu Lys Ser Ile Ala Thr Gln Phe Leu Ser Gly Ser Val Asn Val Lys
305                 310                 315                 320
Asp Ile Glu Ser Ser Val Ser Pro Thr Thr Ser Val His Pro Thr Pro
                325                 330                 335
Thr Ser Val Pro Pro Thr Pro Thr Lys Ser Ser Pro Gly Asn Lys Met
            340                 345                 350
Lys Ile Gln Ile Gly Asp Val Lys Ala Asn Gln Gly Asp Thr Val Ile
        355                 360                 365
Val Pro Ile Thr Phe Asn Glu Val Pro Val Met Gly Val Asn Asn Cys
    370                 375                 380
Asn Phe Thr Leu Ala Tyr Asp Lys Asn Ile Met Glu Phe Ile Ser Ala
385                 390                 395                 400
Asp Ala Gly Asp Ile Val Thr Leu Pro Met Ala Asn Tyr Ser Tyr Asn
                405                 410                 415
Met Pro Ser Asp Gly Leu Val Lys Phe Leu Tyr Asn Asp Gln Ala Gln
            420                 425                 430
Gly Ala Met Ser Ile Lys Glu Asp Gly Thr Phe Ala Asn Val Lys Phe
        435                 440                 445
Lys Ile Lys Gln Ser Ala Ala Phe Gly Lys Tyr Ser Val Gly Ile Lys
    450                 455                 460
Ala Ile Gly Ser Ile Ser Ala Leu Ser Asn Ser Lys Leu Ile Pro Ile
465                 470                 475                 480
Glu Ser Ile Phe Lys Asp Gly Ser Ile Thr Val Thr Asn Lys Pro Ile
                485                 490                 495
Val Asn Ile Glu Ile Gly Lys Val Lys Val Lys Ala Gly Asp Lys Ile
            500                 505                 510
Lys Val Pro Val Glu Ile Lys Asp Ile Pro Ser Ile Gly Ile Asn Asn
        515                 520                 525
Cys Asn Phe Thr Leu Lys Tyr Asn Ser Asn Val Leu Lys Tyr Val Ser
    530                 535                 540
Asn Glu Ala Gly Thr Ile Val Pro Ala Pro Leu Ala Asn Leu Ser Ile
```

```
              545                 550                 555                 560
            Asn Lys Pro Asp Glu Gly Ile Ile Lys Leu Leu Phe Ser Asp Ala Ser
                              565                 570                 575
            Gln Gly Gly Met Pro Ile Lys Asp Asn Gly Ile Phe Val Asn Leu Glu
                              580                 585                 590
            Phe Gln Ala Val Asn Asp Ala Asn Ile Gly Val Tyr Gly Leu Glu Leu
                              595                 600                 605
            Asp Thr Ile Gly Ala Phe Ser Gly Ile Ser Ser Ala Lys Met Thr Ser
                              610                 615                 620
            Ile Glu Pro Gln Phe Asn Asn Gly Ser Ile Glu Ile Phe Asn Ser Ala
            625                 630                 635                 640
            Gln Thr Pro Val Pro Ser Asn Thr Glu Val Gln Thr Pro Thr Asn Thr
                              645                 650                 655
            Ile Ser Val Thr Pro Thr Asn Asn Ser Thr Pro Thr Asn Asn Ser Thr
                              660                 665                 670
            Pro Lys Pro Asn Pro Leu Tyr Asn Leu Asn Val Asn Ile Gly Glu Ile
                              675                 680                 685
            Ser Gly Glu Ala Gly Gly Val Ile Glu Val Pro Ile Glu Phe Lys Asn
                690                 695                 700
            Val Pro Asp Phe Gly Ile Asn Asn Cys Asp Phe Ser Val Lys Tyr Asp
            705                 710                 715                 720
            Lys Ser Ile Phe Glu Tyr Val Thr Tyr Glu Ala Gly Ser Ile Val Lys
                              725                 730                 735
            Asp Ser Ile Val Asn Leu Ala Cys Met Glu Asn Ser Gly Ile Ile Asn
                              740                 745                 750
            Leu Leu Phe Asn Asp Ala Thr Gln Ser Ser Pro Ile Lys Asn Asn
                              755                 760                 765
            Gly Val Phe Ala Lys Leu Lys Phe Lys Ile Asn Ser Asn Ala Ala Ser
                770                 775                 780
            Gly Thr Tyr Gln Ile Asn Ala Glu Gly Tyr Gly Lys Phe Ser Gly Asn
            785                 790                 795                 800
            Leu Asn Gly Lys Leu Thr Ser Ile Asn Pro Ile Phe Glu Asn Gly Ile
                              805                 810                 815
            Ile Asn Ile Gly Asn Val Thr Val Lys Pro Thr Ser Thr Pro Ala Asp
                              820                 825                 830
            Ser Ser Thr Ile Thr Pro Thr Ala Thr Pro Thr Ala Thr Pro Thr Ile
                              835                 840                 845
            Lys Gly Thr Pro Thr Val Thr Pro Ile Tyr Trp Met Asn Val Leu Ile
                850                 855                 860
            Gly Asn Met Asn Ala Ala Ile Gly Glu Glu Val Val Pro Ile Glu
            865                 870                 875                 880
            Phe Lys Asn Val Pro Pro Phe Gly Ile Asn Asn Cys Asp Phe Lys Leu
                              885                 890                 895
            Val Tyr Asp Ser Asn Ala Leu Glu Leu Lys Lys Val Glu Ala Gly Asp
                              900                 905                 910
            Ile Val Pro Glu Pro Leu Ala Asn Leu Ser Ser Asn Lys Ser Glu Gly
                              915                 920                 925
            Lys Ile Gln Phe Leu Phe Asn Asp Ala Ser Gln Gly Ser Met Gln Ile
                              930                 935                 940
            Glu Asn Gly Gly Val Phe Ala Lys Ile Thr Phe Lys Val Lys Ser Thr
            945                 950                 955                 960
            Ala Ala Ser Gly Ile Tyr Asn Ile Arg Lys Asp Ser Val Gly Ser Phe
                              965                 970                 975
```

```
Ser Gly Leu Ile Asp Asn Lys Met Thr Ser Ile Gly Pro Lys Phe Thr
                980             985                 990

Asp Gly Ser Ile Val Val Gly Thr Val Thr Pro Thr Ala Thr Ala Thr
         995                 1000                1005

Pro Ser Ala Ile Val Thr Thr Ile Thr Pro Thr Ala Thr Thr Lys
    1010            1015            1020

Pro Ile Ala Thr Pro Thr Ile Lys Gly Thr Pro Thr Ala Thr Pro
    1025            1030            1035

Met Tyr Trp Met Asn Val Val Ile Gly Lys Met Asn Ala Glu Val
    1040            1045            1050

Gly Gly Glu Val Val Val Pro Ile Glu Phe Asn Asn Val Pro Ser
    1055            1060            1065

Phe Gly Ile Asn Asn Cys Asp Phe Lys Leu Val Tyr Asp Ala Thr
    1070            1075            1080

Ala Leu Glu Leu Lys Asn Val Glu Ala Gly Asp Ile Ile Lys Thr
    1085            1090            1095

Pro Leu Ala Asn Phe Ser Asn Asn Lys Ser Glu Glu Gly Lys Ile
    1100            1105            1110

Ser Phe Leu Phe Asn Asp Ala Ser Gln Gly Ser Met Gln Ile Glu
    1115            1120            1125

Asn Gly Gly Val Phe Ala Lys Ile Thr Phe Lys Val Lys Ser Thr
    1130            1135            1140

Thr Ala Thr Gly Val Tyr Asp Leu Arg Lys Asp Leu Val Gly Ser
    1145            1150            1155

Phe Ser Gly Leu Lys Asp Asn Lys Met Thr Ser Ile Gly Ala Glu
    1160            1165            1170

Phe Thr Asn Gly Ser Ile Thr Val Ala Ala Thr Ala Pro Thr Val
    1175            1180            1185

Thr Pro Thr Val Asn Ala Thr Pro Ser Ala Ala Thr Pro Thr Val
    1190            1195            1200

Thr Pro Thr Ala Thr Ala Thr Pro Ser Val Thr Ile Pro Thr Val
    1205            1210            1215

Thr Pro Thr Ala Thr Ala Thr Pro Ser Val Thr Ile Pro Thr Val
    1220            1225            1230

Thr Pro Thr Ala Thr Ala Thr Pro Ser Ala Ala Thr Pro Thr Val
    1235            1240            1245

Thr Pro Thr Ala Thr Ala Thr Pro Ser Val Thr Ile Pro Thr Val
    1250            1255            1260

Thr Pro Thr Val Thr Ala Thr Pro Ser Asp Thr Ile Pro Thr Val
    1265            1270            1275

Thr Pro Thr Ala Thr Ala Thr Pro Ser Ala Ile Val Thr Thr Ile
    1280            1285            1290

Thr Pro Thr Ala Thr Ala Lys Pro Ile Ala Thr Pro Thr Ile Lys
    1295            1300            1305

Gly Thr Pro Thr Ala Thr Pro Met Tyr Trp Met Asn Val Val Ile
    1310            1315            1320

Gly Lys Met Asn Ala Glu Val Gly Gly Glu Val Val Val Pro Ile
    1325            1330            1335

Glu Phe Lys Asn Val Pro Ser Phe Gly Ile Asn Asn Cys Asp Phe
    1340            1345            1350

Lys Leu Val Tyr Asp Ala Thr Ala Leu Glu Leu Lys Asn Val Glu
    1355            1360            1365
```

```
Ala Gly Asp Ile Ile Lys Thr Pro Leu Ala Asn Phe Ser Asn Asn
    1370            1375                1380
Lys Ser Glu Glu Gly Lys Ile Ser Phe Leu Phe Asn Asp Ala Ser
    1385            1390                1395
Gln Gly Ser Met Gln Ile Glu Asn Gly Gly Val Ser Ala Lys Ile
    1400            1405                1410
Thr Phe Lys Val Lys Ser Thr Ala Ile Gly Val Tyr Asp Ile
    1415            1420                1425
Arg Lys Asp Leu Ile Gly Ser Phe Ser Gly Leu Lys Asp Ser Lys
    1430            1435                1440
Met Thr Ser Ile Gly Ala Glu Phe Thr Asn Gly Ser Ile Thr Val
    1445            1450                1455
Ala Thr Thr Ala Pro Thr Val Thr Pro Thr Ala Thr Ala Thr Pro
    1460            1465                1470
Ser Val Thr Ile Pro Thr Val Thr Pro Thr Ala Thr Ala Thr Pro
    1475            1480                1485
Gly Thr Ala Thr Pro Gly Thr Ala Thr Pro Thr Ala Thr Ala Thr
    1490            1495                1500
Pro Gly Ala Ala Thr Pro Thr Glu Thr Ala Thr Pro Ser Val Met
    1505            1510                1515
Ile Pro Thr Val Thr Pro Thr Ala Thr Ala Thr Pro Thr Ala Thr
    1520            1525                1530
Ala Thr Pro Thr Val Lys Gly Thr Pro Thr Ile Lys Pro Val Tyr
    1535            1540                1545
Lys Met Asn Val Val Ile Gly Arg Val Asn Val Val Ala Gly Glu
    1550            1555                1560
Glu Val Val Val Pro Val Glu Phe Lys Asn Ile Pro Ala Ile Gly
    1565            1570                1575
Val Asn Asn Cys Asn Phe Val Leu Glu Tyr Asp Ala Asn Val Leu
    1580            1585                1590
Glu Val Lys Lys Val Asp Ala Gly Glu Ile Val Pro Asp Ala Leu
    1595            1600                1605
Ile Asn Phe Gly Ser Asn Asn Ser Asp Glu Gly Lys Val Tyr Phe
    1610            1615                1620
Leu Phe Asn Asp Ala Leu Gln Gly Arg Met Gln Ile Ala Asn Asp
    1625            1630                1635
Gly Ile Phe Ala Asn Ile Thr Phe Lys Val Lys Ser Ser Ala Ala
    1640            1645                1650
Ala Gly Ile Tyr Asn Ile Arg Lys Asp Ser Val Gly Ala Phe Ser
    1655            1660                1665
Gly Leu Val Asp Lys Leu Val Pro Ile Ser Ala Glu Phe Thr Asp
    1670            1675                1680
Gly Ser Ile Ser Val Glu Ser Ala Lys Ser Thr Pro Thr Ala Thr
    1685            1690                1695
Ala Thr Gly Thr Asn Val Thr Pro Thr Val Ala Ala Thr Val Thr
    1700            1705                1710
Pro Thr Ala Thr Pro Ala Ser Thr Thr Pro Thr Ala Thr Pro Thr
    1715            1720                1725
Ala Thr Ser Thr Val Lys Gly Thr Pro Thr Ala Thr Pro Leu Tyr
    1730            1735                1740
Ser Met Asn Val Ile Ile Gly Lys Val Asn Ala Glu Ala Ser Gly
    1745            1750                1755
Glu Val Val Val Pro Val Glu Phe Lys Asp Val Pro Ser Ile Gly
```

```
                1760                1765                1770
Ile Asn Asn Cys Asn Phe Ile Leu Glu Tyr Asp Ala Ser Ala Leu
    1775                1780                1785

Glu Leu Asp Ser Ala Glu Ala Gly Ile Val Pro Val Pro Leu
    1790                1795                1800

Gly Asn Phe Ser Ser Asn Asn Lys Asp Glu Gly Lys Ile Tyr Phe
    1805                1810                1815

Leu Phe Ser Asp Gly Thr Gln Gly Arg Met Gln Ile Val Asn Asp
    1820                1825                1830

Gly Ile Phe Ala Lys Ile Lys Phe Lys Val Lys Ser Thr Ala Ser
    1835                1840                1845

Asp Gly Thr Tyr Tyr Ile Arg Lys Asp Ser Val Gly Ala Phe Ser
    1850                1855                1860

Gly Leu Ile Glu Lys Lys Ile Ile Lys Ile Gly Ala Glu Phe Thr
    1865                1870                1875

Asp Gly Ser Ile Thr Val Arg Ser Leu Thr Pro Thr Pro Thr Val
    1880                1885                1890

Thr Pro Asn Val Ala Ser Pro Thr Pro Thr Lys Val Val Ala Glu
    1895                1900                1905

Pro Thr Ser Asn Gln Pro Ala Gly Pro Gly Pro Ile Thr Gly Thr
    1910                1915                1920

Ile Pro Thr Ala Thr Thr Thr Ala Thr Ala Thr Pro Thr Lys Ala
    1925                1930                1935

Ser Val Ala Thr Ala Thr Pro Thr Ala Thr Pro Ile Val Val Val
    1940                1945                1950

Glu Pro Thr Ile Val Arg Pro Gly Tyr Asn Lys Asp Ala Asp Leu
    1955                1960                1965

Ala Val Phe Ile Ser Ser Asp Lys Ser Arg Tyr Glu Glu Ser Ser
    1970                1975                1980

Ile Ile Thr Tyr Ser Ile Glu Tyr Lys Asn Ile Gly Lys Val Asn
    1985                1990                1995

Ala Thr Asn Val Lys Ile Ala Ala Gln Ile Pro Lys Phe Thr Lys
    2000                2005                2010

Val Tyr Asp Ala Ala Lys Gly Ala Val Lys Gly Ser Glu Ile Val
    2015                2020                2025

Trp Met Ile Gly Asn Leu Ala Val Gly Glu Ser Tyr Thr Lys Glu
    2030                2035                2040

Tyr Lys Val Lys Val Asp Ser Leu Thr Lys Ser Glu Glu Tyr Thr
    2045                2050                2055

Asp Asn Thr Val Thr Ile Ser Ser Asp Gln Thr Val Asp Ile Pro
    2060                2065                2070

Glu Asn Ile Thr Thr Gly Asn Asp Asp Lys Ser Thr Ile Arg Val
    2075                2080                2085

Met Leu Tyr Ser Asn Arg Phe Thr Pro Gly Ser His Ser Ser Tyr
    2090                2095                2100

Ile Leu Gly Tyr Lys Asp Lys Thr Phe Lys Pro Lys Gln Asn Val
    2105                2110                2115

Thr Arg Ala Glu Val Ala Ala Met Phe Ala Arg Ile Met Gly Leu
    2120                2125                2130

Thr Val Lys Asp Gly Ala Lys Ser Ser Tyr Lys Asp Val Ser Asn
    2135                2140                2145

Lys His Trp Ala Leu Lys Tyr Ile Glu Ala Val Thr Lys Ser Gly
    2150                2155                2160
```

```
Ile Phe Lys Gly Tyr Lys Asp Ser Thr Phe His Pro Asn Ala Pro
    2165                2170                2175

Ile Thr Arg Ala Glu Leu Ser Thr Val Ile Phe Asn Tyr Leu His
    2180                2185                2190

Leu Asn Asn Ile Ala Pro Ser Lys Val His Phe Thr Asp Ile Asn
    2195                2200                2205

Lys His Trp Ala Lys Asn Tyr Ile Glu Glu Ile Tyr Arg Phe Lys
    2210                2215                2220

Leu Ile Gln Gly Tyr Ser Asp Gly Ser Phe Lys Pro Asn Asn Asn
    2225                2230                2235

Ile Thr Arg Ala Glu Val Val Thr Met Ile Asn Arg Met Leu Tyr
    2240                2245                2250

Arg Gly Pro Leu Lys Val Lys Val Gly Ser Phe Pro Asp Val Ser
    2255                2260                2265

Pro Lys Tyr Trp Ala Tyr Gly Asp Ile Glu Glu Ala Ser Arg Asn
    2270                2275                2280

His Lys Tyr Thr Arg Asp Glu Lys Asp Gly Ser Glu Ile Leu Ile
    2285                2290                2295

Glu

<210> SEQ ID NO 16
<211> LENGTH: 541
<212> TYPE: PRT
<213> ORGANISM: Artificial Sequence
<220> FEATURE:
<223> OTHER INFORMATION: Synthetic peptide.

<400> SEQUENCE: 16

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205
```

```
Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Glu Lys Ile Arg Leu Arg Pro Gly Gly Lys
    450                 455                 460

Lys Lys Tyr Lys Leu Lys His Ile Val Ala Ser Val Gly Phe Pro Val
465                 470                 475                 480

Thr Pro Gln Val Pro Leu Arg Pro Met Thr Tyr Lys Ala Ala Val Asp
                485                 490                 495

Leu Ser His Phe Leu Lys Glu Lys Gly Gly Leu Ala Ser His Thr Gln
            500                 505                 510

Gly Tyr Phe Pro Asp Trp Gln Asn Tyr Thr Pro Gly Pro Gly Val Arg
        515                 520                 525

Tyr Pro Leu Thr Phe Gly Trp Leu Tyr Lys Leu Ala Ser
530                 535                 540

<210> SEQ ID NO 17
<211> LENGTH: 534
<212> TYPE: PRT
<213> ORGANISM: Artificial Sequence
<220> FEATURE:
<223> OTHER INFORMATION: Synthetic peptide.

<400> SEQUENCE: 17

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30
```

Gly Met Gly Leu Ser Trp Ile Arg Gln Pro Ser Gly Lys Gly Leu Glu
            35                  40                  45

Trp Leu Ala His Ile Tyr Trp Asp Asp Lys Arg Tyr Asn Pro Ser
 50                  55                  60

Leu Lys Ser Arg Leu Thr Ile Ser Lys Asp Thr Ser Ser Asn Gln Val
 65                  70                  75                  80

Phe Leu Lys Ile Thr Ile Val Asp Thr Ala Asp Ala Ala Thr Tyr Tyr
                    85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                    325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                    405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys Ala Ser Glu Lys Ile Arg Leu Arg Pro Gly Gly Lys

```
                    450                 455                 460
Lys Lys Tyr Lys Leu Lys His Ile Val Ala Ser Ser Val Ser Pro
465                 470                 475                 480

Thr Thr Ser Val His Pro Thr Pro Thr Ser Val Pro Pro Thr Pro Thr
                    485                 490                 495

Lys Ser Ser Pro Ala Ser His Thr Gln Gly Tyr Phe Pro Asp Trp Gln
                500                 505                 510

Asn Tyr Thr Pro Gly Pro Gly Val Arg Tyr Pro Leu Thr Phe Gly Trp
                515                 520                 525

Leu Tyr Lys Leu Ala Ser
            530

<210> SEQ ID NO 18
<211> LENGTH: 626
<212> TYPE: PRT
<213> ORGANISM: Artificial Sequence
<220> FEATURE:
<223> OTHER INFORMATION: Synthetic peptide.

<400> SEQUENCE: 18

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
```

```
                    275                 280                 285
Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Gln Thr Pro Thr Asn Thr Ile Ser Val Thr
    450                 455                 460

Pro Thr Asn Asn Ser Thr Pro Thr Asn Asn Ser Asn Pro Lys Pro Asn
465                 470                 475                 480

Pro Ala Ser Glu Lys Ile Arg Leu Arg Pro Gly Lys Lys Lys Tyr
                485                 490                 495

Lys Leu Lys His Ile Val Ala Ser Ser Ser Val Ser Pro Thr Thr Ser
            500                 505                 510

Val His Pro Thr Pro Thr Ser Val Pro Pro Thr Pro Thr Lys Ser Ser
        515                 520                 525

Pro Ala Ser Asn Pro Pro Ile Pro Val Gly Glu Ile Tyr Lys Arg Trp
    530                 535                 540

Ile Ile Leu Gly Leu Asn Lys Ile Val Arg Met Tyr Ser Pro Thr Ser
545                 550                 555                 560

Ile Leu Asp Ala Ser Pro Thr Ser Thr Pro Ala Asp Ser Ser Thr Ile
                565                 570                 575

Thr Pro Thr Ala Thr Pro Thr Ala Thr Pro Thr Ile Lys Gly Ala Ser
            580                 585                 590

Val Gly Phe Pro Val Thr Pro Gln Val Pro Leu Arg Pro Met Thr Tyr
        595                 600                 605

Lys Ala Ala Val Asp Leu Ser His Phe Leu Lys Glu Lys Gly Gly Leu
    610                 615                 620

Ala Ser
625

<210> SEQ ID NO 19
<211> LENGTH: 608
<212> TYPE: PRT
<213> ORGANISM: Artificial Sequence
<220> FEATURE:
<223> OTHER INFORMATION: Synthetic peptide.

<400> SEQUENCE: 19

Gln Val Thr Leu Lys Glu Ser Gly Pro Gly Ile Leu Gln Pro Ser Gln
```

-continued

```
1               5                   10                  15
Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
            35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                    85                  90                  95

Cys Ala Arg Ser Ser His Tyr Tyr Gly Tyr Gly Tyr Gly Gly Tyr Phe
                100                 105                 110

Asp Val Trp Gly Ala Gly Thr Thr Val Thr Val Ser Ser Ala Lys Thr
                115                 120                 125

Lys Gly Pro Ser Val Phe Pro Leu Ala Pro Cys Ser Arg Ser Thr Ser
            130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
                195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
                275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                    325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                    405                 410                 415

Val Asp Lys Ser Arg Trp Gln Glu Gly Asn Val Phe Ser Cys Ser Val
                420                 425                 430
```

```
Met His Glu Ala Leu His Asn His Tyr Thr Gln Lys Ser Leu Ser Leu
        435                 440                 445

Ser Leu Gly Lys Ala Ser Ala Ile Phe Gln Ser Ser Met Thr Lys Ile
        450                 455                 460

Leu Glu Pro Phe Arg Lys Gln Asn Pro Asp Ile Val Ile Tyr Gln Tyr
465                 470                 475                 480

Met Asp Asp Leu Tyr Ala Ser Glu Lys Ile Arg Leu Arg Pro Gly Gly
                485                 490                 495

Lys Lys Lys Tyr Lys Leu Lys His Ile Val Ala Ser Val Gly Phe Pro
                500                 505                 510

Val Thr Pro Gln Val Pro Leu Arg Pro Met Thr Tyr Lys Ala Ala Val
            515                 520                 525

Asp Leu Ser His Phe Leu Lys Glu Lys Gly Gly Leu Ala Ser His Thr
            530                 535                 540

Gln Gly Tyr Phe Pro Asp Trp Gln Asn Tyr Thr Pro Gly Pro Gly Val
545                 550                 555                 560

Arg Tyr Pro Leu Thr Phe Gly Trp Leu Tyr Lys Leu Ala Ser Asn Pro
                565                 570                 575

Pro Ile Pro Val Gly Glu Ile Tyr Lys Arg Trp Ile Ile Leu Gly Leu
                580                 585                 590

Asn Lys Ile Val Arg Met Tyr Ser Pro Thr Ser Ile Leu Asp Ala Ser
                595                 600                 605

<210> SEQ ID NO 20
<211> LENGTH: 745
<212> TYPE: PRT
<213> ORGANISM: Artificial Sequence
<220> FEATURE:
<223> OTHER INFORMATION: Synthetic peptide.

<400> SEQUENCE: 20

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Gly Tyr Phe
                100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190
```

-continued

```
Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Gln Thr Pro Thr Asn Thr Ile Ser Val Thr
    450                 455                 460

Pro Thr Asn Asn Ser Thr Pro Thr Asn Asn Ser Asn Pro Lys Pro Asn
465                 470                 475                 480

Pro Ala Ser Glu Lys Ile Arg Leu Arg Pro Gly Gly Lys Lys Lys Tyr
                485                 490                 495

Lys Leu Lys His Ile Val Ala Ser Ser Val Ser Pro Thr Thr Ser
            500                 505                 510

Val His Pro Thr Pro Thr Ser Val Pro Pro Thr Pro Thr Lys Ser Ser
        515                 520                 525

Pro Ala Ser Asn Pro Pro Ile Pro Val Gly Glu Ile Tyr Lys Arg Trp
    530                 535                 540

Ile Ile Leu Gly Leu Asn Lys Ile Val Arg Met Tyr Ser Pro Thr Ser
545                 550                 555                 560

Ile Leu Asp Ala Ser Pro Thr Ser Thr Pro Ala Asp Ser Ser Thr Ile
                565                 570                 575

Thr Pro Thr Ala Thr Pro Thr Ala Thr Pro Thr Ile Lys Gly Ala Ser
            580                 585                 590

His Thr Gln Gly Tyr Phe Pro Asp Trp Gln Asn Tyr Thr Pro Gly Pro
        595                 600                 605
```

```
Gly Val Arg Tyr Pro Leu Thr Phe Gly Trp Leu Tyr Lys Leu Ala Ser
    610                 615                 620

Thr Val Thr Pro Thr Ala Thr Ala Thr Pro Ser Ala Ile Val Thr Thr
625                 630                 635                 640

Ile Thr Pro Thr Ala Thr Thr Lys Pro Ala Ser Val Gly Phe Pro Val
                645                 650                 655

Thr Pro Gln Val Pro Leu Arg Pro Met Thr Tyr Lys Ala Ala Val Asp
            660                 665                 670

Leu Ser His Phe Leu Lys Glu Lys Gly Leu Ala Ser Thr Asn Gly
        675                 680                 685

Ser Ile Thr Val Ala Ala Thr Ala Pro Thr Val Thr Pro Thr Val Asn
690                 695                 700

Ala Thr Pro Ser Ala Ala Ala Ser Ala Ile Phe Gln Ser Ser Met Thr
705                 710                 715                 720

Lys Ile Leu Glu Pro Phe Arg Lys Gln Asn Pro Asp Ile Val Ile Tyr
                725                 730                 735

Gln Tyr Met Asp Asp Leu Tyr Ala Ser
            740                 745

<210> SEQ ID NO 21
<211> LENGTH: 72
<212> TYPE: DNA
<213> ORGANISM: Artificial Sequence
<220> FEATURE:
<223> OTHER INFORMATION: Synthetic oligonucleotide.

<400> SEQUENCE: 21
gctagtgaga agatccggct gcggcccggc ggcaagaaga agtacaagct gaagcacatc     60
gtggctagct ga                                                         72

<210> SEQ ID NO 22
<211> LENGTH: 111
<212> TYPE: DNA
<213> ORGANISM: Artificial Sequence
<220> FEATURE:
<223> OTHER INFORMATION: Synthetic oligonucleotide.

<400> SEQUENCE: 22
gctagtgtgg gcttccccgt gaccccccag gtgcccctgc ggcccatgac ctacaaggcc     60
gccgtggacc tgagccactt cctgaaggag aagggcggcc tggctagctg a             111

<210> SEQ ID NO 23
<211> LENGTH: 108
<212> TYPE: DNA
<213> ORGANISM: Artificial Sequence
<220> FEATURE:
<223> OTHER INFORMATION: Synthetic oligonucleotide.

<400> SEQUENCE: 23
gctagtgcca tcttccagag cagcatgacc aagatcctgg agcccttccg gaagcagaac     60
cccgacatcg tgatctacca gtacatggac gacctgtacg ctagctga                 108

<210> SEQ ID NO 24
<211> LENGTH: 198
<212> TYPE: DNA
<213> ORGANISM: Artificial Sequence
<220> FEATURE:
<223> OTHER INFORMATION: Synthetic oligonucleotide.

<400> SEQUENCE: 24
```

```
gctagtcaga ccccaccaa caccatcagc gtgaccccca ccaacaacag cacccccacc      60
aacaacagca accccaagcc caaccccgct agtaaccccc ccatccccgt gggcgagatc     120
tacaagcggt ggatcatcct gggcctgaac aagatcgtgc ggatgtacag ccccaccagc    180
atcctggacg ctagctga                                                  198
```

<210> SEQ ID NO 25
<211> LENGTH: 255
<212> TYPE: DNA
<213> ORGANISM: Artificial Sequence
<220> FEATURE:
<223> OTHER INFORMATION: Synthetic oligonucleotide.

<400> SEQUENCE: 25

```
gctagtcaga ccccaccaa caccatcagc gtgaccccca ccaacaacag cacccccacc      60
aacaacagca accccaagcc caaccccgct agtgagaaga tccggctgcg gcccggcggc    120
aagaagaagt acaagctgaa gcacatcgtg gctagtcaca cccagggcta cttccccgac    180
tggcagaact acacccccgg ccccggcgtg cggtaccccc tgaccttcgg ctggctgtac    240
aagctggcta gctga                                                     255
```

<210> SEQ ID NO 26
<211> LENGTH: 882
<212> TYPE: DNA
<213> ORGANISM: Artificial Sequence
<220> FEATURE:
<223> OTHER INFORMATION: Synthetic oligonucleotide.

<400> SEQUENCE: 26

```
gctagtcaga ccccaccaa caccatcagc gtgaccccca ccaacaacag cacccccacc      60
aacaacagca accccaagcc caaccccgct agtgagaaga tccggctgcg gcccggcggc    120
aagaagaagt acaagctgaa gcacatcgtg gctagtagca gcgtgagccc caccaccagc    180
gtgcacccca ccccaccag cgtgcccccc accccacca agagcagccc cgctagtaac    240
ccccccatcc ccgtgggcga gatctacaag cggtggatca tcctgggcct gaacaagatc    300
gtgcggatgt acagccccac cagcatcctg gacgctagtc ccaccagcac ccccgccgac    360
agcagcacca tcaccccac cgccaccccc accgccaccc ccaccatcaa gggcgctagt    420
cacacccagg gctacttccc cgactggcag aactacaccc ccggccccgg cgtgcggtac    480
cccctgacct tcggctggct gtacaagctg gctagtaccg tgaccccac cgccaccgcc    540 accccagcg ccatcgtgac caccatcacc ccaccgcca ccaagcc cgctagtgtg    600 ggcttccccg tgacccccca ggtgcccctg cggcccatga cctacaaggc cgccgtggac    660
ctgagccact tcctgaagga aaggggcggc ctggctagta ccaacggcag catcaccgtg    720
gccgccaccg ccccaccgt gaccccacc gtgaacgcca cccagcgc cgccgctagt    780 gccatcttcc agagcagcat gaccaagatc ctggagccct tccggaagca gaaccccgac    840
atcgtgatct accagtacat ggacgacctg tacgctagct ga                       882
```

<210> SEQ ID NO 27
<211> LENGTH: 108
<212> TYPE: DNA
<213> ORGANISM: Artificial Sequence
<220> FEATURE:
<223> OTHER INFORMATION: Synthetic oligonucleotide.

<400> SEQUENCE: 27

```
gctagtgtgg gcttccccgt gacccccag gtgcccctgc ggcccatgac ctacaaggcc      60
```

```
gccgtggacc tgagccactt cctgaaggag aagggcggcc tggctagc            108
```

<210> SEQ ID NO 28
<211> LENGTH: 102
<212> TYPE: DNA
<213> ORGANISM: Artificial Sequence
<220> FEATURE:
<223> OTHER INFORMATION: Synthetic oligonucleotide.

<400> SEQUENCE: 28

```
gctagtcaca cccagggcta cttccccgac tggcagaact acaccccgg ccccggcgtg    60 cggtaccccc tgaccttcgg ctggctgtac aagctggcta gc                     102
```

<210> SEQ ID NO 29
<211> LENGTH: 69
<212> TYPE: DNA
<213> ORGANISM: Artificial Sequence
<220> FEATURE:
<223> OTHER INFORMATION: Synthetic oligonucleotide.

<400> SEQUENCE: 29

```
gctagtgaga agatccggct gcggcccggc ggcaagaaga agtacaagct gaagcacatc   60
gtggctagc                                                          69
```

<210> SEQ ID NO 30
<211> LENGTH: 108
<212> TYPE: DNA
<213> ORGANISM: Artificial Sequence
<220> FEATURE:
<223> OTHER INFORMATION: Synthetic oligonucleotide.

<400> SEQUENCE: 30

```
gctagtaacc cccccatccc cgtgggcgag atctacaagc ggtggatcat cctgggcctg   60
aacaagatcg tgcggatgta cagccccacc agcatcctgg acgctagc              108
```

<210> SEQ ID NO 31
<211> LENGTH: 105
<212> TYPE: DNA
<213> ORGANISM: Artificial Sequence
<220> FEATURE:
<223> OTHER INFORMATION: Synthetic oligonucleotide.

<400> SEQUENCE: 31

```
gctagtgcca tcttccagag cagcatgacc aagatcctgg agcccttccg gaagcagaac   60
cccgacatcg tgatctacca gtacatggac gacctgtacg ctagc                 105
```

<210> SEQ ID NO 32
<211> LENGTH: 87
<212> TYPE: DNA
<213> ORGANISM: Artificial Sequence
<220> FEATURE:
<223> OTHER INFORMATION: Synthetic oligonucleotide.

<400> SEQUENCE: 32

```
gctagtagca gcgtgagccc caccaccagc gtgcacccca ccccaccag cgtgcccccc    60 acccccacca agagcagccc cgctagc                                      87
```

<210> SEQ ID NO 33
<211> LENGTH: 87
<212> TYPE: DNA
<213> ORGANISM: Artificial Sequence
<220> FEATURE:

-continued

<223> OTHER INFORMATION: Synthetic oligonucleotide.

<400> SEQUENCE: 33
gctagtccca ccagcacccc cgccgacagc agcaccatca cccccaccgc acccccacc 60 gccaccccca ccatcaaggg cgctagc 87

<210> SEQ ID NO 34
<211> LENGTH: 87
<212> TYPE: DNA
<213> ORGANISM: Artificial Sequence
<220> FEATURE:
<223> OTHER INFORMATION: Synthetic oligonucleotide.

<400> SEQUENCE: 34
gctagtaccg tgaccccac cgccaccgcc accccagcg ccatcgtgac caccatcacc 60
cccaccgcca ccaagcc cgctagc 87

<210> SEQ ID NO 35
<211> LENGTH: 87
<212> TYPE: DNA
<213> ORGANISM: Artificial Sequence
<220> FEATURE:
<223> OTHER INFORMATION: Synthetic oligonucleotide.

<400> SEQUENCE: 35
gctagtacca acggcagcat caccgtggcc gccaccgccc ccaccgtgac ccccaccgtg 60
aacgccaccc ccagcgccgc cgctagc 87

<210> SEQ ID NO 36
<211> LENGTH: 745
<212> TYPE: PRT
<213> ORGANISM: Artificial Sequence
<220> FEATURE:
<223> OTHER INFORMATION: Synthetic peptide.

<400> SEQUENCE: 36

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Tyr Phe
            100                 105                 110

Asp Val Trp Gly Ala Gly Thr Thr Val Thr Val Ser Ser Ala Lys Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

```
Thr Phe Pro Ala Val Leu Gln Ser Ser Gly Leu Tyr Ser Leu Ser Ser
                180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
        210                 215                 220

Ser Lys Tyr Gly Pro Pro Cys Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Gln Thr Pro Thr Asn Thr Ile Ser Val Thr
450                 455                 460

Pro Thr Asn Asn Ser Thr Pro Thr Asn Asn Ser Asn Pro Lys Pro Asn
465                 470                 475                 480

Pro Ala Ser Glu Lys Ile Arg Leu Arg Pro Gly Gly Lys Lys Lys Tyr
                485                 490                 495

Lys Leu Lys His Ile Val Ala Ser Ser Val Ser Pro Thr Thr Ser
            500                 505                 510

Val His Pro Thr Pro Thr Ser Val Pro Pro Thr Pro Thr Lys Ser Ser
        515                 520                 525

Pro Ala Ser Asn Pro Pro Ile Pro Val Gly Glu Ile Tyr Lys Arg Trp
            530                 535                 540

Ile Ile Leu Gly Leu Asn Lys Ile Val Arg Met Tyr Ser Pro Thr Ser
545                 550                 555                 560

Ile Leu Asp Ala Ser Pro Thr Ser Thr Pro Ala Asp Ser Ser Thr Ile
                565                 570                 575

Thr Pro Thr Ala Thr Pro Thr Ala Thr Pro Thr Ile Lys Gly Ala Ser
            580                 585                 590

His Thr Gln Gly Tyr Phe Pro Asp Trp Gln Asn Tyr Thr Pro Gly Pro
```

```
                595                 600                 605
Gly Val Arg Tyr Pro Leu Thr Phe Gly Trp Leu Tyr Lys Leu Ala Ser
    610                 615                 620

Thr Val Thr Pro Thr Ala Thr Ala Thr Pro Ser Ala Ile Val Thr Thr
625                 630                 635                 640

Ile Thr Pro Thr Ala Thr Thr Lys Pro Ala Ser Val Gly Phe Pro Val
                645                 650                 655

Thr Pro Gln Val Pro Leu Arg Pro Met Thr Tyr Lys Ala Ala Val Asp
                660                 665                 670

Leu Ser His Phe Leu Lys Glu Lys Gly Gly Leu Ala Ser Thr Asn Gly
                675                 680                 685

Ser Ile Thr Val Ala Ala Thr Ala Pro Thr Val Thr Pro Thr Val Asn
690                 695                 700

Ala Thr Pro Ser Ala Ala Ala Ser Ala Ile Phe Gln Ser Ser Met Thr
705                 710                 715                 720

Lys Ile Leu Glu Pro Phe Arg Lys Gln Asn Pro Asp Ile Val Ile Tyr
                725                 730                 735

Gln Tyr Met Asp Asp Leu Tyr Ala Ser
                740                 745

<210> SEQ ID NO 37
<211> LENGTH: 739
<212> TYPE: PRT
<213> ORGANISM: Artificial Sequence
<220> FEATURE:
<223> OTHER INFORMATION: Synthetic peptide.

<400> SEQUENCE: 37

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Tyr Ile Asn Ser Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
```

-continued

```
                210                 215                 220
Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
        435                 440                 445

Gln Thr Pro Thr Asn Thr Ile Ser Val Thr Pro Thr Asn Asn Ser Thr
450                 455                 460

Pro Thr Asn Asn Ser Asn Pro Lys Pro Asn Pro Ala Ser Glu Lys Ile
465                 470                 475                 480

Arg Leu Arg Pro Gly Lys Lys Lys Tyr Lys Leu Lys His Ile Val
                485                 490                 495

Ala Ser Ser Ser Val Ser Pro Thr Thr Ser Val His Pro Thr Pro Thr
            500                 505                 510

Ser Val Pro Pro Thr Pro Thr Lys Ser Ser Pro Ala Ser Asn Pro Pro
        515                 520                 525

Ile Pro Val Gly Glu Ile Tyr Lys Arg Trp Ile Ile Leu Gly Leu Asn
530                 535                 540

Lys Ile Val Arg Met Tyr Ser Pro Thr Ser Ile Leu Asp Ala Ser Pro
545                 550                 555                 560

Thr Ser Thr Pro Ala Asp Ser Ser Thr Ile Thr Pro Thr Ala Thr Pro
                565                 570                 575

Thr Ala Thr Pro Thr Ile Lys Gly Ala Ser His Thr Gln Gly Tyr Phe
            580                 585                 590

Pro Asp Trp Gln Asn Tyr Thr Pro Gly Pro Gly Val Arg Tyr Pro Leu
        595                 600                 605

Thr Phe Gly Trp Leu Tyr Lys Leu Ala Ser Thr Val Thr Pro Thr Ala
    610                 615                 620

Thr Ala Thr Pro Ser Ala Ile Val Thr Thr Ile Thr Pro Thr Ala Thr
625                 630                 635                 640
```

```
Thr Lys Pro Ala Ser Val Gly Phe Pro Val Thr Pro Gln Val Pro Leu
                645                 650                 655

Arg Pro Met Thr Tyr Lys Ala Ala Val Asp Leu Ser His Phe Leu Lys
                660                 665                 670

Glu Lys Gly Gly Leu Ala Ser Thr Asn Gly Ser Ile Thr Val Ala Ala
                675                 680                 685

Thr Ala Pro Thr Val Thr Pro Thr Val Asn Ala Thr Pro Ser Ala Ala
                690                 695                 700

Ala Ser Ala Ile Phe Gln Ser Ser Met Thr Lys Ile Leu Glu Pro Phe
705                 710                 715                 720

Arg Lys Gln Asn Pro Asp Ile Val Ile Tyr Gln Tyr Met Asp Asp Leu
                725                 730                 735

Tyr Ala Ser

<210> SEQ ID NO 38
<211> LENGTH: 234
<212> TYPE: PRT
<213> ORGANISM: Artificial Sequence
<220> FEATURE:
<223> OTHER INFORMATION: Synthetic peptide.

<400> SEQUENCE: 38

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Ser Ala Ser Gln Gly
                35                  40                  45

Ile Ser Asn Tyr Leu Asn Trp Tyr Gln Gln Lys Pro Asp Gly Thr Val
            50                  55                  60

Lys Leu Leu Ile Tyr Tyr Thr Ser Ile Leu His Ser Gly Val Pro Ser
65                  70                  75                  80

Arg Phe Ser Gly Ser Gly Ser Gly Thr Asp Tyr Ser Leu Thr Ile Gly
                85                  90                  95

Asn Leu Glu Pro Glu Asp Ile Ala Thr Tyr Tyr Cys Gln Gln Phe Asn
                100                 105                 110

Lys Leu Pro Pro Thr Phe Gly Gly Gly Thr Lys Leu Glu Ile Lys Arg
                115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
                195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230

<210> SEQ ID NO 39
<211> LENGTH: 467
```

-continued

```
<212> TYPE: PRT
<213> ORGANISM: Artificial Sequence
<220> FEATURE:
<223> OTHER INFORMATION: Synthetic peptide.

<400> SEQUENCE: 39

Met Asn Leu Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Tyr Ile Asn Ser Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Arg Arg Gly Leu Pro Phe His Ala Met Asp Tyr Trp
        115                 120                 125

Gly Gln Gly Thr Ser Val Thr Val Ser Ser Ala Lys Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Glu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380
```

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
            450                 455                 460

Lys Ala Ser
465

<210> SEQ ID NO 40
<211> LENGTH: 705
<212> TYPE: DNA
<213> ORGANISM: Artificial Sequence
<220> FEATURE:
<223> OTHER INFORMATION: Synthetic oligonucleotide.

<400> SEQUENCE: 40
atgatgtcct ctgctcagtt ccttggtctc ctgttgctct gttttcaagg taccagatgt      60
gatatccaga tgacacagac tacatcctcc ctgtctgcct ctctaggaga cagagtcacc     120
atcagttgca gtgcaagtca gggcattagc aattatttaa actggtatca gcagaaacca     180
gatggaactg ttaaactcct gatctattac acatcaattt acactcagg agtcccatca      240 aggttcagtg gcagtgggtc tgggacagat tattctctca ccatcggcaa cctggaacct     300
gaagatattg ccacttacta ttgtcagcag tttaataagc ttcctccgac gttcggtgga     360
ggcaccaaac tcgagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cccctgacg     600 ctgagcaaag cagactacga aaacacaaa gtctatgcct gcgaagtcac ccatcagggc      660
ctgagctcgc ccgtcacaaa gagcttcaac aggggagagt gttag                    705

<210> SEQ ID NO 41
<211> LENGTH: 1404
<212> TYPE: DNA
<213> ORGANISM: Artificial Sequence
<220> FEATURE:
<223> OTHER INFORMATION: Synthetic oligonucleotide.

<400> SEQUENCE: 41
atgaacttgg ggctcagctt gattttcctt gtccttgttt taaaaggtgt ccagtgtgaa      60
gtgaagctgg tggagtctgg gggaggctta gtgcagcctg agggtccct gaaactctcc     120 tgtgcaacct ctggattcac tttcagtgac tattacatgt attgggttcg ccagactcca     180
gagaagaggc tggagtgggt cgcatacatt aattctggtg gtggtagcac ctattatcca     240
gacactgtaa agggccgatt caccatctcc agagacaatg ccaagaacac cctgtacctg     300
caaatgagcc ggctgaagtc tgaggacaca gccatgtatt actgtgcaag acgggggtta     360
ccgttccatg ctatggacta ttggggtcaa ggaacctcag tcaccgtctc ctcagccaaa     420
acgaagggcc catccgtctt ccccctggcg ccctgctcca ggagcacctc cgagagcaca     480
gccgccctgg gctgcctggt caaggactac ttccccgaac cggtgacggt gtcgtggaac     540
```

```
tcaggcgccc tgaccagcgg cgtgcacacc ttcccggctg tcctacagtc ctcaggactc    600
tactccctca gcagcgtggt gaccgtgccc tccagcagct tgggcacgaa gacctacacc    660
tgcaacgtag atcacaagcc cagcaacacc aaggtggaca gagagttga gtccaaatat    720 ggtcccccat gcccaccctg cccagcacct gagttcgaag ggggaccatc agtcttcctg    780
ttccccccaa aacccaagga cactctcatg atctcccgga cccctgaggt cacgtgcgtg    840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caaagggcag   1080
ccccgagagc cacaggtgta caccctgccc ccatcccagg aggagatgac caagaaccag   1140
gtcagcctga cctgcctggt caaaggcttc taccccagcg acatcgccgt ggagtgggag   1200
agcaatgggc agccggagaa caactacaag accacgcctc ccgtgctgga ctccgacggc   1260
tccttcttcc tctacagcag gctaaccgtg gacaagagca ggtggcagga ggggaatgtc   1320
ttctcatgct ccgtgatgca tgaggctctg cacaaccact acacacagaa gagcctctcc   1380
ctgtctctgg gtaaagctag ctga                                         1404
```

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide.

<400> SEQUENCE: 42

Tyr Thr Ser Ile Leu His Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 43

Gln Gln Phe Asn Lys Leu Pro Pro Thr
1               5

<210> SEQ ID NO 44
<211> LENGTH: 10
<212> TYPE: PRT
<213> ORGANISM: Artificial Sequence
<220> FEATURE:
<223> OTHER INFORMATION: Synthetic peptide.

<400> SEQUENCE: 44

Gly Phe Thr Phe Ser Asp Tyr Tyr Met Tyr
1               5                   10

<210> SEQ ID NO 45
<211> LENGTH: 17
<212> TYPE: PRT
<213> ORGANISM: Artificial Sequence
<220> FEATURE:
<223> OTHER INFORMATION: Synthetic peptide.

<400> SEQUENCE: 45

```
Tyr Ile Asn Ser Gly Gly Gly Ser Thr Tyr Tyr Pro Asp Thr Val Lys
1               5                   10                  15
Gly
```

<210> SEQ ID NO 46
<211> LENGTH: 10
<212> TYPE: PRT
<213> ORGANISM: Artificial Sequence
<220> FEATURE:
<223> OTHER INFORMATION: Synthetic peptide.

<400> SEQUENCE: 46

```
Arg Gly Leu Pro Phe His Ala Met Asp Tyr
1               5                   10
```

<210> SEQ ID NO 47
<211> LENGTH: 10
<212> TYPE: PRT
<213> ORGANISM: Artificial Sequence
<220> FEATURE:
<223> OTHER INFORMATION: Synthetic peptide.

<400> SEQUENCE: 47

```
Arg Gly Leu Pro Phe His Ala Met Asp Tyr
1               5                   10
```

<210> SEQ ID NO 48
<211> LENGTH: 36
<212> TYPE: DNA
<213> ORGANISM: Artificial Sequence
<220> FEATURE:
<223> OTHER INFORMATION: Synthetic oligonucleotide.

<400> SEQUENCE: 48
ggatggtggg aagatggata cagttggtgc agcatc                              36

<210> SEQ ID NO 49
<211> LENGTH: 31
<212> TYPE: DNA
<213> ORGANISM: Artificial Sequence
<220> FEATURE:
<223> OTHER INFORMATION: Synthetic oligonucleotide.

<400> SEQUENCE: 49
ccaggcatcc tagagtcacc gaggagccag t                                   31

<210> SEQ ID NO 50
<211> LENGTH: 70
<212> TYPE: DNA
<213> ORGANISM: Artificial Sequence
<220> FEATURE:
<223> OTHER INFORMATION: Synthetic oligonucleotide.

<400> SEQUENCE: 50
gctagcgata caacagaacc tgcaacacct acaacacctg taacaacacc gacaacaaca    60
cttctagcgc                                                           70

<210> SEQ ID NO 51
<211> LENGTH: 186
<212> TYPE: DNA
<213> ORGANISM: Artificial Sequence
<220> FEATURE:
<223> OTHER INFORMATION: Synthetic oligonucleotide.

<400> SEQUENCE: 51

```
gacaccaccg aggcccgcca cccccacccc cccgtgacca ccccaccac caccgaccgg    60 aagggcacca ccgccgagga gctggccggc atcggcatcc tgaccgtgat cctgggcggc   120
aagcggacca acaacagcac ccccaccaag ggcgaattct gcagatatcc atcacactgg   180
cggccg                                                              186
```

<210> SEQ ID NO 52
<211> LENGTH: 61
<212> TYPE: PRT
<213> ORGANISM: Artificial Sequence
<220> FEATURE:
<223> OTHER INFORMATION: Synthetic peptide.

<400> SEQUENCE: 52

```
Asp Thr Thr Glu Ala Arg His Pro His Pro Pro Val Thr Thr Pro Thr
 1               5                  10                  15

Thr Asp Arg Lys Gly Thr Thr Ala Glu Glu Leu Ala Gly Ile Gly Ile
            20                  25                  30

Leu Thr Val Ile Leu Gly Gly Lys Arg Thr Asn Asn Ser Thr Pro Thr
        35                  40                  45

Lys Gly Glu Phe Cys Arg Tyr Pro Ser His Trp Arg Pro
    50                  55                  60
```

<210> SEQ ID NO 53
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 53

```
Met Lys Ala Asn Leu Leu Val Leu Leu Cys Ala Leu Ala Ala Ala Asp
 1               5                  10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg
    50                  55                  60
```

<210> SEQ ID NO 54
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 54

```
Leu Lys Gly Ile Ala Pro Leu Gln Leu Gly Lys Cys Asn Ile Ala Gly
 1               5                  10                  15

Trp Leu Leu Gly Asn Pro Glu Cys Asp Pro Leu Leu Pro Val Arg Ser
            20                  25                  30

Trp Ser Tyr Ile Val Glu Thr Pro Asn Ser Glu Asn Gly Ile Cys Tyr
        35                  40                  45

Pro Gly Asp Phe Ile Asp Tyr Glu Glu Leu Arg Glu
    50                  55                  60
```

<210> SEQ ID NO 55
<211> LENGTH: 60
<212> TYPE: PRT

```
<213> ORGANISM: Artificial Sequence
<220> FEATURE:
<223> OTHER INFORMATION: Synthetic peptide.

<400> SEQUENCE: 55

Gln Leu Ser Ser Val Ser Ser Phe Glu Arg Phe Glu Ile Phe Pro Lys
1               5                   10                  15

Glu Ser Ser Trp Pro Asn His Asn Thr Asn Gly Val Thr Ala Ala Cys
                20                  25                  30

Ser His Glu Gly Lys Ser Ser Phe Tyr Arg Asn Leu Leu Trp Leu Thr
            35                  40                  45

Glu Lys Glu Gly Ser Tyr Pro Lys Leu Lys Asn Ser
        50                  55                  60

<210> SEQ ID NO 56
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 56

Tyr Val Asn Lys Lys Gly Lys Glu Val Leu Val Leu Trp Gly Ile His
1               5                   10                  15

His Pro Pro Asn Ser Lys Glu Gln Gln Asn Leu Tyr Gln Asn Glu Asn
                20                  25                  30

Ala Tyr Val Ser Val Val Thr Ser Asn Tyr Asn Arg Arg Phe Thr Pro
            35                  40                  45

Glu Ile Ala Glu Arg Pro Lys Val Arg Asp Gln Ala
        50                  55                  60

<210> SEQ ID NO 57
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 57

Gly Arg Met Asn Tyr Tyr Trp Thr Leu Leu Lys Pro Gly Asp Thr Ile
1               5                   10                  15

Ile Phe Glu Ala Asn Gly Asn Leu Ile Ala Pro Met Tyr Ala Phe Ala
                20                  25                  30

Leu Ser Arg Gly Phe Gly Ser Gly Ile Ile Thr Ser Asn Ala Ser Met
            35                  40                  45

His Glu Cys Asn Thr Lys Cys Gln Thr Pro Leu Gly
        50                  55                  60

<210> SEQ ID NO 58
<211> LENGTH: 40
<212> TYPE: PRT
<213> ORGANISM: Artificial Sequence
<220> FEATURE:
<223> OTHER INFORMATION: Synthetic peptide.

<400> SEQUENCE: 58

Ala Ile Asn Ser Ser Leu Pro Tyr Gln Asn Ile His Pro Val Thr Ile
1               5                   10                  15

Gly Glu Cys Pro Lys Tyr Val Arg Ser Ala Lys Leu Arg Met Val Thr
                20                  25                  30

Gly Leu Arg Asn Ile Pro Ser Ile
```

<210> SEQ ID NO 59
<211> LENGTH: 17
<212> TYPE: PRT
<213> ORGANISM: Artificial Sequence
<220> FEATURE:
<223> OTHER INFORMATION: Synthetic peptide.

<400> SEQUENCE: 59

Ser Ser Phe Glu Arg Phe Glu Ile Phe Pro Lys Glu Ser Ser Trp Pro
1               5                   10                  15
Asn

<210> SEQ ID NO 60
<211> LENGTH: 17
<212> TYPE: PRT
<213> ORGANISM: Artificial Sequence
<220> FEATURE:
<223> OTHER INFORMATION: Synthetic peptide.

<400> SEQUENCE: 60

Gly Asn Leu Ile Ala Pro Trp Tyr Ala Phe Ala Leu Ser Arg Gly Phe
1               5                   10                  15
Gly

<210> SEQ ID NO 61
<211> LENGTH: 17
<212> TYPE: PRT
<213> ORGANISM: Artificial Sequence
<220> FEATURE:
<223> OTHER INFORMATION: Synthetic peptide.

<400> SEQUENCE: 61

Trp Tyr Ala Phe Ala Leu Ser Arg Gly Phe Gly Ser Gly Ile Ile Thr
1               5                   10                  15
Ser

<210> SEQ ID NO 62
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 62

Met Ala Ser Gln Gly Thr Lys Arg Ser Tyr Glu Gln Met Glu Thr Asp
1               5                   10                  15
Gly Glu Arg Gln Asn Ala Thr Glu Ile Arg Ala Ser Val Gly Lys Met
                20                  25                  30
Ile Gly Gly Ile Gly Arg Phe Tyr Ile Gln Met Cys Thr Glu Leu Lys
            35                  40                  45
Leu Ser Asp Tyr Glu Gly Arg Leu Ile Gln Asn Ser
        50                  55                  60

<210> SEQ ID NO 63
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 63

```
Leu Thr Ile Glu Arg Met Val Leu Ser Ala Phe Asp Glu Arg Arg Asn
1               5                   10                  15

Lys Tyr Leu Glu Glu His Pro Ser Ala Gly Lys Asp Pro Lys Lys Thr
            20                  25                  30

Gly Gly Pro Ile Tyr Arg Arg Val Asn Gly Lys Trp Met Arg Glu Leu
        35                  40                  45

Ile Leu Tyr Asp Lys Glu Glu Ile Arg Arg Ile Trp
50                  55                  60

<210> SEQ ID NO 64
<211> LENGTH: 58
<212> TYPE: PRT
<213> ORGANISM: Artificial Sequence
<220> FEATURE:
<223> OTHER INFORMATION: Synthetic peptide.

<400> SEQUENCE: 64

Arg Gln Ala Asn Asn Gly Asp Asp Ala Thr Ala Gly Leu Thr His Met
1               5                   10                  15

Met Ile Trp His Ser Asn Leu Asn Asp Ala Thr Tyr Gln Arg Thr Arg
            20                  25                  30

Ala Leu Val Arg Thr Gly Met Asp Pro Arg Met Cys Ser Leu Met Gln
        35                  40                  45

Gly Ser Thr Leu Pro Arg Arg Ser Gly Ala
    50                  55

<210> SEQ ID NO 65
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 65

Ala Ala Val Lys Gly Val Gly Thr Met Val Met Glu Leu Val Arg Met
1               5                   10                  15

Ile Lys Arg Gly Ile Asn Asp Arg Asn Phe Trp Arg Gly Glu Asn Gly
            20                  25                  30

Arg Lys Thr Arg Ile Ala Tyr Glu Arg Met Cys Asn Ile Leu Lys Gly
        35                  40                  45

Lys Phe Gln Thr Ala Ala Gln Lys Ala Met Met Asp
    50                  55                  60

<210> SEQ ID NO 66
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 66

Gln Val Arg Glu Ser Arg Asn Pro Gly Asn Ala Glu Phe Glu Asp Leu
1               5                   10                  15

Thr Phe Leu Ala Arg Ser Ala Leu Ile Leu Arg Gly Ser Val Ala His
            20                  25                  30

Lys Ser Cys Leu Pro Ala Cys Val Tyr Gly Pro Ala Val Ala Ser Gly
        35                  40                  45

Tyr Asp Phe Glu Arg Glu Gly Tyr Ser Leu Val Gly
    50                  55                  60
```

```
<210> SEQ ID NO 67
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 67

Ile Asp Pro Phe Arg Leu Leu Gln Asn Ser Gln Val Tyr Ser Leu Ile
1               5                   10                  15

Arg Pro Asn Glu Asn Pro Ala His Lys Ser Gln Leu Val Trp Met Ala
            20                  25                  30

Cys His Ser Ala Ala Phe Glu Asp Leu Arg Val Leu Ser Phe Ile Lys
        35                  40                  45

Gly Thr Lys Val Leu Pro Arg Gly Lys Leu Ser Thr
    50                  55                  60

<210> SEQ ID NO 68
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 68

Arg Gly Val Gln Ile Ala Ser Asn Glu Asn Met Glu Thr Met Glu Ser
1               5                   10                  15

Ser Thr Leu Glu Leu Arg Ser Arg Tyr Trp Ala Ile Arg Thr Arg Ser
            20                  25                  30

Gly Gly Asn Thr Asn Gln Gln Arg Ala Ser Ala Gly Gln Ile Ser Ile
        35                  40                  45

Gln Pro Thr Phe Ser Val Gln Arg Asn Leu Pro Phe
    50                  55                  60

<210> SEQ ID NO 69
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 69

Asp Arg Thr Thr Ile Met Ala Ala Phe Asn Gly Asn Thr Glu Gly Arg
1               5                   10                  15

Thr Ser Asp Met Arg Thr Glu Ile Ile Arg Met Met Glu Ser Ala Arg
            20                  25                  30

Pro Glu Asp Val Ser Phe Gln Gly Arg Gly Val Phe Glu Leu Ser Asp
        35                  40                  45

Glu Lys Ala Ala Ser Pro Ile Val Pro Ser Phe Asp
    50                  55                  60

<210> SEQ ID NO 70
<211> LENGTH: 18
<212> TYPE: PRT
<213> ORGANISM: Artificial Sequence
<220> FEATURE:
<223> OTHER INFORMATION: Synthetic peptide.

<400> SEQUENCE: 70

Met Ser Asn Glu Gly Ser Tyr Phe Phe Gly Asp Asn Ala Glu Glu Tyr
1               5                   10                  15

Asp Asn
```

```
<210> SEQ ID NO 71
<211> LENGTH: 17
<212> TYPE: PRT
<213> ORGANISM: Artificial Sequence
<220> FEATURE:
<223> OTHER INFORMATION: Synthetic peptide.

<400> SEQUENCE: 71

Gly Lys Trp Val Arg Glu Leu Val Leu Tyr Asp Lys Glu Glu Ile Arg
1               5                   10                  15

Arg

<210> SEQ ID NO 72
<211> LENGTH: 17
<212> TYPE: PRT
<213> ORGANISM: Artificial Sequence
<220> FEATURE:
<223> OTHER INFORMATION: Synthetic peptide.

<400> SEQUENCE: 72

Arg Thr Gly Met Asp Pro Arg Met Cys Ser Leu Met Gln Gly Ser Thr
1               5                   10                  15

Leu

<210> SEQ ID NO 73
<211> LENGTH: 17
<212> TYPE: PRT
<213> ORGANISM: Artificial Sequence
<220> FEATURE:
<223> OTHER INFORMATION: Synthetic peptide.

<400> SEQUENCE: 73

Met Cys Asn Ile Leu Lys Gly Lys Phe Gln Thr Ala Ala Gln Lys Ala
1               5                   10                  15

Met

<210> SEQ ID NO 74
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 74

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val
        50                  55                  60

<210> SEQ ID NO 75
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 75

Leu Thr Ala Ala His Cys Ile Arg Asn Lys Ser Val Ile Leu Leu Gly
```

```
                1               5                   10                  15
Arg His Ser Leu Phe His Pro Glu Asp Thr Gly Gln Val Phe Gln Val
                                20                  25                  30

Ser His Ser Phe Pro His Pro Leu Tyr Asp Met Ser Leu Leu Lys Asn
                35                  40                  45

Arg Phe Leu Arg Pro Gly Asp Asp Ser Ser His Asp
    50                  55                  60
```

<210> SEQ ID NO 76
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 76

```
Leu Met Leu Leu Arg Leu Ser Glu Pro Ala Glu Leu Thr Asp Ala Val
1               5                   10                  15

Lys Val Met Asp Leu Pro Thr Gln Glu Pro Ala Leu Gly Thr Thr Cys
                20                  25                  30

Tyr Ala Ser Gly Trp Gly Ser Ile Glu Pro Glu Glu Phe Leu Thr Pro
                35                  40                  45

Lys Lys Leu Gln Cys Val Asp Leu His Val Ile Ser
    50                  55                  60
```

<210> SEQ ID NO 77
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 77

```
Asn Asp Val Cys Ala Gln Val His Pro Gln Lys Val Thr Lys Phe Met
1               5                   10                  15

Leu Cys Ala Gly Arg Trp Thr Gly Gly Lys Ser Thr Cys Ser Gly Asp
                20                  25                  30

Ser Gly Gly Pro Leu Val Cys Asn Gly Val Leu Gln Gly Ile Thr Ser
                35                  40                  45

Trp Gly Ser Glu Pro Cys Ala Leu Pro Glu Arg Pro
    50                  55                  60
```

<210> SEQ ID NO 78
<211> LENGTH: 21
<212> TYPE: PRT
<213> ORGANISM: Artificial Sequence
<220> FEATURE:
<223> OTHER INFORMATION: Synthetic peptide.

<400> SEQUENCE: 78

```
Ser Leu Tyr Thr Lys Val Val His Tyr Arg Lys Trp Ile Lys Asp Thr
1               5                   10                  15

Ile Val Ala Asn Pro
                20
```

<210> SEQ ID NO 79
<211> LENGTH: 15
<212> TYPE: PRT
<213> ORGANISM: Artificial Sequence
<220> FEATURE:
<223> OTHER INFORMATION: Synthetic peptide.

```
<400> SEQUENCE: 79

Ala Pro Leu Ile Leu Ser Arg Ile Val Gly Gly Trp Glu Cys Glu
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 80

Glu Cys Glu Lys His Ser Gln Pro Trp Gln Val Leu Val Ala Ser
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: Synthetic peptide.

<400> SEQUENCE: 81

Gly Asp Asp Ser Ser His Asp Leu Met Leu Leu Arg Leu Ser Glu
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 82

Ser His Asp Leu Met Leu Leu Arg Leu Ser Glu Pro Ala Glu Leu
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 83

Ser Gly Asp Ser Gly Gly Pro Leu Val Cys Asn Gly Val Leu Gln
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 84

Gly Ser Glu Pro Cys Ala Leu Pro Glu Arg Pro Ser Leu Tyr Thr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 85
```

```
Glu Arg Pro Ser Leu Tyr Thr Lys Val Val His Tyr Arg Lys Trp
1               5                   10                  15
```

<210> SEQ ID NO 86
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 86

```
Val Val His Tyr Arg Lys Trp Ile Lys Asp Thr Ile Val Ala Asn
1               5                   10                  15
```

<210> SEQ ID NO 87
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 87

```
Met Arg Ser Tyr Arg Phe Ser Asp Tyr Leu His Met Ser Val Ser Phe
1               5                   10                  15

Ser Asn Asp Met Asp Leu Phe Cys Gly Glu Asp Ser Gly Val Phe Ser
                20                  25                  30

Gly Glu Ser Thr Val Asp Phe Ser Ser Glu Val Asp Ser Trp Pro
            35                  40                  45

Gly Asp Ser Ile Ala Cys Phe Ile Glu Asp Glu Arg
        50                  55                  60
```

<210> SEQ ID NO 88
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 88

```
His Phe Val Pro Gly His Asp Tyr Leu Ser Arg Phe Gln Thr Arg Ser
1               5                   10                  15

Leu Asp Ala Ser Ala Arg Glu Asp Ser Val Ala Trp Ile Leu Lys Val
                20                  25                  30

Gln Ala Tyr Tyr Asn Phe Gln Pro Leu Thr Tyr Leu Ala Val Asn
            35                  40                  45

Tyr Met Asp Arg Phe Leu Tyr Ala Arg Arg Leu Pro
        50                  55                  60
```

<210> SEQ ID NO 89
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 89

```
Glu Thr Ser Gly Trp Pro Met Gln Leu Leu Ala Val Ala Cys Leu Ser
1               5                   10                  15

Leu Ala Ala Lys Met Glu Glu Ile Leu Val Pro Ser Leu Phe Asp Phe
                20                  25                  30

Gln Val Ala Gly Val Lys Tyr Leu Phe Glu Ala Lys Thr Ile Lys Arg
            35                  40                  45
```

```
Met Glu Leu Leu Val Leu Ser Val Leu Asp Trp Arg
    50                  55                  60

<210> SEQ ID NO 90
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 90

Leu Arg Ser Val Thr Pro Phe Asp Phe Ile Ser Phe Ala Tyr Lys
1               5                  10                  15

Ile Asp Pro Ser Gly Thr Phe Leu Gly Phe Phe Ile Ser His Ala Thr
            20                  25                  30

Glu Ile Ile Leu Ser Asn Ile Lys Glu Ala Ser Phe Leu Glu Tyr Trp
        35                  40                  45

Pro Ser Ser Ile Ala Ala Ala Ala Ile Leu Cys Val
    50                  55                  60

<210> SEQ ID NO 91
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 91

Ala Asn Glu Leu Pro Ser Leu Ser Ser Val Val Asn Pro His Glu Ser
1               5                  10                  15

Pro Glu Thr Trp Cys Asp Gly Leu Ser Lys Glu Lys Ile Val Arg Cys
            20                  25                  30

Tyr Arg Leu Met Lys Ala Met Ala Ile Glu Asn Asn Arg Leu Asn Thr
        35                  40                  45

Pro Lys Val Ile Ala Lys Leu Arg Val Ser Val Arg
    50                  55                  60

<210> SEQ ID NO 92
<211> LENGTH: 39
<212> TYPE: PRT
<213> ORGANISM: Artificial Sequence
<220> FEATURE:
<223> OTHER INFORMATION: Synthetic peptide.

<400> SEQUENCE: 92

Ala Ser Ser Thr Leu Thr Arg Pro Ser Asp Glu Ser Ser Phe Ser Ser
1               5                  10                  15

Ser Ser Pro Cys Lys Arg Arg Lys Leu Ser Gly Tyr Ser Trp Val Gly
            20                  25                  30

Asp Glu Thr Ser Thr Ser Asn
        35

<210> SEQ ID NO 93
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 93

Asp Arg Val Leu Arg Ala Met Leu Lys Ala Glu Glu Thr Cys Ala
1               5                  10                  15
```

<210> SEQ ID NO 94
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 94

Arg Ala Met Leu Lys Ala Glu Glu Thr Cys Ala Pro Ser Val Ser
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic peptide.

<400> SEQUENCE: 95

Thr Cys Ala Pro Ser Val Ser Tyr Phe Lys Cys Val Gln Lys Glu
1               5                   10                  15

<210> SEQ ID NO 96
<211> LENGTH: 587
<212> TYPE: PRT
<213> ORGANISM: Artificial Sequence
<220> FEATURE:
<223> OTHER INFORMATION: Synthetic peptide.

<400> SEQUENCE: 96

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

```
Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
        260                 265                 270

Gln Phe Asn Trp Tyr Val Asp Gly Val Glu Val His Asn Ala Lys Thr
    275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Gln Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Asn His Tyr Thr Gln Lys Ser Leu Ser Leu Ser Leu Gly Lys Ala Ser
    435                 440                 445

Gln Thr Pro Thr Asn Thr Ile Ser Val Thr Pro Thr Asn Asn Ser Thr
450                 455                 460

Pro Thr Asn Asn Ser Asn Pro Lys Pro Asn Pro Ala Ser Gly Phe Asp
465                 470                 475                 480

His Arg Asp Ser Lys Val Ser Leu Gln Glu Lys Asn Cys Glu Pro Val
            485                 490                 495

Val Pro Asn Ala Pro Pro Ala Tyr Glu Lys Leu Ser Ala Glu Gln Ser
        500                 505                 510

Pro Pro Pro Tyr Ser Pro Ala Ser Thr Asn Gly Ser Ile Thr Val Ala
    515                 520                 525

Ala Thr Ala Pro Thr Val Thr Pro Thr Val Asn Ala Thr Pro Ser Ala
530                 535                 540

Ala Ala Ser Met Pro Arg Glu Asp Ala His Phe Ile Tyr Gly Tyr Pro
545                 550                 555                 560

Lys Lys Gly His Gly His Ser Tyr Thr Thr Ala Glu Glu Ala Ala Gly
            565                 570                 575

Ile Gly Ile Leu Thr Val Ile Leu Gly Ala Ser
        580                 585

<210> SEQ ID NO 97
<211> LENGTH: 656
<212> TYPE: PRT
<213> ORGANISM: Artificial Sequence
<220> FEATURE:
<223> OTHER INFORMATION: Synthetic peptide.

<400> SEQUENCE: 97
```

-continued

```
Glu Val Lys Leu Val Glu Ser Gly Gly Gly Leu Val Gln Pro Gly Gly
1               5                   10                  15
Ser Leu Lys Leu Ser Cys Ala Thr Ser Gly Phe Thr Phe Ser Asp Tyr
            20                  25                  30
Tyr Met Tyr Trp Val Arg Gln Thr Pro Glu Lys Arg Leu Glu Trp Val
        35                  40                  45
Ala Tyr Ile Asn Ser Gly Gly Gly Ser Thr Tyr Tyr Pro Asp Thr Val
    50                  55                  60
Lys Gly Arg Phe Thr Ile Ser Arg Asp Asn Ala Lys Asn Thr Leu Tyr
65                  70                  75                  80
Leu Gln Met Ser Arg Leu Lys Ser Glu Asp Thr Ala Met Tyr Tyr Cys
                85                  90                  95
Ala Arg Arg Gly Leu Pro Phe His Ala Met Asp Tyr Trp Gly Gln Gly
            100                 105                 110
Thr Ser Val Thr Val Ser Ser Ala Lys Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
    210                 215                 220
Cys Pro Pro Cys Pro Ala Pro Glu Phe Glu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
```

```
                420             425             430
Asn His Tyr Thr Gln Lys Ser Leu Ser Leu Gly Lys Ala Ser
            435             440             445

Gln Thr Pro Thr Asn Thr Ile Ser Val Thr Pro Thr Asn Ser Thr
    450             455             460

Pro Thr Asn Asn Ser Asn Pro Lys Pro Asn Pro Ala Ser Gly Phe Asp
465             470             475             480

His Arg Asp Ser Lys Val Ser Leu Gln Glu Lys Asn Cys Glu Pro Val
            485             490             495

Val Pro Asn Ala Pro Pro Ala Tyr Glu Lys Leu Ser Ala Glu Gln Ser
            500             505             510

Pro Pro Pro Tyr Ser Pro Ala Ser Thr Asn Gly Ser Ile Thr Val Ala
            515             520             525

Ala Thr Ala Pro Thr Val Thr Pro Thr Val Asn Ala Thr Pro Ser Ala
            530             535             540

Ala Ala Ser Met Pro Arg Glu Asp Ala His Phe Ile Tyr Gly Tyr Pro
545             550             555             560

Lys Lys Gly His Gly His Ser Tyr Thr Thr Ala Glu Glu Ala Ala Gly
            565             570             575

Ile Gly Ile Leu Thr Val Ile Leu Gly Ala Ser Thr Val Thr Pro Thr
            580             585             590

Ala Thr Ala Thr Pro Ser Ala Ile Val Thr Thr Ile Thr Pro Thr Ala
            595             600             605

Thr Thr Lys Pro Ala Ser Val Leu Leu Leu Ile Gly Cys Trp Tyr Cys
            610             615             620

Arg Arg Arg Asn Gly Tyr Arg Ala Leu Met Asp Lys Ser Leu His Val
625             630             635             640

Gly Thr Gln Cys Ala Leu Thr Arg Arg Cys Pro Gln Glu Gly Ala Ser
            645             650             655

<210> SEQ ID NO 98
<211> LENGTH: 593
<212> TYPE: PRT
<213> ORGANISM: Artificial Sequence
<220> FEATURE:
<223> OTHER INFORMATION: Synthetic peptide.

<400> SEQUENCE: 98

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
```

```
              130                 135                 140
Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
                195                 200                 205

Asn Val Asp His Lys Pro Ser Asn Thr Lys Val Asp Lys Arg Val Glu
                210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
                275                 280                 285

Val His Asn Ala Lys Thr Lys Pro Arg Glu Glu Gln Phe Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Gln Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
                420                 425                 430

Met His Glu Ala Leu His Asn His Tyr Thr Gln Lys Ser Leu Ser Leu
                435                 440                 445

Ser Leu Gly Lys Ala Ser Gln Thr Pro Thr Asn Thr Ile Ser Val Thr
450                 455                 460

Pro Thr Asn Asn Ser Thr Pro Thr Asn Asn Ser Asn Pro Lys Pro Asn
465                 470                 475                 480

Pro Ala Ser Gly Phe Asp His Arg Asp Ser Lys Val Ser Leu Gln Glu
                485                 490                 495

Lys Asn Cys Glu Pro Val Val Pro Asn Ala Pro Ala Tyr Glu Lys
                500                 505                 510

Leu Ser Ala Glu Gln Ser Pro Pro Tyr Ser Pro Ala Ser Thr Asn
                515                 520                 525

Gly Ser Ile Thr Val Ala Ala Thr Ala Pro Thr Val Thr Pro Thr Val
                530                 535                 540

Asn Ala Thr Pro Ser Ala Ala Ala Ser Met Pro Arg Glu Asp Ala His
545                 550                 555                 560
```

```
Phe Ile Tyr Gly Tyr Pro Lys Lys Gly His Gly His Ser Tyr Thr Thr
                565                 570                 575

Ala Glu Glu Ala Ala Gly Ile Gly Ile Leu Thr Val Ile Leu Gly Ala
            580                 585                 590

Ser

<210> SEQ ID NO 99
<211> LENGTH: 660
<212> TYPE: PRT
<213> ORGANISM: Artificial Sequence
<220> FEATURE:
<223> OTHER INFORMATION: Synthetic peptide.

<400> SEQUENCE: 99

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys Ala Ser Gln Thr Pro Thr Asn Thr Ile Ser Val Thr Pro Thr
    450                 455                 460

Asn Asn Ser Thr Pro Thr Asn Asn Ser Asn Pro Lys Pro Asn Pro Ala
465                 470                 475                 480

Ser Gly Phe Asp His Arg Asp Ser Lys Val Ser Leu Gln Glu Lys Asn
                485                 490                 495

Cys Glu Pro Val Val Pro Asn Ala Pro Pro Ala Tyr Glu Lys Leu Ser
            500                 505                 510

Ala Glu Gln Ser Pro Pro Tyr Ser Pro Ala Ser Thr Asn Gly Ser
        515                 520                 525

Ile Thr Val Ala Ala Thr Ala Pro Thr Val Thr Pro Thr Val Asn Ala
    530                 535                 540

Thr Pro Ser Ala Ala Ala Ser Met Pro Arg Glu Asp Ala His Phe Ile
545                 550                 555                 560

Tyr Gly Tyr Pro Lys Lys Gly His Gly His Ser Tyr Thr Thr Ala Glu
                565                 570                 575

Glu Ala Ala Gly Ile Gly Ile Leu Thr Val Ile Leu Gly Ala Ser Thr
            580                 585                 590

Val Thr Pro Thr Ala Thr Ala Thr Pro Ser Ala Ile Val Thr Thr Ile
        595                 600                 605

Thr Pro Thr Ala Thr Thr Lys Pro Ala Ser Val Leu Leu Leu Ile Gly
    610                 615                 620

Cys Trp Tyr Cys Arg Arg Arg Asn Gly Tyr Arg Ala Leu Met Asp Lys
625                 630                 635                 640

Ser Leu His Val Gly Thr Gln Cys Ala Leu Thr Arg Arg Cys Pro Gln
                645                 650                 655

Glu Gly Ala Ser
        660

<210> SEQ ID NO 100
<211> LENGTH: 630
<212> TYPE: DNA
<213> ORGANISM: Artificial Sequence
<220> FEATURE:
<223> OTHER INFORMATION: Synthetic oligonucleotide.

<400> SEQUENCE: 100
aacaccgaca acaacagatg atctggatgc agctagtggg tttgatcatc gggacagcaa     60
agtgtctctt caagagaaaa actgtgaacc tgtggttccc aatgctccac ctgcttatga    120
```

```
gaaactctct gcagaacagt caccaccacc ttattcacct gctagtacca acggcagcat    180
caccgtggcc gccaccgccc ccaccgtgac ccccaccgtg aacgccaccc ccagcgccgc    240
cgctagtatg ccaagagaag atgctcactt catctatggt tacccaagag agggcacgg    300 ccactcttac accacggctg aagaggccgc tgggatcggc atcctgacag tgatcctggg    360
agctagtacc gtgaccccca ccgccaccgc caccccagc gccatcgtga ccaccatcac    420
ccccaccgcc accaccaagc ccgctagtgt cttactgctc atcggctgtt ggtattgtag    480
aagacgaaat ggatacagag ccttgatgga taaaagtctt catgttggca ctcaatgtgc    540
cttaacaaga agatgcccac aagaagggtg agcggccgca tcgaagagct cggtacccgg    600
ggatcctcta gagtcgacct gcaggcatgc                                    630
```

```
<210> SEQ ID NO 101
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 101

Gly Phe Asp His Arg Asp Ser Lys Val Ser Leu Gln Glu Lys Asn Cys
1               5                   10                  15

Glu Pro Val Val Pro Asn Ala Pro Pro Ala Tyr Glu Lys Leu Ser Ala
            20                  25                  30

Glu Gln Ser Pro Pro Pro Tyr Ser Pro Ala Ser Thr Asn Gly Ser Ile
        35                  40                  45

Thr Val Ala Ala Thr Ala Pro Thr Val Thr Pro Thr
    50                  55                  60

<210> SEQ ID NO 102
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 102

Val Asn Ala Thr Pro Ser Ala Ala Ser Met Pro Arg Glu Asp Ala
1               5                   10                  15

His Phe Ile Tyr Gly Tyr Pro Lys Lys Gly His Gly His Ser Tyr Thr
            20                  25                  30

Thr Ala Glu Glu Ala Ala Gly Ile Gly Ile Leu Thr Val Ile Leu Gly
        35                  40                  45

Ala Ser Thr Val Thr Pro Thr Ala Thr Ala Thr Pro
    50                  55                  60

<210> SEQ ID NO 103
<211> LENGTH: 57
<212> TYPE: PRT
<213> ORGANISM: Artificial Sequence
<220> FEATURE:
<223> OTHER INFORMATION: Synthetic peptide.

<400> SEQUENCE: 103

Ser Ala Ile Val Thr Thr Ile Thr Pro Thr Ala Thr Thr Lys Pro Ala
1               5                   10                  15

Ser Val Leu Leu Leu Ile Gly Cys Trp Tyr Cys Arg Arg Arg Asn Gly
            20                  25                  30
```

-continued

Tyr Arg Ala Leu Met Asp Lys Ser Leu His Val Gly Thr Gln Cys Ala
                35                  40                  45

Leu Thr Arg Arg Cys Pro Gln Glu Gly
        50                  55

<210> SEQ ID NO 104
<211> LENGTH: 41
<212> TYPE: PRT
<213> ORGANISM: Artificial Sequence
<220> FEATURE:
<223> OTHER INFORMATION: Synthetic peptide.

<400> SEQUENCE: 104

Gly Phe Asp His Arg Asp Ser Lys Val Ser Leu Gln Glu Lys Asn Cys
1               5                   10                  15

Glu Pro Val Val Pro Asn Ala Pro Ala Tyr Glu Lys Leu Ser Ala
            20                  25                  30

Glu Gln Ser Pro Pro Pro Tyr Ser Pro
        35                  40

<210> SEQ ID NO 105
<211> LENGTH: 29
<212> TYPE: PRT
<213> ORGANISM: Artificial Sequence
<220> FEATURE:
<223> OTHER INFORMATION: Synthetic peptide.

<400> SEQUENCE: 105

Ala Ser Thr Asn Gly Ser Ile Thr Val Ala Ala Thr Ala Pro Thr Val
1               5                   10                  15

Thr Pro Thr Val Asn Ala Thr Pro Ser Ala Ala Ala Ser
            20                  25

<210> SEQ ID NO 106
<211> LENGTH: 38
<212> TYPE: PRT
<213> ORGANISM: Artificial Sequence
<220> FEATURE:
<223> OTHER INFORMATION: Synthetic peptide.

<400> SEQUENCE: 106

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly
        35

<210> SEQ ID NO 107
<211> LENGTH: 29
<212> TYPE: PRT
<213> ORGANISM: Artificial Sequence
<220> FEATURE:
<223> OTHER INFORMATION: Synthetic peptide.

<400> SEQUENCE: 107

Ala Ser Thr Val Thr Pro Thr Ala Thr Ala Thr Pro Ser Ala Ile Val
1               5                   10                  15

Thr Thr Ile Thr Pro Thr Ala Thr Thr Lys Pro Ala Ser
            20                  25

<210> SEQ ID NO 108
<211> LENGTH: 40

```
<212> TYPE: PRT
<213> ORGANISM: Artificial Sequence
<220> FEATURE:
<223> OTHER INFORMATION: Synthetic peptide.

<400> SEQUENCE: 108

Val Leu Leu Ile Gly Cys Trp Tyr Cys Arg Arg Arg Asn Gly Tyr
1               5                   10                  15

Arg Ala Leu Met Asp Lys Ser Leu His Val Gly Thr Gln Cys Ala Leu
            20                  25                  30

Thr Arg Arg Cys Pro Gln Glu Gly
        35                  40

<210> SEQ ID NO 109
<211> LENGTH: 110
<212> TYPE: PRT
<213> ORGANISM: Artificial Sequence
<220> FEATURE:
<223> OTHER INFORMATION: Synthetic peptide.

<400> SEQUENCE: 109

Gly Phe Asp His Arg Asp Ser Lys Val Ser Leu Gln Glu Lys Asn Cys
1               5                   10                  15

Glu Pro Val Val Pro Asn Ala Pro Ala Tyr Glu Lys Leu Ser Ala
            20                  25                  30

Glu Gln Ser Pro Pro Pro Tyr Ser Pro Ala Ser Thr Asn Gly Ser Ile
        35                  40                  45

Thr Val Ala Ala Thr Ala Pro Thr Val Thr Pro Thr Val Asn Ala Thr
    50                  55                  60

Pro Ser Ala Ala Ala Ser Met Pro Arg Glu Asp Ala His Phe Ile Tyr
65                  70                  75                  80

Gly Tyr Pro Lys Lys Gly His Gly His Ser Tyr Thr Thr Ala Glu Glu
                85                  90                  95

Ala Ala Gly Ile Gly Ile Leu Thr Val Ile Leu Gly Ala Ser
            100                 105                 110

<210> SEQ ID NO 110
<211> LENGTH: 675
<212> TYPE: PRT
<213> ORGANISM: Artificial Sequence
<220> FEATURE:
<223> OTHER INFORMATION: Synthetic peptide.

<400> SEQUENCE: 110

Met Asn Leu Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Tyr Ile Asn Ser Gly Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Arg Arg Gly Leu Pro Phe His Ala Met Asp Tyr Trp
```

-continued

```
            115                 120                 125
Gly Gln Gly Thr Ser Val Thr Val Ser Ser Ala Lys Thr Lys Gly Pro
            130                 135                 140
Ser Val Phe Pro Leu Ala Pro Cys Ser Arg Ser Thr Ser Glu Ser Thr
145                 150                 155                 160
Ala Ala Leu Gly Cys Leu Val Lys Asp Tyr Phe Pro Glu Pro Val Thr
                165                 170                 175
Val Ser Trp Asn Ser Gly Ala Leu Thr Ser Gly Val His Thr Phe Pro
                180                 185                 190
Ala Val Leu Gln Ser Ser Gly Leu Tyr Ser Leu Ser Ser Val Val Thr
                195                 200                 205
Val Pro Ser Ser Ser Leu Gly Thr Lys Thr Tyr Thr Cys Asn Val Asp
            210                 215                 220
His Lys Pro Ser Asn Thr Lys Val Asp Lys Arg Val Glu Ser Lys Tyr
225                 230                 235                 240
Gly Pro Pro Cys Pro Pro Cys Pro Ala Pro Glu Phe Glu Gly Gly Pro
                245                 250                 255
Ser Val Phe Leu Phe Pro Pro Lys Pro Lys Asp Thr Leu Met Ile Ser
                260                 265                 270
Arg Thr Pro Glu Val Thr Cys Val Val Val Asp Val Ser Gln Glu Asp
            275                 280                 285
Pro Glu Val Gln Phe Asn Trp Tyr Val Asp Gly Val Glu Val His Asn
            290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Gly Leu Pro Ser Ser Ile Glu Lys
                340                 345                 350
Thr Ile Ser Lys Ala Lys Gly Gln Pro Arg Glu Pro Gln Val Tyr Thr
            355                 360                 365
Leu Pro Pro Ser Gln Glu Glu Met Thr Lys Asn Gln Val Ser Leu Thr
            370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
                420                 425                 430
Ser Arg Trp Gln Glu Gly Asn Val Phe Ser Cys Ser Val Met His Glu
            435                 440                 445
Ala Leu His Asn His Tyr Thr Gln Lys Ser Leu Ser Leu Ser Leu Gly
            450                 455                 460
Lys Ala Ser Gln Thr Pro Thr Asn Thr Ile Ser Val Thr Pro Thr Asn
465                 470                 475                 480
Asn Ser Thr Pro Thr Asn Asn Ser Asn Pro Lys Pro Asn Pro Ala Ser
                485                 490                 495
Gly Phe Asp His Arg Asp Ser Lys Val Ser Leu Gln Glu Lys Asn Cys
                500                 505                 510
Glu Pro Val Val Pro Asn Ala Pro Ala Tyr Glu Lys Leu Ser Ala
            515                 520                 525
Glu Gln Ser Pro Pro Pro Tyr Ser Pro Ala Ser Thr Asn Gly Ser Ile
            530                 535                 540
```

```
Thr Val Ala Ala Thr Ala Pro Thr Val Thr Pro Thr Val Asn Ala Thr
545                 550                 555                 560

Pro Ser Ala Ala Ala Ser Met Pro Arg Glu Asp Ala His Phe Ile Tyr
            565                 570                 575

Gly Tyr Pro Lys Lys Gly His Gly His Ser Tyr Thr Thr Ala Glu Glu
            580                 585                 590

Ala Ala Gly Ile Gly Ile Leu Thr Val Ile Leu Gly Ala Ser Thr Val
        595                 600                 605

Thr Pro Thr Ala Thr Ala Thr Pro Ser Ala Ile Val Thr Thr Ile Thr
        610                 615                 620

Pro Thr Ala Thr Thr Lys Pro Ala Ser Val Leu Leu Leu Ile Gly Cys
625                 630                 635                 640

Trp Tyr Cys Arg Arg Arg Asn Gly Tyr Arg Ala Leu Met Asp Lys Ser
            645                 650                 655

Leu His Val Gly Thr Gln Cys Ala Leu Thr Arg Arg Cys Pro Gln Glu
            660                 665                 670

Gly Ala Ser
        675
```

<210> SEQ ID NO 111
<211> LENGTH: 606
<212> TYPE: PRT
<213> ORGANISM: Artificial Sequence
<220> FEATURE:
<223> OTHER INFORMATION: Synthetic peptide.

<400> SEQUENCE: 111

```
Met Asn Leu Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser Asp Tyr Tyr Met Tyr Trp Val Arg Gln Thr Pro Glu Lys Arg Leu
50                  55                  60

Glu Trp Val Ala Tyr Ile Asn Ser Gly Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
            100                 105                 110

Tyr Tyr Cys Ala Arg Arg Gly Leu Pro Phe His Ala Met Asp Tyr Trp
        115                 120                 125

Gly Gln Gly Thr Ser Val Thr Val Ser Ser Ala Lys Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
210                 215                 220
```

His Lys Pro Ser Asn Thr Lys Val Asp Lys Arg Val Glu Ser Lys Tyr
225                 230                 235                 240

Gly Pro Pro Cys Pro Cys Pro Ala Pro Glu Phe Glu Gly Gly Pro
            245                 250                 255

Ser Val Phe Leu Phe Pro Pro Lys Pro Lys Asp Thr Leu Met Ile Ser
        260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
        290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
            325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
            435                 440                 445

Ala Leu His Asn His Tyr Thr Gln Lys Ser Leu Ser Leu Ser Leu Gly
            450                 455                 460

Lys Ala Ser Gln Thr Pro Thr Asn Thr Ile Ser Val Thr Pro Thr Asn
465                 470                 475                 480

Asn Ser Thr Pro Thr Asn Asn Ser Asn Pro Lys Pro Asn Pro Ala Ser
                485                 490                 495

Gly Phe Asp His Arg Asp Ser Lys Val Ser Leu Gln Glu Lys Asn Cys
            500                 505                 510

Glu Pro Val Val Pro Asn Ala Pro Ala Tyr Glu Lys Leu Ser Ala
        515                 520                 525

Glu Gln Ser Pro Pro Tyr Ser Pro Ala Ser Thr Asn Gly Ser Ile
        530                 535                 540

Thr Val Ala Ala Thr Ala Pro Thr Val Thr Pro Thr Val Asn Ala Thr
545                 550                 555                 560

Pro Ser Ala Ala Ala Ser Met Pro Arg Glu Asp Ala His Phe Ile Tyr
            565                 570                 575

Gly Tyr Pro Lys Lys Gly His Gly His Ser Tyr Thr Thr Ala Glu Glu
            580                 585                 590

Ala Ala Gly Ile Gly Ile Leu Thr Val Ile Leu Gly Ala Ser
        595                 600                 605

<210> SEQ ID NO 112
<211> LENGTH: 661
<212> TYPE: PRT
<213> ORGANISM: Artificial Sequence
<220> FEATURE:

<223> OTHER INFORMATION: Synthetic peptide.

<400> SEQUENCE: 112

```
Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400
```

```
Thr Pro Ala Glu Val Ser Ile Val Val Leu Ser Gly Thr Ala Ala
            405                 410                 415

Gln Val Thr Thr Thr Glu Trp Val Glu Thr Thr Ala Arg Glu Leu Pro
        420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
        500                 505                 510

Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
                580                 585                 590

Leu Gly Gln Val Pro Leu Ile Val Gly Ile Leu Leu Val Leu Met Ala
            595                 600                 605

Val Val Leu Ala Ser Leu Ile Tyr Arg Arg Arg Leu Met Lys Gln Asp
        610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 113
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 113

Ile Met Asp Gln Val Pro Phe Ser Val
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 114

Ile Thr Asp Gln Val Pro Phe Ser Val
1               5

<210> SEQ ID NO 115
```

```
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 115

Tyr Leu Glu Pro Gly Pro Val Thr Val
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 116

Tyr Leu Glu Pro Gly Pro Val Thr Ala
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic peptide.

<400> SEQUENCE: 117

Lys Thr Trp Gly Gln Tyr Trp Gln Val
1               5

<210> SEQ ID NO 118
<211> LENGTH: 1160
<212> TYPE: PRT
<213> ORGANISM: Artificial Sequence
<220> FEATURE:
<223> OTHER INFORMATION: Synthetic peptide.

<400> SEQUENCE: 118

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
        435                 440                 445

Asp Thr Thr Glu Pro Ala Thr Pro Thr Thr Pro Val Thr Thr Pro Thr
    450                 455                 460

Thr Thr Lys Val Pro Arg Asn Gln Asp Trp Leu Gly Val Ser Arg Gln
465                 470                 475                 480

Leu Arg Thr Lys Ala Trp Asn Arg Gln Leu Tyr Pro Glu Trp Thr Glu
                485                 490                 495

Ala Gln Arg Leu Asp Cys Trp Arg Gly Gly Gln Val Ser Leu Lys Val
            500                 505                 510

Ser Asn Asp Gly Pro Thr Leu Ile Gly Ala Asn Ala Ser Phe Ser Ile
        515                 520                 525

Ala Leu Asn Phe Pro Gly Ser Gln Lys Val Leu Pro Asp Gly Gln Val
    530                 535                 540

Ile Trp Val Asn Asn Thr Ile Ile Asn Gly Ser Gln Val Trp Gly Gly
545                 550                 555                 560

Gln Pro Val Tyr Pro Gln Glu Thr Asp Asp Ala Cys Ile Phe Pro Asp
                565                 570                 575

Gly Gly Pro Cys Pro Ser Gly Ser Trp Ser Gln Lys Arg Ser Phe Val
            580                 585                 590
```

Tyr Val Trp Lys Thr Trp Gly Gln Tyr Trp Gln Val Gly Gly Pro
        595                 600                 605

Val Ser Gly Leu Ser Ile Gly Thr Gly Arg Ala Met Leu Gly Thr His
    610                 615                 620

Thr Met Glu Val Thr Val Tyr His Arg Arg Gly Ser Gln Ser Tyr Val
625                 630                 635                 640

Pro Leu Ala His Ser Ser Ala Phe Thr Ile Thr Asp Gln Val Pro
                645                 650                 655

Phe Ser Val Ser Val Ser Gln Leu Arg Ala Leu Asp Gly Gly Asn Lys
            660                 665                 670

His Phe Leu Arg Asn Gln Ala Ser Thr Asn Gly Ser Ile Thr Val Ala
        675                 680                 685

Ala Thr Ala Pro Thr Val Thr Pro Thr Val Asn Ala Thr Pro Ser Ala
    690                 695                 700

Ala Ala Ser Gly Thr Thr Asp Gly His Arg Pro Thr Thr Glu Ala Pro
705                 710                 715                 720

Asn Thr Thr Ala Gly Gln Val Pro Thr Thr Glu Val Val Gly Thr Thr
                725                 730                 735

Pro Gly Gln Ala Pro Thr Ala Glu Pro Ser Gly Thr Thr Ser Val Gln
            740                 745                 750

Val Pro Thr Thr Glu Val Ile Ser Thr Ala Pro Val Gln Met Pro Thr
        755                 760                 765

Ala Glu Ser Thr Gly Met Thr Pro Glu Lys Val Pro Val Ser Glu Val
    770                 775                 780

Met Gly Thr Thr Leu Ala Glu Met Ser Thr Pro Glu Ala Thr Gly Met
785                 790                 795                 800

Thr Pro Ala Glu Val Ser Ile Val Val Leu Ser Gly Thr Thr Ala Ala
                805                 810                 815

Ala Ser Thr Val Thr Pro Thr Ala Thr Ala Thr Pro Ser Ala Ile Val
            820                 825                 830

Thr Thr Ile Thr Pro Thr Ala Thr Thr Lys Pro Ala Ser Gln Val Thr
        835                 840                 845

Thr Thr Glu Trp Val Glu Thr Thr Ala Arg Glu Leu Pro Ile Pro Glu
    850                 855                 860

Pro Glu Gly Pro Asp Ala Ser Ser Ile Met Ser Thr Glu Ser Ile Thr
865                 870                 875                 880

Gly Ser Leu Gly Pro Leu Leu Asp Gly Thr Ala Leu Arg Leu Val
                885                 890                 895

Lys Arg Gln Val Pro Leu Asp Cys Val Leu Tyr Arg Tyr Gly Ser Phe
            900                 905                 910

Ser Val Thr Leu Asp Ile Val Gln Ala Ser Thr Asn Gly Ser Ile Thr
        915                 920                 925

Val Ala Ala Thr Ala Pro Thr Val Thr Pro Thr Val Asn Ala Thr Pro
    930                 935                 940

Ser Ala Ala Ala Ser Gly Ile Glu Ser Ala Glu Ile Leu Gln Ala Val
945                 950                 955                 960

Pro Ser Gly Glu Gly Asp Ala Phe Glu Leu Thr Val Ser Cys Gln Gly
                965                 970                 975

Gly Leu Pro Lys Glu Ala Cys Met Glu Ile Ser Ser Pro Gly Cys Gln
            980                 985                 990

Pro Pro Ala Gln Arg Leu Cys Gln Pro Val Leu Pro Ser Pro Ala Cys
        995                 1000                1005

Gln Leu Val Leu His Gln Ile Leu Lys Gly Gly Ser Gly Thr Tyr

```
             1010                1015                1020

Cys Leu Asn Val Ser Leu Ala Asp Thr Asn Ser Leu Ala Val Val
    1025                1030                1035

Ser Thr Gln Leu Ile Val Pro Gly Ile Leu Leu Thr Gly Gln Glu
    1040                1045                1050

Ala Gly Leu Gly Gln Ala Ser Thr Val Thr Pro Thr Ala Thr Ala
    1055                1060                1065

Thr Pro Ser Ala Ile Val Thr Thr Ile Thr Pro Thr Ala Thr Thr
    1070                1075                1080

Lys Pro Ala Ser Pro Leu Thr Phe Ala Leu Gln Leu His Asp Pro
    1085                1090                1095

Ser Gly Tyr Leu Ala Glu Ala Asp Leu Ser Tyr Thr Trp Asp Phe
    1100                1105                1110

Gly Asp Ser Ser Gly Thr Leu Ile Ser Arg Ala Leu Val Val Thr
    1115                1120                1125

His Thr Tyr Leu Glu Pro Gly Pro Val Thr Ala Gln Val Val Leu
    1130                1135                1140

Gln Ala Ala Ile Pro Leu Thr Ser Cys Gly Ser Ser Pro Val Pro
    1145                1150                1155

Ala Ser
    1160

<210> SEQ ID NO 119
<211> LENGTH: 1161
<212> TYPE: PRT
<213> ORGANISM: Artificial Sequence
<220> FEATURE:
<223> OTHER INFORMATION: Synthetic peptide.

<400> SEQUENCE: 119

Arg Leu Gln Leu Gln Glu Ser Gly Pro Gly Leu Leu Lys Pro Ser Val
1               5                   10                  15

Thr Leu Ser Leu Thr Cys Thr Val Ser Gly Asp Ser Val Ala Ser Ser
            20                  25                  30

Ser Tyr Tyr Trp Gly Trp Val Arg Gln Pro Pro Gly Lys Gly Leu Glu
        35                  40                  45

Trp Ile Gly Thr Ile Asn Phe Ser Gly Asn Met Tyr Tyr Ser Pro Ser
    50                  55                  60

Leu Arg Ser Arg Val Thr Met Ser Ala Asp Met Ser Glu Asn Ser Phe
65                  70                  75                  80

Tyr Leu Lys Leu Asp Ser Val Thr Ala Ala Asp Thr Ala Val Tyr Tyr
                85                  90                  95

Cys Ala Ala Gly His Leu Val Met Gly Phe Gly Ala His Trp Gly Gln
                100                 105                 110

Gly Lys Leu Val Ser Val Ser Pro Ala Ser Thr Lys Gly Pro Ser Val
            115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
```

```
                 195                 200                 205
Pro Ser Asn Thr Lys Val Asp Lys Arg Val Glu Ser Lys Tyr Gly Pro
210                 215                 220

Pro Cys Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                    245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                    325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys Ala
            435                 440                 445

Ser Asp Thr Thr Glu Pro Ala Thr Pro Thr Thr Pro Val Thr Thr Pro
450                 455                 460

Thr Thr Thr Lys Val Pro Arg Asn Gln Asp Trp Leu Gly Val Ser Arg
465                 470                 475                 480

Gln Leu Arg Thr Lys Ala Trp Asn Arg Gln Leu Tyr Pro Glu Trp Thr
                485                 490                 495

Glu Ala Gln Arg Leu Asp Cys Trp Arg Gly Gly Gln Val Ser Leu Lys
                500                 505                 510

Val Ser Asn Asp Gly Pro Thr Leu Ile Gly Ala Asn Ala Ser Phe Ser
            515                 520                 525

Ile Ala Leu Asn Phe Pro Gly Ser Gln Lys Val Leu Pro Asp Gly Gln
530                 535                 540

Val Ile Trp Val Asn Asn Thr Ile Ile Asn Gly Ser Gln Val Trp Gly
545                 550                 555                 560

Gly Gln Pro Val Tyr Pro Gln Glu Thr Asp Asp Ala Cys Ile Phe Pro
                565                 570                 575

Asp Gly Gly Pro Cys Pro Ser Gly Ser Trp Ser Gln Lys Arg Ser Phe
                580                 585                 590

Val Tyr Val Trp Lys Thr Trp Gly Gln Tyr Trp Gln Val Leu Gly Gly
            595                 600                 605

Pro Val Ser Gly Leu Ser Ile Gly Thr Gly Arg Ala Met Leu Gly Thr
610                 615                 620
```

```
His Thr Met Glu Val Thr Val Tyr His Arg Arg Gly Ser Gln Ser Tyr
625                 630                 635                 640

Val Pro Leu Ala His Ser Ser Ala Phe Thr Ile Thr Asp Gln Val
        645                 650                 655

Pro Phe Ser Val Ser Val Ser Gln Leu Arg Ala Leu Asp Gly Gly Asn
            660                 665                 670

Lys His Phe Leu Arg Asn Gln Ala Ser Thr Asn Gly Ser Ile Thr Val
            675                 680                 685

Ala Ala Thr Ala Pro Thr Val Thr Pro Thr Val Asn Ala Thr Pro Ser
690                 695                 700

Ala Ala Ala Ser Gly Thr Thr Asp Gly His Arg Pro Thr Thr Glu Ala
705                 710                 715                 720

Pro Asn Thr Thr Ala Gly Gln Val Pro Thr Thr Glu Val Val Gly Thr
                725                 730                 735

Thr Pro Gly Gln Ala Pro Thr Ala Glu Pro Ser Gly Thr Thr Ser Val
            740                 745                 750

Gln Val Pro Thr Thr Glu Val Ile Ser Thr Ala Pro Val Gln Met Pro
        755                 760                 765

Thr Ala Glu Ser Thr Gly Met Thr Pro Glu Lys Val Pro Val Ser Glu
770                 775                 780

Val Met Gly Thr Thr Leu Ala Glu Met Ser Thr Pro Glu Ala Thr Gly
785                 790                 795                 800

Met Thr Pro Ala Glu Val Ser Ile Val Val Leu Ser Gly Thr Thr Ala
            805                 810                 815

Ala Ala Ser Thr Val Thr Pro Thr Ala Thr Ala Thr Pro Ser Ala Ile
            820                 825                 830

Val Thr Thr Ile Thr Pro Thr Ala Thr Thr Lys Pro Ala Ser Gln Val
            835                 840                 845

Thr Thr Thr Glu Trp Val Glu Thr Thr Ala Arg Glu Leu Pro Ile Pro
850                 855                 860

Glu Pro Glu Gly Pro Asp Ala Ser Ser Ile Met Ser Thr Glu Ser Ile
865                 870                 875                 880

Thr Gly Ser Leu Gly Pro Leu Leu Asp Gly Thr Ala Thr Leu Arg Leu
            885                 890                 895

Val Lys Arg Gln Val Pro Leu Asp Cys Val Leu Tyr Arg Tyr Gly Ser
            900                 905                 910

Phe Ser Val Thr Leu Asp Ile Val Gln Ala Ser Thr Asn Gly Ser Ile
            915                 920                 925

Thr Val Ala Ala Thr Ala Pro Thr Val Thr Pro Thr Val Asn Ala Thr
            930                 935                 940

Pro Ser Ala Ala Ala Ser Gly Ile Glu Ser Ala Glu Ile Leu Gln Ala
945                 950                 955                 960

Val Pro Ser Gly Glu Gly Asp Ala Phe Glu Leu Thr Val Ser Cys Gln
            965                 970                 975

Gly Gly Leu Pro Lys Glu Ala Cys Met Glu Ile Ser Ser Pro Gly Cys
            980                 985                 990

Gln Pro Pro Ala Gln Arg Leu Cys  Gln Pro Val Leu Pro  Ser Pro Ala
            995                 1000                1005

Cys Gln  Leu Val Leu His Gln  Ile Leu Lys Gly Gly  Ser Gly Thr
            1010                1015                1020

Tyr Cys  Leu Asn Val Ser Leu  Ala Asp Thr Asn Ser  Leu Ala Val
            1025                1030                1035
```

```
Val Ser Thr Gln Leu Ile Val Pro Gly Ile Leu Leu Thr Gly Gln
    1040                1045                1050

Glu Ala Gly Leu Gly Gln Ala Ser Thr Val Thr Pro Thr Ala Thr
    1055                1060                1065

Ala Thr Pro Ser Ala Ile Val Thr Thr Ile Thr Pro Thr Ala Thr
    1070                1075                1080

Thr Lys Pro Ala Ser Pro Leu Thr Phe Ala Leu Gln Leu His Asp
    1085                1090                1095

Pro Ser Gly Tyr Leu Ala Glu Ala Asp Leu Ser Tyr Thr Trp Asp
    1100                1105                1110

Phe Gly Asp Ser Ser Gly Thr Leu Ile Ser Arg Ala Leu Val Val
    1115                1120                1125

Thr His Thr Tyr Leu Glu Pro Gly Pro Val Thr Ala Gln Val Val
    1130                1135                1140

Leu Gln Ala Ala Ile Pro Leu Thr Ser Cys Gly Ser Ser Pro Val
    1145                1150                1155

Pro Ala Ser
    1160
```

<210> SEQ ID NO 120
<211> LENGTH: 2142
<212> TYPE: DNA
<213> ORGANISM: Artificial Sequence
<220> FEATURE:
<223> OTHER INFORMATION: Synthetic oligonucleotide.

<400> SEQUENCE: 120

```
gatacaacag aacctgcaac acctacaaca cctgtaacaa caccgacaac aacaaaagta    60
cccagaaacc aggactggct tggtgtctca aggcaactca gaaccaaagc ctggaacagg   120
cagctgtatc cagagtggac agaagcccag agacttgact gctggagagg tggtcaagtg   180
tccctcaagg tcagtaatga tgggcctaca ctgattggtg caaatgcctc cttctctatt   240
gccttgaact tccctggaag ccaaaaggta ttgccagatg ggcaggttat ctgggtcaac   300
aataccatca tcaatgggag ccaggtgtgg ggaggacagc cagtgtatcc ccaggaaact   360
gacgatgcct gcatcttccc tgatggtgga ccttgcccat ctggctcttg gtctcagaag   420
agaagctttg tttatgtctg gaagacctgg ggccaatact ggcaagttct aggggggccca   480 gtgtctgggc tgagcattgg acaggcagg caatgctgg gcacacacac catggaagtg   540
actgtctacc atcgccgggg atcccagagc tatgtgcctc ttgctcattc cagctcagcc   600
ttcaccatta ctgaccaggt gccttctctc gtgagcgtgt cccagttgcg ggccttggat   660
ggagggaaca agcacttcct gagaaatcag gctagtacca acggcagcat caccgtggcc   720
gccaccgccc ccaccgtgac ccccaccgtg aacgccaccc cagcgccgc cgctagtggc   780 accacagatg ggcacaggcc aactgcagag gcccctaaca ccacagctgg ccaagtgcct   840
actacagaag ttgtgggtac tacacctggt caggcgccaa ctgcagagcc ctctggaacc   900
acatctgtgc aggtgccaac cactgaagtc ataagcactg cacctgtgca gatgccaact   960
gcagagagca caggtatgac acctgagaag gtgccagttt cagaggtcat gggtaccaca  1020
ctggcagaga tgtcaactcc agaggctaca ggtatgacac tgcagaggt atcaattgtg  1080 gtgctttctg gaaccacagc tgcagctagt accgtgaccc ccaccgccac cgccaccccc  1140
agcgccatcg tgaccaccat caccccacc gccaccacca gcccgctag tcaggtaaca  1200 actacagagt gggtggagac cacagctaga gagctaccta tcccctgagcc tgaaggtcca  1260
```

```
gatgccagct caatcatgtc tacgaaagt attacaggtt ccctgggccc cctgctggat    1320
ggtacagcca ccttaaggct ggtgaagaga caagtccccc tggattgtgt tctgtatcga    1380
tatggttcct tttccgtcac cctggacatt gtccaggcta gtaccaacgg cagcatcacc    1440
gtggccgcca ccgcccccac cgtgaccccc accgtgaacg ccaccccag cgccgccgct    1500 agtggtattg aaagtgccga gatcctgcag gctgtgccgt ccggtgaggg ggatgcattt    1560
gagctgactg tgtcctgcca aggcgggctg cccaaggaag cctgcatgga gatctcatcg    1620
ccagggtgcc agcccctgc ccagcggctg tgccagcctg tgctacccag cccagcctgc    1680
cagctggttc tgcaccagat actgaagggg ggctcgggga catactgcct caatgtgtct    1740
ctggctgata ccaacagcct ggcagtggtc agcacccagc ttatcgtgcc tgggattctt    1800
ctcacaggtc aagaagcagg ccttgggcag taagctagta ccgtgacccc caccgccacc    1860 gccacccca gcgccatcgt gaccaccatc accccaccg ccaccaccaa gcccgctagt    1920
cctctgacct ttgccctcca gctccatgac cctagtggct atctggctga agctgacctc    1980
tcctacacct gggactttgg agacagtagt ggaaccctga tctctcgggc acytgtggtc    2040
actcatactt acctggagcc tggcccagtc actgcccagg tggtcctgca ggctgccatt    2100
cctctcacct cctgtggctc ctccccagtt ccagctagct ga                     2142

<210> SEQ ID NO 121
<211> LENGTH: 690
<212> TYPE: DNA
<213> ORGANISM: Artificial Sequence
<220> FEATURE:
<223> OTHER INFORMATION: Synthetic oligonucleotide.

<400> SEQUENCE: 121
gatacaacag aacctgcaac acctacaaca cctgtaacaa caccgacaac aacaaaagta      60
cccagaaacc aggactggct tggtgtctca aggcaactca gaaccaaagc ctggaacagg     120
cagctgtatc cagagtggac agaagcccag agacttgact gctggagagg tggtcaagtg     180
tccctcaagg tcagtaatga tgggcctaca ctgattggtg caaatgcctc cttctctatt     240
gccttgaact tccctggaag ccaaaaggta ttgccagatg ggcaggttat ctgggtcaac     300
aataccatca tcaatgggag ccaggtgtgg ggaggacagc cagtgtatcc ccaggaaact     360
gacgatgcct gcatcttccc tgatggtgga ccttgcccat ctggctcttg gtctcagaag     420
agaagctttg tttatgtctg gaagacctgg ggccaatact ggcaagttct aggggggccca     480 gtgtctgggc tgagcattgg gacaggcagg gcaatgctgg gcacacacac catgaaagtg     540
actgtctacc atcgccgggg atcccagagc tatgtgcctc ttgctcattc cagctcagcc     600
ttcaccatta ctgaccaggt gccttctctc gtgagcgtgt cccagttgcg ggccttggat     660
ggagggaaca agcacttcct gagaaatcag                                     690

<210> SEQ ID NO 122
<211> LENGTH: 230
<212> TYPE: PRT
<213> ORGANISM: Artificial Sequence
<220> FEATURE:
<223> OTHER INFORMATION: Synthetic peptide.

<400> SEQUENCE: 122

Asp Thr Thr Glu Pro Ala Thr Pro Thr Thr Pro Val Thr Thr Pro Thr
1               5                  10                   15

Thr Thr Lys Val Pro Arg Asn Gln Asp Trp Leu Gly Val Ser Arg Gln
            20                  25                  30
```

Leu Arg Thr Lys Ala Trp Asn Arg Gln Leu Tyr Pro Glu Trp Thr Glu
            35                  40                  45

Ala Gln Arg Leu Asp Cys Trp Arg Gly Gly Gln Val Ser Leu Lys Val
    50                  55                  60

Ser Asn Asp Gly Pro Thr Leu Ile Gly Ala Asn Ala Ser Phe Ser Ile
65                  70                  75                  80

Ala Leu Asn Phe Pro Gly Ser Gln Lys Val Leu Pro Asp Gly Gln Val
                85                  90                  95

Ile Trp Val Asn Asn Thr Ile Ile Asn Gly Ser Gln Val Trp Gly Gly
            100                 105                 110

Gln Pro Val Tyr Pro Gln Glu Thr Asp Asp Ala Cys Ile Phe Pro Asp
        115                 120                 125

Gly Gly Pro Cys Pro Ser Gly Ser Trp Ser Gln Lys Arg Ser Phe Val
    130                 135                 140

Tyr Val Trp Lys Thr Trp Gly Gln Tyr Trp Gln Val Leu Gly Gly Pro
145                 150                 155                 160

Val Ser Gly Leu Ser Ile Gly Thr Gly Arg Ala Met Leu Gly Thr His
                165                 170                 175

Thr Met Glu Val Thr Val Tyr His Arg Arg Gly Ser Ser Tyr Val
        180                 185                 190

Pro Leu Ala His Ser Ser Ala Phe Thr Ile Thr Asp Gln Val Pro
        195                 200                 205

Phe Ser Val Ser Val Ser Gln Leu Arg Ala Leu Asp Gly Gly Asn Lys
    210                 215                 220

His Phe Leu Arg Asn Gln
225                 230

<210> SEQ ID NO 123
<211> LENGTH: 327
<212> TYPE: DNA
<213> ORGANISM: Artificial Sequence
<220> FEATURE:
<223> OTHER INFORMATION: Synthetic oligonucleotide.

<400> SEQUENCE: 123
ggcaccacag atgggcacag gccaactgca gaggccccta acaccacagc tggccaagtg      60
cctactacag aagttgtggg tactacacct ggtcaggcgc caactgcaga gccctctgga     120
accacatctg tgcaggtgcc aaccactgaa gtcataagca ctgcacctgt gcagatgcca     180
actgcagaga gcacaggtat gacacctgag aaggtgccag tttcagaggt catgggtacc     240
acactggcag agatgtcaac tccagaggct acaggtatga cacctgcaga ggtatcaatt     300
gtggtgcttt ctggaaccac agctgca                                        327

<210> SEQ ID NO 124
<211> LENGTH: 109
<212> TYPE: PRT
<213> ORGANISM: Artificial Sequence
<220> FEATURE:
<223> OTHER INFORMATION: Synthetic peptide.

<400> SEQUENCE: 124

Gly Thr Thr Asp Gly His Arg Pro Thr Ala Glu Ala Pro Asn Thr Thr
1               5                   10                  15

Ala Gly Gln Val Pro Thr Thr Glu Val Val Gly Thr Thr Pro Gly Gln
            20                  25                  30

Ala Pro Thr Ala Glu Pro Ser Gly Thr Thr Ser Val Gln Val Pro Thr

```
                35                  40                  45
Thr Glu Val Ile Ser Thr Ala Pro Val Gln Met Pro Thr Ala Glu Ser
         50                  55                  60
Thr Gly Met Thr Pro Glu Lys Val Pro Val Ser Glu Val Met Gly Thr
 65                  70                  75                  80
Thr Leu Ala Glu Met Ser Thr Pro Glu Ala Thr Gly Met Thr Pro Ala
                 85                  90                  95
Glu Val Ser Ile Val Val Leu Ser Gly Thr Thr Ala Ala
            100                 105
```

<210> SEQ ID NO 125
<211> LENGTH: 225
<212> TYPE: DNA
<213> ORGANISM: Artificial Sequence
<220> FEATURE:
<223> OTHER INFORMATION: Synthetic oligonucleotide.

<400> SEQUENCE: 125

```
caggtaacaa ctacagagtg ggtggagacc acagctagag agctacctat ccctgagcct      60
gaaggtccag atgccagctc aatcatgtct acggaaagta ttacaggttc cctgggcccc     120
ctgctggatg gtacagccac cttaaggctg gtgaagagac aagtccccct ggattgtgtt     180
ctgtatcgat atggttcctt ttccgtcacc ctggacattg tccag                     225
```

<210> SEQ ID NO 126
<211> LENGTH: 75
<212> TYPE: PRT
<213> ORGANISM: Artificial Sequence
<220> FEATURE:
<223> OTHER INFORMATION: Synthetic peptide.

<400> SEQUENCE: 126

```
Gln Val Thr Thr Thr Glu Trp Val Glu Thr Thr Ala Arg Glu Leu Pro
  1               5                  10                  15
Ile Pro Glu Pro Glu Gly Pro Asp Ala Ser Ser Ile Met Ser Thr Glu
                 20                  25                  30
Ser Ile Thr Gly Ser Leu Gly Pro Leu Leu Asp Gly Thr Ala Thr Leu
             35                  40                  45
Arg Leu Val Lys Arg Gln Val Pro Leu Asp Cys Val Leu Tyr Arg Tyr
         50                  55                  60
Gly Ser Phe Ser Val Thr Leu Asp Ile Val Gln
 65                  70                  75
```

<210> SEQ ID NO 127
<211> LENGTH: 327
<212> TYPE: DNA
<213> ORGANISM: Artificial Sequence
<220> FEATURE:
<223> OTHER INFORMATION: Synthetic oligonucleotide.

<400> SEQUENCE: 127

```
ggtattgaaa gtgccgagat cctgcaggct gtgccgtccg gtgagggggga tgcatttgag      60 ctgactgtgt cctgccaagg cgggctgccc aaggaagcct gcatggagat ctcatcgcca     120
gggtgccagc ccctgcccca gcggctgtgc cagcctgtgc tacccagccc agcctgccag     180
ctggttctgc accagatact gaagggtggc tcggggacat actgcctcaa tgtgtctctg     240
gctgatacca cagcctggc agtggtcagc acccagctta tcgtgcctgg gattcttctc     300
acaggtcaag aagcaggcct tgggcag                                         327
```

<210> SEQ ID NO 128
<211> LENGTH: 109
<212> TYPE: PRT
<213> ORGANISM: Artificial Sequence
<220> FEATURE:
<223> OTHER INFORMATION: Synthetic peptide.

<400> SEQUENCE: 128

Gly Ile Glu Ser Ala Glu Ile Leu Gln Ala Val Pro Ser Gly Glu Gly
1               5                   10                  15

Asp Ala Phe Glu Leu Thr Val Ser Cys Gln Gly Gly Leu Pro Lys Glu
            20                  25                  30

Ala Cys Met Glu Ile Ser Ser Pro Gly Cys Gln Pro Ala Gln Arg
        35                  40                  45

Leu Cys Gln Pro Val Leu Pro Ser Pro Ala Cys Gln Leu Val Leu His
    50                  55                  60

Gln Ile Leu Lys Gly Gly Ser Gly Thr Tyr Cys Leu Asn Val Ser Leu
65                  70                  75                  80

Ala Asp Thr Asn Ser Leu Ala Val Val Ser Thr Gln Leu Ile Val Pro
                85                  90                  95

Gly Ile Leu Leu Thr Gly Gln Glu Ala Gly Leu Gly Gln
            100                 105

<210> SEQ ID NO 129
<211> LENGTH: 219
<212> TYPE: DNA
<213> ORGANISM: Artificial Sequence
<220> FEATURE:
<223> OTHER INFORMATION: Synthetic oligonucleotide.

<400> SEQUENCE: 129
cctctgacct ttgccctcca gctccatgac cctagtggct atctggctga agctgacctc        60
tcctacacct gggactttgg agacagtagt ggaaccctga tctctcgggc acytgtggtc       120
actcatactt acctggagcc tggcccagtc actgcccagg tggtcctgca ggctgccatt       180
cctctcacct cctgtggctc ctccccagtt ccagctagc                              219

<210> SEQ ID NO 130
<211> LENGTH: 73
<212> TYPE: PRT
<213> ORGANISM: Artificial Sequence
<220> FEATURE:
<223> OTHER INFORMATION: Synthetic peptide.
<220> FEATURE:
<221> NAME/KEY: misc_feature
<222> LOCATION: (38)..(38)
<223> OTHER INFORMATION: Xaa can be any naturally occurring amino acid

<400> SEQUENCE: 130

Pro Leu Thr Phe Ala Leu Gln Leu His Asp Pro Ser Gly Tyr Leu Ala
1               5                   10                  15

Glu Ala Asp Leu Ser Tyr Thr Trp Asp Phe Gly Asp Ser Ser Gly Thr
            20                  25                  30

Leu Ile Ser Arg Ala Xaa Val Val Thr His Thr Tyr Leu Glu Pro Gly
        35                  40                  45

Pro Val Thr Ala Gln Val Val Leu Gln Ala Ala Ile Pro Leu Thr Ser
    50                  55                  60

Cys Gly Ser Ser Pro Val Pro Ala Ser
65                  70

```
<210> SEQ ID NO 131
<211> LENGTH: 438
<212> TYPE: PRT
<213> ORGANISM: Artificial Sequence
<220> FEATURE:
<223> OTHER INFORMATION: Synthetic peptide.

<400> SEQUENCE: 131

Met Ala Leu Arg Val Thr Arg Asn Ser Lys Ile Asn Ala Glu Asn Lys
1               5                   10                  15

Ala Lys Ile Asn Met Ala Gly Ala Lys Arg Val Pro Thr Ala Pro Ala
            20                  25                  30

Ala Thr Ser Lys Pro Gly Leu Arg Pro Arg Thr Ala Leu Gly Asp Ile
        35                  40                  45

Gly Asn Lys Val Ser Glu Gln Leu Gln Ala Lys Met Pro Met Lys Lys
    50                  55                  60

Glu Ala Lys Pro Ser Ala Thr Gly Lys Val Ile Asp Lys Lys Leu Pro
65                  70                  75                  80

Lys Pro Leu Glu Lys Val Pro Met Leu Val Pro Val Pro Val Ser Glu
                85                  90                  95

Pro Val Pro Glu Pro Glu Pro Glu Pro Glu Pro Glu Pro Val Lys Glu
            100                 105                 110

Glu Lys Leu Ser Pro Glu Pro Ile Leu Val Asp Thr Ala Ser Pro Ser
        115                 120                 125

Pro Met Glu Thr Ser Gly Cys Ala Pro Ala Glu Glu Asp Leu Cys Gln
    130                 135                 140

Ala Phe Ser Asp Val Ile Leu Ala Val Asn Asp Val Asp Ala Glu Asp
145                 150                 155                 160

Gly Ala Asp Pro Asn Leu Cys Ser Glu Tyr Val Lys Asp Ile Tyr Ala
                165                 170                 175

Tyr Leu Arg Gln Leu Glu Glu Glu Gln Ala Val Arg Pro Lys Tyr Leu
            180                 185                 190

Leu Gly Arg Glu Val Thr Gly Asn Met Arg Ala Ile Leu Ile Asp Trp
        195                 200                 205

Leu Val Gln Val Gln Met Lys Phe Arg Leu Leu Gln Glu Thr Met Tyr
    210                 215                 220

Met Thr Val Ser Ile Ile Asp Arg Phe Met Gln Asn Asn Cys Val Pro
225                 230                 235                 240

Lys Lys Met Leu Gln Leu Val Gly Val Thr Ala Met Phe Ile Ala Ser
                245                 250                 255

Lys Tyr Glu Glu Met Tyr Pro Pro Glu Ile Gly Asp Phe Ala Phe Val
            260                 265                 270

Thr Asp Asn Thr Tyr Thr Lys His Gln Ile Arg Gln Met Glu Met Lys
        275                 280                 285

Ile Leu Arg Ala Leu Asn Phe Gly Leu Gly Arg Pro Leu Pro Leu His
    290                 295                 300

Phe Leu Arg Arg Ala Ser Lys Ile Gly Glu Val Asp Val Glu Gln His
305                 310                 315                 320

Thr Leu Ala Lys Tyr Leu Met Glu Thr Met Leu Asp Tyr Asp Met Val
                325                 330                 335

His Phe Pro Pro Ser Gln Ile Ala Ala Gly Ala Phe Cys Leu Ala Leu
            340                 345                 350

Lys Ile Leu Asp Asn Gly Glu Trp Thr Pro Thr Leu Gln His Tyr Leu
        355                 360                 365

Ser Tyr Thr Glu Glu Ser Leu Leu Pro Val Met Gln His Leu Ala Lys
```

```
                370                 375                 380
Asn Val Met Val Asn Gln Gly Leu Thr Lys His Met Thr Val Lys
385                 390                 395                 400

Asn Lys Tyr Ala Thr Ser Lys His Ala Lys Ile Ser Thr Leu Pro Gln
                405                 410                 415

Leu Asn Ser Ala Leu Val Gln Asp Leu Ala Lys Ala Val Ala Lys Val
                420                 425                 430

His His His His His His
            435

<210> SEQ ID NO 132
<211> LENGTH: 50
<212> TYPE: PRT
<213> ORGANISM: Artificial Sequence
<220> FEATURE:
<223> OTHER INFORMATION: Synthetic peptide.

<400> SEQUENCE: 132

Met Glu Met Lys Ile Leu Arg Ala Leu Asn Phe Gly Leu Gly Arg Pro
1               5                   10                  15

Leu Pro Leu His Phe Leu Arg Arg Ala Ser Lys Ile Gly Glu Val Asp
                20                  25                  30

Val Glu Gln His Thr Leu Ala Lys Tyr Leu Met Glu Leu Thr Met Leu
            35                  40                  45

Asp Tyr
    50

<210> SEQ ID NO 133
<211> LENGTH: 36
<212> TYPE: PRT
<213> ORGANISM: Artificial Sequence
<220> FEATURE:
<223> OTHER INFORMATION: Synthetic peptide.

<400> SEQUENCE: 133

Asp Trp Leu Val Gln Val Gln Met Lys Phe Arg Leu Leu Gln Glu Thr
1               5                   10                  15

Met Tyr Met Thr Val Ser Ile Ile Asp Arg Phe Met Gln Asn Asn Cys
                20                  25                  30

Val Pro Lys Lys
        35

<210> SEQ ID NO 134
<211> LENGTH: 594
<212> TYPE: PRT
<213> ORGANISM: Artificial Sequence
<220> FEATURE:
<223> OTHER INFORMATION: Synthetic peptide.

<400> SEQUENCE: 134

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Tyr Ile Asn Ser Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80
```

```
Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
        435                 440                 445

Gln Thr Pro Thr Asn Thr Ile Ser Val Thr Pro Thr Asn Asn Ser Thr
    450                 455                 460

Pro Thr Asn Asn Ser Asn Pro Lys Pro Asn Pro Ala Ser Asp Trp Leu
465                 470                 475                 480

Val Gln Val Gln Met Lys Phe Arg Leu Leu Gln Glu Thr Met Tyr Met
                485                 490                 495
```

```
Thr Val Ser Ile Ile Asp Arg Phe Met Gln Asn Asn Cys Val Pro Lys
            500                 505                 510

Lys Ala Ser Met Glu Met Lys Ile Leu Arg Ala Leu Asn Phe Gly Leu
        515                 520                 525

Gly Arg Pro Leu Pro Leu His Phe Leu Arg Arg Ala Ser Lys Ile Gly
        530                 535                 540

Glu Val Asp Val Glu Gln His Thr Leu Ala Lys Tyr Leu Met Glu Leu
545                 550                 555                 560

Thr Met Leu Asp Tyr Ala Ser Thr Asn Asp Ser Ile Thr Val Ala Ala
                565                 570                 575

Thr Ala Pro Thr Val Thr Pro Thr Val Asn Ala Thr Pro Ser Ala Ala
            580                 585                 590

Ala Ser
```

<210> SEQ ID NO 135
<211> LENGTH: 1842
<212> TYPE: DNA
<213> ORGANISM: Artificial Sequence
<220> FEATURE:
<223> OTHER INFORMATION: Synthetic oligonucleotide.

<400> SEQUENCE: 135

```
atgaacttgg ggctcagctt gattttcctt gtccttgttt taaaaggtgt ccagtgtgaa      60
gtgaagctgg tggagtctgg gggaggctta gtgcagcccg agggtccct gaaactctcc     120
tgtgcaacct ctggattcac tttcagtgac tattacatgt attgggttcg ccagactcca     180
gagaagaggc tggagtgggt cgcatacatt aattctggtg gtggtagcac ctattatcca     240
gacactgtaa agggccgatt caccatctcc agagacaatg ccaagaacac cctgtacctg     300
caaatgagcc ggctgaagtc tgaggacaca gccatgtatt actgtgcaag acggggggta     360
ccgttccatg ctatggacta ttggggtcaa ggaacctcag tcaccgtctc ctcagccaaa     420
acgaagggcc catccgtctt ccccctggcg ccctgctcca ggagcacctc cgagagcaca     480
gccgccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct gggcacgaag acctacacc     660
tgcaacgtag atcacaagcc cagcaacacc aaggtggaca gagagttga gtccaaatat     720
ggtcccccat gcccacctg cccagcacct gagttcgaag ggggaccatc agtcttcctg     780
ttccccccaa aacccaagga cactctcatg atctcccgga cccctgaggt cacgtgcgtg     840
gtggtggacg tgagccagga agaccccgag gtccagttca actggtacgt ggatggcgtg     900
gaggtgcata atgccaagac aaagccgcgg gaggagcagt tcaacagcac gtaccgtgtg     960
gtcagcgtcc tcaccgtcct gcaccaggac tggctgaacg gcaaggagta caagtgcaag    1020
gtctccaaca aaggcctccc gtcctccatc gagaaaacca tctccaaagc caaagggcag    1080
ccccgagagc cacaggtgta caccctgccc ccatcccagg aggagatgac caagaaccag    1140
gtcagcctga cctgcctggt caaaggcttc taccccagcg acatcgccgt ggagtgggag    1200
agcaatgggc agccggagaa caactacaag accacgcctc ccgtgctgga ctccgacggc    1260
tccttcttcc tctacagcag gctaaccgtg gacaagagca ggtggcagga ggggaatgtc    1320
ttctcatgct ccgtgatgca tgaggctctg cacaaccact acacacagaa gagcctctcc    1380
ctgtctctgg gtaaagctag tcagaccccc accaacacca tcagcgtgac ccccaccaac    1440
aacagcaccc ccaccaacaa cagcaacccc aagcccaacc ccgctagtga ctggctagta    1500
```

-continued

```
caggttcaaa tgaaattcag gttgttgcag agaccatgt acatgactgt ctccattatt    1560
gatcggttca tgcagaataa ttgtgtgccc aagaaggcta gtatggaaat gaagattcta    1620
agagctttaa actttggtct gggtcggcct ctacctttgc acttccttcg gagagcatct    1680
aagattggag aggttgatgt cgagcaacat actttggcca aatacctgat ggaactaact    1740
atgttggact atgctagtac caacgacagc atcaccgtgg ccgccaccgc ccccaccgtg    1800 accccaccg tgaacgccac cccagcgcc gccgctagct ga    1842
```

<210> SEQ ID NO 136
<211> LENGTH: 542
<212> TYPE: PRT
<213> ORGANISM: Artificial Sequence
<220> FEATURE:
<223> OTHER INFORMATION: Synthetic peptide.

<400> SEQUENCE: 136

```
Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
        435                 440                 445

Gln Thr Pro Thr Asn Thr Ile Ser Val Thr Pro Thr Asn Asn Ser Thr
    450                 455                 460

Pro Thr Asn Asn Ser Asn Pro Lys Pro Asn Pro Ala Ser Asp Trp Leu
465                 470                 475                 480

Val Gln Val Gln Met Lys Phe Arg Leu Leu Gln Glu Thr Met Tyr Met
                485                 490                 495

Thr Val Ser Ile Ile Asp Arg Phe Met Gln Asn Asn Cys Val Pro Lys
            500                 505                 510

Lys Ala Ser Thr Val Thr Pro Thr Ala Thr Thr Pro Ser Ala Ile
        515                 520                 525

Val Thr Thr Ile Thr Pro Thr Ala Thr Thr Lys Pro Ala Ser
    530                 535                 540

<210> SEQ ID NO 137
<211> LENGTH: 1686
<212> TYPE: DNA
<213> ORGANISM: Artificial Sequence
<220> FEATURE:
<223> OTHER INFORMATION: Synthetic oligonucleotide.

<400> SEQUENCE: 137
atgaacttgg ggctcagctt gattttcctt gtccttgttt taaaaggtgt ccagtgtgaa      60
gtgaagctgg tggagtctgg gggaggctta gtgcagcccg agggtccct  gaaactctcc     120 tgtgcaacct ctggattcac tttcagtgac tattacatgt attgggttcg ccagactcca     180
gagaagaggc tggagtgggt cgcatacatt aattctggtg gtggtagcac ctattatcca     240
gacactgtaa aggccgatt caccatctcc agagacaatg ccaagaacac cctgtacctg      300
caaatgagcc ggctgaagtc tgaggacaca gccatgtatt actgtgcaag acgggggtta     360
ccgttccatg ctatggacta ttggggtcaa ggaacctcag tcaccgtctc ctcagccaaa     420
acgaagggcc catccgtctt ccccctggcg ccctgctcca ggagcacctc cgagagcaca     480
gccgccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct gggcacgaa  gacctacacc     660 tgcaacgtag atcacaagcc cagcaacacc aaggtggaca agagagttga gtccaaatat     720
```

```
ggtcccccat gcccaccctg cccagcacct gagttcgaag ggggaccatc agtcttcctg      780
ttccccccaa acccaagga cactctcatg atctcccgga cccctgaggt cacgtgcgtg      840
gtggtggacg tgagccagga agaccccgag gtccagttca actggtacgt ggatggcgtg      900
gaggtgcata atgccaagac aaagccgcgg gaggagcagt tcaacagcac gtaccgtgtg      960
gtcagcgtcc tcaccgtcct gcaccaggac tggctgaacg gcaaggagta caagtgcaag     1020
gtctccaaca aggcctccc gtcctccatc gagaaaacca tctccaaagc caagggcag     1080 ccccgagagc cacaggtgta caccctgccc ccatcccagg aggagatgac caagaaccag     1140
gtcagcctga cctgcctggt caaaggcttc tacccagcg acatcgccgt ggagtgggag     1200
agcaatgggc agccggagaa caactacaag accacgcctc ccgtgctgga ctccgacggc     1260
tccttcttcc tctacagcag gctaaccgtg gacaagagca ggtggcagga ggggaatgtc     1320
ttctcatgct ccgtgatgca tgaggctctg cacaaccact acacacagaa gagcctctcc     1380
ctgtctctgg gtaaagctag tcagacccc accaacacca tcagcgtgac ccccaccaac     1440
aacagcaccc ccaccaacaa cagcaacccc aagcccaacc ccgctagtga ctggctagta     1500
caggttcaaa tgaaattcag gttgttgcag gagaccatgt acatgactgt ctccattatt     1560
gatcggttca tgcagaataa ttgtgtgccc aagaaggcta gtaccgtgac ccccaccgcc     1620
accgccaccc ccagcgccat cgtgaccacc atcaccccca ccgccaccac caagcccgct     1680
agctga                                                                1686
```

<210> SEQ ID NO 138
<211> LENGTH: 556
<212> TYPE: PRT
<213> ORGANISM: Artificial Sequence
<220> FEATURE:
<223> OTHER INFORMATION: Synthetic peptide.

<400> SEQUENCE: 138

```
Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190
Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys Ala Ser
            435                 440                 445

Gln Thr Pro Thr Asn Thr Ile Ser Val Thr Pro Thr Asn Asn Ser Thr
        450                 455                 460

Pro Thr Asn Asn Ser Asn Pro Lys Pro Asn Pro Ala Ser Met Glu Met
465                 470                 475                 480

Lys Ile Leu Arg Ala Leu Asn Phe Gly Leu Gly Arg Pro Leu Pro Leu
                485                 490                 495

His Phe Leu Arg Arg Ala Ser Lys Ile Gly Glu Val Asp Val Glu Gln
                500                 505                 510

His Thr Leu Ala Lys Tyr Leu Met Glu Leu Thr Met Leu Asp Tyr Ala
            515                 520                 525

Ser Thr Asn Gly Ser Ile Thr Val Ala Ala Thr Ala Pro Thr Val Thr
        530                 535                 540

Pro Thr Val Asn Ala Thr Pro Ser Ala Ala Ser
545                 550                 555

<210> SEQ ID NO 139
<211> LENGTH: 1728
<212> TYPE: DNA
<213> ORGANISM: Artificial Sequence
<220> FEATURE:
<223> OTHER INFORMATION: Synthetic oligonucleotide.
```

<400> SEQUENCE: 139

```
atgaacttgg ggctcagctt gattttcctt gtccttgttt taaaaggtgt ccagtgtgaa      60
gtgaagctgg tggagtctgg gggaggctta gtgcagcccg agggtccct gaaactctcc      120
tgtgcaacct ctggattcac tttcagtgac tattacatgt attgggttcg ccagactcca     180
gagaagaggc tggagtgggt cgcatacatt aattctggtg gtggtagcac ctattatcca     240
gacactgtaa agggccgatt caccatctcc agagacaatg ccaagaacac cctgtacctg     300
caaatgagcc ggctgaagtc tgaggacaca gccatgtatt actgtgcaag acggggtta     360
ccgttccatg ctatggacta ttggggtcaa ggaacctcag tcaccgtctc ctcagccaaa     420
acgaagggcc catccgtctt cccctggcg ccctgctcca ggagcacctc cgagagcaca     480
gccgccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct gggcacgaa gacctacacc      660
tgcaacgtag atcacaagcc cagcaacacc aaggtggaca gagagttga gtccaaatat     720
ggtcccccat gcccaccctg cccagcacct gagttcgaag gggaccatc agtcttcctg     780
ttccccccaa aacccaagga cactctcatg atctcccgga cccctgaggt cacgtgcgtg     840
gtggtggacg tgagccagga agaccccgag gtccagttca actggtacgt ggatggcgtg     900
gaggtgcata atgccaagac aaagccgcgg gaggagcagt tcaacagcac gtaccgtgtg     960
gtcagcgtcc tcaccgtcct gcaccaggac tggctgaacg gcaaggagta caagtgcaag     1020
gtctccaaca aaggcctccc gtcctccatc gagaaaacca tctccaaagc caaagggcag     1080
ccccgagagc cacaggtgta caccctgccc ccatcccagg aggagatgac caagaaccag     1140
gtcagcctga cctgcctggt caaaggcttc taccccagcg acatcgccgt ggagtgggag     1200
agcaatgggc agccggagaa caactacaag accacgcctc ccgtgctgga ctccgacggc     1260
tccttcttcc tctacagcag gctaaccgtg gacaagagca ggtggcagga ggggaatgtc     1320
ttctcatgct ccgtgatgca tgaggctctg cacaaccact acacacagaa gagcctctcc     1380
ctgtctctgg gtaaagctag tcagacccc accaacacca tcagcgtgac ccccaccaac     1440
aacagcaccc ccaccaacaa cagcaacccc aagcccaacc ccgctagtat ggaaatgaag     1500
attctaagag ctttaaactt tggtctgggt cggcctctac cttgcacttc ccttcggaga     1560
gcatctaaga ttggagaggt tgatgtcgag caacatactt tggccaaata cctgatggaa     1620
ctaactatgt tggactatgc tagtaccaac ggcagcatca ccgtggccgc caccgccccc     1680
accgtgaccc ccaccgtgaa cgccacccc agcgccgccg ctagctga                  1728
```

<210> SEQ ID NO 140
<211> LENGTH: 294
<212> TYPE: PRT
<213> ORGANISM: Artificial Sequence
<220> FEATURE:
<223> OTHER INFORMATION: Synthetic peptide.

<400> SEQUENCE: 140

```
Glu His Gln Leu Leu Cys Cys Glu Val Glu Thr Ile Arg Arg Ala Tyr
1               5                   10                  15

Pro Asp Ala Asn Leu Leu Asn Asp Arg Val Leu Arg Ala Met Leu Lys
            20                  25                  30

Ala Glu Glu Thr Cys Ala Pro Ser Val Ser Tyr Phe Lys Cys Val Gln
        35                  40                  45
```

```
Lys Glu Val Leu Pro Ser Met Arg Lys Ile Val Ala Thr Trp Met Leu
 50                  55                  60

Glu Val Cys Glu Glu Gln Lys Cys Glu Glu Val Phe Pro Leu Ala
 65                  70                  75                  80

Met Asn Tyr Leu Asp Arg Phe Leu Ser Leu Glu Pro Val Lys Lys Ser
                 85                  90                  95

Arg Leu Gln Leu Leu Gly Ala Thr Cys Met Phe Val Ala Ser Lys Met
                100                 105                 110

Lys Glu Thr Ile Pro Leu Thr Ala Glu Lys Leu Cys Ile Tyr Thr Asp
                115                 120                 125

Asn Ser Ile Arg Pro Glu Glu Leu Leu Gln Met Glu Leu Leu Leu Val
130                 135                 140

Asn Lys Leu Lys Trp Asn Leu Ala Ala Met Thr Pro His Asp Phe Ile
145                 150                 155                 160

Glu His Phe Leu Ser Lys Met Pro Glu Ala Glu Glu Asn Lys Gln Ile
                165                 170                 175

Ile Arg Lys His Ala Gln Thr Phe Val Ala Leu Cys Ala Thr Asp Val
                180                 185                 190

Lys Phe Ile Ser Asn Pro Pro Ser Met Val Ala Ala Gly Ser Val Val
                195                 200                 205

Ala Ala Val Gln Gly Leu Asn Leu Arg Ser Pro Asn Asn Phe Leu Ser
210                 215                 220

Tyr Tyr Arg Leu Thr Arg Phe Leu Ser Arg Val Ile Lys Cys Asp Pro
225                 230                 235                 240

Asp Cys Leu Arg Ala Cys Gln Glu Gln Ile Glu Ala Leu Leu Glu Ser
                245                 250                 255

Ser Leu Arg Gln Ala Gln Gln Asn Met Asp Pro Lys Ala Ala Glu Glu
                260                 265                 270

Glu Glu Glu Glu Glu Glu Val Asp Leu Ala Cys Thr Pro Thr Asp
                275                 280                 285

Val Arg Asp Val Asp Ile
                290

<210> SEQ ID NO 141
<211> LENGTH: 48
<212> TYPE: PRT
<213> ORGANISM: Artificial Sequence
<220> FEATURE:
<223> OTHER INFORMATION: Synthetic peptide.

<400> SEQUENCE: 141

Met Glu His Gln Leu Leu Cys Cys Glu Val Glu Thr Ile Arg Arg Ala
 1               5                  10                  15

Tyr Pro Asp Ala Asn Leu Leu Asn Asp Arg Val Leu Arg Ala Met Leu
                 20                  25                  30

Lys Ala Glu Glu Thr Cys Ala Pro Ser Val Ser Tyr Phe Lys Cys Val
                 35                  40                  45

<210> SEQ ID NO 142
<211> LENGTH: 95
<212> TYPE: PRT
<213> ORGANISM: Artificial Sequence
<220> FEATURE:
<223> OTHER INFORMATION: Synthetic peptide.

<400> SEQUENCE: 142

Gln Lys Glu Val Leu Pro Ser Met Arg Lys Ile Val Ala Thr Trp Met
 1               5                  10                  15
```

```
Leu Glu Val Cys Glu Glu Gln Lys Cys Glu Glu Val Phe Pro Leu
            20                  25                  30

Ala Met Asn Tyr Leu Asp Arg Phe Leu Ser Leu Glu Pro Val Lys Lys
        35                  40                  45

Ser Arg Leu Gln Leu Leu Gly Ala Thr Cys Met Phe Val Ala Ser Lys
 50                  55                  60

Met Lys Glu Thr Ile Pro Leu Thr Ala Glu Lys Leu Cys Ile Tyr Thr
 65                  70                  75                  80

Asp Asn Ser Ile Arg Pro Glu Leu Leu Gln Met Glu Leu Leu
                85                  90                  95

<210> SEQ ID NO 143
<211> LENGTH: 60
<212> TYPE: PRT
<213> ORGANISM: Artificial Sequence
<220> FEATURE:
<223> OTHER INFORMATION: Synthetic peptide.

<400> SEQUENCE: 143

Leu Val Asn Lys Leu Lys Trp Asn Leu Ala Ala Met Thr Pro His Asp
1               5                  10                  15

Phe Ile Glu His Phe Leu Ser Lys Met Pro Glu Ala Glu Glu Asn Lys
            20                  25                  30

Gln Ile Ile Arg Lys His Ala Gln Thr Phe Val Ala Leu Cys Ala Thr
        35                  40                  45

Asp Val Lys Phe Ile Ser Asn Pro Pro Ser Met Val
    50                  55                  60

<210> SEQ ID NO 144
<211> LENGTH: 92
<212> TYPE: PRT
<213> ORGANISM: Artificial Sequence
<220> FEATURE:
<223> OTHER INFORMATION: Synthetic peptide.

<400> SEQUENCE: 144

Ala Ala Gly Ser Val Val Ala Ala Val Gln Gly Leu Asn Leu Arg Ser
1               5                  10                  15

Pro Asn Asn Phe Leu Ser Tyr Tyr Arg Leu Thr Arg Phe Leu Ser Arg
            20                  25                  30

Val Ile Lys Cys Asp Pro Asp Cys Leu Arg Ala Cys Gln Glu Gln Ile
        35                  40                  45

Glu Ala Leu Leu Glu Ser Ser Leu Arg Gln Ala Gln Gln Asn Met Asp
 50                  55                  60

Pro Lys Ala Ala Glu Glu Glu Glu Glu Glu Glu Glu Val Asp Leu
 65                  70                  75                  80

Ala Cys Thr Pro Thr Asp Val Arg Asp Val Asp Ile
                85                  90

<210> SEQ ID NO 145
<211> LENGTH: 27
<212> TYPE: PRT
<213> ORGANISM: Artificial Sequence
<220> FEATURE:
<223> OTHER INFORMATION: Synthetic peptide.

<400> SEQUENCE: 145

Gln Thr Pro Thr Asn Thr Ile Ser Val Thr Pro Thr Asn Asn Ser Thr
1               5                  10                  15
```

```
Pro Thr Asn Asn Ser Asn Pro Lys Pro Asn Pro
            20                  25
```

<210> SEQ ID NO 146
<211> LENGTH: 560
<212> TYPE: PRT
<213> ORGANISM: Artificial Sequence
<220> FEATURE:
<223> OTHER INFORMATION: Synthetic peptide.

<400> SEQUENCE: 146

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Tyr Phe
            100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
        210                 215                 220

Ser Lys Tyr Gly Pro Pro Cys Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350
```

```
Val Tyr Thr Leu Pro Pro Ser Gln Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
    435                 440                 445

Ser Leu Gly Lys Ala Ser Gln Thr Pro Thr Asn Thr Ile Ser Val Thr
    450                 455                 460

Pro Thr Asn Asn Ser Thr Pro Thr Asn Asn Ser Asn Pro Lys Pro Asn
465                 470                 475                 480

Pro Ala Ser Met Glu His Gln Leu Leu Cys Cys Glu Val Glu Thr Ile
                485                 490                 495

Arg Arg Ala Tyr Pro Asp Ala Asn Leu Leu Asn Asp Arg Val Leu Arg
                500                 505                 510

Ala Met Leu Lys Ala Glu Glu Thr Cys Ala Pro Ser Val Ser Tyr Phe
        515                 520                 525

Lys Cys Val Ala Ser Thr Asn Gly Ser Ile Thr Val Ala Ala Thr Ala
            530                 535                 540

Pro Thr Val Thr Pro Thr Val Asn Ala Thr Pro Ser Ala Ala Ala Ser
545                 550                 555                 560

<210> SEQ ID NO 147
<211> LENGTH: 759
<212> TYPE: PRT
<213> ORGANISM: Artificial Sequence
<220> FEATURE:
<223> OTHER INFORMATION: Synthetic peptide.

<400> SEQUENCE: 147

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
            165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
            435                 440                 445

Ser Leu Gly Lys Ala Ser Gln Thr Pro Thr Asn Thr Ile Ser Val Thr
            450                 455                 460

Pro Thr Asn Asn Ser Thr Pro Thr Asn Asn Ser Asn Pro Lys Pro Asn
465                 470                 475                 480

Pro Ala Ser Gln Lys Glu Val Leu Pro Ser Met Arg Lys Ile Val Ala
            485                 490                 495

Thr Trp Met Leu Glu Val Cys Glu Glu Gln Lys Cys Glu Glu Glu Val
            500                 505                 510

Phe Pro Leu Ala Met Asn Tyr Leu Asp Arg Phe Leu Ser Leu Glu Pro
            515                 520                 525

Val Lys Lys Ser Arg Leu Gln Leu Leu Gly Ala Thr Cys Met Phe Val
            530                 535                 540

Ala Ser Lys Met Lys Glu Thr Ile Pro Leu Thr Ala Glu Lys Leu Cys
545                 550                 555                 560

Ile Tyr Thr Asp Asn Ser Ile Arg Pro Glu Glu Leu Leu Gln Met Glu
            565                 570                 575

Leu Leu Leu Val Asn Lys Leu Lys Trp Asn Leu Ala Ala Met Thr Pro
```

```
                580             585             590
His Asp Phe Ile Glu His Phe Leu Ser Lys Met Pro Glu Ala Glu Glu
            595                 600             605

Asn Lys Gln Ile Ile Arg Lys His Ala Gln Thr Phe Ala Leu Cys
            610             615                 620

Ala Thr Asp Val Lys Phe Ile Ser Asn Pro Ser Met Val Ala Ala
625                 630             635                 640

Gly Ser Val Val Ala Ala Val Gln Gly Leu Asn Leu Arg Ser Pro Asn
                645             650             655

Asn Phe Leu Ser Tyr Tyr Arg Leu Thr Arg Phe Leu Ser Arg Val Ile
                660             665             670

Lys Cys Asp Pro Asp Cys Leu Arg Ala Cys Gln Gln Ile Glu Ala
                675             680             685

Leu Leu Glu Ser Ser Leu Arg Gln Ala Gln Gln Asn Met Asp Pro Lys
                690             695             700

Ala Ala Glu Glu Glu Glu Glu Glu Glu Val Asp Leu Ala Cys
705                 710             715                 720

Thr Pro Thr Asp Val Arg Asp Val Asp Ile Ala Ser Thr Asn Gly Ser
                725             730             735

Ile Thr Val Ala Ala Thr Ala Pro Thr Val Thr Pro Thr Val Asn Ala
                740             745             750

Thr Pro Ser Ala Ala Ala Ser
            755

<210> SEQ ID NO 148
<211> LENGTH: 468
<212> TYPE: PRT
<213> ORGANISM: Artificial Sequence
<220> FEATURE:
<223> OTHER INFORMATION: Synthetic peptide.

<400> SEQUENCE: 148

Met Asn Leu Gly Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
                20                  25                  30

Pro Gly Gly Ser Leu Lys Leu Ser Cys Ala Thr Ser Gly Phe Thr Phe
            35                  40                  45

Ser Asp Tyr Tyr Met Tyr Trp Val Arg Gln Thr Pro Glu Lys Arg Leu
        50                  55                  60

Glu Trp Val Ala Tyr Ile Asn Ser Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Arg Leu Lys Ser Glu Asp Thr Ala Met
                100                 105                 110

Tyr Tyr Cys Ala Arg Arg Gly Leu Pro Phe His Ala Met Asp Tyr Trp
            115                 120                 125

Gly Gln Gly Thr Ser Val Thr Phe Val Ser Ser Ala Lys Thr Lys Gly
        130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
```

```
                180             185             190
Pro Ala Val Leu Gln Ser Ser Gly Leu Tyr Ser Leu Ser Val Val
            195                 200                 205
Thr Val Pro Ser Ser Ser Leu Gly Thr Lys Thr Tyr Thr Cys Asn Val
            210                 215                 220
Asp His Lys Pro Ser Asn Thr Lys Val Asp Lys Arg Val Glu Ser Lys
225                 230                 235                 240
Tyr Gly Pro Pro Cys Pro Pro Cys Pro Ala Pro Glu Phe Glu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser Gln Glu
            275                 280                 285
Asp Pro Glu Val Gln Phe Asn Trp Tyr Val Asp Gly Val Glu Val His
            290                 295                 300
Asn Ala Lys Thr Lys Pro Arg Glu Glu Gln Phe Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Gly Leu Pro Ser Ser Ile Glu
                340                 345                 350
Lys Thr Ile Ser Lys Ala Lys Gly Gln Pro Arg Glu Pro Gln Val Tyr
            355                 360                 365
Thr Leu Pro Pro Ser Gln Glu Glu Met Thr Lys Asn Gln Val Ser Leu
            370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Arg Leu Thr Val Asp
            420                 425                 430
Lys Ser Arg Trp Gln Glu Gly Asn Val Phe Ser Cys Ser Val Met His
            435                 440                 445
Glu Ala Leu His Asn His Tyr Thr Gln Lys Ser Leu Ser Leu Ser Leu
            450                 455                 460
Gly Lys Ala Ser
465

<210> SEQ ID NO 149
<211> LENGTH: 234
<212> TYPE: PRT
<213> ORGANISM: Artificial Sequence
<220> FEATURE:
<223> OTHER INFORMATION: Synthetic peptide.

<400> SEQUENCE: 149

Met Met Ser Ser Ala Gln Phe Leu Gly Leu Leu Leu Leu Cys Phe Gln
1               5                   10                  15
Gly Thr Arg Cys Asp Ile Gln Met Thr Gln Thr Thr Ser Ser Leu Ser
                20                  25                  30
Ala Ser Leu Gly Asp Arg Val Thr Ile Ser Cys Ser Ala Ser Gln Gly
            35                  40                  45
Ile Ser Asn Tyr Leu Asn Trp Tyr Gln Gln Lys Pro Asp Gly Thr Val
        50                  55                  60
Lys Leu Leu Ile Tyr Tyr Thr Ser Ile Leu His Ser Gly Val Pro Ser
```

```
            65                  70                  75                  80
Arg Phe Ser Gly Ser Gly Ser Gly Thr Asp Tyr Ser Leu Thr Ile Gly
                85                  90                  95

Asn Leu Glu Pro Glu Asp Ile Ala Thr Tyr Tyr Cys Gln Gln Phe Asn
            100                 105                 110

Lys Leu Pro Pro Thr Phe Gly Gly Gly Thr Lys Leu Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 150
<211> LENGTH: 203
<212> TYPE: PRT
<213> ORGANISM: Artificial Sequence
<220> FEATURE:
<223> OTHER INFORMATION: Synthetic peptide.

<400> SEQUENCE: 150

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Val Leu His Trp Val Lys Gln Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Gly Tyr Pro Ala Tyr Ser Gly Tyr Ala Met Asp
        115                 120                 125

Tyr Trp Gly Gln Gly Thr Ser Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Lys Gly Glu Phe Val
```

<210> SEQ ID NO 151
<211> LENGTH: 234
<212> TYPE: PRT
<213> ORGANISM: Artificial Sequence
<220> FEATURE:
<223> OTHER INFORMATION: Synthetic peptide.

<400> SEQUENCE: 151

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys His His Gly Asn
            100                 105                 110

Thr Leu Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 152
<211> LENGTH: 235
<212> TYPE: PRT
<213> ORGANISM: Artificial Sequence
<220> FEATURE:
<223> OTHER INFORMATION: Synthetic peptide.

<400> SEQUENCE: 152

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Leu Ser Ala Ser Pro Gly Glu Lys Val Thr Met Thr Cys Ser Ala Ser
        35                  40                  45

Ser Ser Val Ser Tyr Met Tyr Arg Tyr Gln Gln Lys Pro Gly Ser Ser
    50                  55                  60

```
Pro Lys Pro Trp Ile Tyr Gly Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Ser Met Glu Ala Glu Asp Ala Ala Thr Tyr Tyr Cys Gln Gln Tyr
             100                 105                 110

His Ser Tyr Pro Leu Thr Phe Gly Ala Gly Thr Lys Leu Glu Leu Lys
         115                 120                 125

Arg Ala Asp Ala Ala Pro Thr Val Ser Ile Phe Pro Pro Ser Ser Glu
     130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                 165                 170                 175

Gln Asn Gly Val Leu Asn Ser Trp Thr Asp Gln Asp Ser Lys Asp Ser
             180                 185                 190

Thr Tyr Ser Met Ser Ser Thr Leu Thr Leu Thr Lys Asp Glu Tyr Glu
         195                 200                 205

Arg His Asn Ser Tyr Thr Cys Glu Ala Thr His Lys Thr Ser Thr Ser
     210                 215                 220

Pro Ile Val Lys Ser Phe Asn Arg Asn Glu Cys
225                 230                 235

<210> SEQ ID NO 153
<211> LENGTH: 196
<212> TYPE: PRT
<213> ORGANISM: Artificial Sequence
<220> FEATURE:
<223> OTHER INFORMATION: Synthetic peptide.

<400> SEQUENCE: 153

Met Gly Trp Ser Trp Ile Phe Leu Phe Leu Leu Ser Gly Thr Ala Gly
  1               5                  10                  15

Val Leu Ser Glu Val Gln Leu Gln Gln Ser Gly Pro Glu Leu Val Lys
                 20                  25                  30

Pro Gly Ala Ser Val Lys Ile Ser Cys Lys Ala Ser Gly Tyr Ser Phe
             35                  40                  45

Thr Gly Tyr Tyr Met His Trp Val Lys Gln Ser His Val Lys Ser Leu
         50                  55                  60

Glu Trp Ile Gly Arg Ile Asn Pro Tyr Asn Gly Ala Thr Ser Tyr Asn
 65                  70                  75                  80

Gln Asn Phe Lys Asp Lys Ala Ser Leu Thr Val Asp Lys Ser Ser Ser
                 85                  90                  95

Thr Ala Tyr Met Glu Leu His Ser Leu Thr Ser Glu Asp Ser Ala Val
             100                 105                 110

Tyr Tyr Cys Ala Arg Glu Asp Tyr Val Tyr Trp Gly Gln Gly Thr Thr
         115                 120                 125

Leu Thr Val Ser Ser Ala Lys Thr Thr Pro Pro Ser Val Tyr Pro Leu
     130                 135                 140

Ala Pro Gly Ser Ala Ala Gln Thr Asn Ser Met Val Thr Leu Gly Cys
145                 150                 155                 160

Leu Val Lys Gly Tyr Phe Pro Glu Pro Val Thr Val Thr Trp Asn Ser
                 165                 170                 175

Gly Ser Leu Ser Ser Gly Val His Thr Phe Pro Ala Val Leu Gln Lys
             180                 185                 190
```

Gly Glu Phe Val
    195

<210> SEQ ID NO 154
<211> LENGTH: 238
<212> TYPE: PRT
<213> ORGANISM: Artificial Sequence
<220> FEATURE:
<223> OTHER INFORMATION: Synthetic peptide.

<400> SEQUENCE: 154

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Ala
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 155
<211> LENGTH: 705
<212> TYPE: DNA
<213> ORGANISM: Artificial Sequence
<220> FEATURE:
<223> OTHER INFORMATION: Synthetic oligonucleotide.

<400> SEQUENCE: 155
atgatgtcct ctgctcagtt ccttggtctc ctgttgctct gttttcaagg taccagatgt      60
gatatccaga tgacacagac tacatcctcc ctgtctgcct ctctaggaga cagagtcacc     120
atcagttgca gtgcaagtca gggcattagc aattatttaa actggtatca gcagaaacca     180
gatggaactg ttaaactcct gatctattac acatcaattt acactcagg agtcccatca      240 aggttcagtg gcagtgggtc tgggacagat tattctctca ccatcggcaa cctggaacct     300
gaagatattg ccacttacta ttgtcagcag tttaataagc ttcctccgac gttcggtgga     360

```
ggcaccaaac tcgagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg dataacgccc tccaatcggg taactcccag    540
gagagtgtca cagagcagga cagcaaggac agcacctaca gcctcagcag cacccctgacg    600 ctgagcaaag cagactacga gaaacacaaa gtctatgcct gcgaagtcac ccatcagggc    660
ctgagctcgc ccgtcacaaa gagcttcaac aggggagagt gttag                    705
```

<210> SEQ ID NO 156
<211> LENGTH: 1404
<212> TYPE: DNA
<213> ORGANISM: Artificial Sequence
<220> FEATURE:
<223> OTHER INFORMATION: Synthetic oligonucleotide.

<400> SEQUENCE: 156

```
atgaacttgg ggctcagctt gattttcctt gtccttgttt taaaaggtgt ccagtgtgaa     60
gtgaagctgg tggagtctgg gggaggctta gtgcagcctg agggtccct gaaactctcc     120 tgtgcaacct ctggattcac tttcagtgac tattacatgt attgggttcg ccagactcca    180
gagaagaggc tggagtgggt cgcatacatt aattctggtg gtggtagcac ctattatcca    240
gacactgtaa agggccgatt caccatctcc agagacaatg ccaagaacac cctgtacctg    300
caaatgagcc ggctgaagtc tgaggacaca gccatgtatt actgtgcaag acgggggtta    360
ccgttccatg ctatggacta ttggggtcaa ggaacctcag tcaccgtctc ctcagccaaa    420
acgaagggcc catccgtctt ccccctggcg ccctgctcca ggagcacctc cgagagcaca    480
gccgccctgg gctgcctggt caaggactac ttccccgaac cggtgacggt gtcgtggaac    540
tcaggcgccc tgaccagcgg cgtgcacacc ttcccggctg tcctacagtc ctcaggactc    600
tactccctca gcagcgtggt gaccgtgccc tccagcagct gggcacgaa gacctacacc     660 tgcaacgtag atcacaagcc cagcaacacc aaggtggaca gagagttga gtccaaatat     720 ggtccccat gcccaccctg cccagcacct gagttcgaag ggggaccatc agtcttcctg     780
ttccccccaa aacccaagga cactctcatg atctcccgga cccctgaggt cacgtgcgtg    840
gtggtggacg tgagccagga agaccccgag gtccagttca actggtacgt ggatggcgtg    900
gaggtgcata atgccaagac aaagccgcgg gaggagcagt tcaacagcac gtaccgtgtg    960
gtcagcgtcc tcaccgtcct gcaccaggac tggctgaacg gcaaggagta caagtgcaag   1020
gtctccaaca aaggcctccc gtcctccatc gagaaaacca tctccaaagc caaagggcag   1080
ccccgagagc cacaggtgta caccctgccc ccatcccagg aggagatgac caagaaccag   1140
gtcagcctga cctgcctggt caaaggcttc taccccagcg acatcgccgt ggagtgggag   1200
agcaatgggc agccggagaa caactacaag accacgcctc ccgtgctgga ctccgacggc   1260
tccttcttcc tctacagcag gctaaccgtg gacaagagca ggtggcagga ggggaatgtc   1320
ttctcatgct ccgtgatgca tgaggctctg cacaaccact acacacagaa gagcctctcc   1380
ctgtctctgg gtaaagctag ctga                                          1404
```

<210> SEQ ID NO 157
<211> LENGTH: 1410
<212> TYPE: DNA
<213> ORGANISM: Artificial Sequence
<220> FEATURE:
<223> OTHER INFORMATION: Synthetic oligonucleotide.

<400> SEQUENCE: 157

```
atggaatgga gttggatatt tctctttctt ctgtcaggaa ctgcaggtgt ccactctgag      60
gtccagctgc agcagtctgg acctgagctg gtaaagcctg ggcttcagt gaagatgtcc      120
tgcaaggctt ctggatacac attcactgac tatgttttgc actgggtgaa acagaagcct    180
gggcagggcc ttgagtggat tggatatatt aatccttaca tgatggtac taagtacaat     240
gagaagttca aggcaaggc cacactgact tcagacaaat cctccagcac agcctacatg     300
gagctcagca gcctgacctc tgaggactct gcggtctatt actgtgcaag ggctatccg     360
gcctactctg gtatgctat ggactactgg ggtcaaggaa cctcagtcac cgtctcctca    420
gccaaaacga agggcccatc cgtcttcccc ctggcgccct gctccaggag cacctccgag   480
agcacagccg ccctgggctg cctggtcaag gactacttcc ccgaaccggt gacggtgtcg   540
tggaactcag gcgccctgac cagcggcgtg cacaccttcc cggctgtcct acagtcctca    600
ggactctact ccctcagcag cgtggtgacc gtgccctcca gcagcttggg cacgaagacc    660
tacacctgca acgtagatca caagcccagc aacaccaagg tggacaagag agttgagtcc    720
aaatatggtc cccatgccc accctgccca gcacctgagt tcgaagggg accatcagtc     780
ttcctgttcc ccccaaaacc caaggacact ctcatgatct cccggacccc tgaggtcacg    840
tgcgtggtgg tggacgtgag ccaggaagac cccgaggtcc agttcaactg gtacgtggat    900
ggcgtggagg tgcataatgc caagacaaag ccgcgggagg agcagttcaa cagcacgtac    960
cgtgtggtca gcgtcctcac cgtcctgcac caggactggc tgaacggcaa ggagtacaag   1020
tgcaaggtct ccaacaaagg cctcccgtcc tccatcgaga aaaccatctc caaagccaaa  1080
gggcagcccc gagagccaca ggtgtacacc ctgcccccat cccaggagga tgaccaag    1140
aaccaggtca gcctgacctg cctggtcaaa ggcttctacc ccagcgacat cgccgtggag   1200
tgggagagca atgggcagcc ggagaacaac tacaagacca cgcctcccgt gctggactcc   1260
gacggctcct tcttcctcta cagcaggcta accgtggaca gagcaggtg gcaggagggg   1320
aatgtcttct catgctccgt gatgcatgag gctctgcaca accactacac acagaagagc   1380
ctctccctgt ctctgggtaa agctagctga                                    1410
```

<210> SEQ ID NO 158
<211> LENGTH: 708
<212> TYPE: DNA
<213> ORGANISM: Artificial Sequence
<220> FEATURE:
<223> OTHER INFORMATION: Synthetic oligonucleotide.

<400> SEQUENCE: 158

```
atggatttc aagtgcagat tttcagcttc ctgctaatca gtgcctcagt cataatgtcc      60
agggacaaa ttgttctcac ccagtctcca gcaatcctgt ctgcatctcc aggggagaag   120
gtcaccatga cctgcagtgc cagctcaagt gtaagttaca tgtacaggta ccagcagaag   180
ccaggatcct cacccaaacc ctggatttat ggcacatcca acctggcttc tggagtccct   240
gctcgcttca gtggcagtgg atctgggacc tcttattctc tcacaatcag cagcatggag   300
gctgaagatg ctgccactta ttactgccag caatatcata gttacccgct cacgttcggt   360
gctgggacca agctcgagat caaacgaact gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct cagcctcag cagcacctg    600
```

```
acgctgagca aagcagacta cgagaaacac aaagtctatg cctgcgaagt cacccatcag    660
ggcctgagct cgcccgtcac aaagagcttc aacaggggag agtgttag                708

<210> SEQ ID NO 159
<211> LENGTH: 705
<212> TYPE: DNA
<213> ORGANISM: Artificial Sequence
<220> FEATURE:
<223> OTHER INFORMATION: Synthetic oligonucleotide.

<400> SEQUENCE: 159
atgatgtcct ctgctcagtt ccttggtctc ctgttgctct gttttcaagg taccagatgt     60
gatatccaga tgacacagac tacatcctcc ctgtctgcct ctctgggaga cagagtcacc    120
atcagttgca gggcaagtca ggacattagc aattatttaa actggtatca gcagaaacca    180
gatggaactg ttaaactcct gatctactac acatcaagat tacactcagg agtcccatca    240
aggttcagtg gcagtgggtc tggaacagat tattctctca ccattagcaa cctggagcaa    300
gaagatattg ccacttactt ttgccatcat ggtaatacgc ttccgtggac gttcggtgga    360
ggcaccaagc tcgagatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctatgcct gcgaagtcac ccatcagggc    660
ctgagctcgc ccgtcacaaa gagcttcaac aggggagagt gttag                   705

<210> SEQ ID NO 160
<211> LENGTH: 1389
<212> TYPE: DNA
<213> ORGANISM: Artificial Sequence
<220> FEATURE:
<223> OTHER INFORMATION: Synthetic oligonucleotide.

<400> SEQUENCE: 160
atgggatgga gctggatctt tctctttctc ctgtcaggaa ctgcaggtgt cctctctgag     60
gtccagctgc aacagtctgg acctgagctg gtgaagcctg ggcttcagt gaagatatcc    120 tgcaaggctt ctggttactc attcactggc tactacatgc actgggtgaa gcaaagccat    180
gtaaagagcc ttgagtggat tggacgtatt aatccttaca atggtgctac tagctacaac    240
cagaatttca aggacaaggc cagcttgact gtagataagt cctccagcac agcctacatg    300
gagctccaca gcctgacatc tgaggactct gcagtctatt actgtgcaag agaggactac    360
gtctactggg gccaaggcac cactctcaca gtctcctcag ccaaaacgaa gggcccatcc    420
gtcttccccc tggcgccctg ctccaggagc acctccgaga gcacagccgc cctgggctgc    480
ctggtcaagg actacttccc cgaaccggtg acggtgtcgt ggaactcagg cgccctgacc    540
agcggcgtgc acaccttccc ggctgtccta cagtcctcag gactctactc cctcagcagc    600
gtggtgaccg tgccctccag cagcttgggc acgaagacct acacctgcaa cgtagatcac    660
aagcccagca acaccaaggt ggacaagaga gttgagtcca aatatggtcc cccatgccca    720
ccctgcccag cacctgagtt cgaaggggga ccatcagtct tcctgttccc cccaaaaccc    780
aaggacactc tcatgatctc ccggaccccct gaggtcacgt gcgtggtggt ggacgtgagc    840
caggaagacc ccgaggtcca gttcaactgg tacgtggatg gcgtggaggt gcataatgcc    900
```

```
aagacaaagc cgcgggagga gcagttcaac agcacgtacc gtgtggtcag cgtcctcacc    960
gtcctgcacc aggactggct gaacggcaag gagtacaagt gcaaggtctc caacaaaggc   1020
ctcccgtcct ccatcgagaa aaccatctcc aaagccaaag ggcagccccg agagccacag   1080
gtgtacaccc tgcccccatc ccaggaggag atgaccaaga accaggtcag cctgacctgc   1140
ctggtcaaag gcttctaccc cagcgacatc gccgtggagt gggagagcaa tgggcagccg   1200
gagaacaact acaagaccac gcctcccgtg ctggactccg acggctcctt cttcctctac   1260
agcaggctaa ccgtggacaa gagcaggtgg caggagggga atgtcttctc atgctccgtg   1320
atgcatgagg ctctgcacaa ccactacaca cagaagagcc tctccctgtc tctgggtaaa   1380
gctagctga                                                          1389

<210> SEQ ID NO 161
<211> LENGTH: 717
<212> TYPE: DNA
<213> ORGANISM: Artificial Sequence
<220> FEATURE:
<223> OTHER INFORMATION: Synthetic oligonucleotide.

<400> SEQUENCE: 161
atgaagttgc ctgttaggct gttggtgctg atgttctgga ttcctgcttc cagcagtgat     60
gttgtgatga cccaaactcc actctccctg cctgtcagtc ttggagatca agcctccatc    120
tcttgcagat ctagtcagag ccttgtacac agtaatggaa acacctattt acattggtac    180
ctgcagaagc caggccagtc tccaaagctc ctgatctaca agtttccaac cgattttct    240 ggggtcccag acaggttcag tggcagtgga tcagggacag atttcgcact caagatcagt    300
agagtggagg ctgaggatct gggagtttat ttctgctctc aaagtacaca tgttccgtgg    360
acgttcggtg gaggcaccaa gctcgagatc aaacgaactg tggctgcacc atctgtcttc    420
atcttcccgc catctgatga gcagttgaaa tctggaactg cctctgttgt gtgcctgctg    480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca aagtctatgc ctgcgaagtc    660
acccatcagg gcctgagctc gcccgtcaca aagagcttca cagggggaga gtgttag      717
```